United States Patent
Olivier et al.

(10) Patent No.: US 12,404,297 B2
(45) Date of Patent: *Sep. 2, 2025

(54) SALTS AND CRYSTAL FORMS OF GABA-$_A$ POSITIVE ALLOSTERIC MODULATOR

(71) Applicant: Praxis Precision Medicines, Inc., Boston, MA (US)

(72) Inventors: Nelson B. Olivier, Stoughton, MA (US); Kiran Reddy, Charlestown, MA (US); Gabriel Martinez Botella, Wayland, MA (US); Magnus Ronn, Melrose, MA (US); Paul A. Laskar, Napa, CA (US)

(73) Assignee: PRAXIS PRECISION MEDICINES, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/529,117

(22) Filed: Dec. 5, 2023

(65) Prior Publication Data
US 2024/0140985 A1     May 2, 2024

Related U.S. Application Data

(63) Continuation of application No. 17/143,602, filed on Jan. 7, 2021, now abandoned, which is a continuation of application No. 16/698,057, filed on Nov. 27, 2019, now Pat. No. 10,927,141, which is a continuation of application No. 16/517,369, filed on Jul. 19, 2019, now Pat. No. 10,562,930.

(60) Provisional application No. 62/725,805, filed on Aug. 31, 2018.

(51) Int. Cl.
| C07J 43/00 | (2006.01) |
| A61K 9/20 | (2006.01) |
| A61K 31/4164 | (2006.01) |
| C07D 233/60 | (2006.01) |

(52) U.S. Cl.
CPC ............... *C07J 43/003* (2013.01); *A61K 9/20* (2013.01); *A61K 31/4164* (2013.01); *C07B 2200/13* (2013.01)

(58) Field of Classification Search
CPC .. A61K 31/4164; C07J 43/003; C07D 233/60
See application file for complete search history.

(56) References Cited

U.S. PATENT DOCUMENTS

| 5,925,630 A | 7/1999 | Upasani et al. |
| 5,939,545 A | 8/1999 | Upasani et al. |
| 6,780,853 B1 | 8/2004 | Upasani et al. |
| 10,562,930 B1 | 2/2020 | Olivier et al. |
| 10,927,141 B2 | 2/2021 | Olivier et al. |
| 11,697,669 B2 | 7/2023 | Neville et al. |
| 2004/0034002 A1 | 2/2004 | Hogenkamp |
| 2005/0101614 A1 | 5/2005 | Lin et al. |
| 2006/0074059 A1 | 4/2006 | Goliber et al. |
| 2007/0015789 A1 | 1/2007 | Barth et al. |
| 2007/0112017 A1 | 5/2007 | Barlow et al. |
| 2009/0074677 A1 | 3/2009 | Marx et al. |
| 2009/0118248 A1 | 5/2009 | Chang et al. |
| 2009/0131383 A1 | 5/2009 | Woodward |
| 2012/0276196 A1 | 11/2012 | Woodward |
| 2014/0315992 A1 | 10/2014 | Hakonarson et al. |
| 2017/0151191 A1 | 6/2017 | Charney et al. |
| 2017/0240589 A1 | 8/2017 | Martinez Botella et al. |
| 2017/0348327 A1 | 12/2017 | Kanes et al. |
| 2018/0028519 A1 | 2/2018 | Mouthon et al. |
| 2018/0071315 A1 | 3/2018 | Cashman et al. |
| 2019/0008760 A1 | 1/2019 | Meltzer et al. |
| 2019/0091231 A1 | 3/2019 | During |
| 2019/0160078 A1 | 5/2019 | Masuoka et al. |
| 2020/0071350 A1 | 3/2020 | Olivier et al. |
| 2020/0188358 A1 | 6/2020 | Loya et al. |
| 2020/0255471 A1 | 8/2020 | Olivier et al. |
| 2020/0323823 A1 | 10/2020 | Loya et al. |

FOREIGN PATENT DOCUMENTS

| JP | 2002543218 A | 12/2002 |
| JP | 2008542419 A | 11/2008 |
| WO | 1998005337 A1 | 2/1998 |
| WO | 00/66614 A1 | 11/2000 |
| WO | 2000066614 A2 | 11/2000 |
| WO | 2004072079 A1 | 8/2004 |
| WO | 2005105822 A2 | 11/2005 |
| WO | 2006131392 A1 | 12/2006 |
| WO | 2016061527 A1 | 4/2016 |
| WO | 2020047434 A1 | 3/2020 |
| WO | 2020124094 A1 | 6/2020 |
| WO | 2020131918 A1 | 6/2020 |

(Continued)

OTHER PUBLICATIONS

Dewey et al., "GABAergic inhibition of endogenous dopamine release measured in vivo with 11C-raclopride and positron emission tomography," The Journal of Neuroscience, Oct. 1992, 12(10): 3773-3780.

Extended European Search Report for European Application No. 19842855.9 dated Jul. 31, 2020.

Hosie et al., "Endogenous neurosteroids regulate GABAA receptors through two discrete transmembrane sites," Nature, 2006, 444:486-489.

International Search Report and Written Opinion of the International Searching Authority for International Application No. PCT/US2019/049103, dated Nov. 15, 2019.

International Search Report and Written Opinion of the International Searching Authority for International Application No. PCT/US2019/066642, dated Feb. 21, 2020.

(Continued)

Primary Examiner — Adam C Milligan
Assistant Examiner — Karen Cheng
(74) Attorney, Agent, or Firm — MH2 Technology Law Group, LLP

(57) ABSTRACT

The invention relates to salts of Compound 1, crystalline forms thereof, methods of their preparation, pharmaceutical compositions thereof and methods of their use.

17 Claims, 125 Drawing Sheets

(56) References Cited

FOREIGN PATENT DOCUMENTS

| WO | 2020180955 A1 | 9/2020 |
| WO | 2020185710 A1 | 9/2020 |
| WO | 2021025985 A1 | 2/2021 |
| WO | 2021067702 A1 | 4/2021 |
| WO | 2021168106 A1 | 8/2021 |
| WO | 2022006541 A1 | 1/2022 |
| WO | 2022040545 A1 | 2/2022 |
| WO | 2022178000 A1 | 8/2022 |
| WO | 2022232104 A1 | 11/2022 |
| WO | 2023159094 A2 | 8/2023 |
| WO | 2023211856 A1 | 11/2023 |

OTHER PUBLICATIONS

Krupitsky et al., "Injectable extended-release naltrexone for opioid dependence: a double-blind, placebo-controlled, multicentre randomised trial," Lancet (2006) 377, 1506-1513.

Luscher et al., "The GABAergic deficit hypothesis of major depressive disorder," Mol Psychiatry, 2011, 16 (4):383-406.

Maki et al., "Guidelines for the Evaluation and Treatment of Perimenopausal Depression: Summary and Recommendations," Journal of Women's Health, 2019, vol. 28, No. 2, pp. 117-134.

Ross and Peselow, "The Neurobiology of Addictive Disorders," Clin Neuropharmacol (2009) 32(5), 269-276.

Schmidt et al., "Comparative Evaluation of the Datex-Ohmeda S/5 Entropy Module and the Bispectral Index® Monitor during Propofol-Remifentanil Anesthesia," Anesthesiology 2004; 101 : 1283-1290.

Sinha et al., "Sex steroid hormones, stress response, and drug craving in cocaine-dependent women: Implications for relapse susceptibility," Exp Clin Psychopharm (2007) 15:445-452.

Vanover et al., "Behavioral characterization of Co 134444 (3a-hydroxy-21-( 1 '-imidazolyl)-3· - methoxymethyl-5a-pregnan-20-one), a novel sedative-hypnotic neuroactive steroid," Psychopharmacology (2001) 155:285-291.

Anderson, B.D., et al. (C.G. Wermuth, Editor), "Preparation of water-soluble organic compound by salt formation," Saishin Soyaku Kagaku Last Volume [The Practice of Medicinal Chemistry], Jan. 25, 1999, pp. 347-365, Japan ISBN: 4-924746-80-0. (See pp. 1-3 of translation of Japanese Notice of Reasons for Refusal dated Dec. 26, 2023 for a concise explanation of the relevance of this document, which is referred to as Document 4 in the Japanese Notice of Reasons for Refusal.).

Fujishiro, Ryo (Examiner), Japanese Notice of Reasons for Refusal for Japanese Application No. 2022-199092, dated Dec. 26, 2023, with English translation, 8 pages.

Hirayama, "Handbook of Organic Compound Crystal Preparation—Principle and Know-how," Maruzen Co., Ltd., 2008, pp. 57-84, Japan ISBN: 978-4-621-07991-1. (See pp. 1-3 of translation of Japanese Notice of Reasons for Refusal dated Dec. 26, 2023 for a concise explanation of the relevance of this document, which is referred to as Document 5 in the Japanese Notice of Reasons for Refusal.).

Loya, Carlos, et al., "Methods of Treatment with Neuroactive Steroids," U.S. Appl. No. 18/555,222, filed Oct. 12, 2023, 164 pages.

Maruzen Planetary Co., Ltd., "A polymorphism of medicines and crystallisation," 2002, pp. 1, 56-102 and 304-317. (See pp. 1-3 of translation of Japanese Notice of Reasons for Refusal dated Dec. 26, 2023 for a concise explanation of the relevance of this document, which is referred to as Document 3 in the Japanese Notice of Reasons for Refusal.).

Marx, C., et al., "Neuroactive Steroids are Altered in Schizophrenia and Bipolar Disorder: Relevance to Pathophysiology and Therapeutics," Neuropsychopharmacology, 31:1249-1263, 2006 (Published online Nov. 23, 2005).

Matos, Taina (Authorized Officer), International Search Report and Written Opinion of the International Searching Authority for International Application No. PCT/US2022/026289, dated Jun. 24, 2022, 10 pages.

Mauro, John Matthew (Examiner), Non-Final Office Action issued in U.S. Appl. No. 17/824,205 mailed on Nov. 9, 2022, 11 pages.

Neville, Doris, et al., "Hemi-Citrate Salts of GABA-A Positive Allosteric Modulator and Crystalline Form Thereof," U.S. Appl. No. 18/546,800, filed Aug. 17, 2023, 97 pages.

Rodriquez, Kari (Authorized Officer), International Search Report and Written Opinion of the International Searching Authority for International Application No. PCT/US2022/016612, dated May 4, 2022, 12 pages.

Vanover et al., "Response-Rate Suppression in Operant Paradigm as Predictor of Soporific Potency in Rats and Identification of Three Novel Sedative-Hypnotic Neuroactive Steroids," The Journal of Pharmacology and Experimental Therapeutics, 291(3): 1317-1323, 1999 (Accepted for Publication Aug. 31, 1999).

Takesada, Ayumi {Examiner), Notice of Rejection issued in Japanese Patent Application No. 2020-517339 dated Apr. 26, 2022, with English language translation, 6 pages.

Australian Bureau of Statistics, (2008). "National Survey of Mental Health and Wellbeing: Summary of results," Available on line at <https://www.abs.gov.au/statistics/health/mental-health/national-survey-mental-health-and-wellbeing-summary-results/latest-release>, 30 pages.

Buysse et al., (1989). "The Pittsburgh Sleep Quality Index: a New Instrument for Psychiatric Practice and Research," Psychiatry Res., 28(2):193-213.

Dolomanov et al., (2009). "OLEX2: a complete structure solution, refinement and analysis program," Appl. Cryst., 42:339-341.

Drugs.com, (2018). "Depression Overview: Symptoms and Diagnosis," Available online at <https://www.drugs.com/depression.html>, 8 pages.

Fava et al., (2009). "Reliability and Validity of the Massachusetts General Hospital Cognitive and Physical Functioning Questionnaire," Psychothera Psychosom., 78:91-97.

Garratt et al., (1995). "Measuring sexual functioning in premenopausal women," Br J Obstet Gynaecol., 102:311-316.

Gordon et al., (2015). "Ovarian Hormone Fluctuation, Neurosteroids, and HPA Axis Dysregulation in Perimenopausal Depression: A Novel Heuristic Model," Am. J. Psychiatry, 172(3):227-236.

Hamilton, (1959). "The Assessment of Anxiety States by Rating," Br J Med Psychol., 32(1 ):50-5. Abstract Only.

Hamilton, (1960). "A Rating Scale for Depression," J Neurol Neurosurg Psychiatry, 23:56-62.

Hamilton, (1967). "Development of a rating scale; for primary depressive illness," Br. J. Soc. Clin. Psychol., 6 (4):278-296, 1 page.

Harlow et al., (2012). "Executive summary of the Stages of Reproductive Aging Workshop +10: addressing the unfinished agenda of staging reproductive aging," Climacteric, 15:105-114, 18 pages.

Hoddes et al., (1973). "Quantification of Sleepiness: A New Approach," Psychophysiology, 10(4):431-436.

Khodadoustan et al., (2017). "Evaluation of the effect of time dependent dosing on pharmacokinetic and pharmacodynamics of amlodipine in normotensive and hypertensive human subjects," Clinical and Experimental Hypertension, 39:520-526.

Kulkarni et al., (2018). "Development and validation of a new rating scale for perimenopausal depression-the Meno-D," Transl Psychiatry, 8(1 ):123, 9 pages.

Monaghan et al., (2005). "Ganaxolone: a novel positive allosteric modulator of the GABAA receptor complex for the treatment of epilepsy," Expert Opinion on investigational Drugs, 8, 1 page. Abstract only.

Montgomery et al., (1979). "New Depression Scale Designed to be Sensitive to Change," Br. J. Psychiatry, 134:382-9.

Pallarito, (2017). "12 Types of Depression, and What You Need to Know About Each," Available online at <https://www.health.com/condition/depression/types-of-depression>, 6 pages.

Pedrelli et al., (2014). "Reliability and Validity of the Symptoms of Depression Questionnaire (SDQ)," CNS Spectr., 19 (6):535-546, 17 pages.

Rush et al., (2006). "Acute and longer-term outcomes in depressed outpatients requiring one or several treatment steps: a STAR*D report," Am J Psychiatry, 163: 1905-1917.

Salvi et al., (2009). "Pharmacological Treatments for Tinnitus: New and Old," Drug Future, 34(5):381-400, 35 pages.

(56) References Cited

OTHER PUBLICATIONS

Shacham, (1983). "A shortened version of the Profile of Mood States," J of Personality Assessment, 4 7:305-306.
Shah et al., (2006). "Analytical techniques for quantification of amorphous/crystalline phases in pharmaceutical solids," J. Pharm. Sci., 95(8):1641-1665.
Spitzer et al., (2006). "A brief measure for assessing generalized anxiety disorder," Arch Inern Med., 166:1092-1097.
Williams et al., (2008). "Development and reliability of a structured interview guide for the Montgomery-Asberg Depression Rating Scale (SIGMA)," Br. J. of Psychiatry, 192:52-58.
Final Office Action received for U.S. Appl. No. 16/912,327 mailed on Jan. 26, 2021, 12 pages.
International Search Report and Written Opinion for International Application PCT/US2020/020938 mailed on Jun. 4, 2020, 8 pages.
International Search Report and Written Opinion for International Application PCT/US2020/044455 mailed on Dec. 29, 2020, 11 pages.
International Search Report and Written Opinion for International Application PCT/US2020/053951 mailed on Jan. 8, 2021, 8 pages.
International Search Report and Written Opinion for International Application PCT/US2021/018568 mailed on Jun. 11, 2021, 10 pages.
International Search Report and Written Opinion for International Patent Application No. PCT/US2021/040343 mailed Oct. 13, 2021, 8 pages.
Non-Final Office Action received for U.S. Appl. No. 16/698,057 mailed on Jun. 16, 2020, 8 pages.
Non-Final Office Action received for U.S. Appl. No. 16/912,327 mailed on Oct. 8, 2020, 12 pages.

SALTS AND CRYSTAL FORMS OF GABA-$_A$ POSITIVE ALLOSTERIC MODULATOR

CROSS-REFERENCE TO RELATED APPLICATIONS

This application is a continuation of U.S. application Ser. No. 17/143,602, filed Jan. 7, 2021, which is a continuation of U.S. application Ser. No. 16/698,057, filed Nov. 27, 2019 (now U.S. Pat. No. 10,927,141), which is a continuation of U.S. application Ser. No. 16/517,369, filed Jul. 19, 2019 (now U.S. Pat. No. 10,562,930), which claims priority to U.S. Provisional Application No. 62/725,805, filed Aug. 31, 2018, all of which are hereby incorporated by reference in their entireties herein.

FIELD OF THE DISCLOSURE

The present disclosure relates to salts of 3α-hydroxy-3β-methoxymethyl-21-(1'-imidazolyl)-5α-pregnan-20-one, crystal forms thereof and processes for preparing such salts and crystal forms.

BACKGROUND OF THE DISCLOSURE

3α-Hydroxy-3β-methoxymethyl-21-(1'-imidazolyl)-5α-pregnan-20-one (Compound 1) is a synthetic neuroactive steroid. Its primary molecular target is the γ-aminobutyric acid type A (GABA$_A$) receptor, where it acts as a positive allosteric modulator (PAM) of channel function. The structural formula of Compound 1 appears below.

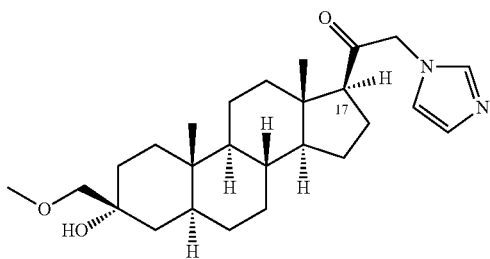

Neuroactive steroid GABA$_A$ PAMs have demonstrated clinical efficacy in epilepsy, post-partum depression, and major depression.

There is a need for isolable, stable and water-soluble Compound 1 salts and processes for making the same.

SUMMARY OF THE DISCLOSURE

This disclosure provides salts of Compound 1 and methods of making such salts. In some embodiments, the salts of Compound 1 are crystalline. The disclosure also provides pharmaceutical compositions comprising salts of Compound 1.

In some embodiments, the present disclosure provides hydrobromide, citrate, malate, maleate, mesylate, phosphate, tartrate, hydrochloride, tosylate, glucuronate, ethanesulfonate, fumarate, sulfate, napthalene-2-sulfonate, ascorbate, oxalate, napthalene-1,5-disulfonate, malonate, aminosalicylate, benzenesulfonate, isethionate, gentisate, 1-hydroxy-2-naphthoate, dichloroacetate, cyclamate, and ethane-1,2-disulfonate salts of Compound 1.

In some embodiments, the present disclosure provides crystalline forms of hydrobromide, citrate, malate, maleate, mesylate, phosphate, tartrate, hydrochloride, tosylate, glucuronate, ethanesulfonate, fumarate, sulfate, napthalene-2-sulfonate, ascorbate, oxalate, napthalene-1,5-di sulfonate, malonate, aminosalicylate, benzenesulfonate, isethionate, gentisate, 1-hydroxy-2-naphthoate, dichloroacetate, cyclamate, and ethane-1,2-disulfonate salts of Compound 1.

In some embodiments, the present disclosure provides hydrobromide salts of Compound 1. In some embodiments, the present disclosure provides crystalline forms of hydrobromide salts of Compound 1 ("Compound 1 HBr"). In one embodiment, the present disclosure provides Compound 1 HBr (Form A). In one embodiment, the present disclosure provides Compound 1 HBr (Form B). In one embodiment, the present disclosure provides Compound 1 HBr (Form C). In one embodiment, the present disclosure provides Compound 1 HBr (Form D). In one embodiment, the present disclosure provides Compound 1 HBr (Form E).

In some embodiments, the present disclosure provides citrate salts of Compound 1. In some embodiments, the present disclosure provides crystalline forms of citrate salts of Compound 1 ("Compound 1 Citrate"). In one embodiment, the present disclosure provides Compound 1 Citrate (Form A). In one embodiment, the present disclosure provides Compound 1 Citrate (Form B). In one embodiment, the present disclosure provides Compound 1 Citrate (Form C).

The present disclosure provides methods of administering salts of Compound 1. In some embodiments, the salts of Compound 1 are orally administered. The present disclosure also provides methods of treating a disease, disorder, or condition comprising administering a therapeutically effective amount of a salt of Compound 1. In certain embodiments, the disease, disorder, or condition is selected from epilepsy, post-partum depression, major depressive disorder, bipolar disorder, treatment resistant depression and anxiety.

DETAILED DESCRIPTION OF THE DRAWINGS

DETAILED DESCRIPTION OF THE DISCLOSURE

Definitions

Figure 1:
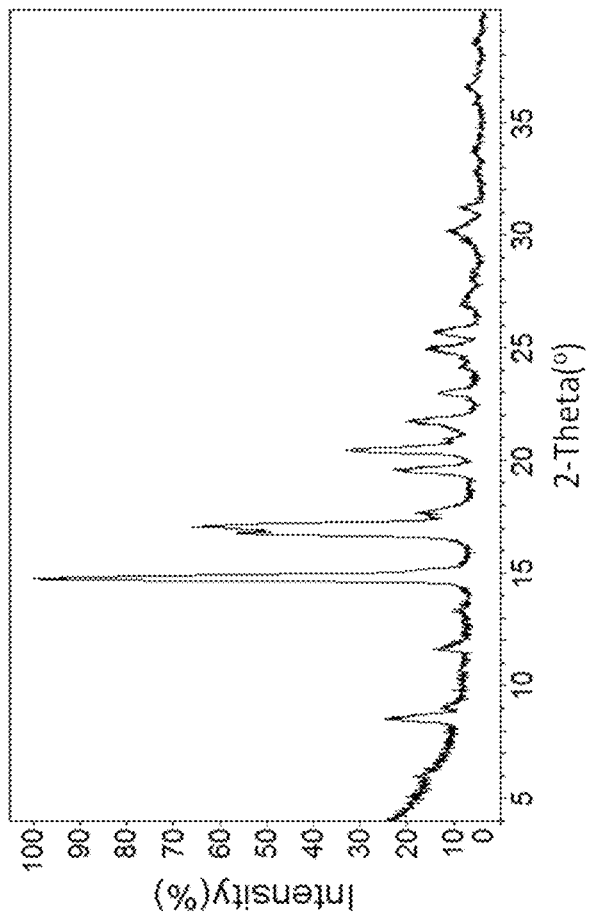
FIG. 1 shows an x-ray powder diffraction (XRPD) pattern of Compound 1 free base (Pattern A).

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

Throughout this disclosure, various patents, patent applications and publications (including non-patent publications) are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The terms "administer," "administering" or "administration" as used herein refer to either directly administering Compound 1 or pharmaceutically acceptable salt thereof or a composition comprising Compound 1 or pharmaceutically acceptable salt to a patient.

The terms "aprotic solvent," "nonprotic solvent" or "non-protic solvent" as used herein refers to an organic solvent or a mixture of organic solvents that is not readily deprotonated in the presence of a strongly basic reactant. Non-limiting examples of non-protic solvents include ethers, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, methyl isobutyl ketone, hexachloroacetone, acetone, ethyl methyl ketone, methyl ethyl ketone (MEK), ethyl acetate, isopropyl acetate, sulfolane, N,N-dimethylpropionamide, tetramethylurea, nitromethane, nitrobenzene, or hexamethylphosphoramide, diethoxymethane, tetrahydrofuran, 1,3-dioxane, 1,4-dioxane, furan, diethyl ether, tetrahydropyran, diisopropyl ether, dibutyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, and the like.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound, or a salt, solvate or ester thereof, that, when administered to a patient, is capable of performing the intended result. For example, an effective amount of a salt of Compound 1 is that amount that is required to reduce at least one symptom of depression in a patient. The actual amount that comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The term "isomer" refers to compounds having the same chemical formula but may have different stereochemical formula, structural formula, or special arrangements of atoms. Examples of isomers include stereoisomers, diastereomers, enantiomers, conformational isomers, rotamers, geometric isomers, and atropisomers.

The term "peak" refers to a line having a substantial intensity in the XRPD diffractogram (or pattern) obtained from a sample using standard XRPD collection techniques. For example, a peak is a line in the XRPD diffractogram having an intensity that is, for example, at least about 10% of the intensity of the largest peak in the XRPD diffractogram.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "protic solvent" as used herein refers to a solvent or a solvent mixture that is capable of functioning as an acid for purposes of protonating any unreacted, strongly basic reaction intermediates. Non-limiting examples of protic solvents include water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, and the like.

The term "salts" as used herein embraces pharmaceutically acceptable salts commonly used to form addition salts of free bases. The nature of the salt is not critical provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. In a salt, proton transfer occurs between Compound 1 free base and an organic acid or an inorganic acid. However, in some cases proton transfer is incomplete. In such cases, Compound 1 and the "co-former" molecules in the solid (i.e., "co-crystal") interact through non-ionic forces such as hydrogen bonding.

Where an acid co-former is a solid at about 23° C. (i.e., room temperature) and there is no, or partial, proton transfer between Compound 1 and the acid co-former, a co-crystal of the co-former and Compound 1 is provided. As used herein, the term "salt" encompasses co-crystal forms of Compound 1.

The term "substantially similar" as used herein means an analytical spectrum, such as XRPD pattern, DSC thermogram, etc., which resembles the reference spectrum to a great degree in both the peak locations and their intensity.

The term "treating" as used herein with regard to a patient, refers to improving at least one symptom of the patient's disorder. Treating can be curing, improving, or at least partially ameliorating a disorder.

The term "therapeutic effect" as used herein refers to a desired or beneficial effect provided by the method and/or the composition. For example, the method for treating depression provides a therapeutic effect when the method reduces at least one symptom of depression in a patient.

As used herein, the symbol "≤" means "not more than" or "equal to or less than"; "<" means "less than"; "≥" means "not less than" or "equal to or more than"; and ">" means "more than". Furthermore, the numerical numbers, when used herein in connection with purity or impurity content, include not only the exact number but also the approximate range around the number. For example, the phrase "purity of 99.0%" denotes a purity of about 99.0%.

Salts of Compound 1

Compound 1 is a neuroactive steroid GABA-A positive allosteric modulator (PAM) with high potency similar to clinical stage neuroactive steroids (allopregnanolone, ganaxolone, SAGE-217, alphaxolone). Compound 1 is poorly soluble at the pH found in the lower GI tract, which may limit Compound 1's oral bioavailability.

The synthesis of Compound 1 is described in U.S. Publication Nos. 2004/034002 and 2009/0118248; crystalline polymorph of Compound 1 free base is described in U.S. Publication No. 2006/0074059 and pharmaceutical compositions containing Compound 1 are described in U.S. Publication No. 2009/0131383, which are hereby incorporated by reference in their entirety for all purposes.

The present disclosure provides salts of Compound 1 and crystalline forms thereof.

Crystalline Salts of Compound 1

In some embodiments, the present disclosure provides crystalline forms of a salt of Compound 1. Polymorphism can be characterized as the ability of a compound to crystallize into different crystal forms while maintaining the same structural formula (i.e., the covalent bonds in the compound are the same in different crystal forms). A crystalline polymorph of a given drug substance is chemically identical to any other crystalline polymorph of that drug substance in containing the same atoms bonded to one another in the same way, but differs in its crystal forms, which can affect one or more physical properties, such as stability, solubility, melting point, bulk density, flow properties, etc., or pharmacological properties such as bioavailability, etc.

In some embodiments, the crystalline forms are characterized by the interlattice plane intervals determined by an X-ray powder diffraction pattern (XRPD). The XRPD diffractogram is typically represented by a diagram plotting the intensity of the peaks versus the location of the peaks, i.e., diffraction angle 2θ (two-theta) in degrees. The characteristic peaks of a given XRPD diffractogram can be selected according to the peak locations and their relative intensity to conveniently distinguish this crystalline structure from others. The % intensity of the peaks relative to the most intense peak may be represented as I/Io.

Those skilled in the art recognize that the measurements of the XRPD peak locations and/or intensity for a given crystalline form of the same compound will vary within a margin of error. The values of degree 2θ allow appropriate error margins. Typically, the error margins are represented by "±". For example, the degree 2θ of about "8.716±0.3" denotes a range from about 8.716+0.3, i.e., about 9.016, to about 8.716-0.3, i.e., about 8.416. Depending on the sample preparation technique, the calibration technique applied to the instrument, human operational variation, and etc., those skilled in the art recognize that the appropriate error of margins for an XRPD can be about ±0.7; ±0.6; ±0.5; ±0.4; ±0.3; ±0.2; ±0.1; ±0.05; or less.

Additional details of the methods and equipment used for the XRPD analysis are described in the Examples section.

In some embodiments, the crystalline forms are characterized by Differential Scanning calorimetry (DSC). The DSC thermogram is typically expressed by a diagram plotting the normalized heat flow in units of Watts/gram ("W/g") versus the measured sample temperature in degree C. The DSC thermogram is usually evaluated for extrapolated onset and end (outset) temperatures, peak temperature, and heat of fusion. A peak characteristic value of a DSC thermogram is often used as the characteristic peak to distinguish this crystalline structure from others.

Those skilled in the art recognize that the measurements of the DSC thermogram for a given crystalline form of the same compound will vary within a margin of error. The values of a single peak characteristic value, expressed in degree C., allow appropriate error margins. Typically, the error margins are represented by "±". For example, the single peak characteristic value of about "53.09±2.0" denotes a range from about 53.09+2, i.e., about 55.09, to about 53.09-2, i.e., about 51.09. Depending on the sample preparation techniques, the calibration techniques applied to the instruments, human operational variations, and etc., those skilled in the art recognize that the appropriate error of margins for a single peak characteristic value can be ±2.5; ±2.0; ±1.5; ±1.0; ±0.5; or less.

Additional details of the methods and equipment used for the DSC thermogram analysis are described in the Examples section.

Hydrobromide Salt

In some embodiments, the present disclosure provides a hydrobromide salt of Compound 1 ("Compound 1 HBr"). In some embodiments, the present disclosure provides a crystalline form of Compound 1 HBr.

In one embodiment, the present disclosure provides Compound 1 HBr (Form A). In some embodiments, the Compound 1 HBr (Form A) exhibits an XRPD comprising one or more peaks at about 7.6, 15.2, 16.3, 19.8 and 22.9 degrees two-theta with the margin of error of about ±0.5; about ±0.4; about ±0.3; about ±0.2; about ±0.1; about ±0.05; or less. In another embodiment, the XRPD of the Compound 1 HBr (Form A) further comprises one or more peaks at about 15.5, 19.2, 20.6, 26.1, and 31.3 degrees two-theta with the margin of error of about ±0.5; about ±0.4; about ±0.3; about ±0.2; about ±0.1; about ±0.05; or less. In yet another embodiment, the Compound 1 HBr (Form A) exhibits an XRPD comprising peaks shown in Table 1 below:

TABLE 1

XRPD Table of Compound 1 HBr (Form A)

| 2-Theta | Intensity % |
| --- | --- |
| 7.6 | 100 |
| 9.6 | 11.4 |
| 11.6 | 3.1 |
| 11.9 | 2.8 |
| 13.2 | 2.8 |
| 13.9 | 5.6 |
| 15.2 | 47.9 |
| 15.5 | 24.4 |
| 16.3 | 82.8 |
| 18.5 | 2.0 |
| 19.2 | 11.6 |
| 19.8 | 28.8 |
| 20.6 | 15.0 |
| 21.2 | 2.9 |
| 22.3 | 3.3 |
| 22.9 | 53.3 |
| 23.2 | 3.4 |
| 23.7 | 11.1 |
| 24.6 | 3.7 |
| 25.4 | 1.6 |
| 26.1 | 20.7 |
| 26.4 | 4.8 |
| 27.0 | 4.4 |
| 27.4 | 2.5 |
| 28.0 | 2.0 |
| 28.9 | 6.0 |
| 30.3 | 3.1 |
| 30.7 | 4.7 |
| 31.3 | 15.6 |
| 31.7 | 2.1 |
| 32.5 | 1.5 |
| 33.0 | 4.4 |
| 33.6 | 1.5 |
| 34.0 | 2.1 |
| 34.7 | 3.9 |
| 35.6 | 2.2 |
| 39.1 | 4.8 |

Some embodiments provide Compound 1 HBr (Form A), wherein in the range from 15.2±0.2 to 16.3±0.2 degrees two-theta in the XRPD pattern, the Form A exhibits only three peaks.

Figure 2:
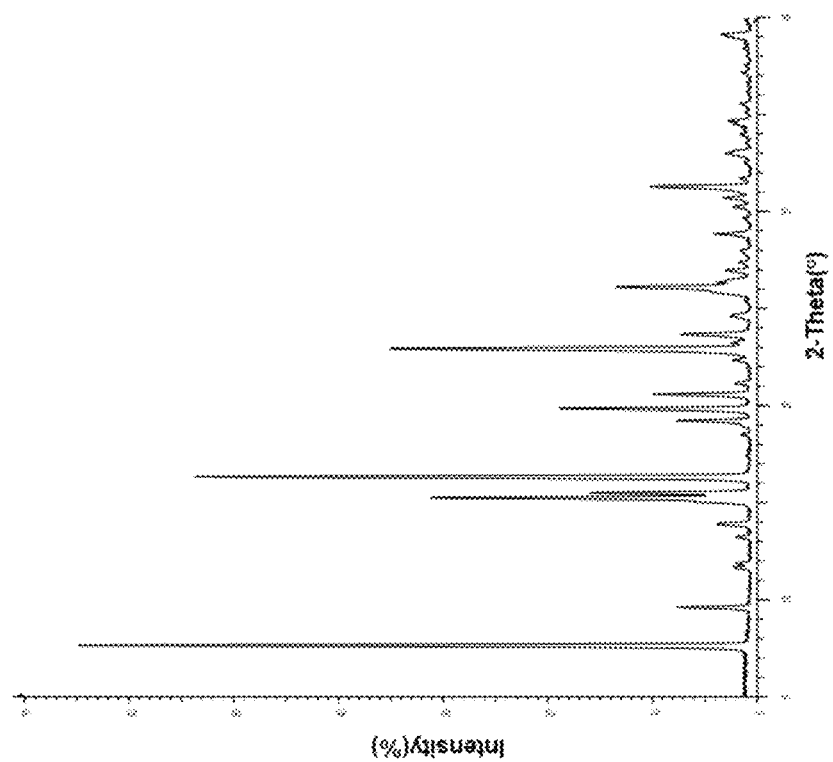
FIG. 2 shows an XRPD pattern of Compound 1 HBr (Form A).

In some embodiments, the Compound 1 HBr (Form A) exhibits an XRPD that is substantially similar to FIG. 2.

In some embodiments, the Compound 1 HBr (Form A) exhibits a DSC thermogram comprising a sharp endotherm at about 243.1° C. with the error of margin of about ±2.5; about ±2.0; about ±1.5; about ±1.0; about ±0.5; or less. In some embodiments, the Compound 1 HBr (Form A) exhibits a DSC thermogram that is substantially similar to FIG. 3.

Figure 3:
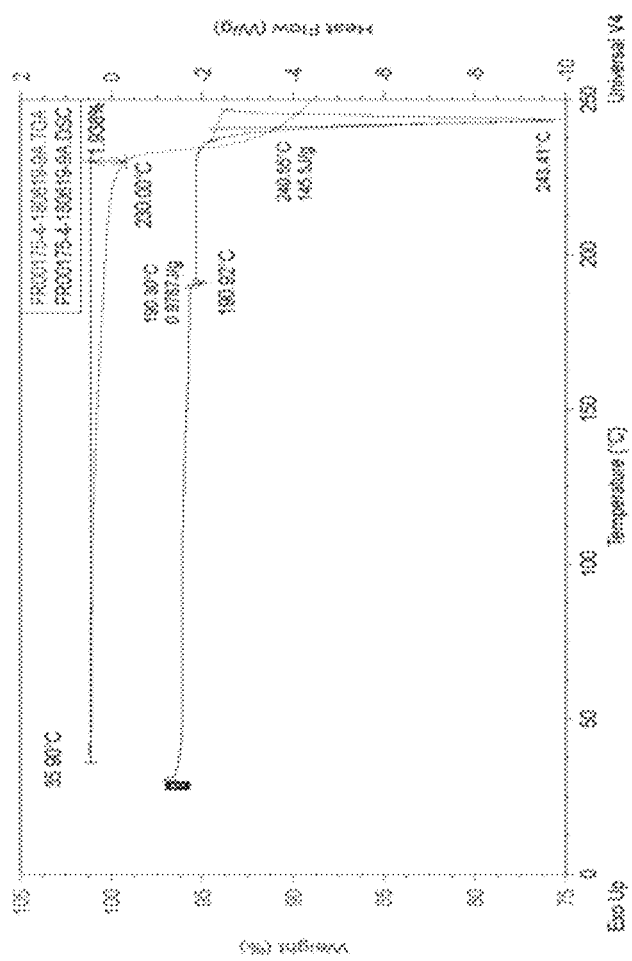
FIG. 3 shows a differential scanning calorimetry (DSC) thermogram and a thermogravimetric analysis (TGA) thermogram of Compound 1 HBr (Form A).

In some embodiments, the Compound 1 HBr (Form A) exhibits a TGA thermogram that is substantially similar to FIG. 3. In other embodiments, the TGA thermogram of the Compound 1 HBr (Form A) exhibits a weight loss of about 0.0 to 1.9% in the temperature range of 25 to 230° C.

Figure 4:
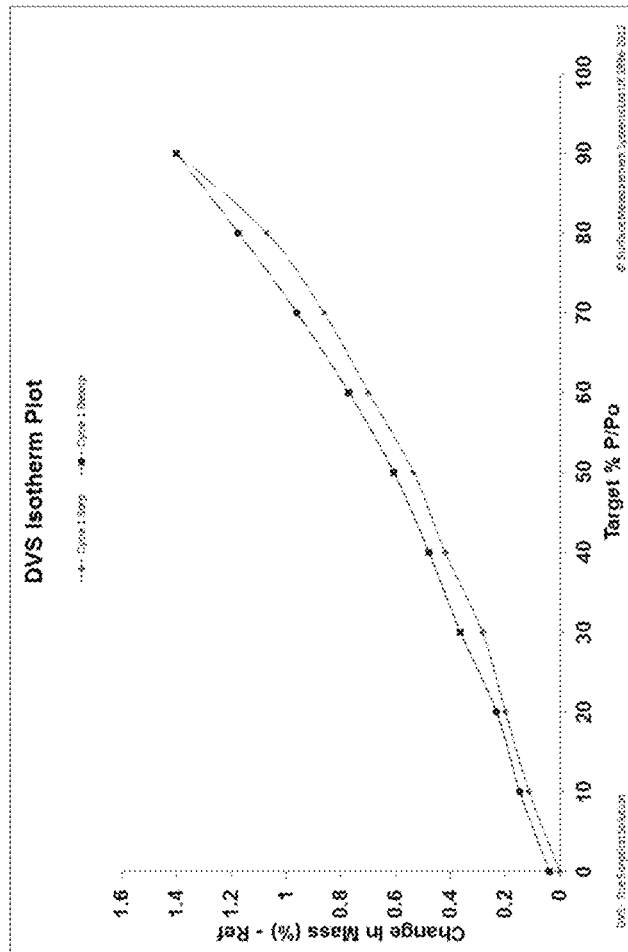
FIG. 4 shows a dynamic vapor sorption (DVS) isotherm plot for Compound 1 HBr (Form A).

In some embodiments, the Compound 1 HBr (Form A) exhibits a DVS isotherm plot that is substantially similar to FIG. 4. In other embodiments, the Compound 1 HBr (Form A) exhibits a gravimetric moisture sorption of about 1.1% (by weight) at 80% Relative Humidity.

In one embodiment, the present disclosure provides Compound 1 HBr (Form B). In some embodiments, the Compound 1 HBr (Form B) exhibits an XRPD comprising one or more peaks at about 3.6, 16.3, 17.7, 21.4 and 23.5 degrees two-theta with the margin of error of about ±0.5; about ±0.4; about ±0.3; about ±0.2; about ±0.1; about ±0.05; or less. In another embodiment, the XRPD of the Compound 1 HBr (Form B) further comprises one or more peaks at about 14.4, 18.7, 24.8, 27.3 and 28.2 degrees two-theta with the margin of error of about ±0.5; about ±0.4; about ±0.3; about ±0.2; about ±0.1; about ±0.05; or less. In yet another embodiment, the Compound 1 HBr (Form B) exhibits an XRPD comprising peaks shown in Table 2 below:

TABLE 2

XRPD Table of Compound 1 HBr (Form B)

| 2-Theta | Intensity % |
|---------|-------------|
| 3.6 | 51 |
| 8.9 | 18.8 |
| 14.1 | 17.8 |
| 14.4 | 37.5 |
| 16.3 | 52.6 |
| 16.7 | 19.8 |
| 17.7 | 100 |
| 18.7 | 32.2 |
| 19.3 | 23.6 |
| 19.5 | 20 |
| 21.4 | 76 |
| 21.8 | 17.6 |
| 22.8 | 14.8 |
| 23.5 | 41.8 |
| 24.3 | 14.4 |
| 24.8 | 30.7 |
| 25.7 | 23.9 |
| 25.9 | 11.4 |
| 26.6 | 14 |
| 27.3 | 29.2 |
| 27.7 | 11.2 |
| 28.2 | 28.6 |
| 30.2 | 5.4 |
| 30.3 | 7.5 |
| 30.9 | 12.5 |
| 33.8 | 12.7 |
| 34.5 | 11 |
| 35.0 | 13.1 |
| 35.9 | 11.6 |

Figure 5:
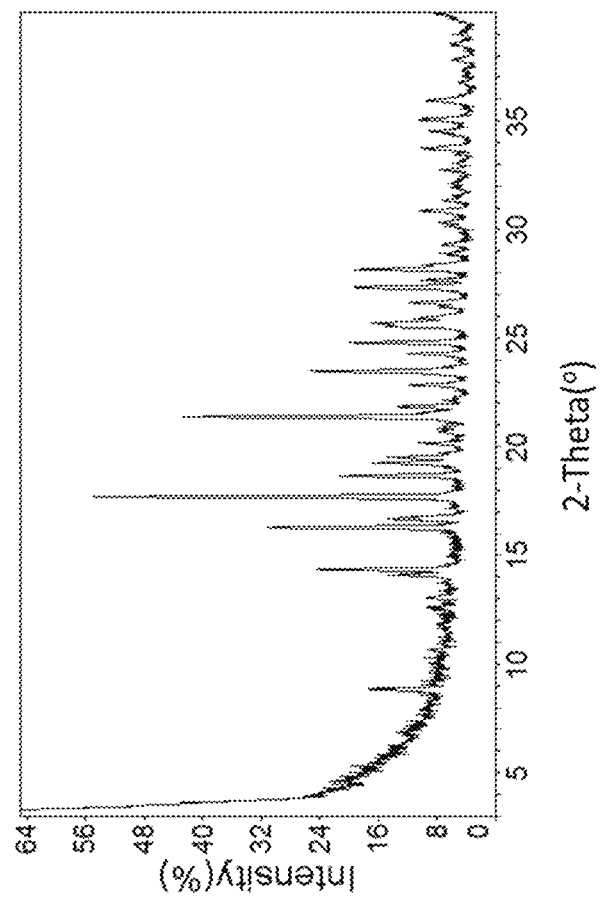
FIG. 5 shows an XRPD pattern of Compound 1 HBr (Form B).

In some embodiments, the Compound 1 HBr (Form B) exhibits an XRPD that is substantially similar to FIG. 5.

In some embodiments, the Compound 1 HBr (Form B) exhibits a DSC thermogram comprising an endotherm at about 121° C. with the error of margin of about ±2.5; about ±2.0; about ±1.5; about ±1.0; about ±0.5; or less. In some embodiments, the Compound 1 HBr (Form B) exhibits a DSC thermogram that is substantially similar to FIG. 6.

Figure 6:
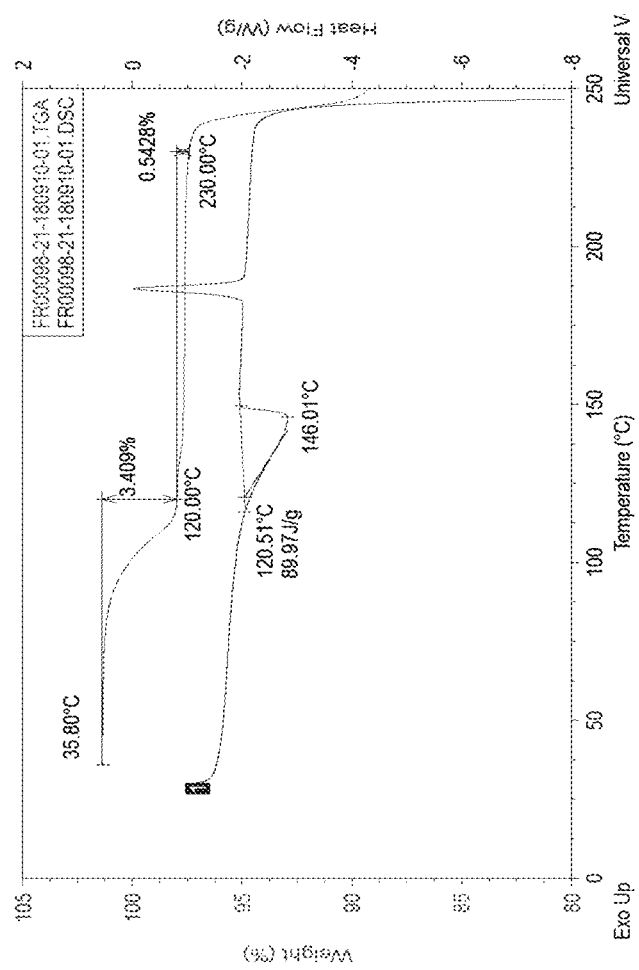
FIG. 6 shows a differential scanning calorimetry (DSC) thermogram and a thermogravimetric analysis (TGA) thermogram of Compound 1 HBr (Form B).

In some embodiments, the Compound 1 HBr (Form B) exhibits a TGA thermogram that is substantially similar to FIG. 6. In other embodiments, the TGA thermogram of the Compound 1 HBr (Form B) exhibits a weight loss of about 0.0 to 3.4% in the temperature range of 25 to 120° C.

Figure 7:
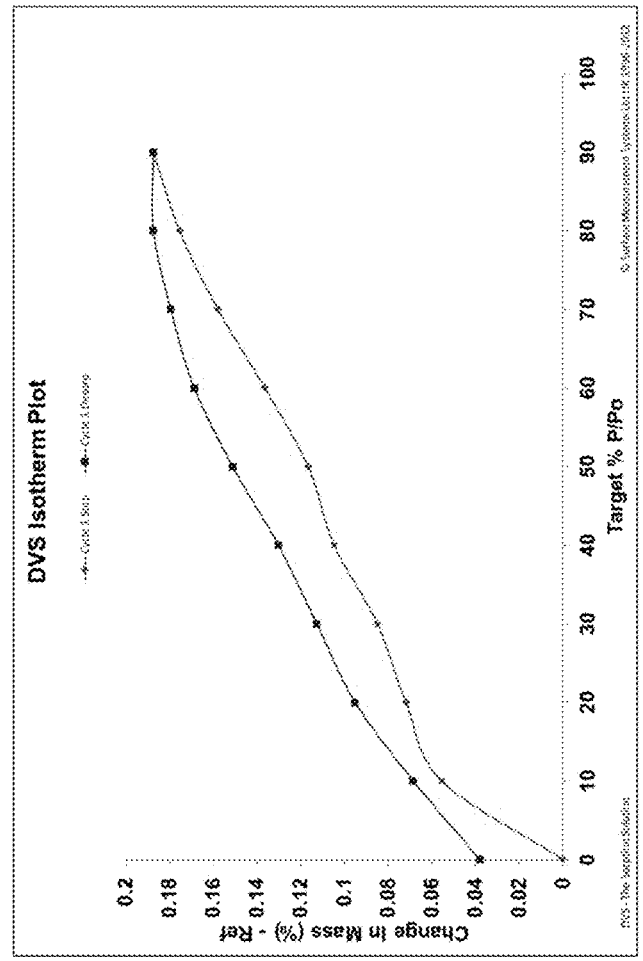
FIG. 7 shows a dynamic vapor sorption (DVS) isotherm plot for Compound 1 HBr (Form B).

In some embodiments, the Compound 1 HBr (Form B) exhibits a DVS isotherm plot that is substantially similar to FIG. 7. In other embodiments, the Compound 1 HBr (Form B) exhibits a gravimetric moisture sorption of about 0.2% (by weight) at 80% Relative Humidity.

In some embodiments, the Compound 1 HBr (Form B) is defined by unit cell parameters substantially similar to the following: a=9.3(4) Å; b=10.8 (4) Å; c=25.2 (11) Å; α=90°; β=90°; γ=90°; Space group $P2_12_12_1$; Molecules/asymmetric unit 1, wherein the crystalline form is at about 120 K.

In one embodiment, the present disclosure provides Compound 1 HBr (Form C). In some embodiments, the Compound 1 HBr (Form C) exhibits an XRPD comprising one or more peaks at about 6.9, 13.8, 20.8, 21.6 and 27.7 degrees two-theta with the margin of error of about ±0.5; about ±0.4; about ±0.3; about ±0.2; about ±0.1; about ±0.05; or less. In another embodiment, the XRPD of the Compound 1 HBr (Form C) further comprises one or more peaks at about 8.8, 25.6, 27.5, 36.2 and 37.3 degrees two-theta with the margin of error of about ±0.5; about ±0.4; about ±0.3; about ±0.2; about ±0.1; about ±0.05; or less. In yet another embodiment, the Compound 1 HBr (Form C) exhibits an XRPD comprising peaks shown in Table 3 below:

TABLE 3

XRPD Table of Compound 1 HBr (Form C)

| 2-Theta | Intensity % |
|---------|-------------|
| 3.4 | 8.3 |
| 6.9 | 62.4 |
| 8.8 | 10.2 |
| 10.9 | 7.0 |
| 13.8 | 32.4 |
| 16.3 | 3.2 |
| 17.7 | 8.9 |
| 19.3 | 5.0 |
| 20.8 | 100 |
| 21.6 | 20.5 |
| 23.6 | 8.5 |
| 23.8 | 3.2 |
| 25.6 | 14.1 |
| 27.5 | 14.8 |
| 27.7 | 70.1 |
| 34.8 | 8.4 |
| 36.2 | 10.2 |
| 37.3 | 14.3 |

Figure 8:
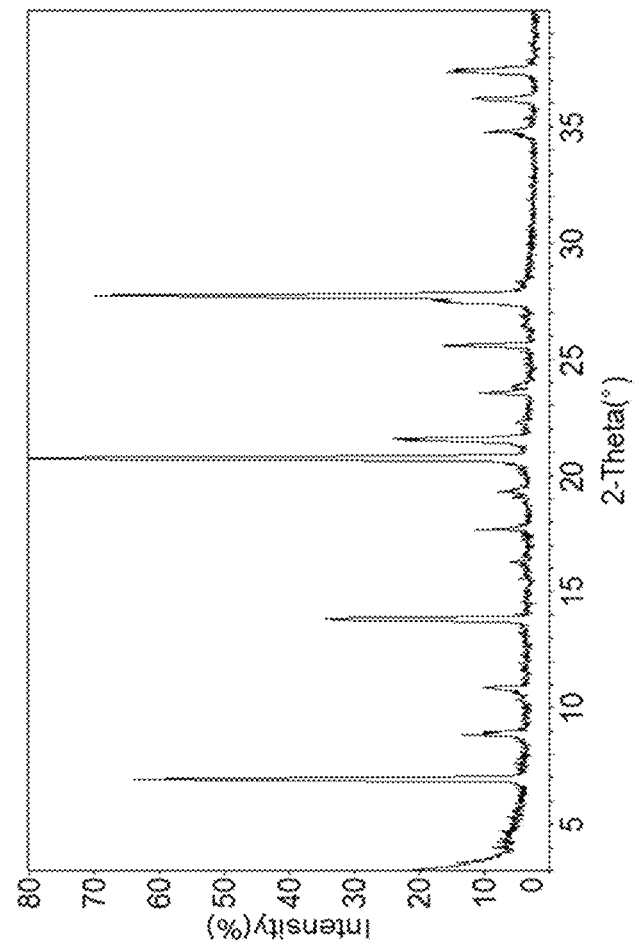
FIG. 8 shows an XRPD pattern of Compound 1 HBr (Form C).

In some embodiments, the Compound 1 HBr (Form C) exhibits an XRPD that is substantially similar to FIG. 8.

In some embodiments, the Compound 1 HBr (Form C) exhibits a DSC thermogram comprising a sharp endotherm at about 141° C. with the error of margin of about ±2.5; about ±2.0; about ±1.5; about ±1.0; about ±0.5; or less. In some embodiments, the Compound 1 HBr (Form C) exhibits a DSC thermogram that is substantially similar to FIG. 9.

Figure 9:
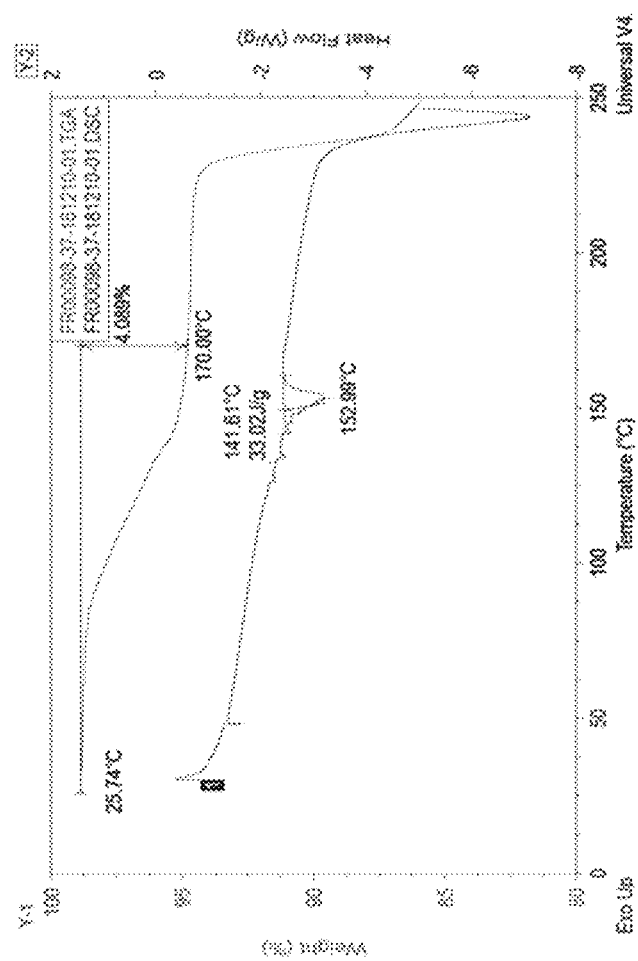
FIG. 9 shows a differential scanning calorimetry (DSC) thermogram and a thermogravimetric analysis (TGA) thermogram of Compound 1 HBr (Form C).

In some embodiments, the Compound 1 HBr (Form C) exhibits a TGA thermogram that is substantially similar to FIG. 9. In other embodiments, the TGA thermogram of the Compound 1 HBr (Form C) exhibits a weight loss of about 0.0 to 4.1% in the temperature range of 25 to 170° C.

Figure 10:
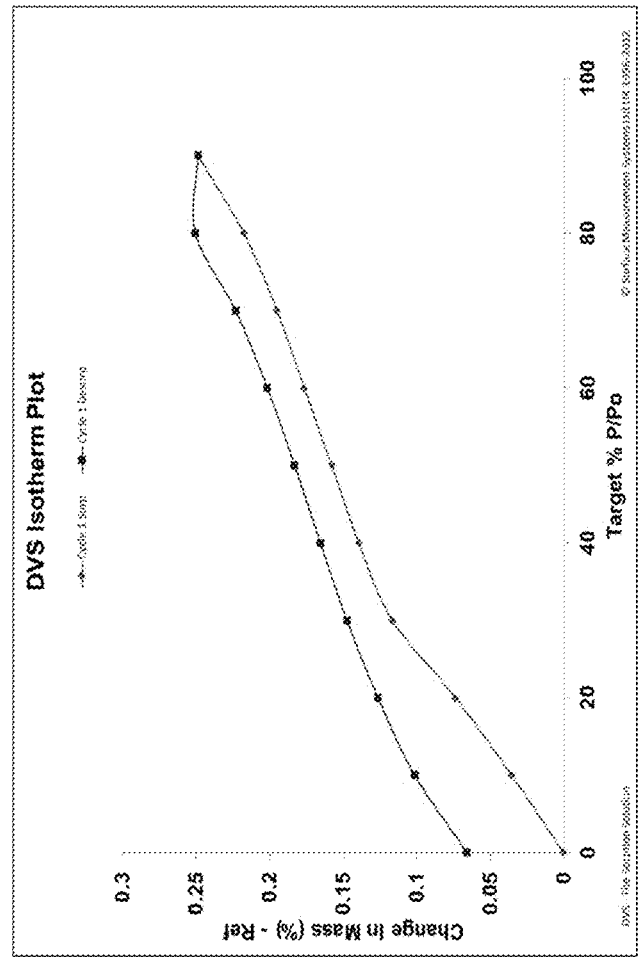
FIG. 10 shows a dynamic vapor sorption (DVS) isotherm plot for Compound 1 HBr (Form C).

In some embodiments, the Compound 1 HBr (Form C) exhibits a DVS isotherm plot that is substantially similar to FIG. 10. In other embodiments, the Compound 1 HBr (Form C) exhibits a gravimetric moisture sorption of about 0.25% (by weight) at 80% Relative Humidity.

In one embodiment, the present disclosure provides Compound 1 HBr (Form D). In some embodiments, the Compound 1 HBr (Form D) exhibits an XRPD comprising one or more peaks at about 14.7, 15.2, 15.6, 16.4, and 23.1 degrees two-theta with the margin of error of about ±0.5; about ±0.4; about ±0.3; about ±0.2; about ±0.1; about ±0.05; or less. In another embodiment, the XRPD of the Compound 1 HBr (Form D) further comprises one or more peaks at about 18.2, 19.9, 21.3, 22.2, and 23.4 degrees two-theta with the margin of error of about ±0.5; about ±0.4; about ±0.3; about ±0.2; about ±0.1; about ±0.05; or less. In yet another embodiment, the Compound 1 HBr (Form D) exhibits an XRPD comprising peaks shown in Table 4 below:

TABLE 4

XRPD Table of Compound 1 HBr (Form D)

| 2-Theta | Intensity % |
|---|---|
| 7.7 | 27.7 |
| 9.1 | 2.6 |
| 9.7 | 12.1 |
| 11.9 | 12.0 |
| 12.7 | 14.5 |
| 13.3 | 6.6 |
| 14.0 | 12.4 |
| 14.7 | 51.5 |
| 15.2 | 100.0 |
| 15.6 | 55.3 |
| 16.1 | 27.9 |
| 16.4 | 52.4 |
| 17.9 | 31.1 |
| 18.2 | 40.0 |
| 18.8 | 34.9 |
| 19.4 | 36.2 |
| 19.9 | 47.0 |
| 20.7 | 23.5 |
| 21.3 | 41.0 |
| 22.2 | 39.1 |
| 23.1 | 56.6 |
| 23.4 | 48.2 |
| 23.8 | 30.7 |
| 24.2 | 24.6 |
| 24.8 | 21.8 |
| 26.2 | 31.4 |
| 26.6 | 20.1 |
| 27.5 | 16.4 |
| 29.0 | 11.3 |
| 29.5 | 18.7 |
| 29.7 | 21.6 |
| 30.4 | 21.1 |
| 31.4 | 14.1 |
| 32.7 | 12.4 |
| 33.5 | 9.7 |
| 35.3 | 10.2 |
| 39.3 | 10.3 |

Figure 11:
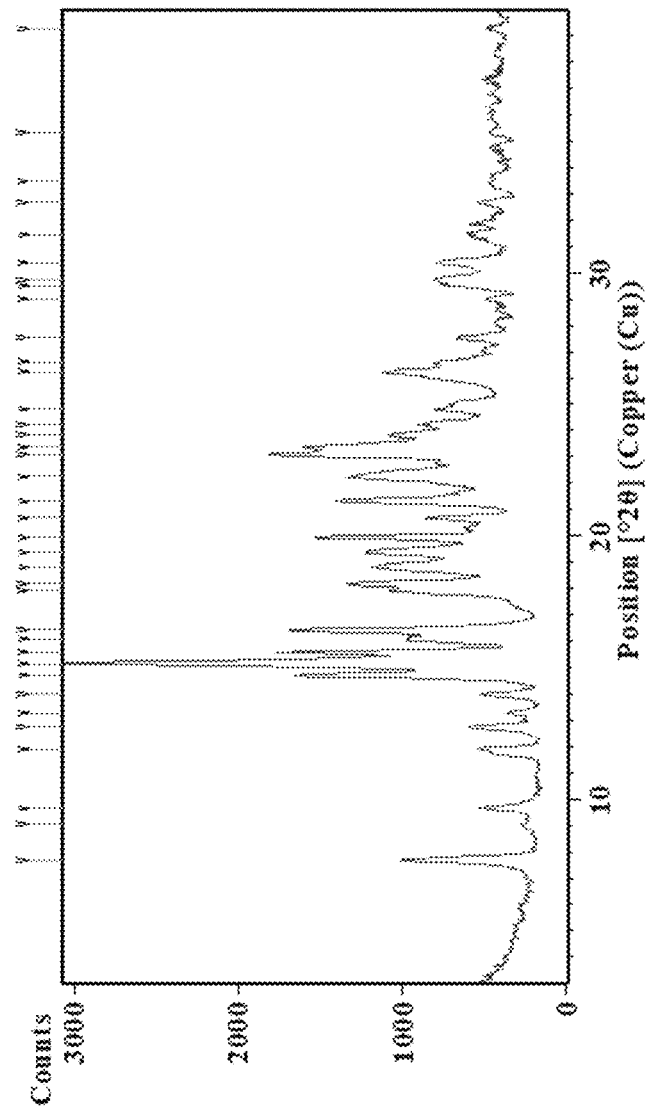
FIG. 11 shows an XRPD pattern of Compound 1 HBr (Form D).

In some embodiments, the Compound 1 HBr (Form D) exhibits an XRPD that is substantially similar to FIG. 11.

In some embodiments, the Compound 1 HBr (Form D) exhibits a DSC thermogram comprising a sharp endotherm at about 248° C. with the error of margin of about ±2.5; about ±2.0; about ±1.5; about ±1.0; about ±0.5; or less. In some embodiments, the Compound 1 HBr (Form D) exhibits a DSC thermogram that is substantially similar to FIG. 12.

Figure 12:
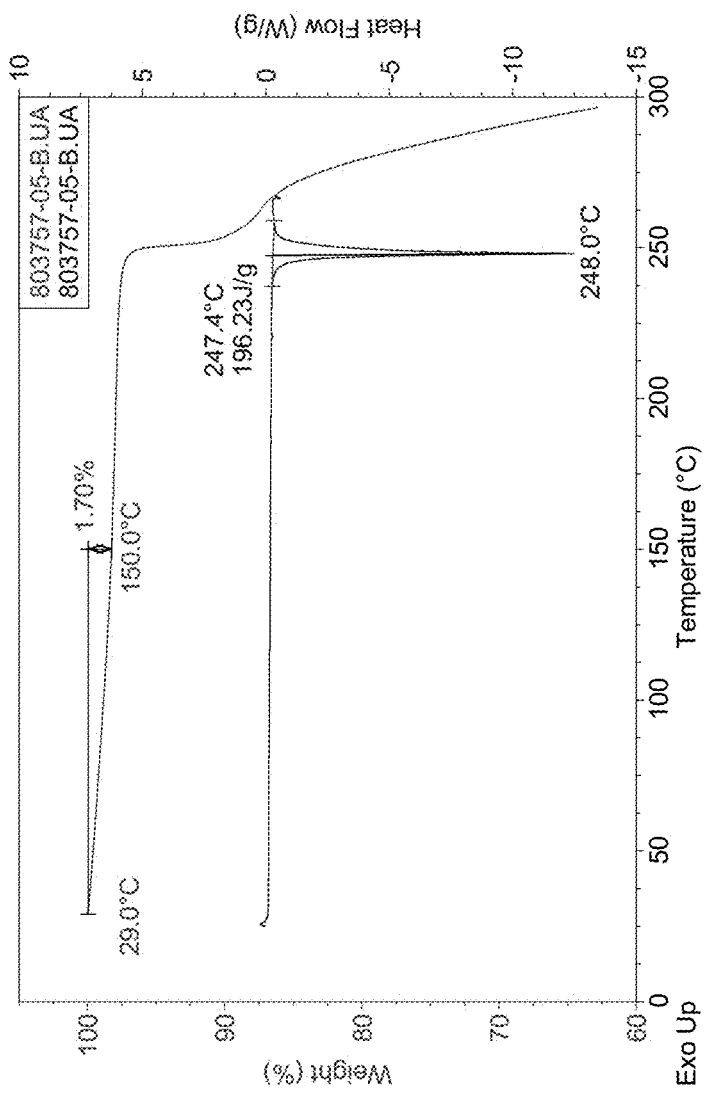
FIG. 12 shows a differential scanning calorimetry (DSC) thermogram and a thermogravimetric analysis (TGA) thermogram of Compound 1 HBr (Form D).

In some embodiments, the Compound 1 HBr (Form D) exhibits a TGA thermogram that is substantially similar to FIG. 12. In other embodiments, the TGA thermogram of the Compound 1 HBr (Form D) exhibits a weight loss of about 0.0 to 1.7% in the temperature range of 29 to 150° C.

In some embodiments, the present disclosure provides Compound 1 HBr (Form E). In some embodiments, the Compound 1 HBr (Form E) exhibits an XRPD comprising one or more peaks at about 7.6, 15.2, 16.3, 22.9 and 23.2 degrees two-theta with the margin of error of about ±0.5; about ±0.4; about ±0.3; about ±0.2; about ±0.1; about ±0.05; or less. In another embodiment, the XRPD of the Compound 1 HBr (Form E) further comprises one or more peaks at about 9.6, 17.4, 22.4, 23.6 and 31.2 degrees two-theta with the margin of error of about ±0.5; about ±0.4; about ±0.3; about ±0.2; about ±0.1; about ±0.05; or less. In yet another embodiment, the Compound 1 HBr (Form E) exhibits an XRPD comprising peaks shown in Table 5 below:

TABLE 5

XRPD Table of Compound 1 HBr (Form E)

| 2-Theta | Intensity % |
|---|---|
| 7.6 | 100 |
| 9.6 | 6.1 |
| 11.7 | 1.4 |
| 12.3 | 4.5 |
| 12.8 | 2.3 |
| 13.1 | 1.9 |
| 14 | 2.3 |
| 15.2 | 58.3 |
| 16.3 | 53.5 |
| 17.4 | 14 |
| 19.2 | 1.6 |
| 19.9 | 4 |
| 20.1 | 5.8 |
| 21.2 | 1.8 |
| 22.4 | 6.8 |
| 22.9 | 47.9 |
| 23.2 | 19.9 |
| 23.6 | 8.2 |
| 23.9 | 2.1 |
| 24.8 | 1.7 |
| 25.4 | 3.5 |
| 25.8 | 2.6 |
| 26.2 | 5.5 |
| 26.5 | 5.2 |
| 26.7 | 1.7 |
| 27.4 | 2.7 |
| 28.4 | 3.2 |
| 29.9 | 4.6 |
| 30.6 | 5 |
| 31.2 | 9 |
| 33.5 | 2.1 |
| 35.1 | 3.5 |
| 36.5 | 2.2 |
| 39 | 3.1 |
| 39.5 | 1.6 |

Some embodiments provide Compound 1 HBr (Form E), wherein in the range from 15.2±0.2 to 16.3±0.2 degrees two-theta in the XRPD pattern, the Form E exhibits only two peaks.

Figure 13:
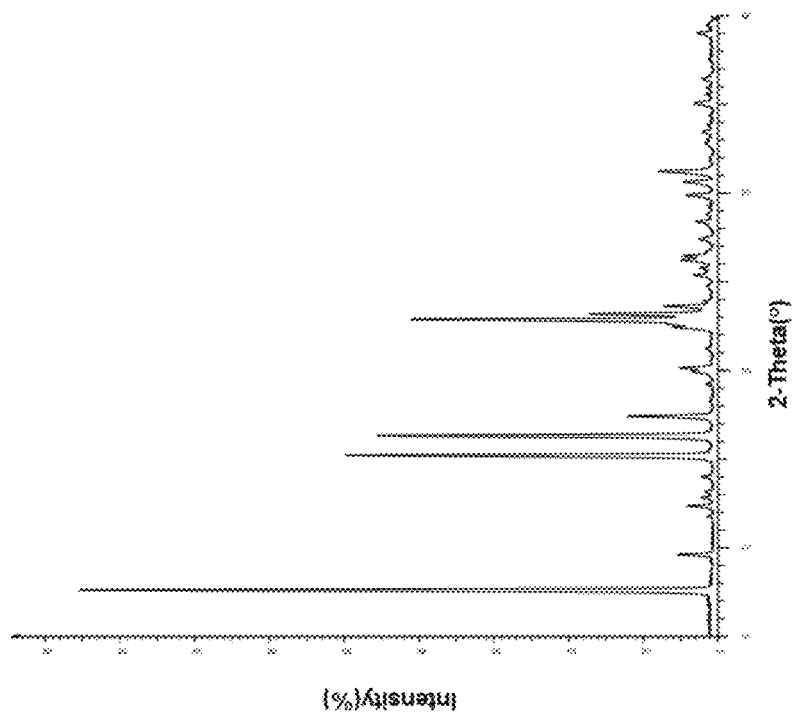
FIG. 13 shows an XRPD pattern of Compound 1 HBr (Form E).

In some embodiments, the Compound 1 HBr (Form E) exhibits an XRPD that is substantially similar to FIG. 13.

In some embodiments, the Compound 1 HBr (Form E) exhibits a DSC thermogram comprising a sharp endotherm at about 245° C. with the error of margin of about ±2.5; about ±2.0; about ±1.5; about ±1.0; about ±0.5; or less. In some embodiments, the Compound 1 HBr (Form E) exhibits a DSC thermogram that is substantially similar to FIG. 14.

Figure 14:
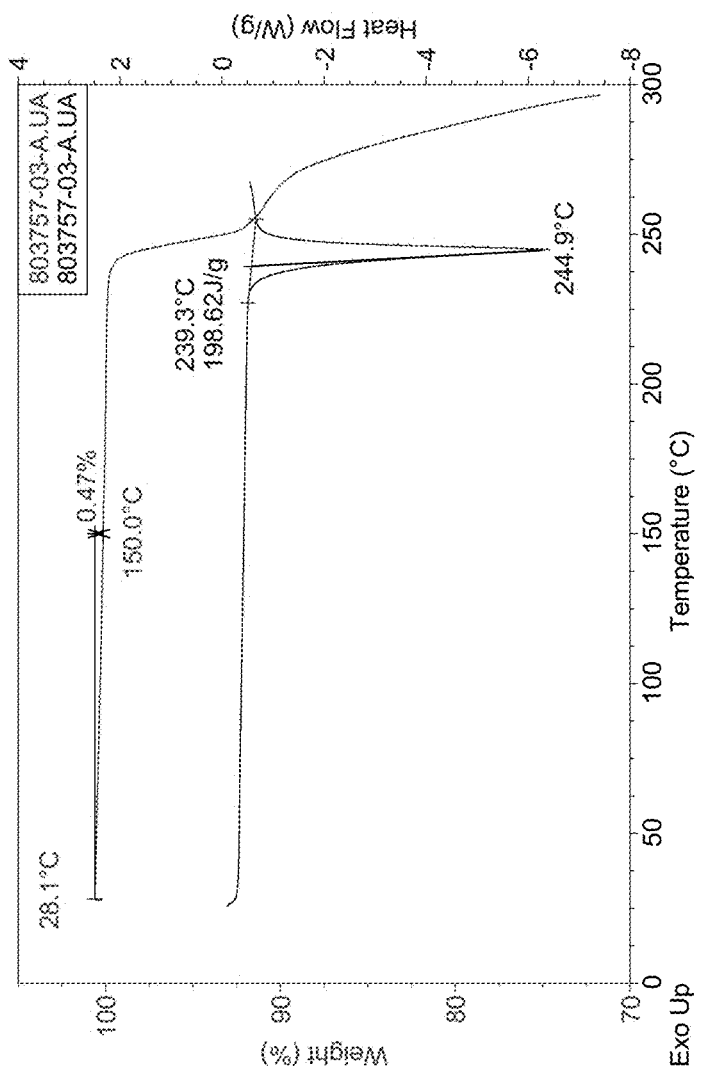
FIG. 14 shows a differential scanning calorimetry (DSC) thermogram and a thermogravimetric analysis (TGA) thermogram of Compound 1 HBr (Form E).

In some embodiments, the Compound 1 HBr (Form E) exhibits a TGA thermogram that is substantially similar to FIG. 14. In other embodiments, the TGA thermogram of the Compound 1 HBr (Form E) exhibits a weight loss of about 0.0 to 0.5% in the temperature range of 28 to 150° C.

In some embodiments, the Compound 1 HBr (Form E) is defined by unit cell parameters substantially similar to the following: a=7.5(10) Å; b=15.0 (2) Å; c=23.0(2) Å; α=90°; β=90°; γ=90°; Space group P2₁2₁2₁; Molecules/asymmetric unit 1, wherein the crystalline form is at about 120 K.

In some embodiments, the Compound 1 HBr (Form E) is defined by unit cell parameters substantially similar to the following: a=23.3(5) Å; b=15.0(3) Å; c=7.5(10) Å; α=90°; β=90°; γ=90°; Space group P2₁2₁2₁; Molecules/asymmetric unit 1, wherein the crystalline form is at about 298 K.

Citrate Salt

In some embodiments, the present disclosure provides a citrate salt of Compound 1 ("Compound 1 Citrate"). In some embodiments, the present disclosure provides a crystalline form of Compound 1 Citrate.

In one embodiment, the present disclosure provides Compound 1 Citrate (Form A). In some embodiments, the Compound 1 Citrate (Form A) exhibits an XRPD comprising one or more peaks at about 5.7, 11.9, 17.1, 20.1, and 20.3 degrees two-theta with the margin of error of about ±0.5; about ±0.4; about ±0.3; about ±0.2; about ±0.1; about ±0.05; or less. In another embodiment, the XRPD of the Compound 1 Citrate (Form A) further comprises one or more peaks at about 12.7, 13.0, 13.6, 15.3, and 16.8 degrees two-theta with the margin of error of about ±0.5; about ±0.4; about ±0.3; about ±0.2; about ±0.1; about ±0.05; or less. In yet another embodiment, the Compound 1 Citrate (Form A) exhibits an XRPD comprising peaks shown in Table 6 below:

TABLE 6

XRPD Table of Compound 1 Citrate (Form A)

| 2-Theta | Intensity (%) |
|---|---|
| 5.7 | 100 |
| 8.2 | 18.5 |
| 10.3 | 4.3 |
| 10.6 | 12 |
| 11.4 | 12.6 |
| 11.9 | 38 |
| 12.5 | 19 |
| 12.7 | 19.6 |
| 13.0 | 22.4 |
| 13.6 | 21.2 |
| 13.9 | 14.1 |
| 14.1 | 14.2 |
| 14.7 | 5 |
| 15.3 | 21.8 |
| 16.8 | 30.6 |
| 17.1 | 39.7 |
| 17.5 | 11.4 |
| 18.0 | 14.1 |
| 18.7 | 10.6 |
| 19.0 | 18.3 |
| 19.4 | 14.5 |
| 19.7 | 12.1 |
| 20.1 | 37.7 |
| 20.3 | 63.7 |
| 20.7 | 11.8 |
| 21.3 | 12.7 |
| 21.6 | 9.9 |
| 22.4 | 11.3 |
| 22.8 | 13.2 |
| 23.4 | 7 |
| 23.9 | 5.2 |
| 24.6 | 5.7 |
| 25.0 | 4.6 |
| 25.8 | 19.3 |
| 26.2 | 6.3 |
| 26.5 | 6.8 |
| 27.2 | 4.8 |
| 28.2 | 6.5 |
| 28.6 | 5.8 |
| 29.5 | 6.7 |
| 30.5 | 5.4 |
| 31.3 | 5.8 |

TABLE 6-continued

XRPD Table of Compound 1 Citrate (Form A)

| 2-Theta | Intensity (%) |
|---|---|
| 32.8 | 4.6 |
| 37.1 | 5.9 |

In some embodiments, the Compound 1 Citrate (Form A) exhibits an XRPD comprising peaks at about: 5.7±0.2; 12.5±0.2 and 13.0±0.2; or 5.7±0.2, 12.5±0.2 and 20.1±0.2; or 5.7±0.2; 12.5±0.2 and 20.3±0.2; or 5.7±0.2; 12.7±0.2 and 13.0±0.2; or 5.7±0.2; 12.7±0.2 and 20.3±0.2; or 5.7±0.2, 13.0±0.2 and 20.3±0.2; or 5.7±0.2, 16.8±0.2 and 20.1±0.2; or 5.7±0.2; 20.1±0.2 and 20.3±0.2; or 12.5±0.2, 13.0±0.2 and 20.3±0.2; or 12.7±0.2, 13.0±0.2 and 20.3±0.2; or 16.8±0.2, 20.1±0.2 and 20.3±0.2 degrees two-theta.

Figure 15:
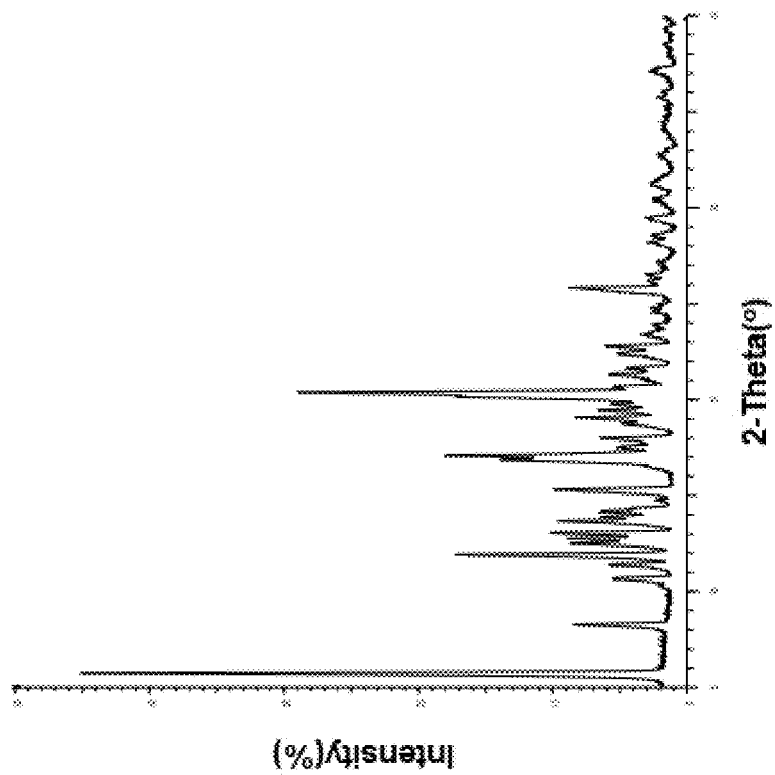
FIG. 15 shows an XRPD pattern of Compound 1 Citrate (Form A).

In some embodiments, the Compound 1 Citrate (Form A) exhibits an XRPD that is substantially similar to FIG. 15.

In some embodiments, the Compound 1 Citrate (Form A) exhibits a DSC thermogram comprising a endotherm at about 89.0° C. with the error of margin of about ±2.5; about ±2.0; about ±1.5; about ±1.0; about ±0.5; or less. In another embodiment, the Compound 1 Citrate (Form A) exhibits a DSC thermogram comprising a sharp endotherm at about 139.5° C. with the error of margin of about ±2.5; about ±2.0; about ±1.5; about ±1.0; about ±0.5; or less. In some embodiments, the Compound 1 Citrate (Form A) exhibits a DSC thermogram that is substantially similar to FIG. 16.

Figure 16:
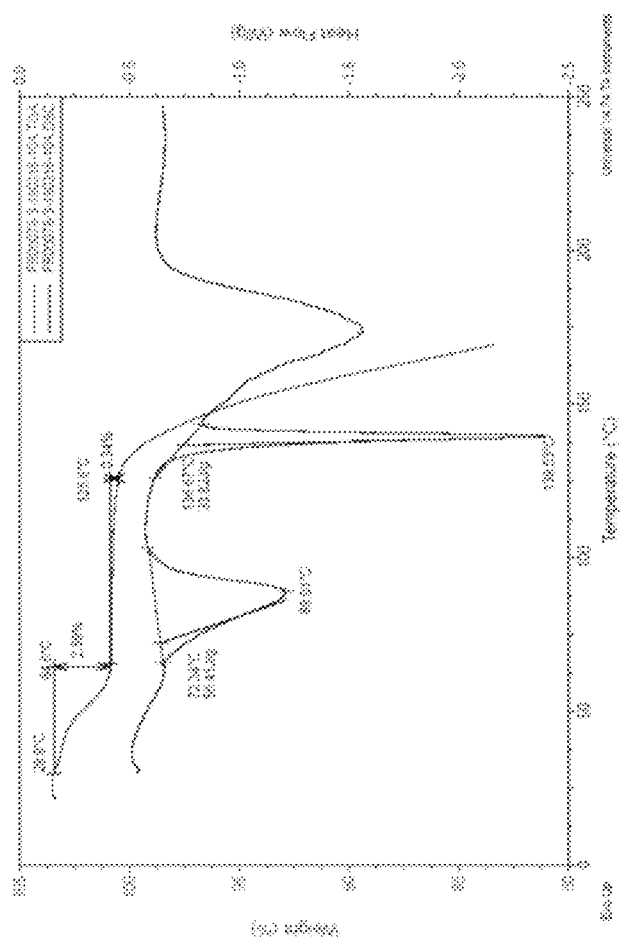
FIG. 16 shows a DSC thermogram and a TGA thermogram of Compound 1 Citrate (Form A).

In some embodiments, the Compound 1 Citrate (Form A) exhibits a TGA thermogram that is substantially similar to FIG. 16. In other embodiments, the TGA thermogram of the Compound 1 Citrate (Form A) exhibits a weight loss of 0.0 to 2.6% in the temperature range of 25 to 65° C.

Figure 17:
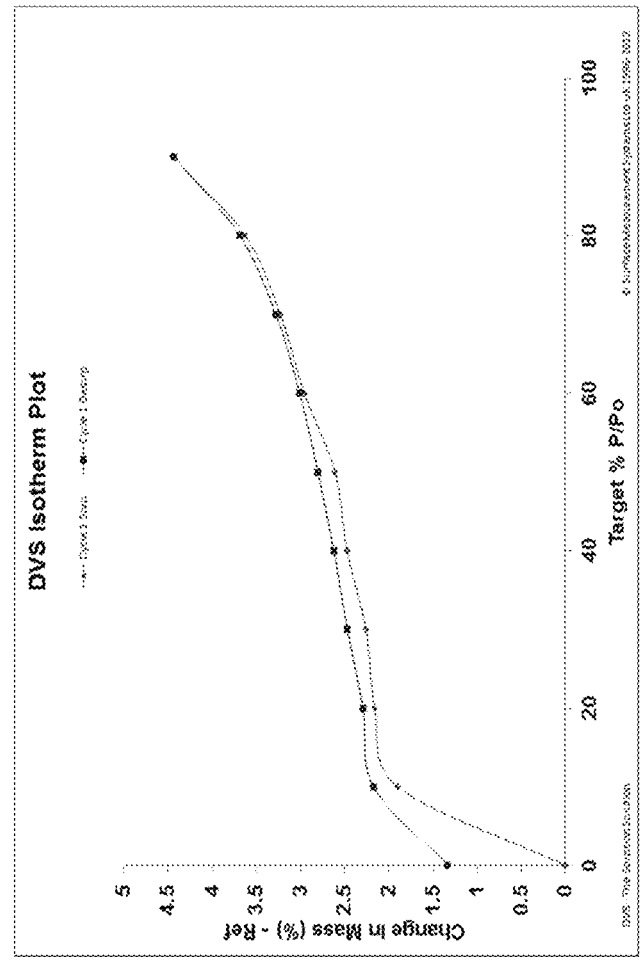
FIG. 17 shows a DVS isotherm plot for Compound 1 Citrate (Form A).

In some embodiments, the Compound 1 Citrate (Form A) exhibits a DVS isotherm plot that is substantially similar to FIG. 17. In other embodiments, the Compound 1-citrate (Form A) exhibits a gravimetric moisture sorption of about 3.6% (by weight) at 80% Relative Humidity.

In some embodiments, the Compound 1 Citrate (Form A) is defined by unit cell parameters substantially similar to the following: a=8.9(10) Å; b=12.2(10) Å; c=16.5(10) Å; α=73.7(10°); β=76.6(10°); γ=83.2 (10°); Space group P1; Molecules/asymmetric unit 2, wherein the crystalline form is at about 120.00 K.

In one embodiment, the present disclosure provides Compound 1 Citrate (Form B). In some embodiments, the Compound 1 Citrate (Form B) exhibits an XRPD comprising one or more peaks at about 5.5, 5.7, 10.9, 16.3 and 20.5 degrees two-theta with the margin of error of about ±0.5; about ±0.4; about ±0.3; about ±0.2; about ±0.1; about ±0.05; or less. In another embodiment, the XRPD of the Compound 1 Citrate (Form B) further comprises one or more peaks at about 3.4, 11.8, 14.6, 17.2 and 21.1 degrees two-theta with the margin of error of about ±0.5; about ±0.4; about ±0.3; about ±0.2; about ±0.1; about ±0.05; or less. In yet another embodiment, the Compound 1 Citrate (Form B) exhibits an XRPD comprising peaks shown in Table 7 below:

TABLE 7

XRPD Table of Compound 1 Citrate (Form B)

| 2-Theta | Intensity % |
|---|---|
| 3.4 | 4.8 |
| 5.5 | 58.1 |

TABLE 7-continued

XRPD Table of Compound 1 Citrate (Form B)

| 2-Theta | Intensity % |
|---|---|
| 5.7 | 42.3 |
| 10.9 | 32.1 |
| 11.4 | 4.3 |
| 11.8 | 8.9 |
| 13.6 | 4.5 |
| 14.6 | 9.7 |
| 14.8 | 3.1 |
| 16.0 | 2.4 |
| 16.3 | 100 |
| 17.2 | 13.3 |
| 20.5 | 29.8 |
| 21.1 | 7.5 |
| 25.6 | 3.2 |
| 25.9 | 4 |
| 27.3 | 4.4 |
| 30.9 | 1.6 |

Figure 18:
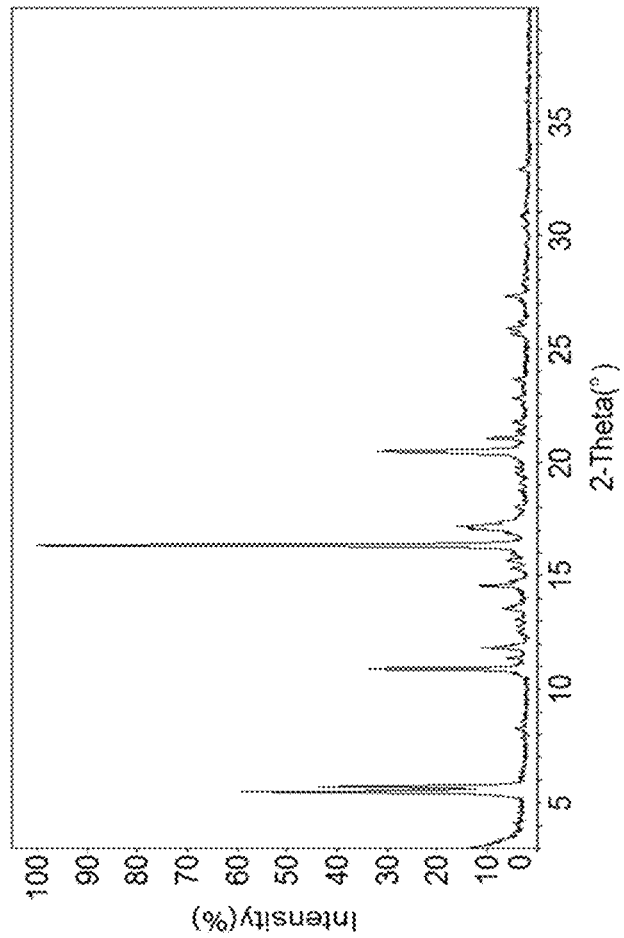
FIG. 18 shows an XRPD pattern of Compound 1 Citrate (Form B).

In some embodiments, the Compound 1 Citrate (Form B) exhibits an XRPD that is substantially similar to FIG. 18.

In some embodiments, the Compound 1 Citrate (Form B) exhibits a DSC thermogram comprising an endotherm at about 77.7° C. with the error of margin of about ±2.5; about ±2.0; about ±1.5; about ±1.0; about ±0.5; or less. In some embodiments, the Compound 1 Citrate (Form B) exhibits a DSC thermogram comprising an endotherm at about 121.5° C. with the error of margin of about ±2.5; about ±2.0; about ±1.5; about ±1.0; about ±0.5; or less. In some embodiments, the Compound 1 Citrate (Form B) exhibits a DSC thermogram comprising an endotherm at about 136.6° C. with the error of margin of about ±2.5; about ±2.0; about ±1.5; about ±1.0; about ±0.5; or less. In some embodiments, the Compound 1 Citrate (Form B) exhibits a DSC thermogram that is substantially similar to FIG. 19.

Figure 19:
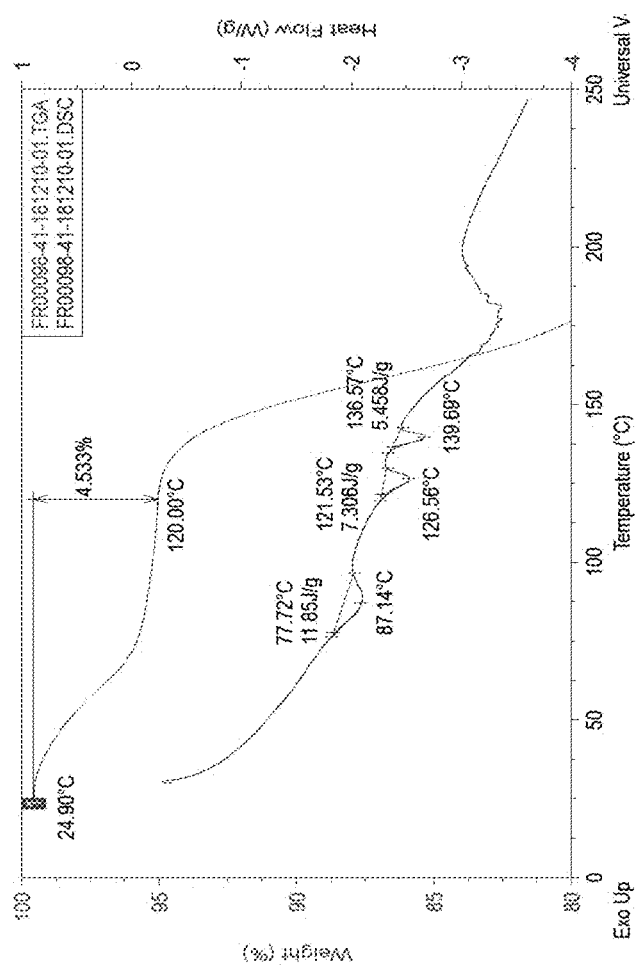
FIG. 19 shows a DSC thermogram and a TGA thermogram of Compound 1 Citrate (Form B).

In some embodiments, the Compound 1 Citrate (Form B) exhibits a TGA thermogram that is substantially similar to FIG. 19. In other embodiments, the TGA thermogram of the Compound 1 Citrate (Form B) exhibits a weight loss of about 0.0 to 4.5% in the temperature range of 25 to 120° C.

Figure 20:
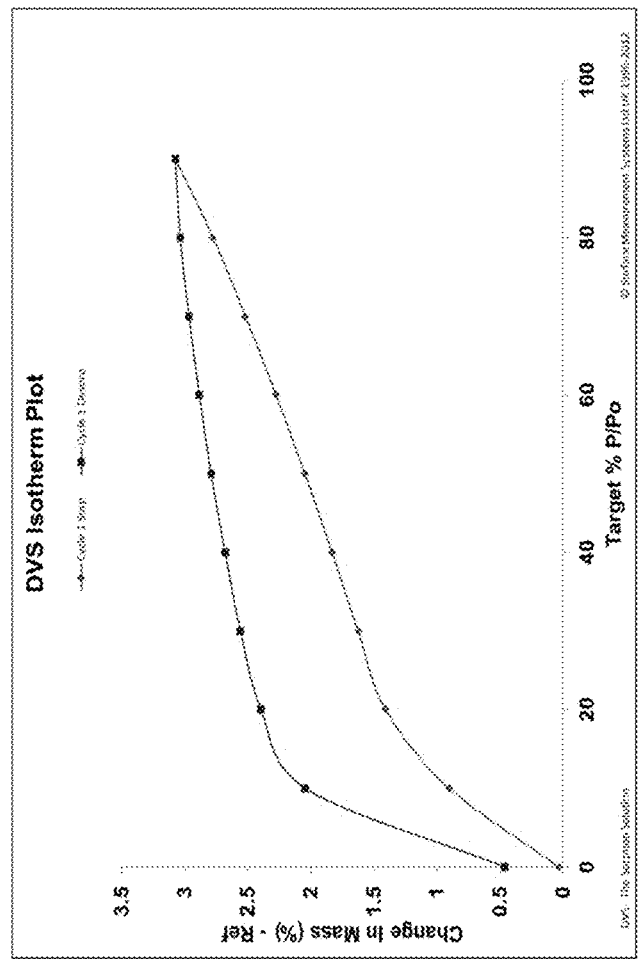
FIG. 20 shows a DVS isotherm plot for Compound 1 Citrate (Form B).

In some embodiments, the Compound 1 Citrate (Form B) exhibits a DVS isotherm plot that is substantially similar to FIG. 20. In other embodiments, the Compound 1 Citrate (Form B) exhibits a gravimetric moisture sorption of about 2.8% (by weight) at 80% Relative Humidity.

In one embodiment, the present disclosure provides Compound 1 Citrate (Form C). In some embodiments, the Compound 1 Citrate (Form C) exhibits an XRPD comprising one or more peaks at about 15.4, 18.7, 19.7, 20.6 and 27.1 degrees two-theta with the margin of error of about ±0.5; about ±0.4; about ±0.3; about ±0.2; about ±0.1; about ±0.05; or less. In another embodiment, the XRPD of the Compound 1 Citrate (Form C) further comprises one or more peaks at about 13.5, 15.5, 16.2, 17.0 and 22.1 degrees two-theta with the margin of error of about ±0.5; about ±0.4; about ±0.3; about ±0.2; about ±0.1; about ±0.05; or less. In yet another embodiment, the Compound 1 Citrate (Form C) exhibits an XRPD comprising peaks shown in Table 8 below.

TABLE 8

XRPD Table of Compound 1 Citrate (Form C)

| 2-Theta | Intensity % |
|---|---|
| 5.1 | 23.1 |
| 5.6 | 7.8 |
| 8.2 | 6.5 |
| 10.3 | 16.4 |
| 11.3 | 9.3 |
| 11.9 | 9.8 |
| 13.5 | 46.3 |
| 14.5 | 21.6 |
| 15.0 | 40.2 |
| 15.4 | 82.4 |
| 15.5 | 66.9 |
| 16.2 | 49.5 |
| 17.0 | 49.5 |
| 17.8 | 42.7 |
| 18.7 | 78.7 |
| 19.7 | 74.8 |
| 20.6 | 100.0 |
| 22.1 | 60.4 |
| 23.4 | 28.7 |
| 24.1 | 11.8 |
| 24.7 | 16.6 |
| 25.8 | 25.3 |
| 26.6 | 23.8 |
| 27.1 | 83.0 |
| 27.7 | 11.5 |
| 28.4 | 21.5 |
| 29.6 | 5.9 |
| 30.2 | 13.4 |
| 31.3 | 7.0 |
| 31.7 | 10.3 |
| 32.2 | 9.7 |
| 32.8 | 7.1 |
| 33.7 | 4.0 |
| 34.2 | 8.2 |
| 34.8 | 8.5 |
| 35.6 | 6.2 |
| 36.6 | 9.3 |
| 37.0 | 7.5 |
| 37.4 | 8.8 |
| 38.4 | 7.9 |
| 39.2 | 8.8 |

Figure 21:
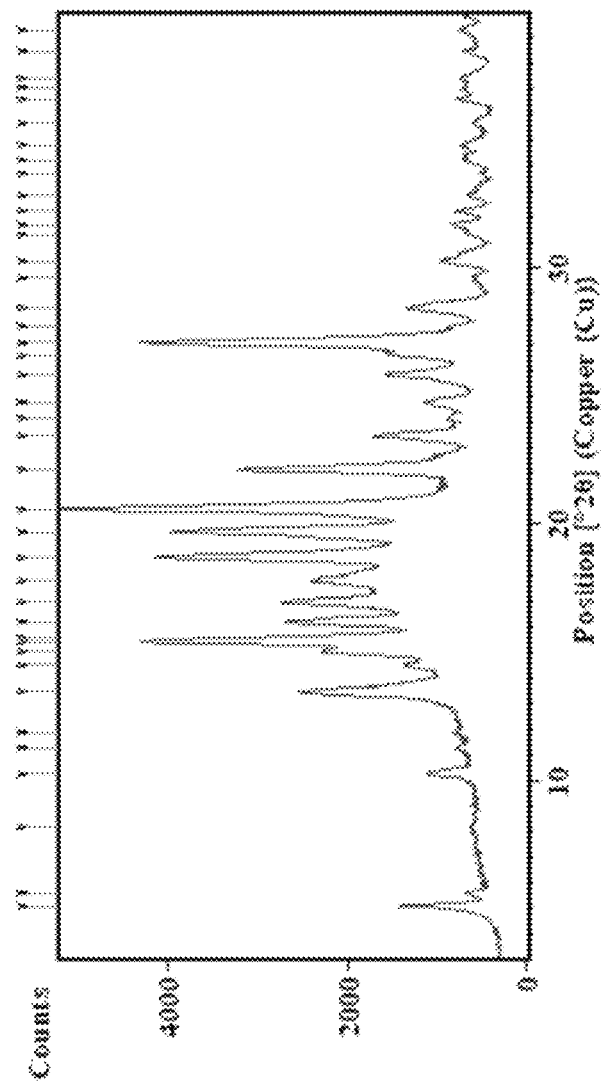
FIG. 21 shows an XRPD pattern of Compound 1 Citrate (Form C).

In some embodiments, the Compound 1 Citrate (Form C) exhibits an XRPD that is substantially similar to FIG. 21.

Mesylate Salt

In some embodiments, the present disclosure provides a mesylate salt of Compound 1 ("Compound 1 Mesylate"). In some embodiments, the present disclosure provides a crystalline form of Compound 1 Mesylate.

In one embodiment, the present disclosure provides Compound 1 Mesylate (Form A). In some embodiments, the Compound 1 Mesylate (Form A) exhibits an XRPD comprising one or more peaks at about 3.6, 7.1, 14.2, 19.1 and 25.9 degrees two-theta with the margin of error of about ±0.5; about ±0.4; about ±0.3; about ±0.2; about ±0.1; about ±0.05; or less. In another embodiment, the XRPD of the Compound 1 Mesylate (Form A) further comprises one or more peaks at about 7.7, 12.7, 17.8, 19.4, and 21.4 degrees two-theta with the margin of error of about ±0.5; about ±0.4; about ±0.3; about ±0.2; about ±0.1; about ±0.05; or less. In yet another embodiment, the Compound 1 Mesylate (Form A) exhibits an XRPD comprising peaks shown in Table 9 below:

TABLE 9

XRPD Table of Compound 1 Mesylate (Form A)

| 2-Theta | Intensity % |
|---------|-------------|
| 3.6 | 14.5 |
| 7.1 | 100 |
| 7.7 | 9.4 |
| 12.0 | 3.7 |
| 12.7 | 8.7 |
| 13.4 | 3.3 |
| 14.2 | 24.3 |
| 17.5 | 2.8 |
| 17.8 | 7.4 |
| 19.1 | 35.4 |
| 19.4 | 10.1 |
| 21.4 | 8.1 |
| 23.6 | 2.2 |
| 25.4 | 4.2 |
| 25.9 | 10.3 |

Figure 22:
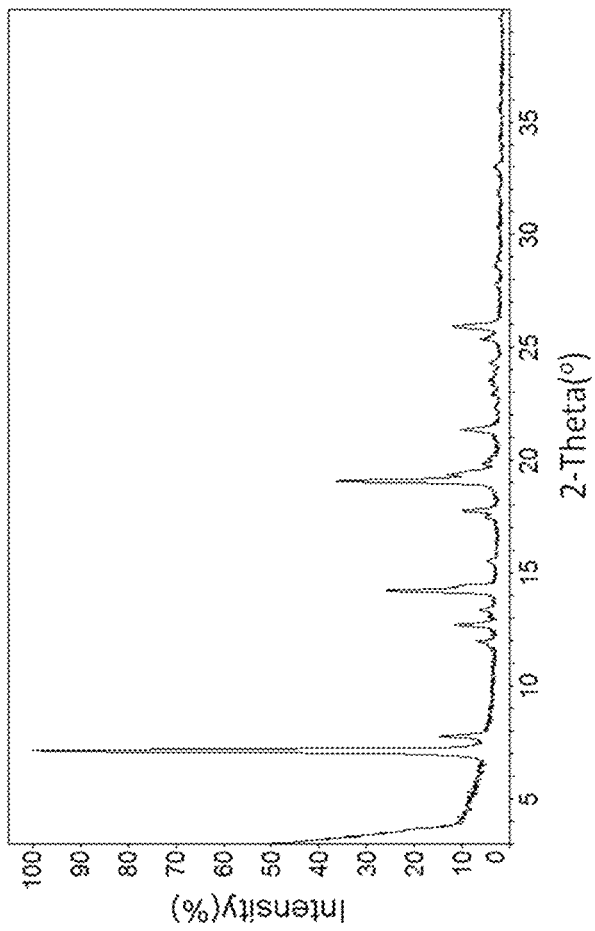
FIG. 22 shows an XRPD pattern of Compound 1 Mesylate (Form A).

In some embodiments, the Compound 1 Mesylate (Form A) exhibits an XRPD that is substantially similar to FIG. 22.

In some embodiments, the Compound 1 Mesylate (Form A) exhibits a DSC thermogram comprising an endotherm at about 170.9° C. with the error of margin of about ±2.5; about ±2.0; about ±1.5; about ±1.0; about ±0.5; or less. In some embodiments, the Compound 1 Mesylate (Form A) exhibits a DSC thermogram comprising a sharp endotherm at about 209.7° C. with the error of margin of about ±2.5; about ±2.0; about ±1.5; about ±1.0; about ±0.5; or less. In some embodiments, the Compound 1 Mesylate (Form A) exhibits a DSC thermogram that is substantially similar to FIG. 23.

Figure 23:
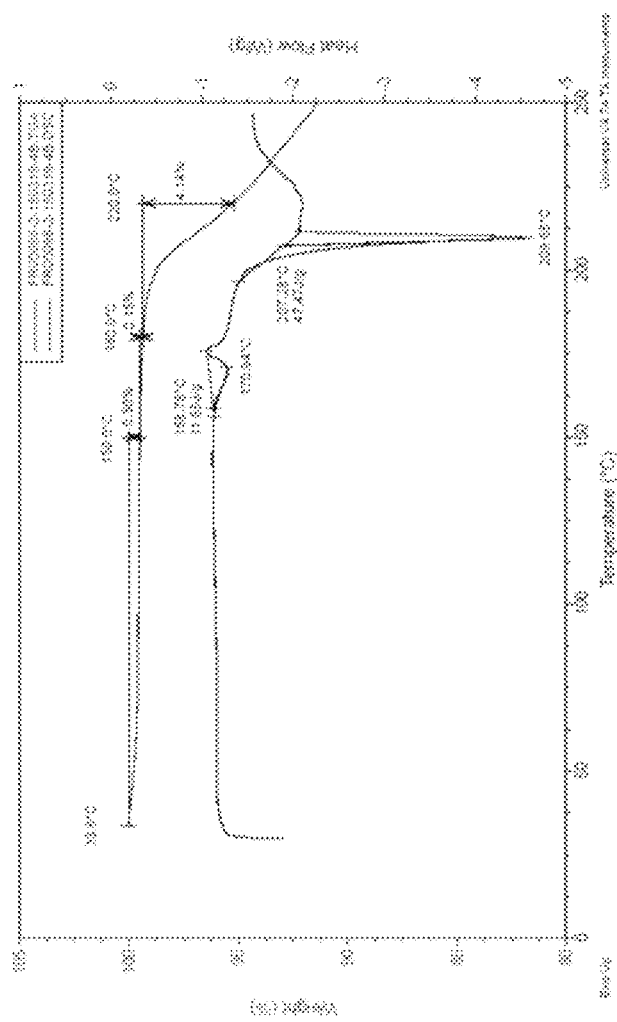
FIG. 23 shows a DSC thermogram and a TGA thermogram of Compound 1 Mesylate (Form A).

In some embodiments, the Compound 1 Mesylate (Form A) exhibits a TGA thermogram that is substantially similar to FIG. 23. In other embodiments, the TGA thermogram of the Compound 1 Mesylate (Form A) exhibits a weight loss of 0.0 to 0.5% in the temperature range of 25 to 150° C.

Figure 24:
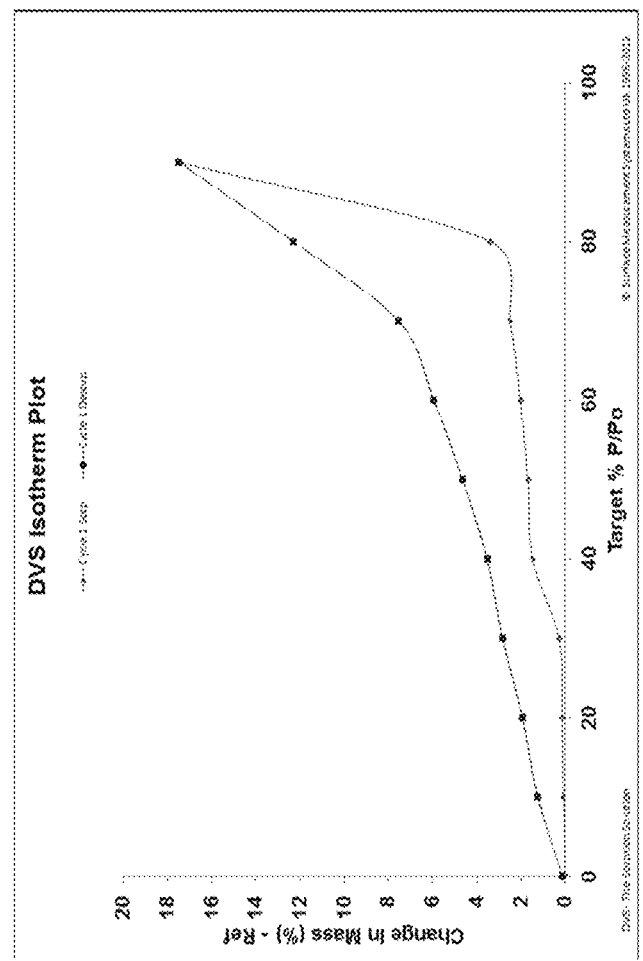
FIG. 24 shows a DVS isotherm plot for Compound 1 Mesylate (Form A).

In some embodiments, the Compound 1 Mesylate (Form A) exhibits a DVS isotherm plot that is substantially similar to FIG. 24. In other embodiments, the Compound 1 Mesylate (Form A) exhibits a gravimetric moisture sorption of about 3.4% (by weight) at 80% Relative Humidity.

In one embodiment, the present disclosure provides Compound 1 Mesylate (Form B). In some embodiments, the Compound 1 Mesylate (Form B) exhibits an XRPD comprising one or more peaks at about 7.1, 14.3, 15.9, 21.4, and 22.6 degrees two-theta with the margin of error of about ±0.5; about ±0.4; about ±0.3; about ±0.2; about ±0.1; about ±0.05; or less. In another embodiment, the Compound 1 Mesylate (Form B) exhibits an XRPD comprising peaks shown in Table 10A below:

TABLE 10A

XRPD Table of Compound 1 Mesylate (Form B)

| 2-Theta | Intensity % |
|---------|-------------|
| 7.1 | 100 |
| 14.3 | 25.8 |
| 15.9 | 11.3 |
| 19.0 | 3.5 |
| 21.4 | 9.1 |
| 22.6 | 6.1 |

Figure 25A:
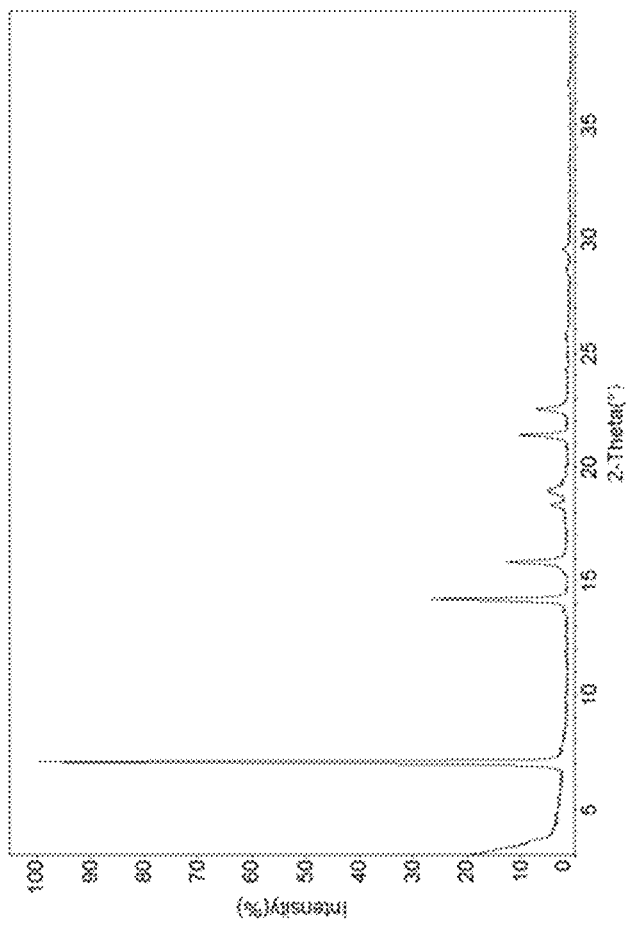
FIG. 25A shows an XRPD pattern of Compound 1 Mesylate (Form B).

In some embodiments, the Compound 1 Mesylate (Form B) exhibits an XRPD that is substantially similar to FIG. 25A.

In some embodiments, the present disclosure provides Compound 1 Mesylate (Form C). In some embodiments, the Compound 1 Mesylate (Form C) exhibits an XRPD comprising one or more peaks at about 7.5, 15.0, 19.4, 22.5, and 30.2 degrees two-theta with the margin of error of about ±0.5; about ±0.4; about ±0.3; about ±0.2; about ±0.1; about ±0.05; or less. In yet another embodiment, the Compound 1 Mesylate (Form C) exhibits an XRPD comprising peaks shown in Table 10B below:

TABLE 10B

XRPD Table of Compound 1 Mesylate (Form C)

| 2-Theta | Intensity % |
|---------|-------------|
| 7.5 | 100 |
| 15.0 | 33.1 |
| 19.4 | 3.1 |
| 22.5 | 13.3 |
| 30.2 | 3 |

Figure 25B:
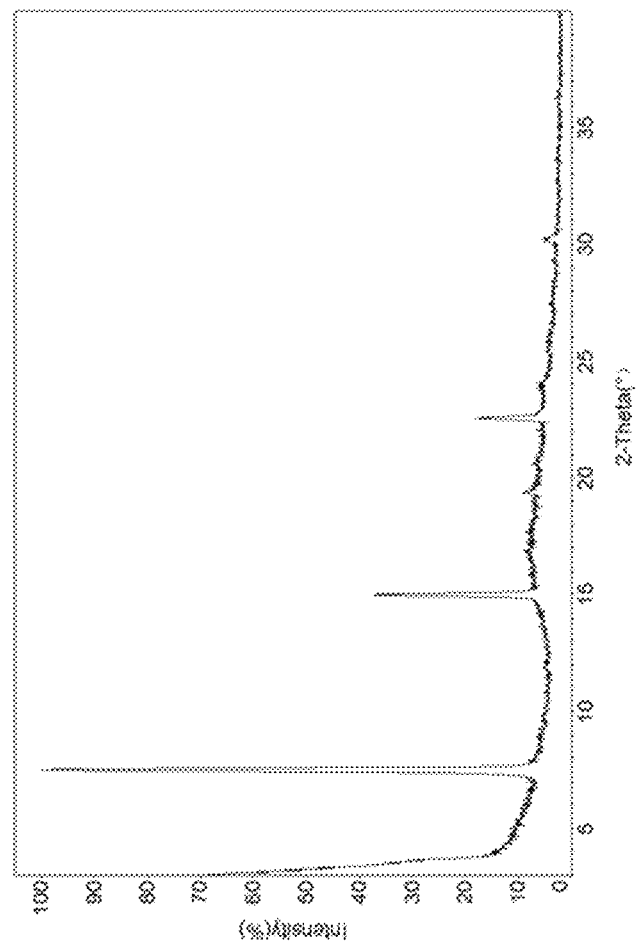
FIG. 25B shows an XRPD pattern of Compound 1 Mesylate (Form C).

In some embodiments, the Compound 1 Mesylate (Form C) exhibits an XRPD that is substantially similar to FIG. 25B.

In one embodiment, the present disclosure provides Compound 1 Mesylate (Form D). In some embodiments, the Compound 1 Mesylate (Form D) exhibits an XRPD comprising one or more peaks at about 7.4, 15.0, and 22.6 degrees two-theta with the margin of error of about ±0.5; about ±0.4; about ±0.3; about ±0.2; about ±0.1; about ±0.05; or less. In yet another embodiment, the Compound 1 Mesylate (Form D) exhibits an XRPD comprising peaks shown in Table 11 below:

TABLE 11

XRPD Table of Compound 1 Mesylate (Form D)

| 2-Theta | Intensity % |
|---------|-------------|
| 7.4 | 100 |
| 15.0 | 21.1 |
| 22.6 | 10 |

Figure 26:
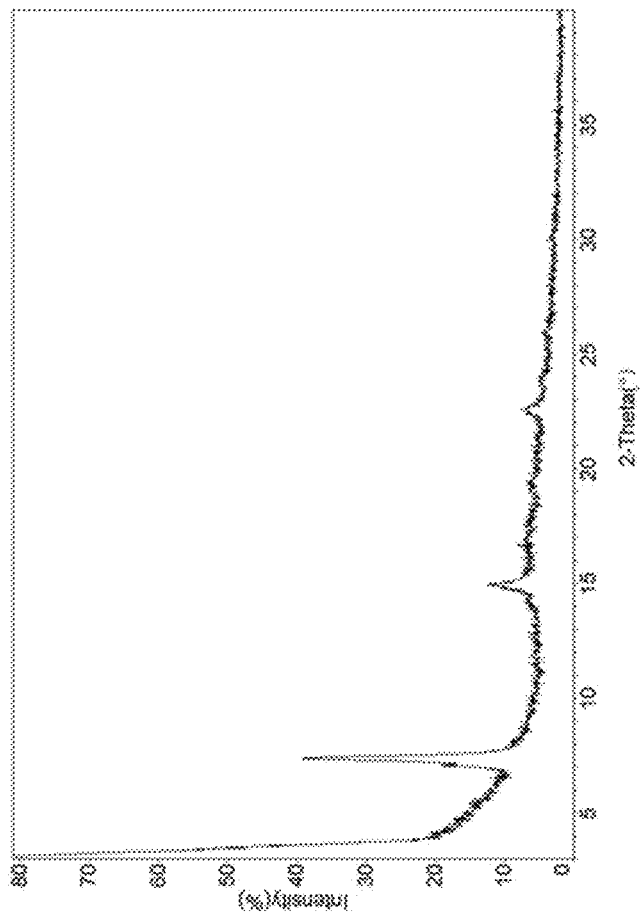
FIG. 26 shows an XRPD pattern of Compound 1 Mesylate (Form D).

In some embodiments, the Compound 1 Mesylate (Form D) exhibits an XRPD that is substantially similar to FIG. 26.

Phosphate Salt

In some embodiments, the present disclosure provides a phosphate salt of Compound 1 ("Compound 1 Phosphate"). In some embodiments, the present disclosure provides a crystalline form of Compound 1 Phosphate.

In one embodiment, the present disclosure provides Compound 1 Phosphate (Form A). In some embodiments, the Compound 1 Phosphate (Form A) exhibits an XRPD comprising one or more peaks at about 3.3, 3.6, 5.4, 9.9, and 13.1 degrees two-theta with the margin of error of about ±0.5; about ±0.4; about ±0.3; about ±0.2; about ±0.1; about ±0.05; or less. In another embodiment, the XRPD of the Compound 1 Phosphate (Form A) further comprises one or more peaks at about 16.1, 17.9, 20.9, 23.7, and 26.4 degrees two-theta with the margin of error of about ±0.5; about ±0.4; about ±0.3; about ±0.2; about ±0.1; about ±0.05; or less. In yet another embodiment, the Compound 1 Phosphate (Form A) exhibits an XRPD comprising peaks shown in Table 12 below:

TABLE 12

XRPD Table of Compound 1 Phosphate (Form A)

| 2-Theta | Intensity % |
|---|---|
| 3.3 | 100 |
| 3.6 | 7.8 |
| 5.4 | 7.2 |
| 6.6 | 1.9 |
| 9.9 | 14.2 |
| 13.1 | 12.7 |
| 15.7 | 1.8 |
| 16.1 | 5.4 |
| 16.4 | 1.7 |
| 17.9 | 3.8 |
| 19.0 | 1.4 |
| 20.4 | 1.9 |
| 20.9 | 2.6 |
| 23.7 | 2.9 |
| 26.4 | 2.3 |
| 26.5 | 1.1 |
| 29.6 | 1.1 |
| 31.0 | 1.3 |

Figure 27:
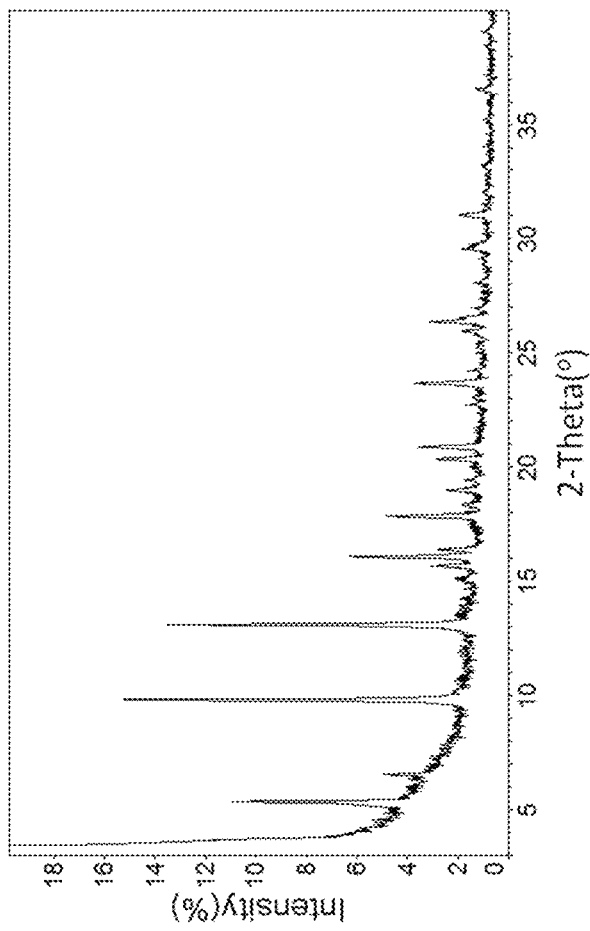
FIG. 27 shows an XRPD pattern of Compound 1 Phosphate (Form A).

In some embodiments, the Compound 1 Phosphate (Form A) exhibits an XRPD that is substantially similar to FIG. 27.

In some embodiments, the Compound 1 Phosphate (Form A) exhibits a DSC thermogram comprising a sharp endotherm at about 217.6° C. with the error of margin of about ±2.5; about ±2.0; about ±1.5; about ±1.0; about ±0.5; or less. In some embodiments, the Compound 1 Phosphate (Form A) exhibits a DSC thermogram that is substantially similar to FIG. 28.

Figure 28:
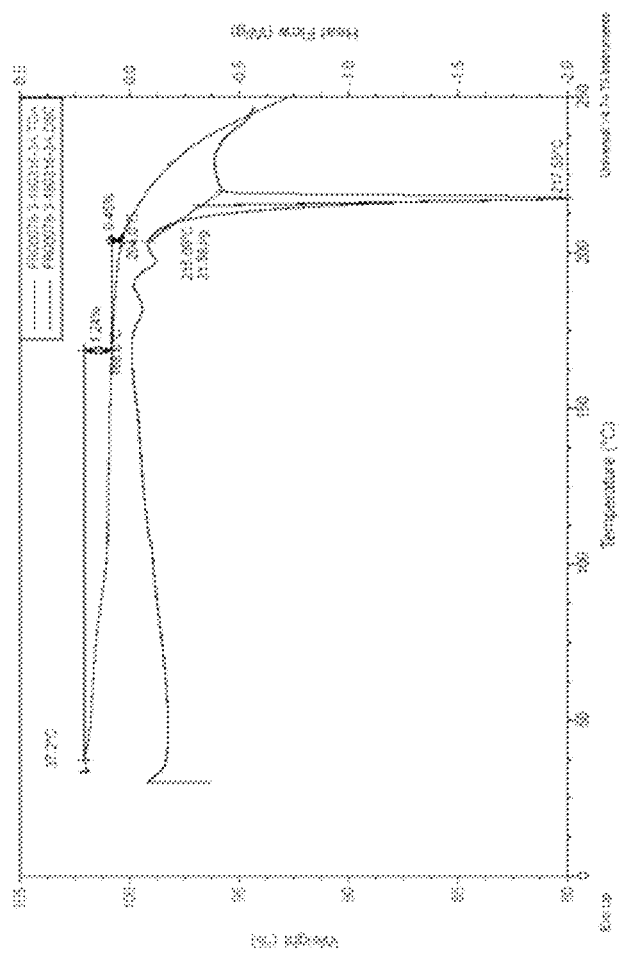
FIG. 28 shows a DSC thermogram and a TGA thermogram of Compound 1 Phosphate (Form A).

In some embodiments, the Compound 1 Phosphate (Form A) exhibits a TGA thermogram that is substantially similar to FIG. 28. In other embodiments, the TGA thermogram of the Compound 1 Phosphate (Form A) exhibits a weight loss of 0.0 to 1.7% in the temperature range of 25 to 204° C.

Figure 29:
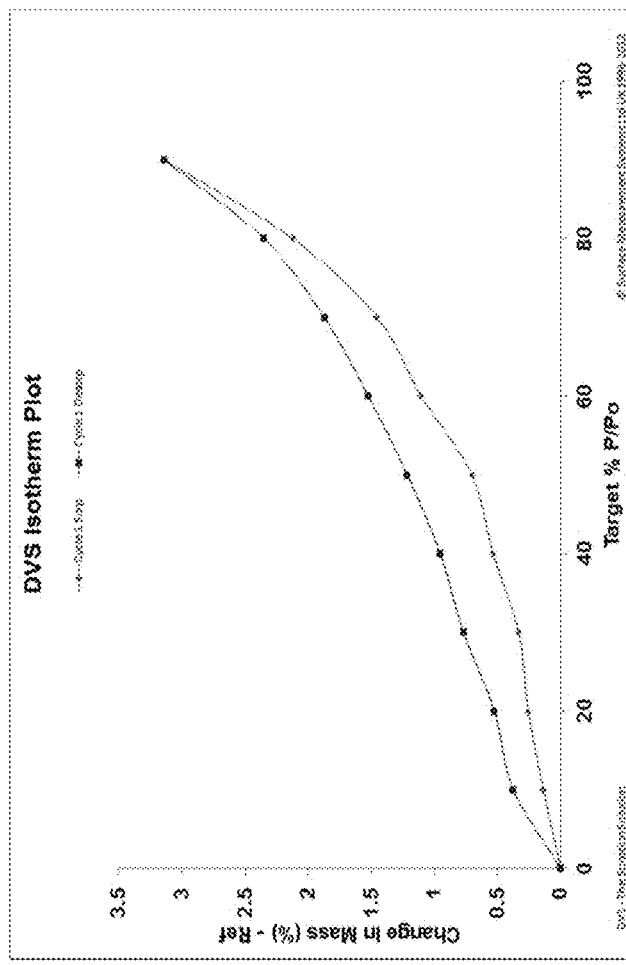
FIG. 29 shows a DVS isotherm plot for Compound 1 Phosphate (Form A).

In some embodiments, the Compound 1 Phosphate (Form A) exhibits a DVS isotherm plot that is substantially similar to FIG. 29. In other embodiments, the Compound 1 Phosphate (Form A) exhibits a gravimetric moisture sorption of about 2.1% (by weight) at 80% Relative Humidity.

Tartrate Salt

In some embodiments, the present disclosure provides a tartrate salt of Compound 1 ("Compound 1 Tartrate"). In some embodiments, the present disclosure provides a D(-)-tartrate salt of Compound 1 ("Compound 1 D(-)-Tartrate"). In some embodiments, the present disclosure provides an L(+)-tartrate salt of Compound 1 ("Compound 1 L(+)-Tartrate").

In some embodiments, the present disclosure provides a crystalline form of Compound 1 Tartrate. In some embodiments, the present disclosure provides a crystalline form of Compound 1 D(-)-Tartrate. In some embodiments, the present disclosure provides a crystalline form of Compound 1 L(+)-Tartrate.

In one embodiment, the present disclosure provides Compound 1 L(+)-Tartrate (Form A). In some embodiments, the Compound 1 L(+)-Tartrate (Form A) exhibits an XRPD comprising one or more peaks at about 3.6, 4.7, 13.9, 18.6, and 22.8 degrees two-theta with the margin of error of about ±0.5; about ±0.4; about ±0.3; about ±0.2; about ±0.1; about ±0.05; or less. In another embodiment, the XRPD of the Compound 1 L(+)-Tartrate (Form A) further comprises one or more peaks at about 14.6, 17.8 and 18.1 degrees two-theta with the margin of error of about ±0.5; about ±0.4; about ±0.3; about ±0.2; about ±0.1; about ±0.05; or less. In yet another embodiment, the Compound 1 L(+)-Tartrate (Form A) exhibits an XRPD comprising peaks shown in Table 13 below:

TABLE 13

XRPD Table of Compound 1 L(+)-Tartrate (Form A)

| 2-Theta | Intensity % |
|---|---|
| 3.6 | 13.6 |
| 4.7 | 100 |
| 13.9 | 82.1 |
| 14.6 | 5.1 |
| 17.8 | 7.6 |
| 18.1 | 3.1 |
| 18.6 | 13 |
| 22.8 | 50.7 |

Figure 30:
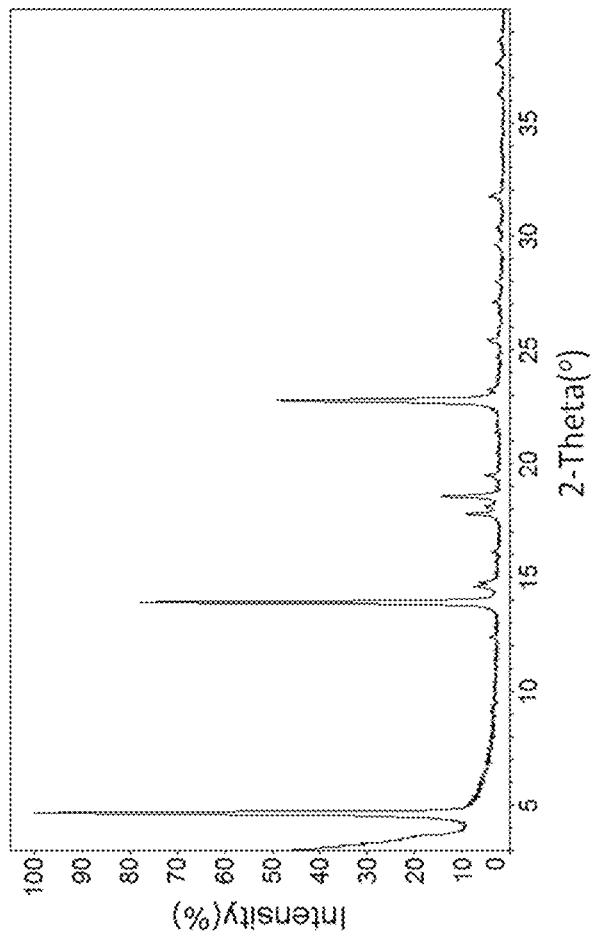
FIG. 30 shows an XRPD pattern of Compound 1 L(+)-Tartrate (Form A).

In some embodiments, the Compound 1 L(+)-Tartrate (Form A) exhibits an XRPD that is substantially similar to FIG. 30.

In some embodiments, the Compound 1 L(+)-Tartrate (Form A) exhibits a DSC thermogram comprising a sharp endotherm at about 207.6° C. with the error of margin of about ±2.5; about ±2.0; about ±1.5; about ±1.0; about ±0.5; or less. In some embodiments, the Compound 1 L(+)-Tartrate (Form A) exhibits a DSC thermogram that is substantially similar to FIG. 31.

Figure 31:
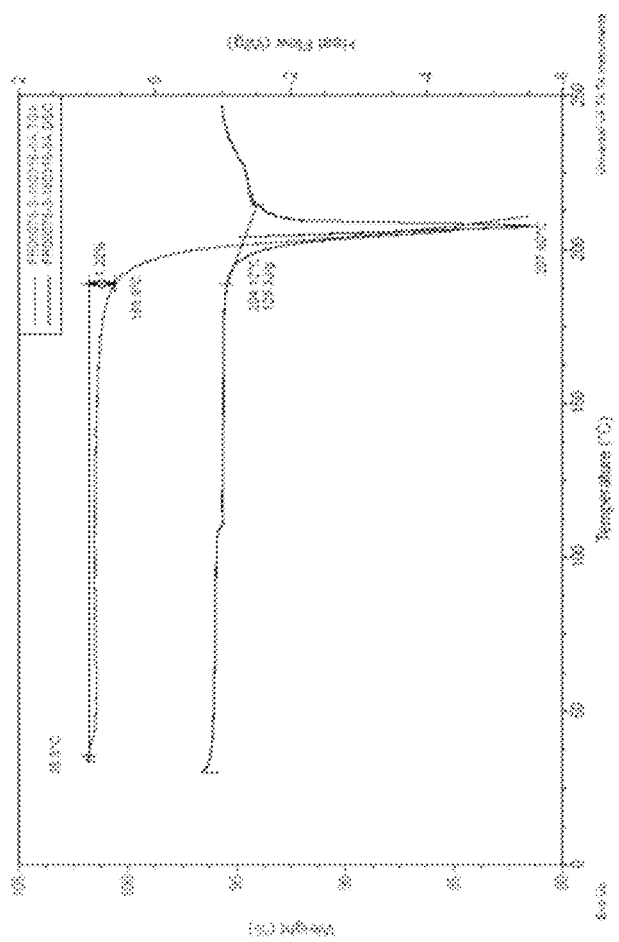
FIG. 31 shows a DSC thermogram and a TGA thermogram of Compound 1 L(+)-Tartrate (Form A).

In some embodiments, the Compound 1 L(+)-Tartrate (Form A) exhibits a TGA thermogram that is substantially similar to FIG. 31. In other embodiments, the TGA thermogram of the Compound 1 L(+)-Tartrate (Form A) exhibits a weight loss of 0.0 to 1.2% in the temperature range of 25 to 189° C.

Figure 32:
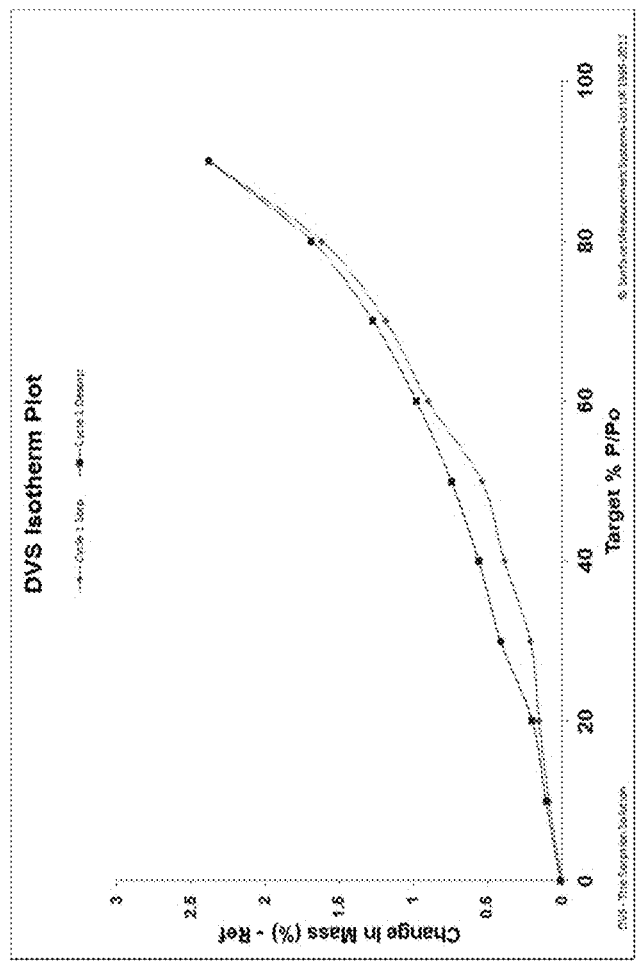
FIG. 32 shows a DVS isotherm plot for Compound 1 L(+)-Tartrate (Form A).

In some embodiments, the Compound 1 L(+)-Tartrate (Form A) exhibits a DVS isotherm plot that is substantially similar to FIG. 32. In other embodiments, the Compound 1 L(+)-Tartrate (Form A) exhibits a gravimetric moisture sorption of about 1.6% (by weight) at 80% Relative Humidity.

In one embodiment, the present disclosure provides Compound 1 L(+)-Tartrate (Form B). In some embodiments, the Compound 1 L(+)-Tartrate (Form B) exhibits an XRPD comprising one or more peaks at about 3.6, 4.6, 12.4, 13.9, and 22.7 degrees two-theta with the margin of error of about ±0.5; about ±0.4; about ±0.3; about ±0.2; about ±0.1; about ±0.05; or less. In another embodiment, the XRPD of the Compound 1 L(+)-Tartrate (Form B) further comprises one or more peaks at about 14.8, 18.3 and 18.5 degrees two-theta with the margin of error of about ±0.5; about ±0.4; about ±0.3; about ±0.2; about ±0.1; about ±0.05; or less. In yet another embodiment, the Compound 1 L(+)-Tartrate (Form B) exhibits an XRPD comprising peaks shown in Table 14 below:

TABLE 14

XRPD Table of Compound 1 L(+)-Tartrate (Form B)

| 2-Theta | Intensity % |
|---|---|
| 3.6 | 65 |
| 4.6 | 100 |
| 12.4 | 22 |
| 13.9 | 50.8 |
| 14.8 | 17.1 |
| 18.3 | 16.9 |
| 18.5 | 20.9 |
| 22.7 | 54.9 |

Figure 33:
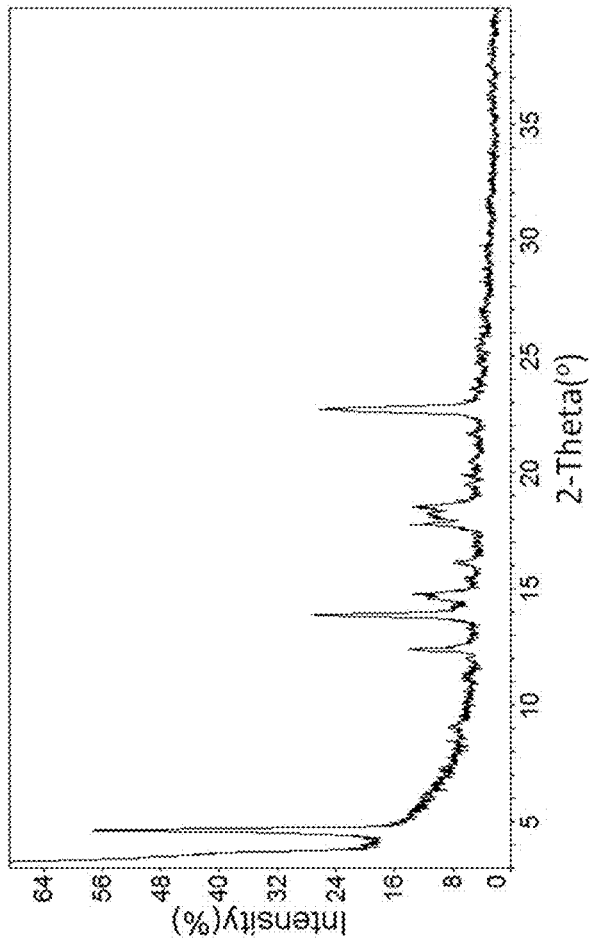
FIG. 33 shows an XRPD pattern of Compound 1 L(+)-Tartrate (Form B).

In some embodiments, the Compound 1 L(+)-Tartrate (Form B) exhibits an XRPD that is substantially similar to FIG. 33.

In some embodiments, the Compound 1 L(+)-Tartrate (Form B) exhibits a DSC thermogram comprising a sharp endotherm at about 207.3° C. with the error of margin of about ±2.5; about ±2.0; about ±1.5; about ±1.0; about ±0.5; or less. In some embodiments, the Compound 1 L(+)-Tartrate (Form B) exhibits a DSC thermogram that is substantially similar to FIG. 34.

Figure 34:
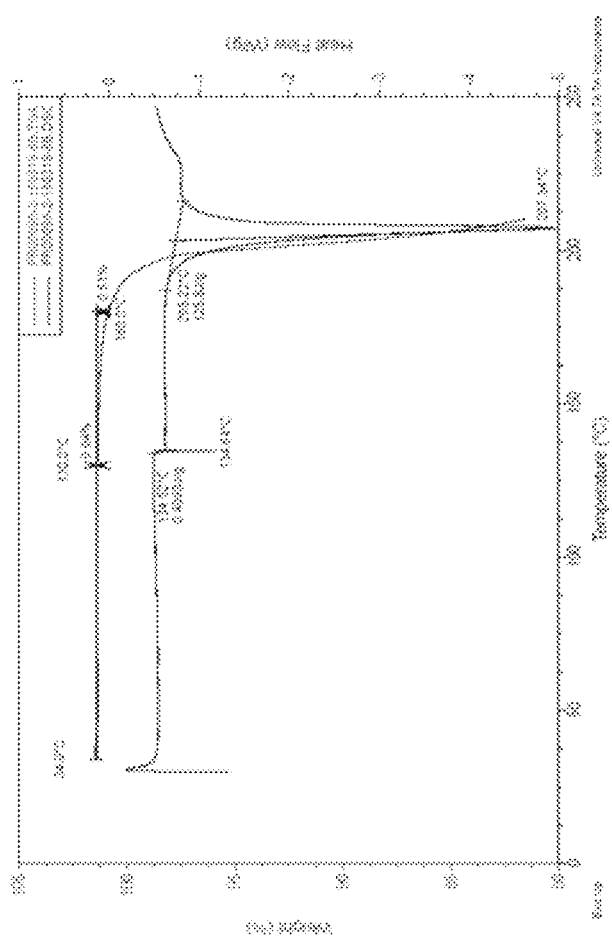
FIG. 34 shows a DSC thermogram and a TGA thermogram of Compound 1 L(+)-Tartrate (Form B).

In some embodiments, the Compound 1 L(+)-Tartrate (Form B) exhibits a TGA thermogram that is substantially similar to FIG. 34. In other embodiments, the TGA thermogram of the Compound 1 L(+)-Tartrate (Form B) exhibits a weight loss of 0.0 to 0.6% in the temperature range of 25 to 180° C.

Figure 35:
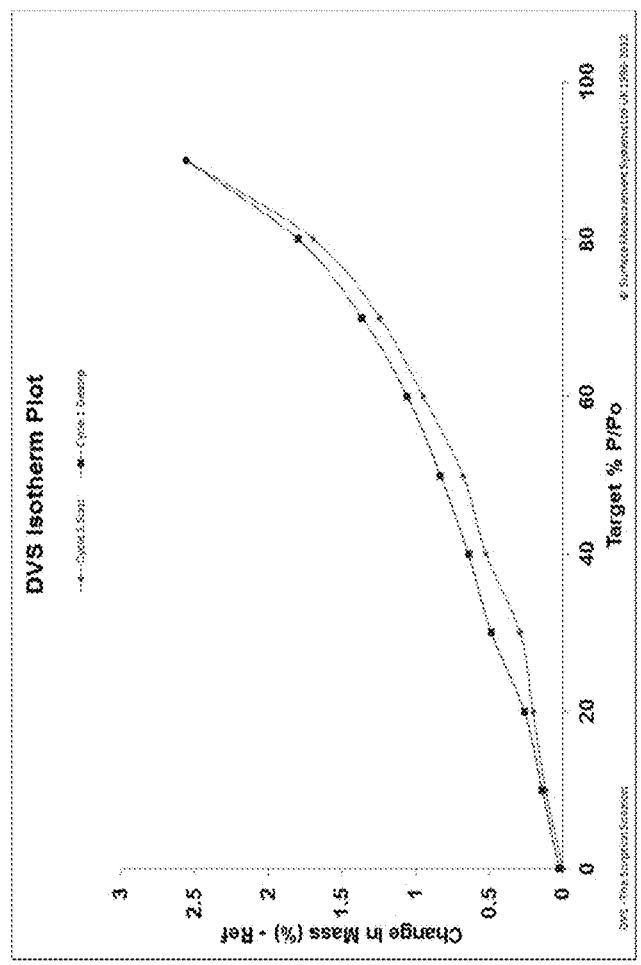
FIG. 35 shows a DVS isotherm plot for Compound 1 L(+)-Tartrate (Form B).

In some embodiments, the Compound 1 L(+)-Tartrate (Form B) exhibits a DVS isotherm plot that is substantially similar to FIG. 35. In other embodiments, the Compound 1 L(+)-Tartrate (Form B) exhibits a gravimetric moisture sorption of about 1.7% (by weight) at 80% Relative Humidity.

Fumarate Salt

In some embodiments, the present disclosure provides a fumarate salt of Compound 1 ("Compound 1 Fumarate"). In some embodiments, the present disclosure provides a crystalline form of Compound 1 Fumarate.

In one embodiment, the present disclosure provides Compound 1 Fumarate (Form A). In some embodiments, the Compound 1 Fumarate (Form A) exhibits an XRPD comprising one or more peaks at about 3.5 and 16.0 degrees two-theta with the margin of error of about ±0.5; about ±0.4; about ±0.3; about ±0.2; about ±0.1; about ±0.05; or less. In yet another embodiment, the Compound 1 Fumarate (Form A) exhibits an XRPD comprising peaks shown in Table 15 below:

TABLE 15

XRPD Table of Compound 1 Fumarate (Form A)

| 2-Theta | Intensity % |
| --- | --- |
| 3.5 | 100 |
| 16.0 | 13.4 |

Figure 36:
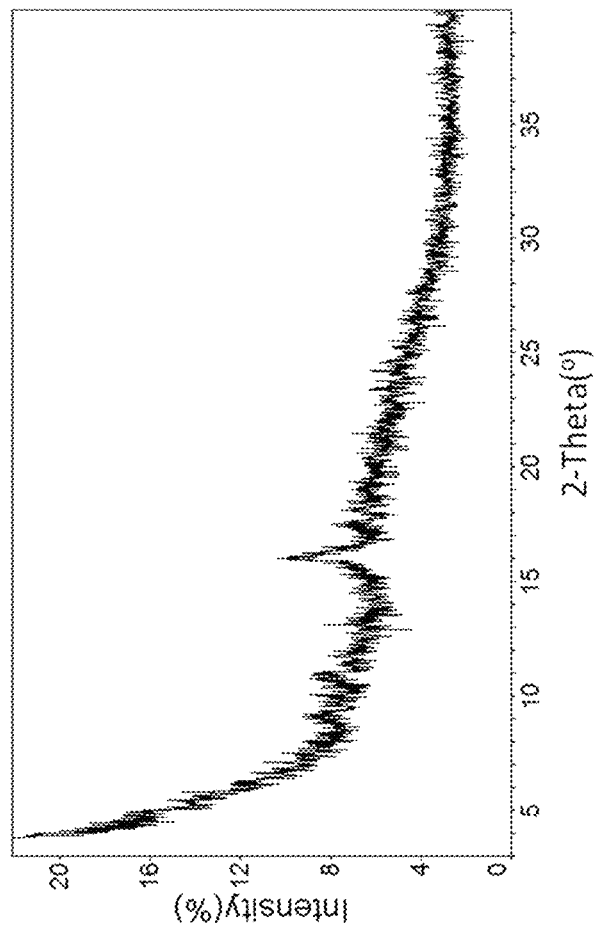
FIG. 36 shows an XRPD pattern of Compound 1 Fumarate (Form A).

In some embodiments, the Compound 1 Fumarate (Form A) exhibits an XRPD that is substantially similar to FIG. 36.

In some embodiments, the Compound 1 Fumarate (Form A) exhibits a DSC thermogram comprising a sharp endotherm at about 87.0° C. with the error of margin of about ±2.5; about ±2.0; about ±1.5; about ±1.0; about ±0.5; or less. In some embodiments, the Compound 1 Fumarate (Form A) exhibits a DSC thermogram that is substantially similar to FIG. 37.

Figure 37:
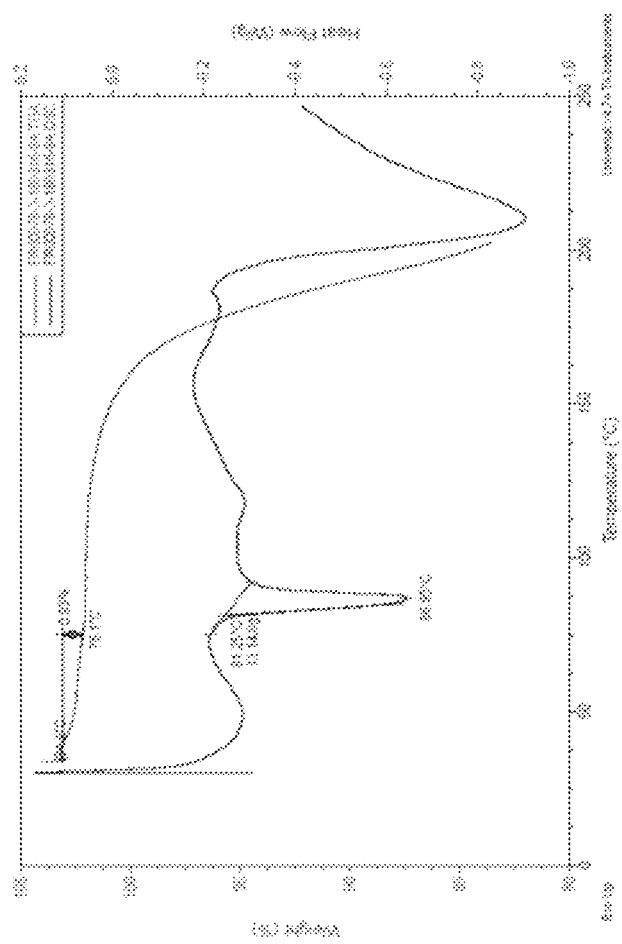
FIG. 37 shows a DSC thermogram and a TGA thermogram of Compound 1 Fumarate (Form A).

In some embodiments, the Compound 1 Fumarate (Form A) exhibits a TGA thermogram that is substantially similar to FIG. 37. In other embodiments, the TGA thermogram of the Compound 1 Fumarate (Form A) exhibits a weight loss of 0.0 to 0.9% in the temperature range of 25 to 75° C.

In some embodiments, the present disclosure provides Compound 1 Fumarate (Form B). In some embodiments, the Compound 1 Fumarate (Form B) exhibits an XRPD comprising one or more peaks at about 3.6, 11.0, 16.2, and 17.5 degrees two-theta with the margin of error of about ±0.5; about ±0.4; about ±0.3; about ±0.2; about ±0.1; about ±0.05; or less. In yet another embodiment, the Compound 1 Fumarate (Form B) exhibits an XRPD comprising peaks shown in Table 16 below:

TABLE 16

XRPD Table of Compound 1 Fumarate (Form B)

| 2-Theta | Intensity % |
| --- | --- |
| 3.6 | 100 |
| 11.0 | 12.8 |
| 16.2 | 23.4 |
| 17.5 | 13.1 |

Figure 38:
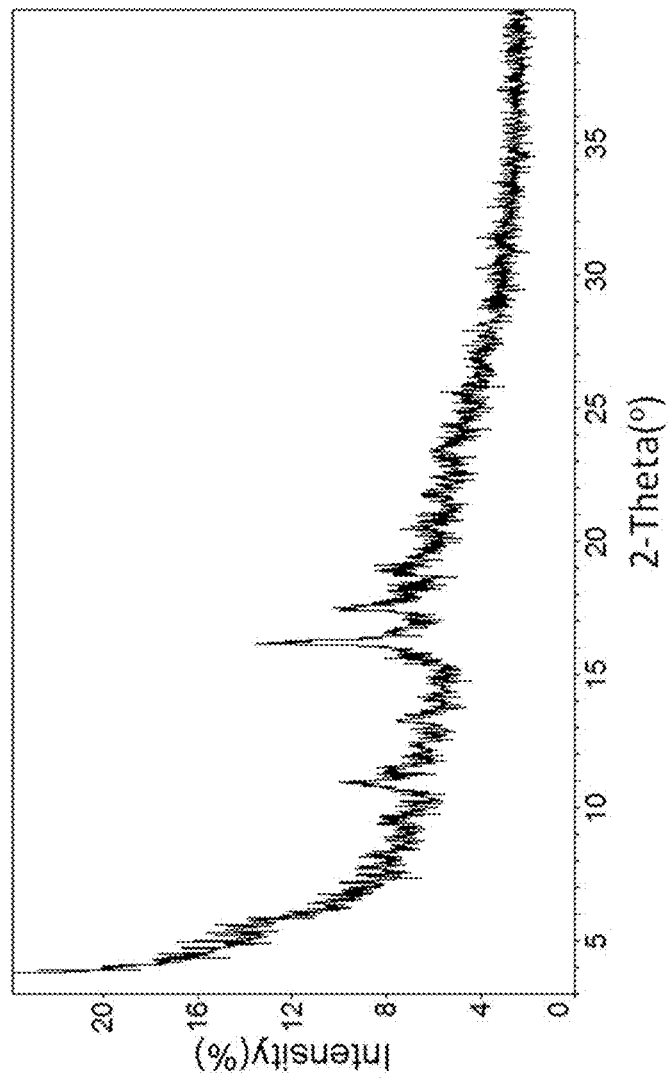
FIG. 38 shows an XRPD pattern of Compound 1 Fumarate (Form B).

In some embodiments, the Compound 1 Fumarate (Form B) exhibits an XRPD that is substantially similar to FIG. 38.

In some embodiments, the Compound 1 Fumarate (Form B) exhibits a DSC thermogram comprising a sharp endotherm at about 89.9° C. with the error of margin of about ±2.5; about ±2.0; about ±1.5; about ±1.0; about ±0.5; or less. In some embodiments, the Compound 1 Fumarate (Form B) exhibits a DSC thermogram that is substantially similar to FIG. 39.

Figure 39:
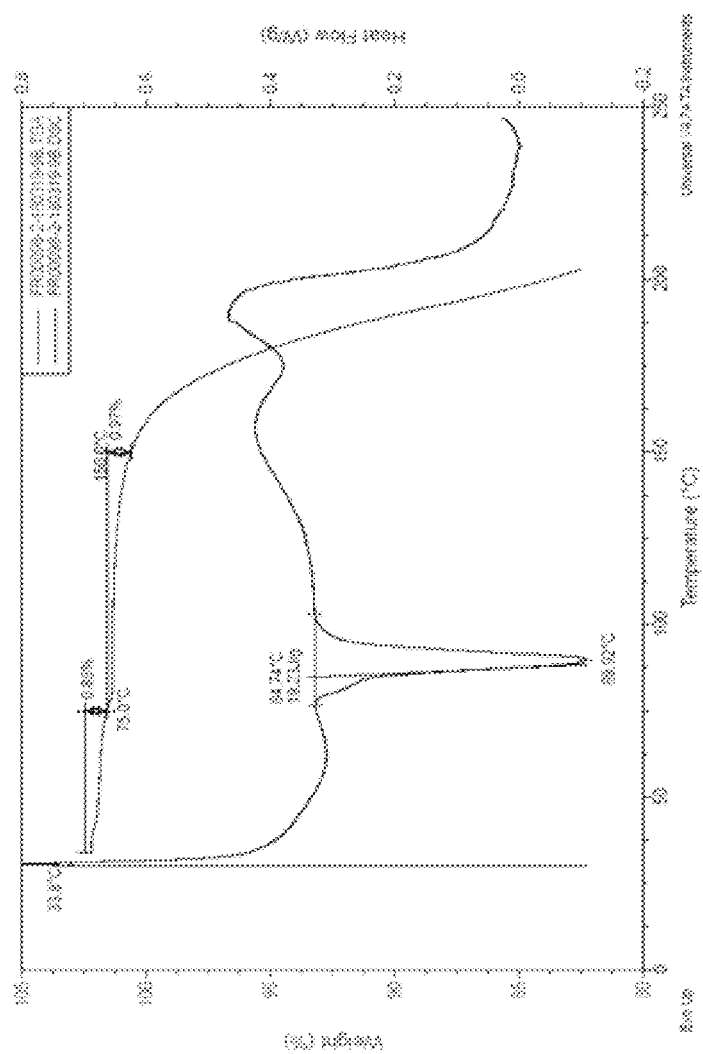
FIG. 39 shows a DSC thermogram and a TGA thermogram of Compound 1 Fumarate (Form B).

In some embodiments, the Compound 1 Fumarate (Form B) exhibits a TGA thermogram that is substantially similar to FIG. 39. In other embodiments, the TGA thermogram of the Compound 1 Fumarate (Form B) exhibits a weight loss of 0.0 to 1.85% in the temperature range of 25 to 150° C.

Figure 40:
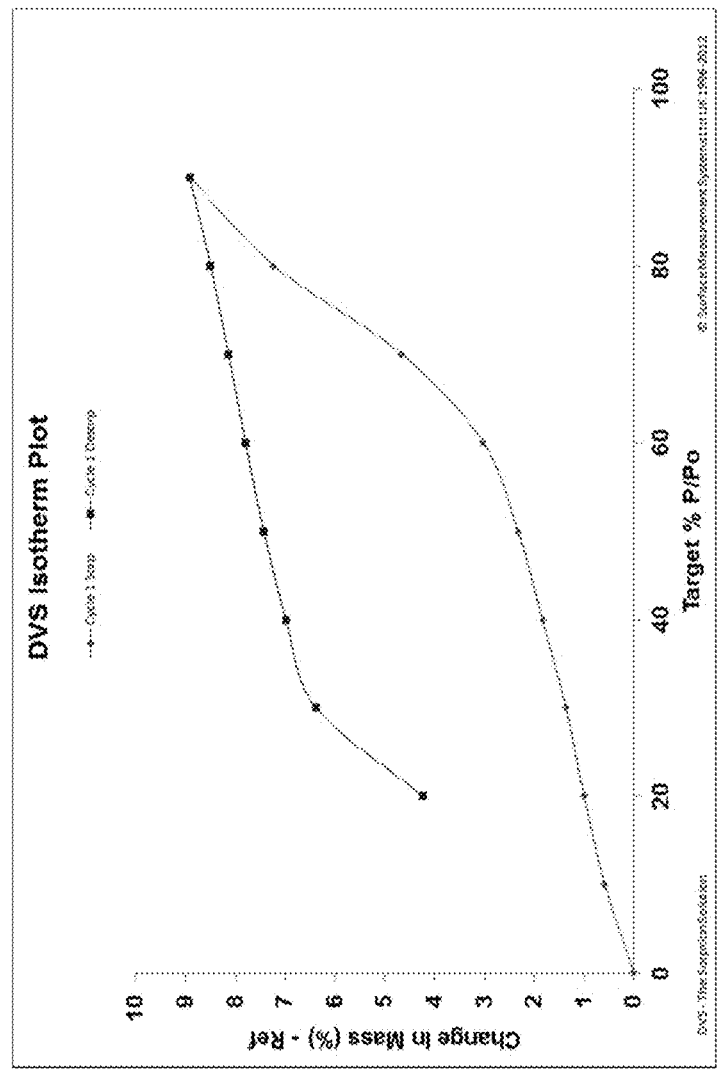
FIG. 40 shows a DVS isotherm plot for Compound 1 Fumarate (Form B).

In some embodiments, the Compound 1 Fumarate (Form B) exhibits a DVS isotherm plot that is substantially similar to FIG. 40. In other embodiments, the Compound 1 Fumarate (Form B) exhibits a gravimetric moisture sorption of about 7.2% (by weight) at 80% Relative Humidity.

In one embodiment, the present disclosure provides Compound 1 Fumarate (Form C). In some embodiments, the Compound 1 Fumarate (Form C) exhibits an XRPD comprising one or more peaks at about 14.5, 15.4, 16.7, 17.6, and 28.8 degrees two-theta with the margin of error of about ±0.5; about ±0.4; about ±0.3; about ±0.2; about ±0.1; about ±0.05; or less. In another embodiment, the XRPD of the Compound 1 Fumarate (Form C) further comprises one or more peaks at about 8.4, 19.7, 20.5, 22.9, and 38.1 degrees two-theta with the margin of error of about ±0.5; about ±0.4; about ±0.3; about ±0.2; about ±0.1; about ±0.05; or less. In yet another embodiment, the Compound 1 Fumarate (Form C) exhibits an XRPD comprising peaks shown in Table 17 below:

TABLE 17

XRPD Table of Compound 1 Fumarate (Form C)

| 2-Theta | Intensity % |
| --- | --- |
| 8.4 | 26.2 |
| 9.8 | 8.9 |
| 12.9 | 10.2 |
| 14.5 | 46.3 |
| 15.4 | 100 |
| 16.7 | 36.6 |
| 17.6 | 44.4 |
| 19.7 | 21.7 |
| 20.5 | 27.9 |
| 21.5 | 12.6 |
| 22.9 | 20.6 |
| 23.3 | 8.2 |

TABLE 17-continued

XRPD Table of Compound 1 Fumarate (Form C)

| 2-Theta | Intensity % |
|---|---|
| 25.2 | 15.8 |
| 25.7 | 12.1 |
| 27.4 | 14.5 |
| 28.8 | 41.6 |
| 38.1 | 28.8 |

Figure 41:
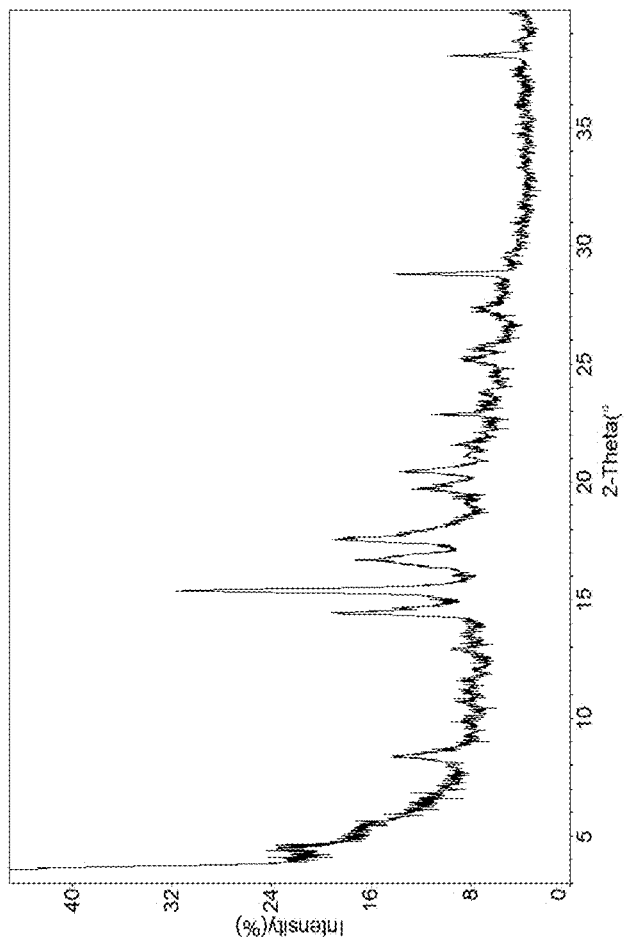
FIG. 41 shows an XRPD pattern of Compound 1 Fumarate (Form C).

In some embodiments, the Compound 1 Fumarate (Form C) exhibits an XRPD that is substantially similar to FIG. 41.

In one embodiment, the present disclosure provides Compound 1 Fumarate (Form D). In some embodiments, the Compound 1 Fumarate (Form D) exhibits an XRPD comprising one or more peaks at about 5.2, 12.2, 15.2, 15.5, and 19.9 degrees two-theta with the margin of error of about ±0.5; about ±0.4; about ±0.3; about ±0.2; about ±0.1; about ±0.05; or less. In another embodiment, the XRPD of the Compound 1 Fumarate (Form D) further comprises one or more peaks at about 10.4, 13.6, 14.2, 21.2, and 22.3 degrees two-theta with the margin of error of about ±0.5; about ±0.4; about ±0.3; about ±0.2; about ±0.1; about ±0.05; or less. In yet another embodiment, the Compound 1 Fumarate (Form D) exhibits an XRPD comprising peaks shown in Table 18 below:

TABLE 18

XRPD Table of Compound 1 Fumarate (Form D)

| 2-Theta | Intensity % |
|---|---|
| 5.2 | 29.5 |
| 10.4 | 23.5 |
| 12.2 | 100 |
| 13.6 | 27.9 |
| 14.2 | 28.8 |
| 15.2 | 42 |
| 15.5 | 40 |
| 16.5 | 19.6 |
| 16.9 | 13.5 |
| 17.2 | 9.6 |
| 19.1 | 11 |
| 19.9 | 40.9 |
| 20.5 | 19.2 |
| 21.2 | 27.9 |
| 22.3 | 21.2 |
| 22.9 | 17.1 |
| 23.5 | 17.4 |
| 24.0 | 21.2 |
| 24.6 | 13.5 |
| 26.2 | 18.5 |
| 26.9 | 14.4 |
| 28.9 | 15.1 |

Figure 42:
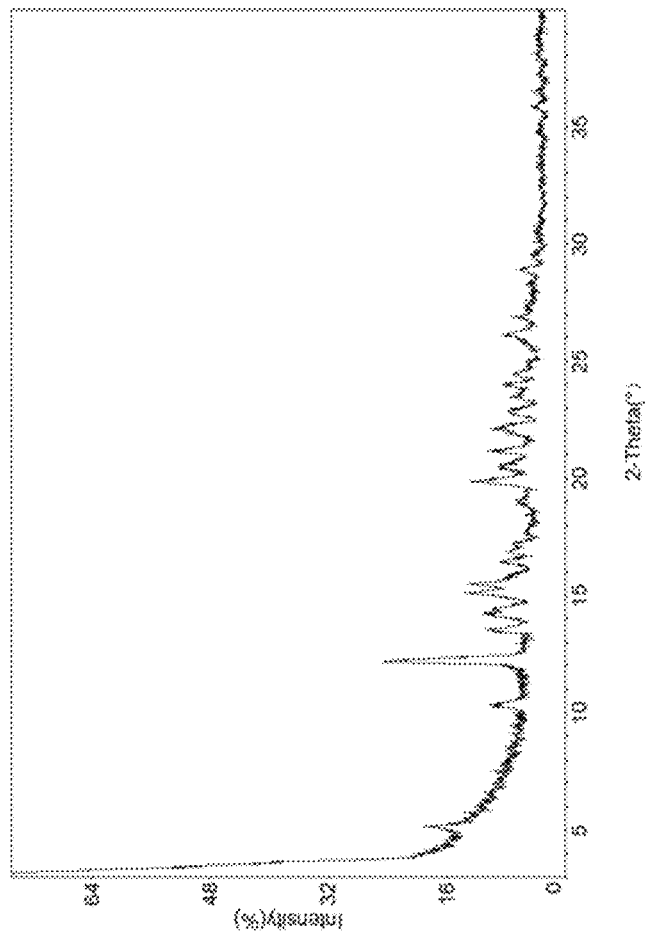
FIG. 42 shows an XRPD pattern of Compound 1 Fumarate (Form D).

In some embodiments, the Compound 1 Fumarate (Form D) exhibits an XRPD that is substantially similar to FIG. 42.

Tosylate SALT

In some embodiments, the present disclosure provides a tosylate salt of Compound 1 ("Compound 1 Tosylate"). In some embodiments, the present disclosure provides a crystalline form of Compound 1 Tosylate.

In one embodiment, the present disclosure provides Compound 1 Tosylate (Form A). In some embodiments, the Compound 1 Tosylate (Form A) exhibits an XRPD comprising one or more peaks at about 3.4, 9.8, 10.3, 12.5, and 15.3 degrees two-theta with the margin of error of about ±0.5; about ±0.4; about ±0.3; about ±0.2; about ±0.1; about ±0.05; or less. In another embodiment, the XRPD of the Compound 1 Tosylate (Form A) further comprises one or more peaks at about 17.4, 17.9, 19.6, 23.2 and 26.0 degrees two-theta with the margin of error of about ±0.5; about ±0.4; about ±0.3; about ±0.2; about ±0.1; about ±0.05; or less.

In yet another embodiment, the Compound 1 Tosylate (Form A) exhibits an XRPD comprising peaks shown in Table 19 below:

TABLE 19

XRPD Table of Compound 1 Tosylate (Form A)

| 2-Theta | Intensity % |
|---|---|
| 3.4 | 100 |
| 9.8 | 3.1 |
| 10.3 | 3 |
| 12.5 | 7 |
| 15.3 | 6.3 |
| 15.8 | 1.1 |
| 16.5 | 0.9 |
| 16.9 | 1.1 |
| 17.4 | 2.2 |
| 17.9 | 1.8 |
| 19.0 | 1.4 |
| 19.6 | 2.6 |
| 20.7 | 1.3 |
| 21.4 | 1.5 |
| 23.2 | 1.7 |
| 23.6 | 1.1 |
| 26.0 | 1.9 |
| 27.2 | 1.1 |
| 27.5 | 1.3 |
| 28.7 | 1 |
| 29.6 | 0.7 |
| 30.7 | 0.9 |

Figure 43:
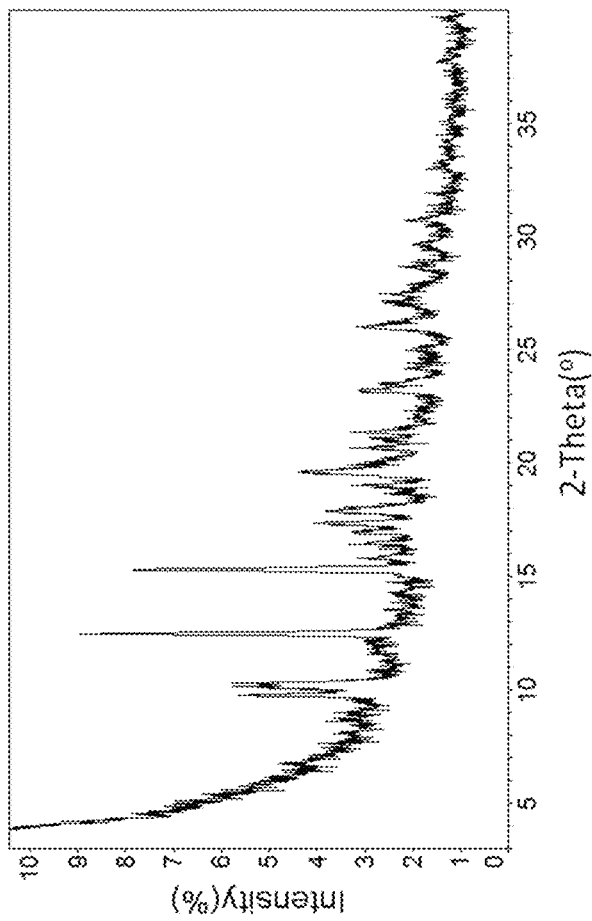
FIG. 43 shows an XRPD pattern of Compound 1 Tosylate (Form A).

In some embodiments, the Compound 1 Tosylate (Form A) exhibits an XRPD that is substantially similar to FIG. 43.

In some embodiments, the Compound 1 Tosylate (Form A) exhibits a DSC thermogram comprising a sharp endotherm at about 186.2° C. with the error of margin of about ±2.5; about ±2.0; about ±1.5; about ±1.0; about ±0.5; or less. In some embodiments, the Compound 1 Tosylate (Form A) exhibits a DSC thermogram that is substantially similar to FIG. 44.

Figure 44:
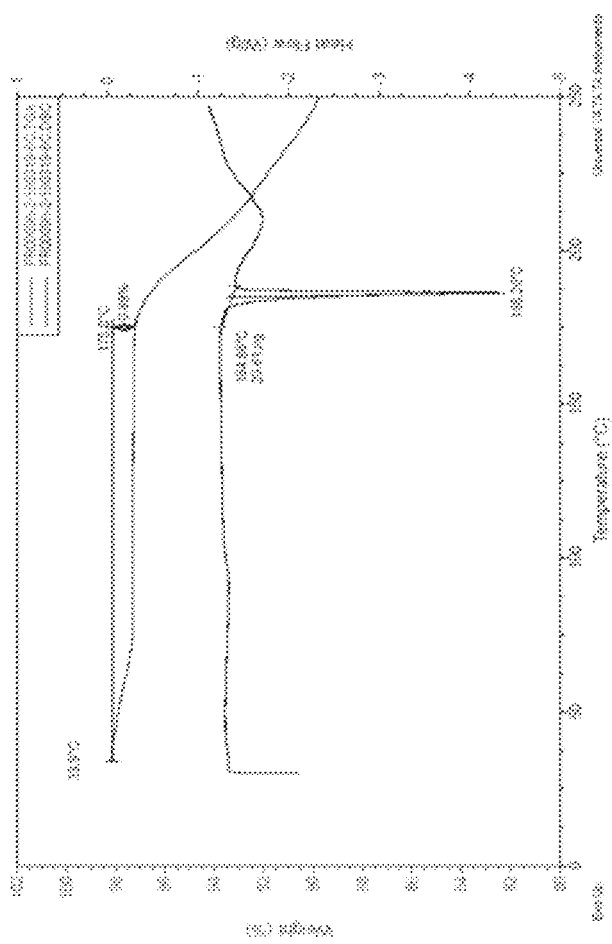
FIG. 44 shows a DSC thermogram and a TGA thermogram of Compound 1 Tosylate (Form A).

In some embodiments, the Compound 1 Tosylate (Form A) exhibits a TGA thermogram that is substantially similar to FIG. 44. In other embodiments, the TGA thermogram of the Compound 1 Tosylate (Form A) exhibits a weight loss of 0.0 to 0.9% in the temperature range of 25 to 175° C.

Figure 45:
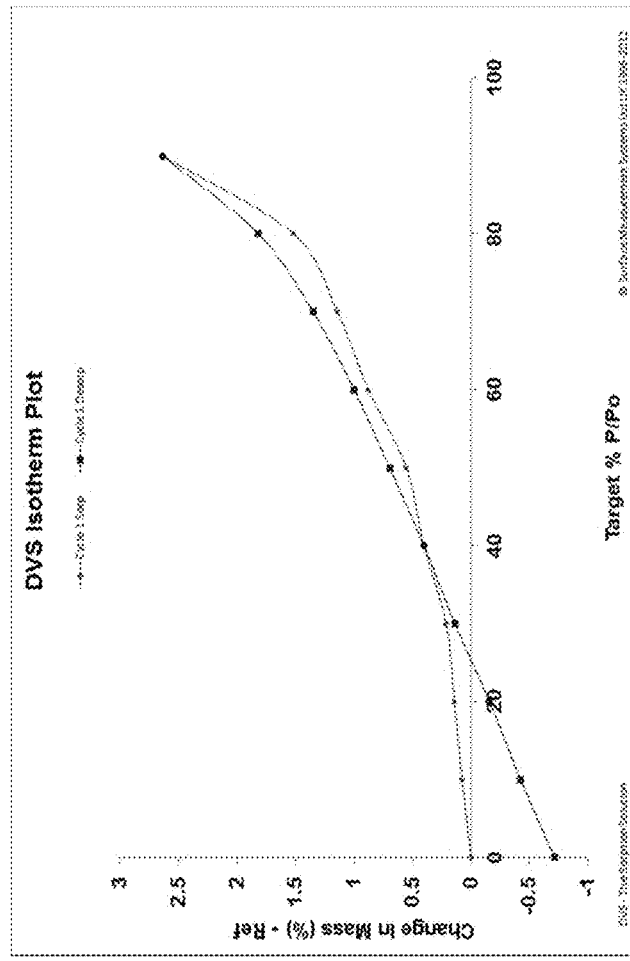
FIG. 45 shows a DVS isotherm plot for Compound 1 Tosylate (Form A).

In some embodiments, the Compound 1 Tosylate (Form A) exhibits a DVS isotherm plot that is substantially similar to FIG. 45. In other embodiments, the Compound 1 Tosylate (Form A) exhibits a gravimetric moisture sorption of about 1.5% (by weight) at 80% Relative Humidity.

In one embodiment, the present disclosure provides Compound 1 Tosylate (Form B). In some embodiments, the Compound 1 Tosylate (Form B) exhibits an XRPD comprising one or more peaks at about 10.0, 15.2, 15.5, 17.2, and 19.4 degrees two-theta with the margin of error of about ±0.5; about ±0.4; about ±0.3; about ±0.2; about ±0.1; about ±0.05; or less. In another embodiment, the XRPD of the Compound 1 Tosylate (Form B) further comprises one or more peaks at about 10.3, 16.7, 19.1, 20.1 and 20.8 degrees two-theta with the margin of error of about ±0.5; about ±0.4; about ±0.3; about ±0.2; about ±0.1; about ±0.05; or less.

In yet another embodiment, the Compound 1 Tosylate (Form B) exhibits an XRPD comprising peaks shown in Table 20 below:

TABLE 20

XRPD Table of Compound 1 Tosylate (Form B)

| 2-Theta | Intensity % |
|---|---|
| 6.8 | 16.7 |
| 9.1 | 24.4 |
| 10.0 | 100 |
| 10.3 | 39.9 |
| 11.0 | 12.8 |
| 11.9 | 23.8 |
| 12.2 | 25.9 |
| 13.0 | 15.5 |
| 13.5 | 19.3 |
| 15.2 | 58.3 |
| 15.5 | 65.5 |
| 16.2 | 27.1 |
| 16.7 | 35.1 |
| 17.2 | 47.9 |
| 18.5 | 23.2 |
| 19.1 | 29.2 |
| 19.4 | 41.7 |
| 19.8 | 28.0 |
| 20.1 | 32.1 |
| 20.8 | 40.2 |
| 21.7 | 25.6 |
| 22.2 | 25.3 |
| 23.2 | 21.7 |
| 24.4 | 20.5 |
| 25.6 | 26.8 |
| 26.2 | 26.8 |
| 27.2 | 18.5 |
| 28.4 | 17.9 |
| 29.0 | 12.8 |

Figure 46:
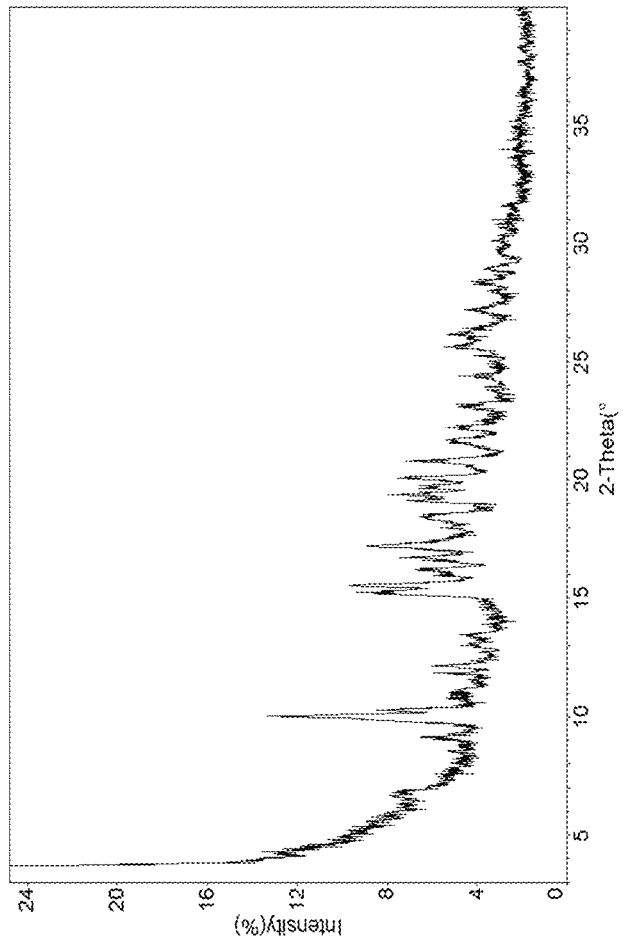
FIG. 46 shows an XRPD pattern of Compound 1 Tosylate (Form B).

In some embodiments, the Compound 1 Tosylate (Form B) exhibits an XRPD that is substantially similar to FIG. 46.

In one embodiment, the present disclosure provides Compound 1 Tosylate (Form C). In some embodiments, the Compound 1 Tosylate (Form C) exhibits an XRPD comprising one or more peaks at about 7.4, 10.2, 12.5, 18.3, and 19.7 degrees two-theta with the margin of error of about ±0.5; about ±0.4; about ±0.3; about ±0.2; about ±0.1; about ±0.05; or less. In another embodiment, the XRPD of the Compound 1 Tosylate (Form C) further comprises one or more peaks at about 9.8, 14.7, 16.6, 17.8, and 23.2 degrees two-theta with the margin of error of about ±0.5; about ±0.4; about ±0.3; about ±0.2; about ±0.1; about ±0.05; or less.

In yet another embodiment, the Compound 1 Tosylate (Form C) exhibits an XRPD comprising peaks shown in Table 21 below:

TABLE 21

XRPD Table of Compound 1 Tosylate (Form C)

| 2-Theta | Intensity % |
|---|---|
| 7.4 | 70 |
| 9.8 | 28.2 |
| 10.2 | 46.9 |
| 10.8 | 16.4 |
| 11.4 | 21.8 |
| 12.5 | 100 |
| 13.1 | 15.6 |
| 13.8 | 17.1 |
| 14.7 | 34.2 |
| 15.3 | 16.7 |
| 16.6 | 40.2 |
| 16.9 | 16 |
| 17.4 | 16.2 |
| 17.8 | 41.6 |
| 18.3 | 65.1 |
| 19.7 | 85.6 |
| 20.3 | 8 |
| 20.7 | 14.2 |
| 21.1 | 18.9 |
| 21.4 | 16 |
| 22.2 | 26.7 |
| 22.8 | 9.3 |
| 23.2 | 46.4 |
| 23.6 | 14.9 |
| 24.2 | 11.8 |
| 24.7 | 16.9 |
| 25.9 | 21.6 |
| 27.2 | 11.3 |
| 27.5 | 20.9 |
| 28.6 | 17.8 |
| 30.5 | 16.2 |
| 30.8 | 13.8 |
| 31.2 | 12.4 |
| 37.8 | 11.1 |

Figure 47:
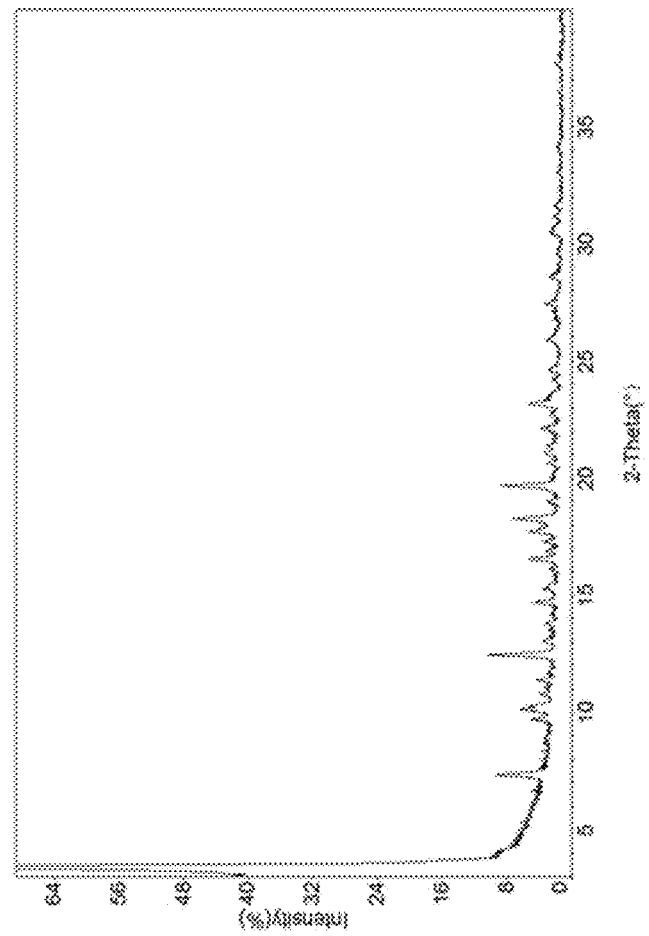
FIG. 47 shows an XRPD pattern of Compound 1 Tosylate (Form C).

In some embodiments, the Compound 1 Tosylate (Form C) exhibits an XRPD that is substantially similar to FIG. 47.

Glucuronate Salt

In some embodiments, the present disclosure provides a glucuronate salt of Compound 1 ("Compound 1 Glucuronate"). In some embodiments, the present disclosure provides a D-glucuronate salt of Compound 1 ("Compound 1 D-Glucuronate"). In some embodiments, the present disclosure provides L-glucuronate salt of Compound 1 ("Compound 1 L-Glucuronate").

In some embodiments, the present disclosure provides a crystalline form of Compound 1 Glucuronate. In some embodiments, the present disclosure provides a crystalline form of Compound 1 D-Glucuronate. In some embodiments, the present disclosure provides a crystalline form of Compound 1 L-Glucuronate.

In one embodiment, the present disclosure provides Compound 1 D-Glucuronate (Form A). In some embodiments, the Compound 1 D-Glucuronate (Form A) exhibits an XRPD comprising one or more peaks at about 4.3, 12.9, 16.8, 20.2 and 20.9 degrees two-theta with the margin of error of about ±0.5; about ±0.4; about ±0.3; about ±0.2; about ±0.1; about ±0.05; or less. In another embodiment, the XRPD of the Compound 1 D-Glucuronate (Form A) further comprises one or more peaks at about 3.3, 14.7, 17.3, 21.6, and 24.8 degrees two-theta with the margin of error of about ±0.5; about ±0.4; about ±0.3; about ±0.2; about ±0.1; about ±0.05; or less.

In yet another embodiment, the Compound 1 D-Glucuronate (Form A) exhibits an XRPD comprising peaks shown in Table 22 below:

TABLE 22

XRPD Table of Compound 1 D-Glucuronate (Form A)

| 2-Theta | Intensity % |
|---|---|
| 3.3 | 30.3 |
| 4.3 | 100 |
| 11.6 | 8.8 |
| 12.9 | 51.1 |
| 13.8 | 11.1 |
| 14.7 | 24.3 |
| 15.0 | 8.3 |
| 15.4 | 18.7 |
| 16.8 | 62.1 |
| 17.3 | 38.5 |
| 20.2 | 49.3 |

TABLE 22-continued

XRPD Table of Compound 1 D-Glucuronate (Form A)

| 2-Theta | Intensity % |
|---|---|
| 20.9 | 99.8 |
| 21.6 | 20.9 |
| 22.4 | 8 |
| 24.2 | 20 |
| 24.8 | 20.5 |
| 25.7 | 5.7 |
| 28.2 | 9.1 |
| 28.8 | 5.7 |
| 30.8 | 9.1 |
| 32.5 | 11.3 |

Figure 48:
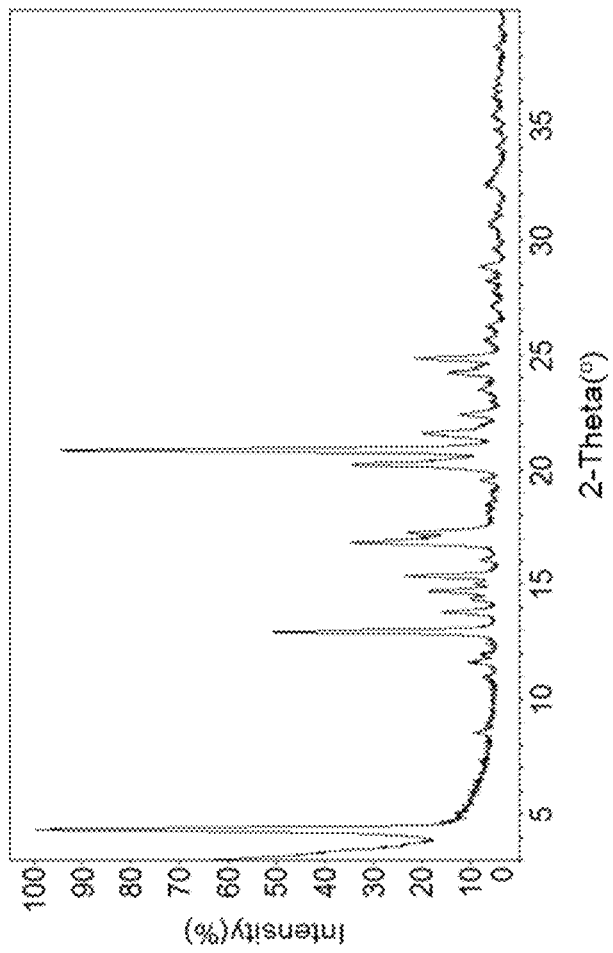
FIG. 48 shows an XRPD pattern of Compound 1 Glucuronate (Form A).

In some embodiments, the Compound 1 D-Glucuronate (Form A) exhibits an XRPD that is substantially similar to FIG. 48.

In some embodiments, the Compound 1 D-Glucuronate (Form A) exhibits a DSC thermogram comprising a endotherm at about 116.2° C. with the error of margin of about ±2.5; about ±2.0; about ±1.5; about ±1.0; about ±0.5; or less. In another embodiment, the Compound 1 D-Glucuronate (Form A) exhibits a DSC thermogram comprising a endotherm at about 139.3° C. with the error of margin of about ±2.5; about ±2.0; about ±1.5; about ±1.0; about ±0.5; or less. In some embodiments, the Compound 1 D-Glucuronate (Form A) exhibits a DSC thermogram that is substantially similar to FIG. 49.

Figure 49:
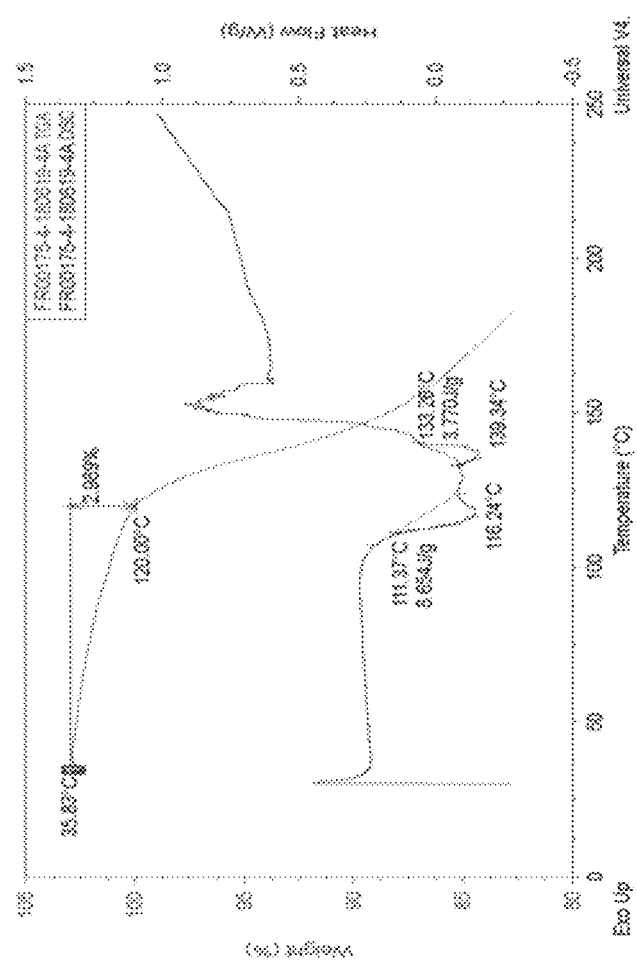
FIG. 49 shows a DSC thermogram and a TGA thermogram of Compound 1 Glucuronate (Form A).

In some embodiments, the Compound 1 D-Glucuronate (Form A) exhibits a TGA thermogram that is substantially similar to FIG. 49. In other embodiments, the TGA thermogram of the Compound 1 D-Glucuronate (Form A) exhibits a weight loss of 0.0 to 3.0% in the temperature range of 25 to 120° C.

Figure 50:
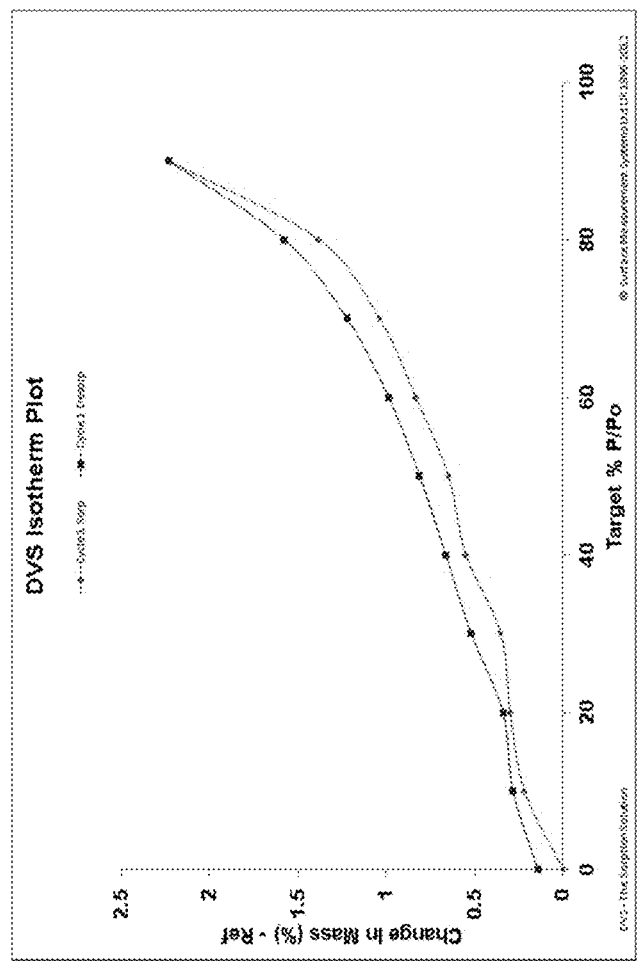
FIG. 50 shows a DVS isotherm plot for Compound 1 Glucuronate (Form A).

In some embodiments, the Compound 1 D-Glucuronate (Form A) exhibits a DVS isotherm plot that is substantially similar to FIG. 50. In other embodiments, the Compound 1 D-Glucuronate (Form A) exhibits a gravimetric moisture sorption of about 1.4% (by weight) at 80% Relative Humidity.

In one embodiment, the present disclosure provides Compound 1 D-Glucuronate (Form B). In some embodiments, the Compound 1 D-Glucuronate (Form B) exhibits an XRPD comprising one or more peaks at about 14.7, 16.7, 17.0, 20.0 and 20.4 degrees two-theta with the margin of error of about ±0.5; about ±0.4; about ±0.3; about ±0.2; about ±0.1; about ±0.05; or less. In another embodiment, the XRPD of the Compound 1 D-Glucuronate (Form B) further comprises one or more peaks at about 8.5, 15.0, 19.5, 22.5 and 24.3 degrees two-theta with the margin of error of about ±0.5; about ±0.4; about ±0.3; about ±0.2; about ±0.1; about ±0.05; or less.

In yet another embodiment, the Compound 1 D-Glucuronate (Form B) exhibits an XRPD comprising peaks shown in Table 23 below:

TABLE 23

XRPD Table of Compound 1 D-Glucuronate (Form B)

| 2-Theta | Intensity % |
|---|---|
| 8.5 | 16.1 |
| 11.7 | 7.1 |
| 14.7 | 100 |
| 15.0 | 24.8 |
| 16.7 | 45.2 |

TABLE 23-continued

XRPD Table of Compound 1 D-Glucuronate (Form B)

| 2-Theta | Intensity % |
|---|---|
| 17.0 | 67.7 |
| 19.1 | 4.7 |
| 19.5 | 18.7 |
| 20.0 | 32.9 |
| 20.4 | 42.3 |
| 21.7 | 11.1 |
| 22.5 | 15.6 |
| 22.9 | 8.5 |
| 24.3 | 18 |
| 24.8 | 7.4 |
| 25.4 | 11.2 |
| 25.6 | 14.2 |
| 26.2 | 14.2 |
| 28.0 | 4.1 |
| 28.8 | 3.8 |
| 30.1 | 6.2 |
| 30.6 | 13.6 |
| 35.2 | 9.1 |
| 35.8 | 6.5 |
| 38.3 | 5.1 |
| 39.2 | 5 |

Figure 51:
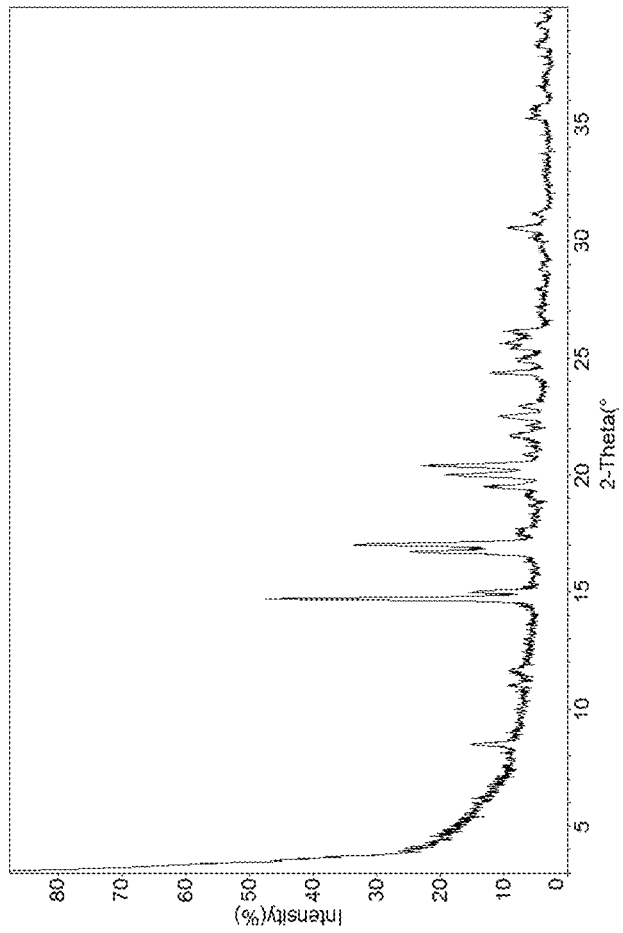
FIG. 51 shows an XRPD pattern of Compound 1 Glucuronate (Form B).

In some embodiments, the Compound 1 D-Glucuronate (Form B) exhibits an XRPD that is substantially similar to FIG. 51.

Ethanesulfonate SALT

In some embodiments, the present disclosure provides an ethanesulfonate salt of Compound 1 ("Compound 1 Ethanesulfonate"). In some embodiments, the present disclosure provides a crystalline form of Compound 1 Ethanesulfonate.

In one embodiment, the present disclosure provides Compound 1 Ethanesulfonate (Form A). In some embodiments, the Compound 1 Ethanesulfonate (Form A) exhibits an XRPD comprising one or more peaks at about 3.4, 3.7, 7.6, 15.3, and 23.0 degrees two-theta with the margin of error of about ±0.5; about ±0.4; about ±0.3; about ±0.2; about ±0.1; about ±0.05; or less. In another embodiment, the XRPD of the Compound 1 Ethanesulfonate (Form A) further comprises one or more peaks at about 23.3 and 30.8 degrees two-theta with the margin of error of about ±0.5; about ±0.4; about ±0.3; about ±0.2; about ±0.1; about ±0.05; or less.

In yet another embodiment, the Compound 1 Ethanesulfonate (Form A) exhibits an XRPD comprising peaks shown in Table 24 below:

TABLE 24

XRPD Table of Compound 1 Ethanesulfonate (Form A)

| 2-Theta | Intensity % |
|---|---|
| 3.4 | 22.4 |
| 3.7 | 11.7 |
| 7.6 | 100 |
| 15.3 | 70.3 |
| 23.0 | 21.6 |
| 23.3 | 1.6 |
| 30.8 | 4.3 |

Figure 52:
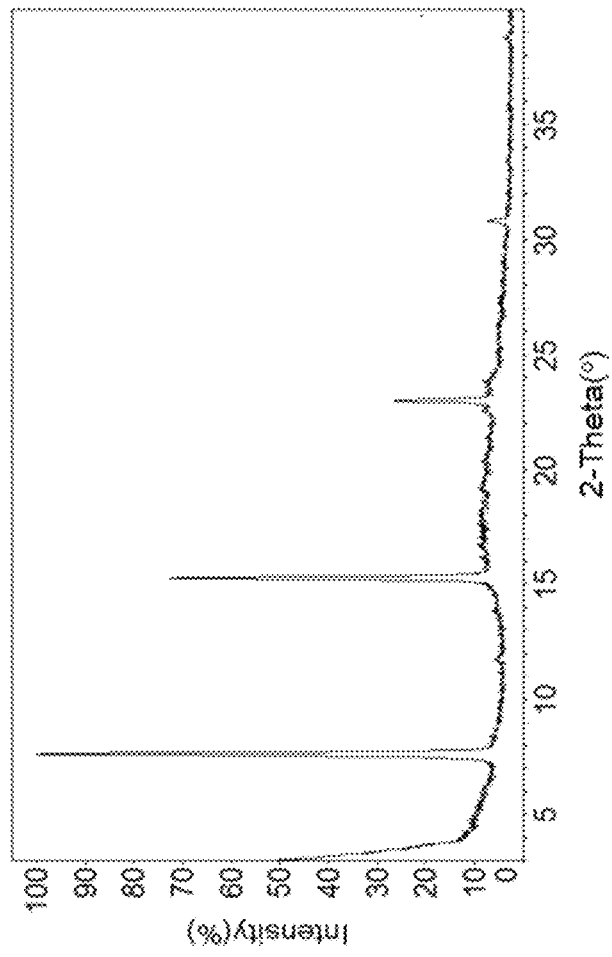
FIG. 52 shows an XRPD pattern of Compound 1 Ethanesulfonate (Form A).

In some embodiments, the Compound 1 Ethanesulfonate (Form A) exhibits an XRPD that is substantially similar to FIG. 52.

In some embodiments, the Compound 1 Ethanesulfonate (Form A) exhibits a DSC thermogram comprising a endotherm at about 177.9° C. with the error of margin of about ±2.5; about ±2.0; about ±1.5; about ±1.0; about ±0.5; or less. In another embodiment, the Compound 1 Ethanesulfonate (Form A) exhibits a DSC thermogram comprising a endotherm at about 207.0° C. with the error of margin of about ±2.5; about ±2.0; about ±1.5; about ±1.0; about ±0.5; or less. In some embodiments, the Compound 1 Ethanesulfonate (Form A) exhibits a DSC thermogram that is substantially similar to FIG. 53.

Figure 53:
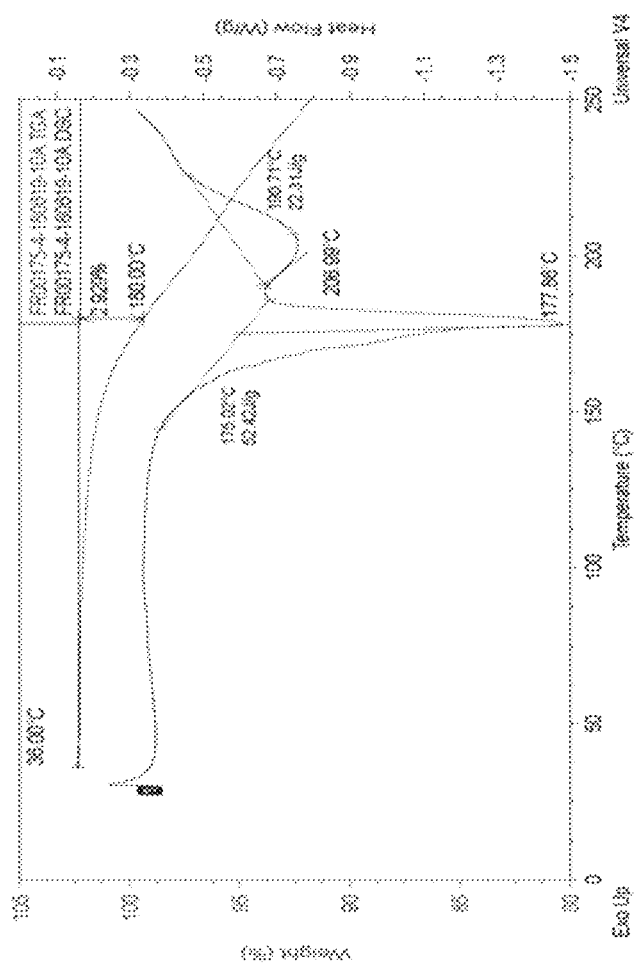
FIG. 53 shows a DSC thermogram and a TGA thermogram of Compound 1 Ethanesulfonate (Form A).

In some embodiments, the Compound 1 Ethanesulfonate (Form A) exhibits a TGA thermogram that is substantially similar to FIG. 53. In other embodiments, the TGA thermogram of the Compound 1 Ethanesulfonate (Form A) exhibits a weight loss of 0.0 to 2.9% in the temperature range of 25 to 180° C.

Figure 54:
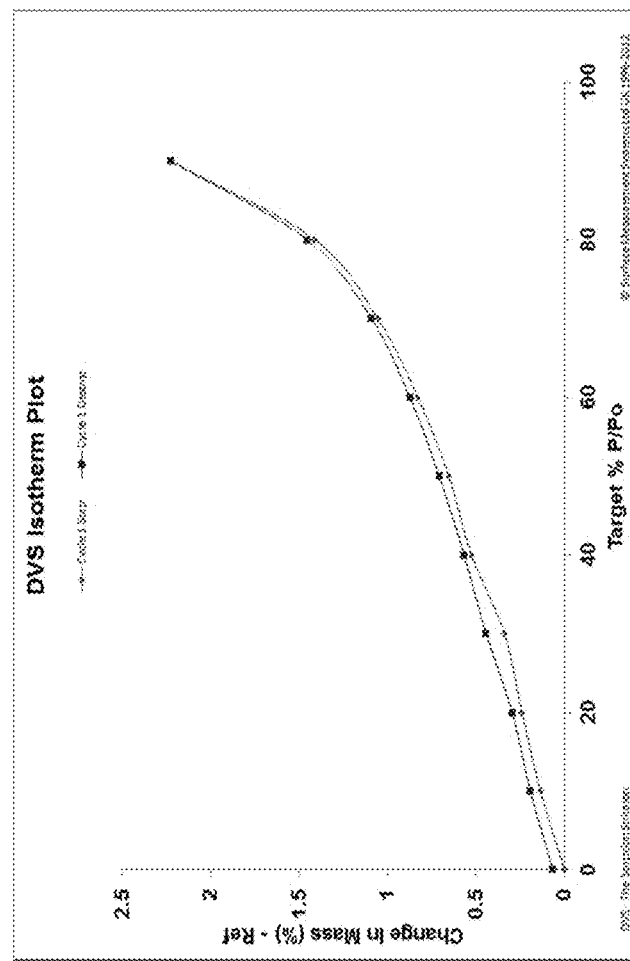
FIG. 54 shows a DVS isotherm plot for Compound 1 Ethanesulfonate (Form A).

In some embodiments, the Compound 1 Ethanesulfonate (Form A) exhibits a DVS isotherm plot that is substantially similar to FIG. 54. In other embodiments, the Compound 1 Ethanesulfonate (Form A) exhibits a gravimetric moisture sorption of about 1.4% (by weight) at 80% Relative Humidity.

Sulfate Salt

In some embodiments, the present disclosure provides a sulfate salt of Compound 1 ("Compound 1 Sulfate"). In some embodiments, the present disclosure provides a crystalline form of Compound 1 Sulfate.

In one embodiment, the present disclosure provides Compound 1 Sulfate (Form A). In some embodiments, the Compound 1 Sulfate (Form A) exhibits an XRPD comprising one or more peaks at about 3.6, 5.2, 7.8, 8.1, and 15.1 degrees two-theta with the margin of error of about ±0.5; about ±0.4; about ±0.3; about ±0.2; about ±0.1; about ±0.05; or less. In another embodiment, the XRPD of the Compound 1 Sulfate (Form A) further comprises one or more peaks at about 14.7, 17.4, 18.2, 18.4, and 19.7 degrees two-theta with the margin of error of about ±0.5; about ±0.4; about ±0.3; about ±0.2; about ±0.1; about ±0.05; or less. In some embodiments, the Compound 1 Sulfate (Form A) exhibits an XRPD comprising peaks shown in Table 25 below:

TABLE 25

XRPD Table of Compound 1 Sulfate (Form A)

| 2-Theta | Intensity % |
| --- | --- |
| 3.6 | 100 |
| 5.2 | 39 |
| 7.8 | 50 |
| 8.1 | 16.4 |
| 14.2 | 9 |
| 14.7 | 9.6 |
| 15.1 | 13.6 |
| 17.4 | 10.3 |
| 18.2 | 10.6 |
| 18.4 | 9.4 |
| 19.7 | 11.3 |
| 20.8 | 9 |
| 21.6 | 8.2 |
| 24.0 | 8.8 |

Figure 55:
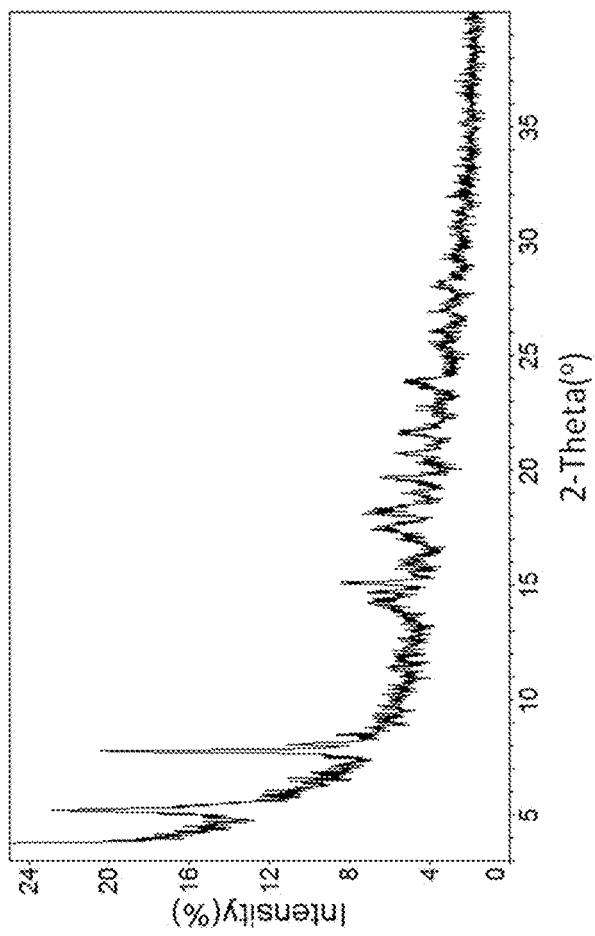
FIG. 55 shows an XRPD pattern of Compound 1 Sulfate (Form A).

In some embodiments, the Compound 1 Sulfate (Form A) exhibits an XRPD that is substantially similar to FIG. 55.

In some embodiments, the Compound 1 Sulfate (Form A) exhibits a DSC thermogram comprising a endotherm at about 167.1° C. with the error of margin of about ±2.5; about ±2.0; about ±1.5; about ±1.0; about ±0.5; or less. In some embodiments, the Compound 1 Sulfate (Form A) exhibits a DSC thermogram that is substantially similar to FIG. 56.

Figure 56:
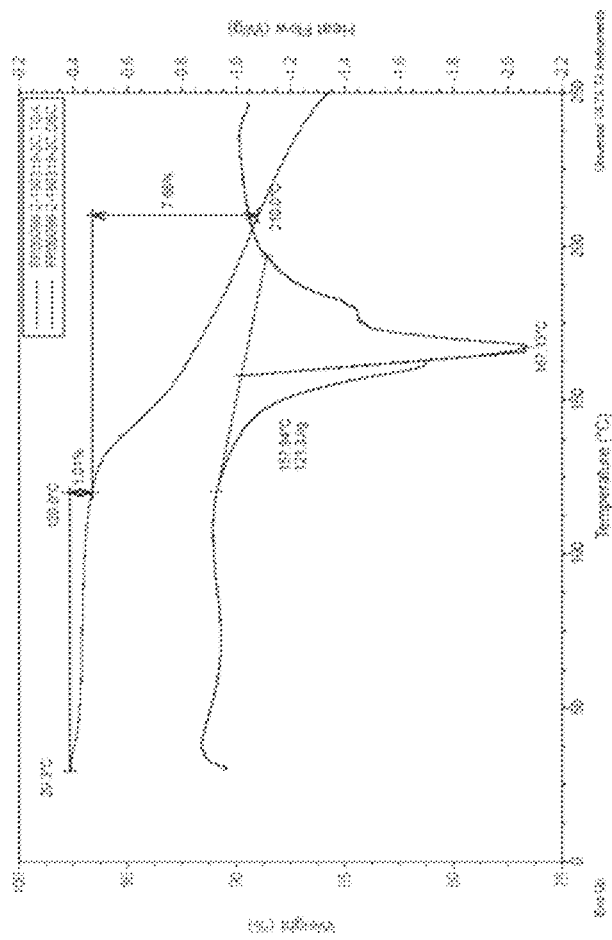
FIG. 56 shows a DSC thermogram and a TGA thermogram of Compound 1 Sulfate (Form A).

In some embodiments, the Compound 1 Sulfate (Form A) exhibits a TGA thermogram that is substantially similar to FIG. 56. In other embodiments, the TGA thermogram of the Compound 1 Sulfate (Form A) exhibits a weight loss of 0.0 to 1.0% in the temperature range of 25 to 120° C.

Figure 57:
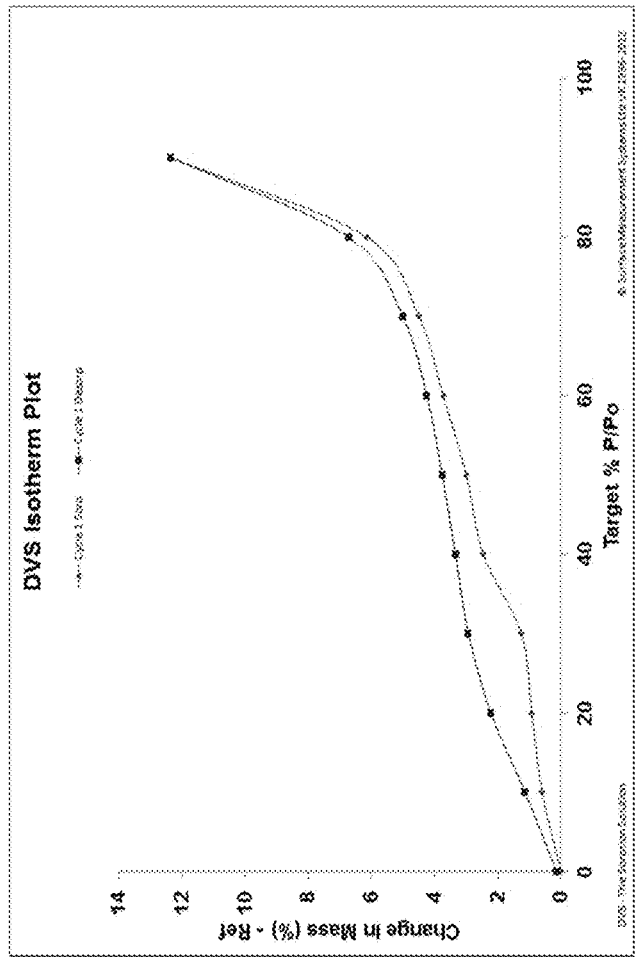
FIG. 57 shows a DVS isotherm plot for Compound 1 Sulfate (Form A).

In some embodiments, the Compound 1 Sulfate (Form A) exhibits a DVS isotherm plot that is substantially similar to FIG. 57. In other embodiments, the Compound 1 Sulfate (Form A) exhibits a gravimetric moisture sorption of about 6.2% (by weight) at 80% Relative Humidity.

Ascorbate Salt

In some embodiments, the present disclosure provides an ascorbate salt of Compound 1 ("Compound 1 Ascorbate"). In some embodiments, the present disclosure provides a crystalline form of Compound 1 Ascorbate.

In one embodiment, the present disclosure provides Compound 1 Ascorbate (Form A). In some embodiments, the Compound 1 Ascorbate (Form A) exhibits an XRPD comprising one or more peaks at about 3.6, 5.6, 16.6, 19.6, and 19.8 degrees two-theta with the margin of error of about ±0.5; about ±0.4; about ±0.3; about ±0.2; about ±0.1; about ±0.05; or less. In another embodiment, the XRPD of the Compound 1 Ascorbate (Form A) further comprises one or more peaks at about 11.5, 11.9, 21.6, 24.1, and 24.5 degrees two-theta with the margin of error of about ±0.5; about ±0.4; about ±0.3; about ±0.2; about ±0.1; about ±0.05; or less.

In some embodiments, the Compound 1 Ascorbate (Form A) exhibits an XRPD comprising peaks shown in Table 26 below:

TABLE 26

XRPD Table of Compound 1 Ascorbate (Form A)

| 2-Theta | Intensity % |
| --- | --- |
| 3.6 | 28.5 |
| 5.6 | 31.7 |
| 9.6 | 9.7 |
| 11.0 | 8.8 |
| 11.5 | 13.8 |
| 11.9 | 13.3 |
| 14.5 | 12.9 |
| 16.6 | 100 |
| 18.9 | 6.3 |
| 19.6 | 31.9 |
| 19.8 | 22.5 |
| 21.6 | 14.7 |
| 22.1 | 5.1 |
| 22.9 | 6 |
| 23.2 | 10.6 |
| 24.1 | 15.1 |
| 24.5 | 21.1 |

Figure 58:
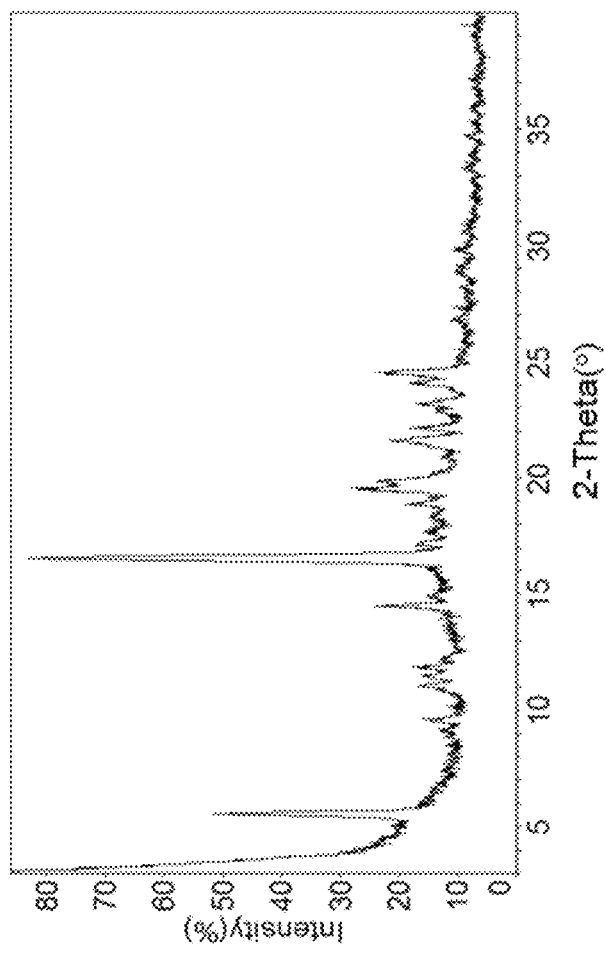
FIG. 58 shows an XRPD pattern of Compound 1 Ascorbate (Form A).

In some embodiments, the Compound 1 Ascorbate (Form A) exhibits an XRPD that is substantially similar to FIG. 58.

In some embodiments, the Compound 1 Ascorbate (Form A) exhibits a DSC thermogram comprising a endotherm at about 46.3° C. with the error of margin of about ±2.5; about ±2.0; about ±1.5; about ±1.0; about ±0.5; or less. In some embodiments, the Compound 1 Ascorbate (Form A) exhibits a DSC thermogram comprising a endotherm at about 124.3° C. with the error of margin of about ±2.5; about ±2.0; about ±1.5; about ±1.0; about ±0.5; or less. In some embodiments, the Compound 1 Ascorbate (Form A) exhibits a DSC thermogram that is substantially similar to FIG. 59.

Figure 59:
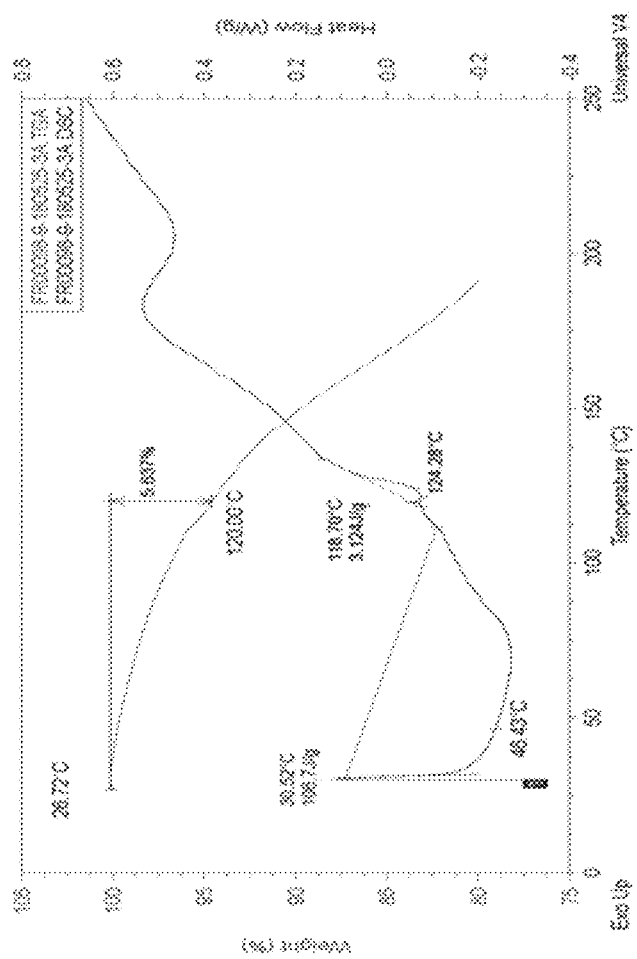
FIG. 59 shows a DSC thermogram and a TGA thermogram of Compound 1 Ascorbate (Form A).

In some embodiments, the Compound 1 Ascorbate (Form A) exhibits a TGA thermogram that is substantially similar to FIG. 59. In other embodiments, the TGA thermogram of the Compound 1 Ascorbate (Form A) exhibits a weight loss of 0.0 to 5.6% in the temperature range of 25 to 120° C.

Figure 60:
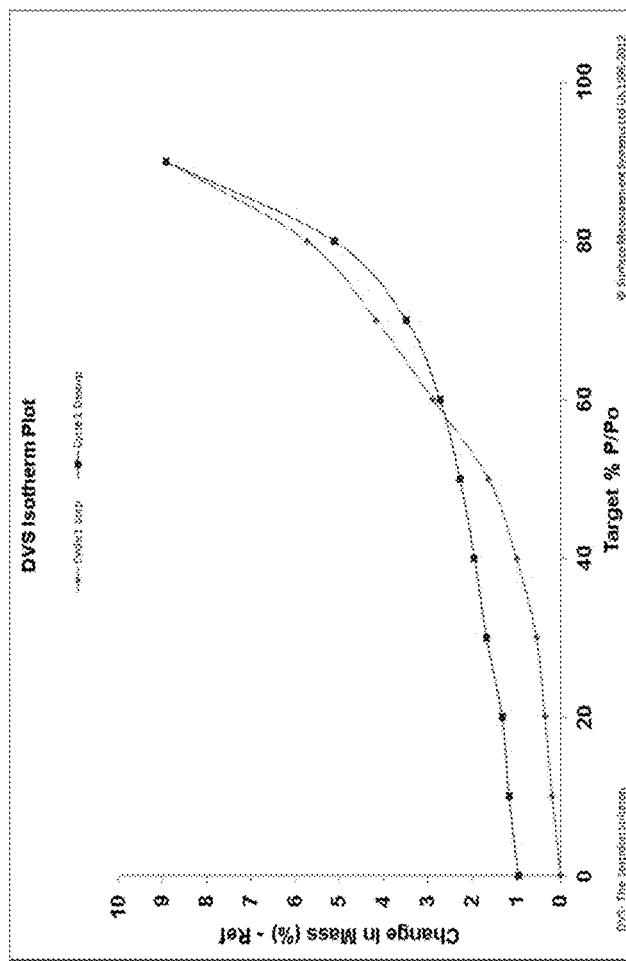
FIG. 60 shows a DVS isotherm plot for Compound 1 Ascorbate (Form A).

In some embodiments, the Compound 1 Ascorbate (Form A) exhibits a DVS isotherm plot that is substantially similar to FIG. 60. In other embodiments, the Compound 1 Ascorbate (Form A) exhibits a gravimetric moisture sorption of about 5.7% (by weight) at 80% Relative Humidity.

In one embodiment, the present disclosure provides Compound 1 Ascorbate (Form B). In some embodiments, the Compound 1 Ascorbate (Form B) exhibits an XRPD comprising one or more peaks at about 5.5, 16.6, 19.7, 20.1, and 28.3 degrees two-theta with the margin of error of about ±0.5; about ±0.4; about ±0.3; about ±0.2; about ±0.1; about ±0.05; or less. In another embodiment, the XRPD of the Compound 1 Ascorbate (Form B) further comprises one or more peaks at about 14.7 and 23.6 degrees two-theta with the margin of error of about ±0.5; about ±0.4; about ±0.3; about ±0.2; about ±0.1; about ±0.05; or less.

In some embodiments, the Compound 1 Ascorbate (Form B) exhibits an XRPD comprising peaks shown in Table 27 below:

TABLE 27

XRPD Table of Compound 1 Ascorbate (Form B)

| 2-Theta | Intensity % |
| --- | --- |
| 5.5 | 74.9 |
| 14.7 | 21.2 |
| 16.6 | 100 |
| 19.7 | 29.6 |
| 20.1 | 38 |
| 23.6 | 22.9 |
| 28.3 | 39.7 |

Figure 61:
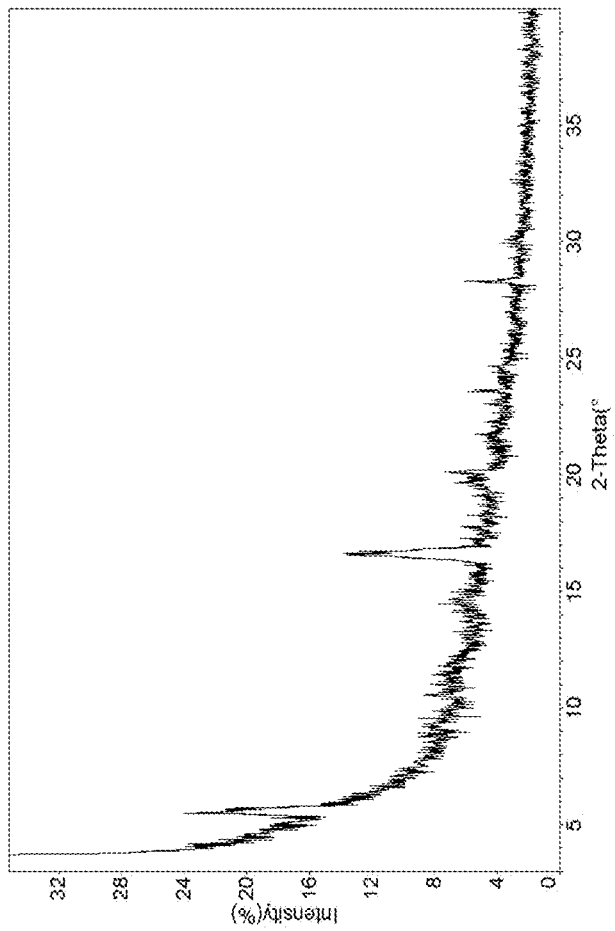
FIG. 61 shows an XRPD pattern of Compound 1 Ascorbate (Form B).

In some embodiments, the Compound 1 Ascorbate (Form B) exhibits an XRPD that is substantially similar to FIG. 61.

Napadisylate Salt

In some embodiments, the present disclosure provides a napadisylate salt of Compound 1 ("Compound 1 Napadisylate"). In some embodiments, the present disclosure provides a crystalline form of Compound 1 Napadisylate.

In one embodiment, the present disclosure provides Compound 1 Napadisylate (Form A). In some embodiments, the Compound 1 Napadisylate (Form A) exhibits an XRPD comprising one or more peaks at about 3.3, 9.4, 14.2, 16.4, and 17.8 degrees two-theta with the margin of error of about ±0.5; about ±0.4; about ±0.3; about ±0.2; about ±0.1; about ±0.05; or less. In another embodiment, the XRPD of the Compound 1 Napadisylate (Form A) further comprises one or more peaks at about 9.7, 17.3, 20.3, 24.4, and 26.1 degrees two-theta with the margin of error of about ±0.5; about ±0.4; about ±0.3; about ±0.2; about ±0.1; about ±0.05; or less. In some embodiments, the Compound 1 Napadisylate (Form A) exhibits an XRPD comprising peaks shown in Table 28 below:

TABLE 28

XRPD Table of Compound 1 Napadisylate (Form A)

| 2-Theta | Intensity % |
| --- | --- |
| 3.3 | 70.6 |
| 3.6 | 18.5 |
| 4.7 | 15.3 |
| 7.1 | 7.7 |
| 9.4 | 38.1 |
| 9.7 | 35.7 |
| 14.2 | 52 |
| 16.4 | 100 |
| 17.3 | 23.3 |
| 17.8 | 77.6 |
| 19.6 | 22.9 |
| 20.3 | 24.5 |

TABLE 28-continued

XRPD Table of Compound 1 Napadisylate (Form A)

| 2-Theta | Intensity % |
| --- | --- |
| 20.8 | 19.9 |
| 22.1 | 12.6 |
| 22.6 | 6.6 |
| 23.0 | 17.3 |
| 24.4 | 23.7 |
| 25.5 | 6.2 |
| 26.1 | 37.4 |
| 27.3 | 19.7 |
| 28.3 | 7.6 |

Figure 62:
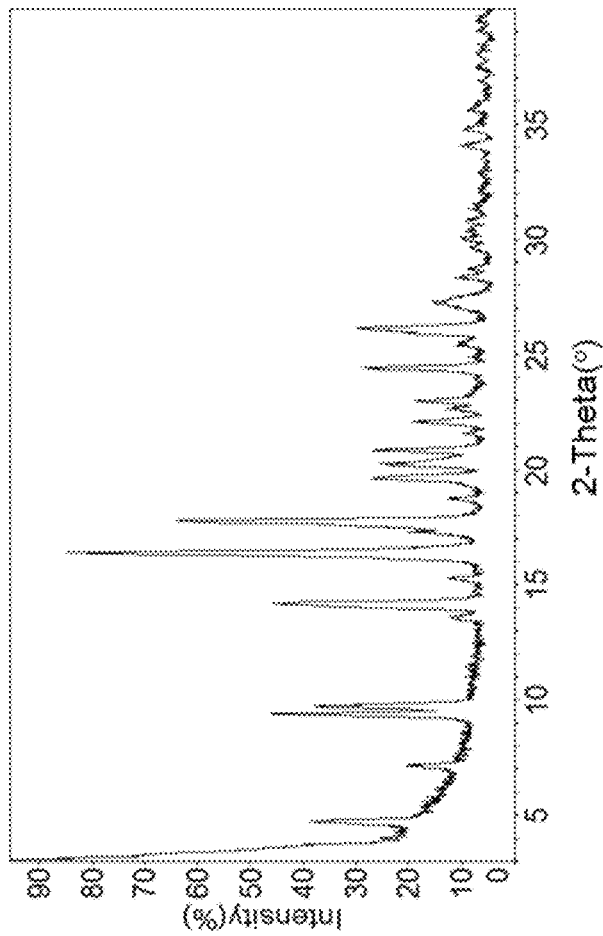
FIG. 62 shows an XRPD pattern of Compound 1 Napadisylate (Form A).

In some embodiments, the Compound 1 Napadisylate (Form A) exhibits an XRPD that is substantially similar to FIG. 62.

In some embodiments, the Compound 1 Napadisylate (Form A) exhibits a DSC thermogram comprising a endotherm at about 41.7° C. with the error of margin of about ±2.5; about ±2.0; about ±1.5; about ±1.0; about ±0.5; or less. In some embodiments, the Compound 1 Napadisylate (Form A) exhibits a DSC thermogram that is substantially similar to FIG. 63.

Figure 63:
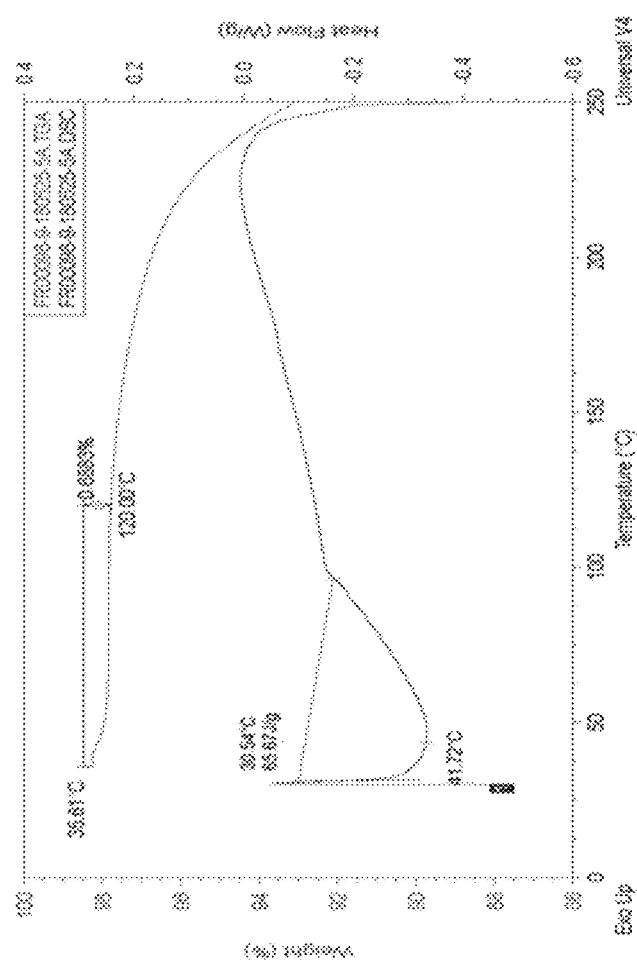
FIG. 63 shows a DSC thermogram and a TGA thermogram of Compound 1 Napadisylate (Form A).

In some embodiments, the Compound 1 Napadisylate (Form A) exhibits a TGA thermogram that is substantially similar to FIG. 63. In other embodiments, the TGA thermogram of the Compound 1 Napadisylate (Form A) exhibits a weight loss of 0.0 to 0.7% in the temperature range of 25 to 120° C.

Figure 64:
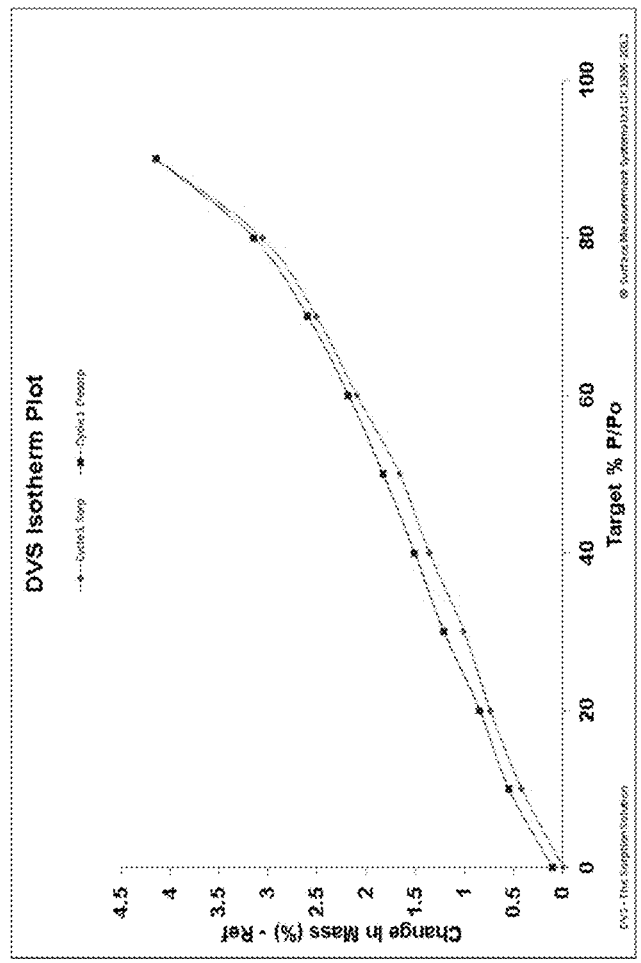
FIG. 64 shows a DVS isotherm plot for Compound 1 Napadisylate (Form A).

In some embodiments, the Compound 1 Napadisylate (Form A) exhibits a DVS isotherm plot that is substantially similar to FIG. 64. In other embodiments, the Compound 1 Napadisylate exhibits a gravimetric moisture sorption of about 3.1% (by weight) at 80% Relative Humidity.

In some embodiments, the present disclosure provides Compound 1 Napadisylate (Form B). In some embodiments, the Compound 1 Napadisylate (Form B) exhibits an XRPD comprising one or more peaks at about 6.0, 14.2, 18.1, 19.0, and 20.3 degrees two-theta with the margin of error of about ±0.5; about ±0.4; about ±0.3; about ±0.2; about ±0.1; about ±0.05; or less. In another embodiment, the XRPD of the Compound 1 Napadisylate (Form B) further comprises one or more peaks at about 12.0, 16.9, 18.4, 19.4, and 24.1 degrees two-theta with the margin of error of about ±0.5; about ±0.4; about ±0.3; about ±0.2; about ±0.1; about ±0.05; or less.

In some embodiments, the Compound 1 Napadisylate (Form B) exhibits an XRPD comprising peaks shown in Table 29 below:

TABLE 29

XRPD Table of Compound 1 Napadisylate (Form B)

| 2-Theta | Intensity % |
| --- | --- |
| 6.0 | 100 |
| 12.0 | 18.2 |
| 13.3 | 14.8 |
| 13.5 | 12.4 |
| 14.2 | 33.8 |
| 16.9 | 23.6 |
| 18.1 | 51.1 |
| 18.4 | 22.9 |
| 19.0 | 26.3 |
| 19.4 | 17 |
| 20.3 | 39.9 |
| 21.7 | 10.5 |

TABLE 29-continued

XRPD Table of Compound 1 Napadisylate (Form B)

| 2-Theta | Intensity % |
| --- | --- |
| 24.1 | 22.4 |
| 25.8 | 11.2 |

Figure 65:
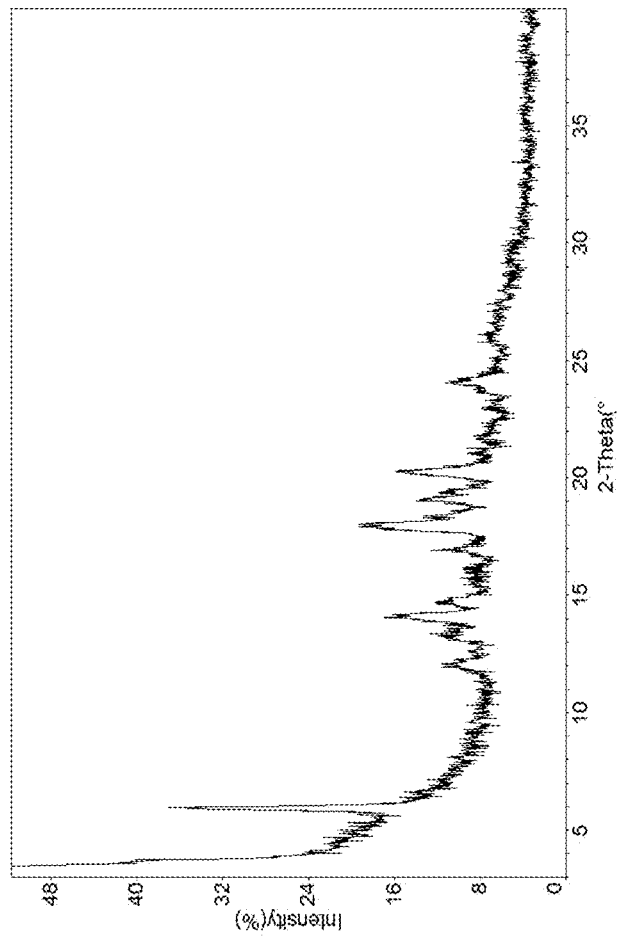
FIG. 65 shows an XRPD pattern of Compound 1 Napadisylate (Form B).

In some embodiments, the Compound 1 Napadisylate (Form B) exhibits an XRPD that is substantially similar to FIG. 65.

Malonate Salt

In some embodiments, the present disclosure provides a malonate salt of Compound 1 ("Compound 1 Malonate"). In some embodiments, the present disclosure provides a crystalline form of Compound 1 Malonate.

In one embodiment, the present disclosure provides Compound 1 Malonate (Form A). In some embodiments, the Compound 1 Malonate (Form A) exhibits an XRPD comprising one or more peaks at about 15.1, 18.0, 18.8, 23.4, and 23.8 degrees two-theta with the margin of error of about ±0.5; about ±0.4; about ±0.3; about ±0.2; about ±0.1; about ±0.05; or less. In another embodiment, the XRPD of the Compound 1 Malonate (Form A) further comprises one or more peaks at about 3.6, 13.8, 15.6, 21.4, and 27.6 degrees two-theta with the margin of error of about ±0.5; about ±0.4; about ±0.3; about ±0.2; about ±0.1; about ±0.05; or less.

In some embodiments, the Compound 1 Malonate (Form A) exhibits an XRPD comprising peaks shown in Table 30 below:

TABLE 30

XRPD Table of Compound 1 Malonate (Form A)

| 2-Theta | Intensity % |
| --- | --- |
| 3.6 | 26.7 |
| 10.9 | 13.6 |
| 11.7 | 6.7 |
| 12.1 | 17.6 |
| 13.8 | 25 |
| 14.6 | 15 |
| 15.1 | 60.1 |
| 15.6 | 29.2 |
| 16.7 | 7.4 |
| 18.0 | 100 |
| 18.8 | 85.6 |
| 20.6 | 18.3 |
| 21.4 | 24.8 |
| 21.7 | 24.1 |
| 23.1 | 17.8 |
| 23.4 | 43.3 |
| 23.8 | 56.3 |
| 25.0 | 8.2 |
| 25.6 | 8.3 |
| 27.6 | 37.3 |
| 29.4 | 17.5 |

Figure 66:
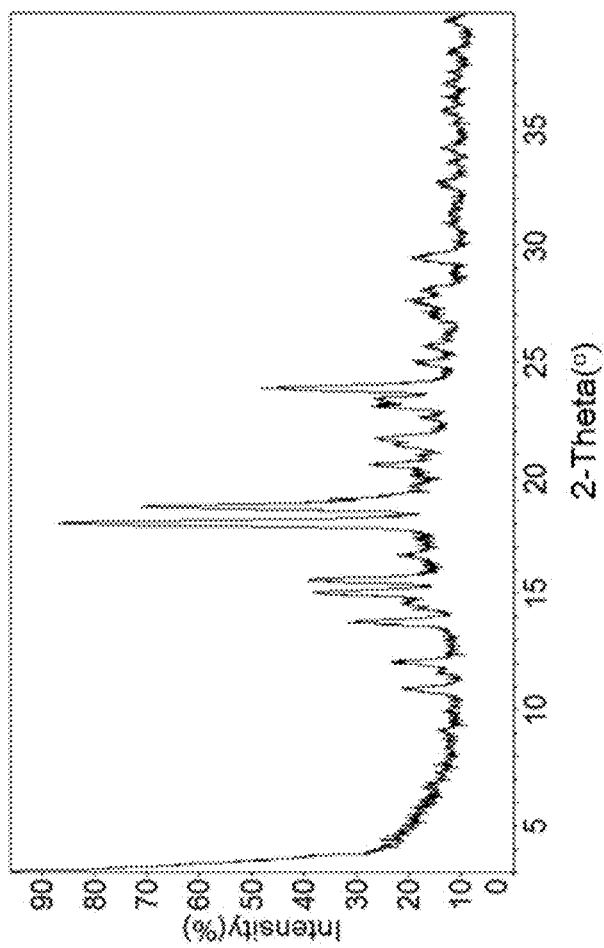
FIG. 66 shows an XRPD pattern of Compound 1 Malonate (Form A).

In some embodiments, the Compound 1 Malonate (Form A) exhibits an XRPD that is substantially similar to FIG. 66.

In some embodiments, the Compound 1 Malonate (Form A) exhibits a DSC thermogram comprising a endotherm at about 36.9° C. with the error of margin of about ±2.5; about ±2.0; about ±1.5; about ±1.0; about ±0.5; or less. In some embodiments, the Compound 1 Malonate (Form A) exhibits a DSC thermogram comprising a endotherm at about 124.6° C. with the error of margin of about ±2.5; about ±2.0; about ±1.5; about ±1.0; about ±0.5; or less. In some embodiments, the Compound 1 Malonate (Form A) exhibits a DSC thermogram that is substantially similar to FIG. 67.

Figure 67:
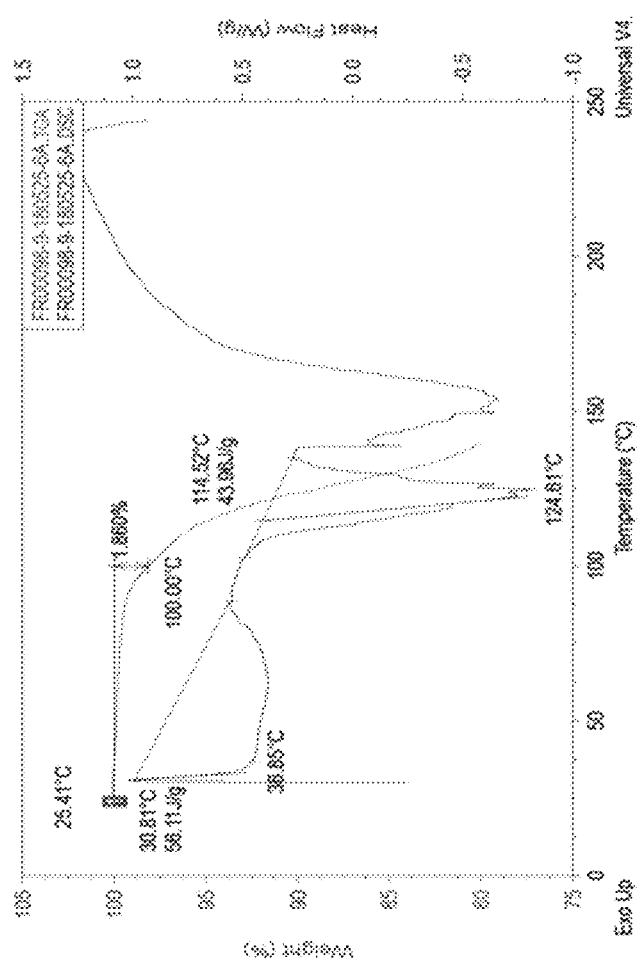
FIG. 67 shows a DSC thermogram and a TGA thermogram of Compound 1 Malonate (Form A).

In some embodiments, the Compound 1 Malonate (Form A) exhibits a TGA thermogram that is substantially similar to FIG. 67. In other embodiments, the TGA thermogram of the Compound 1 Malonate (Form A) exhibits a weight loss of 0.0 to 1.9% in the temperature range of 25 to 120° C.

Besylate Salt

In some embodiments, the present disclosure provides a besylate salt of Compound 1 ("Compound 1 Besylate"). In some embodiments, the present disclosure provides a crystalline form of Compound 1 Besylate.

In one embodiment, the present disclosure provides Compound 1 Besylate (Form A). In some embodiments, the Compound 1 Besylate (Form A) exhibits an XRPD comprising one or more peaks at about 14.7, 15.8, 22.1, 23.2, and 26.6 degrees two-theta with the margin of error of about ±0.5; about ±0.4; about ±0.3; about ±0.2; about ±0.1; about ±0.05; or less. In another embodiment, the XRPD of the Compound 1 Besylate (Form A) further comprises one or more peaks at about 3.7, 16.2, 17.8, 19.5, and 30.4 degrees two-theta with the margin of error of about ±0.5; about ±0.4; about ±0.3; about ±0.2; about ±0.1; about ±0.05; or less.

In some embodiments, the Compound 1 Besylate (Form A) exhibits an XRPD comprising peaks shown in Table 31 below:

TABLE 31

XRPD Table of Compound 1 Besylate (Form A)

| 2-Theta | Intensity % |
| --- | --- |
| 3.3 | 21.9 |
| 3.7 | 7 |
| 7.4 | 100 |
| 14.7 | 41.9 |
| 15.8 | 3.5 |
| 16.2 | 19.3 |
| 17.2 | 5.7 |
| 17.8 | 9.1 |
| 19.5 | 9.3 |
| 22.1 | 21.4 |
| 23.2 | 20.6 |
| 26.6 | 3.8 |
| 29.6 | 3.6 |
| 30.4 | 7.3 |

Figure 68:
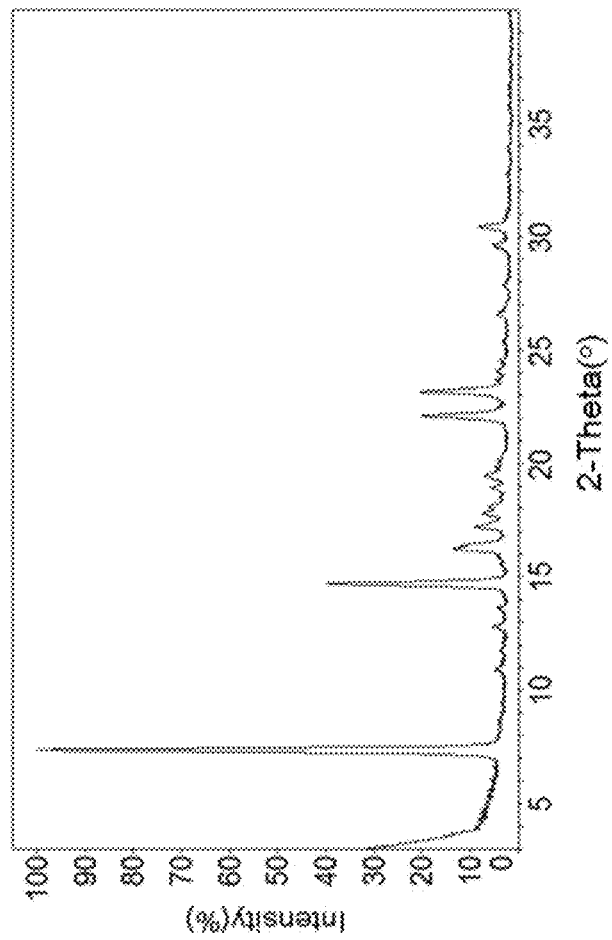
FIG. 68 shows an XRPD pattern of Compound 1 Besylate (Form A).

In some embodiments, the Compound 1 Besylate (Form A) exhibits an XRPD that is substantially similar to FIG. 68.

In some embodiments, the Compound 1 Besylate (Form A) exhibits a DSC thermogram comprising a sharp endotherm at about 194.2° C. with the error of margin of about ±2.5; about ±2.0; about ±1.5; about ±1.0; about ±0.5; or less. In some embodiments, the Compound 1 Besylate (Form A) exhibits a DSC thermogram that is substantially similar to FIG. 69.

Figure 69:
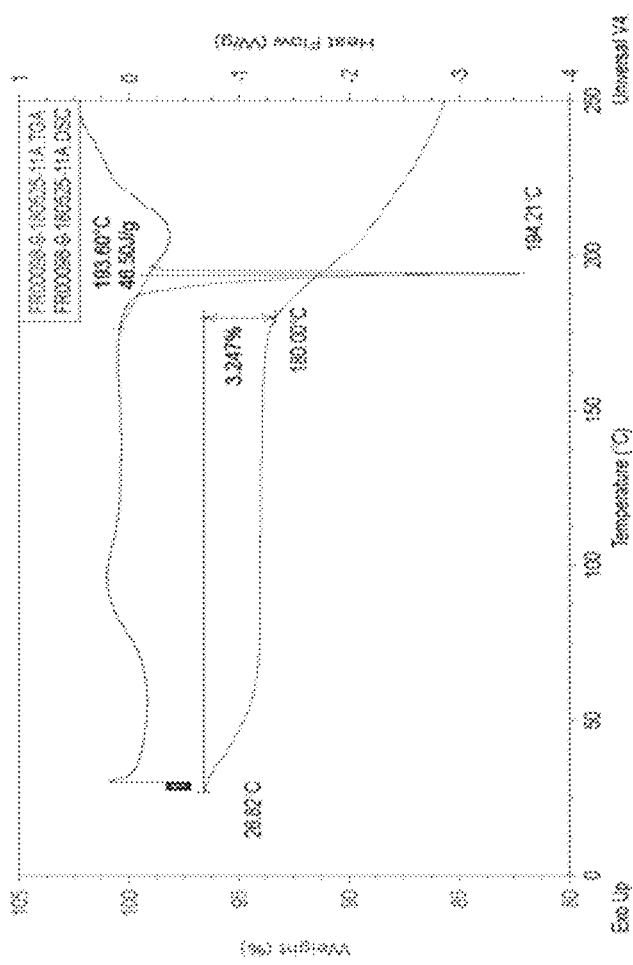
FIG. 69 shows a DSC thermogram and a TGA thermogram of Compound 1 Besylate (Form A).

In some embodiments, the Compound 1 Besylate (Form A) exhibits a TGA thermogram that is substantially similar to FIG. 69. In other embodiments, the TGA thermogram of the Compound 1 Besylate (Form A) exhibits a weight loss of 0.0 to 3.3% in the temperature range of 25 to 120° C.

Figure 70:
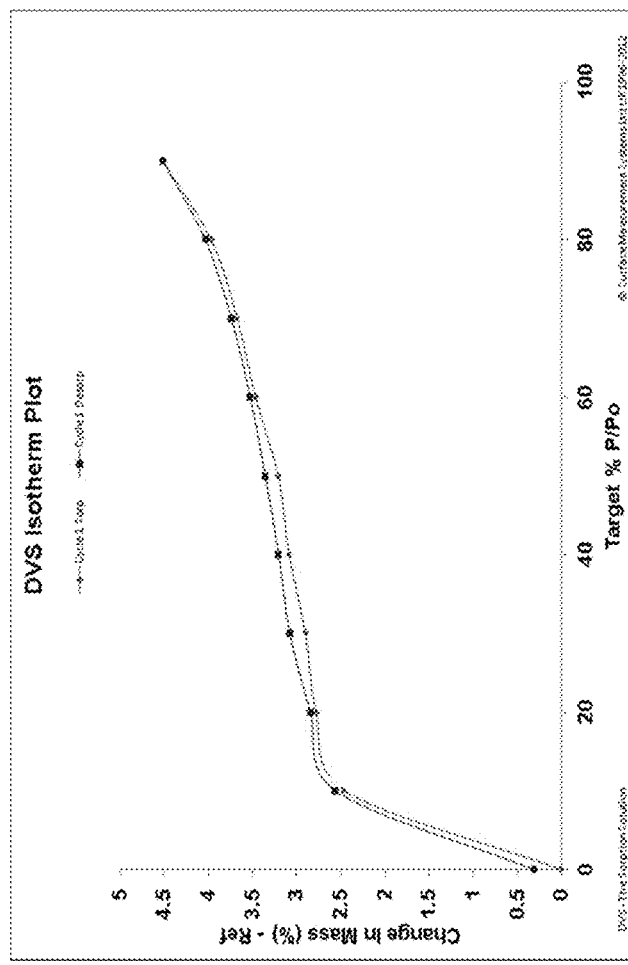
FIG. 70 shows a DVS isotherm plot for Compound 1 Besylate (Form A).

In some embodiments, the Compound 1 Besylate (Form A) exhibits a DVS isotherm plot that is substantially similar to FIG. 70. In other embodiments, the Compound 1 Besylate (Form A) exhibits a gravimetric moisture sorption of about 4.0% (by weight) at 80% Relative Humidity.

In one embodiment, the present disclosure provides Compound 1 Besylate (Form B).

In some embodiments, the Compound 1 Besylate (Form B) exhibits an XRPD comprising one or more peaks at about 7.3, 14.7, 22.1, 23.2, and 29.6 degrees two-theta with the margin of error of about ±0.5; about ±0.4; about ±0.3; about ±0.2; about ±0.1; about ±0.05; or less. In another embodiment, the XRPD of the Compound 1 Besylate (Form B) further comprises one or more peaks at about 7.9, 16.2, 16.4, 17.2, and 30.4 degrees two-theta with the margin of error of about ±0.5; about ±0.4; about ±0.3; about ±0.2; about ±0.1; about ±0.05; or less.

In some embodiments, the Compound 1 Besylate (Form B) exhibits an XRPD comprising peaks shown in Table 32 below:

TABLE 32

XRPD Table of Compound 1 Besylate (Form B)

| 2-Theta | Intensity % |
|---|---|
| 7.3 | 100 |
| 7.9 | 0.5 |
| 14.7 | 51.7 |
| 16.2 | 3.4 |
| 16.4 | 3.0 |
| 17.2 | 2.7 |
| 22.1 | 24.5 |
| 23.2 | 7.7 |
| 29.6 | 4.4 |
| 30.4 | 2.7 |

Figure 71:
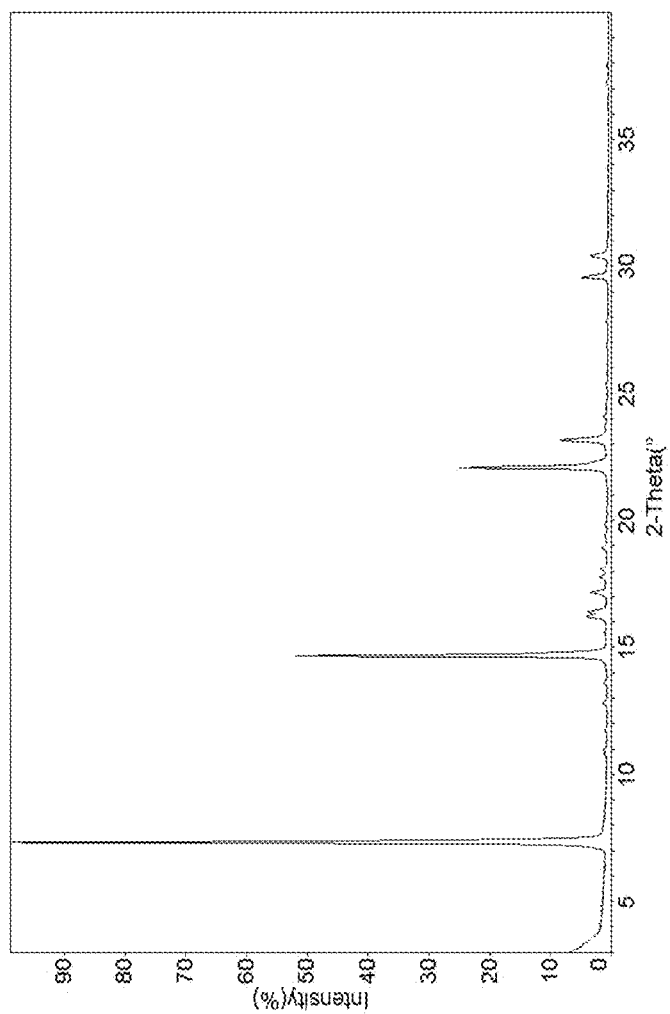
FIG. 71 shows an XRPD pattern of Compound 1 Besylate (Form B).

In some embodiments, the Compound 1 Besylate (Form B) exhibits an XRPD that is substantially similar to FIG. 71.

Isethionate Salt

In some embodiments, the present disclosure provides an isethionate salt of Compound 1 ("Compound 1 Isethionate"). In some embodiments, the present disclosure provides a crystalline form of Compound 1 Isethionate.

In one embodiment, the present disclosure provides Compound 1 Isethionate (Form A).

In some embodiments, the Compound 1 Isethionate (Form A) exhibits an XRPD comprising one or more peaks at about 5.6, 16.7, 16.9, 18, and 20.9 degrees two-theta with the margin of error of about ±0.5; about ±0.4; about ±0.3; about ±0.2; about ±0.1; about ±0.05; or less. In another embodiment, the XRPD of the Compound 1 Isethionate (Form A) further comprises one or more peaks at about 3.7, 15.7, 16.2, 20.7, and 25.1 degrees two-theta with the margin of error of about ±0.5; about ±0.4; about ±0.3; about ±0.2; about ±0.1; about ±0.05; or less.

In some embodiments, the Compound 1 Isethionate (Form A) exhibits an XRPD comprising peaks shown in Table 33 below:

TABLE 33

XRPD Table of Compound 1 Isethionate (Form A)

| 2-Theta | Intensity % |
|---|---|
| 3.7 | 23.7 |
| 5.6 | 26.4 |
| 9.6 | 5 |
| 10.0 | 10.8 |
| 11.2 | 6.8 |
| 13.1 | 17 |
| 14.1 | 9.8 |
| 14.6 | 7.7 |
| 14.7 | 7 |
| 15.7 | 24.8 |
| 16.2 | 18.5 |
| 16.7 | 100 |
| 16.9 | 46.9 |
| 18.1 | 26.1 |
| 19.2 | 10.1 |

TABLE 33-continued

XRPD Table of Compound 1 Isethionate (Form A)

| 2-Theta | Intensity % |
|---|---|
| 19.5 | 6.6 |
| 20.1 | 7.1 |
| 20.3 | 12.5 |
| 20.7 | 19.2 |
| 20.9 | 45.1 |
| 22.4 | 7.2 |
| 25.1 | 23.1 |
| 25.6 | 8.7 |
| 26.1 | 7.9 |
| 27.7 | 12.8 |
| 28.0 | 7.5 |

Figure 72:
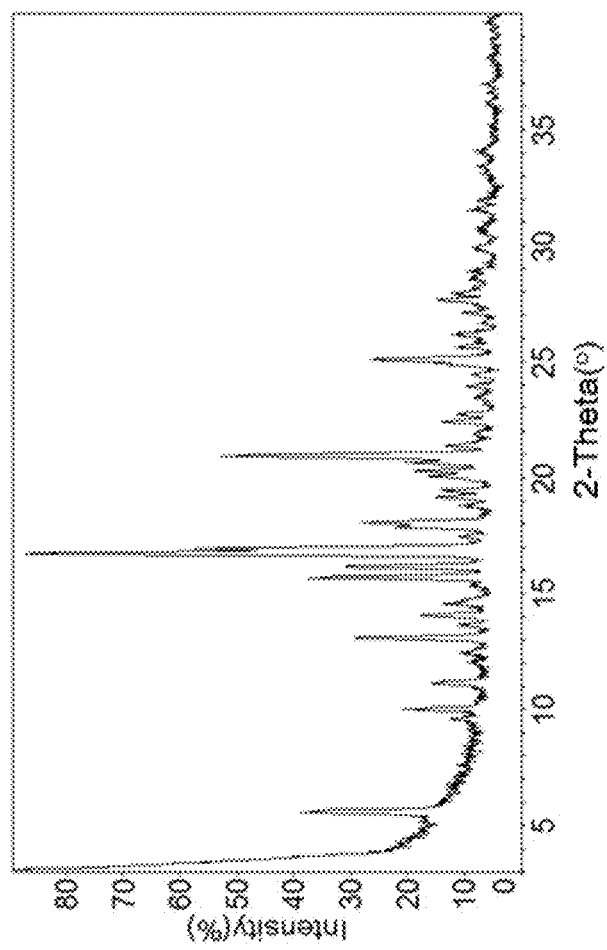
FIG. 72 shows an XRPD pattern of Compound 1 Isethionate (Form A).

In some embodiments, the Compound 1 Isethionate (Form A) exhibits an XRPD that is substantially similar to FIG. 72.

In some embodiments, the Compound 1 Isethionate (Form A) exhibits a DSC thermogram comprising a sharp endotherm at about 153.3° C. with the error of margin of about ±2.5; about ±2.0; about ±1.5; about ±1.0; about ±0.5; or less. In some embodiments, the Compound 1 Isethionate (Form A) exhibits a DSC thermogram that is substantially similar to FIG. 73.

Figure 73:
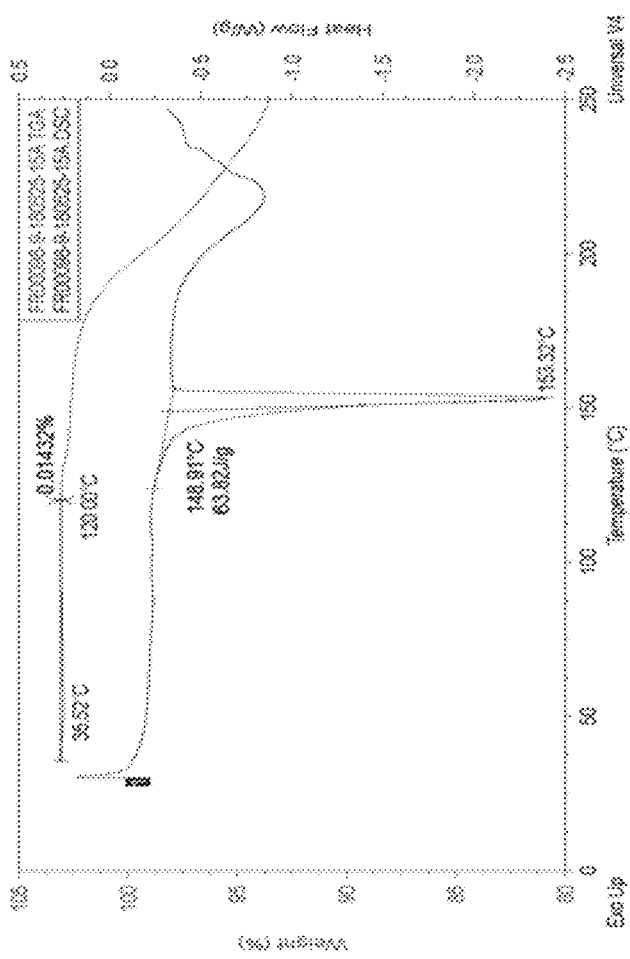
FIG. 73 shows a DSC thermogram and a TGA thermogram of Compound 1 Isethionate (Form A).

In some embodiments, the Compound 1 Isethionate (Form A) exhibits a TGA thermogram that is substantially similar to FIG. 73. In other embodiments, the TGA thermogram of the Compound 1 Isethionate (Form A) exhibits a weight loss of 0.0 to 0.0% in the temperature range of 25 to 120° C.

Figure 74:
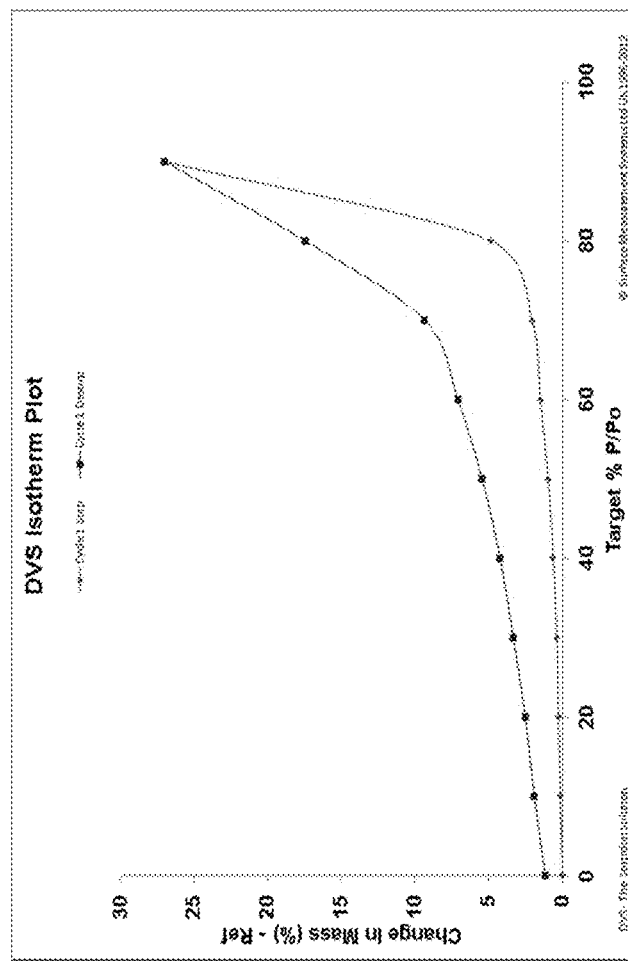
FIG. 74 shows a DVS isotherm plot for Compound 1 Isethionate (Form A).

In some embodiments, the Compound 1 Isethionate (Form A) exhibits a DVS isotherm plot that is substantially similar to FIG. 74. In other embodiments, the Compound 1 Isethionate (Form A) exhibits a gravimetric moisture sorption of about 4.9% (by weight) at 80% Relative Humidity.

In one embodiment, the present disclosure provides Compound 1 Isethionate (Form B). In some embodiments, the Compound 1 Isethionate (Form B) exhibits an XRPD comprising one or more peaks at about 14.5, 15.8, 17.9, 18.1, and 18.6 degrees two-theta with the margin of error of about ±0.5; about ±0.4; about ±0.3; about ±0.2; about ±0.1; about ±0.05; or less. In another embodiment, the XRPD of the Compound 1 Isethionate (Form B) further comprises one or more peaks at about 11.4, 13.1, 14.2, 15.0, and 17.0 degrees two-theta with the margin of error of about ±0.5; about ±0.4; about ±0.3; about ±0.2; about ±0.1; about ±0.05; or less.

In some embodiments, the Compound 1 Isethionate (Form B) exhibits an XRPD comprising peaks shown in Table 34 below:

TABLE 34

XRPD Table of Compound 1 Isethionate (Form B)

| 2-Theta | Intensity % |
|---|---|
| 8.5 | 15.7 |
| 11.4 | 27.1 |
| 13.1 | 29.2 |
| 14.2 | 26.5 |
| 14.5 | 71.4 |
| 15.0 | 23.4 |
| 15.8 | 30.5 |
| 17.0 | 24.0 |
| 17.9 | 100 |
| 18.1 | 54.8 |
| 18.6 | 75.1 |
| 19.5 | 14.8 |

TABLE 34-continued

XRPD Table of Compound 1 Isethionate (Form B)

| 2-Theta | Intensity % |
|---|---|
| 22.1 | 14.8 |
| 24.2 | 16.9 |
| 27.2 | 15.4 |
| 27.5 | 10.5 |

Figure 75:
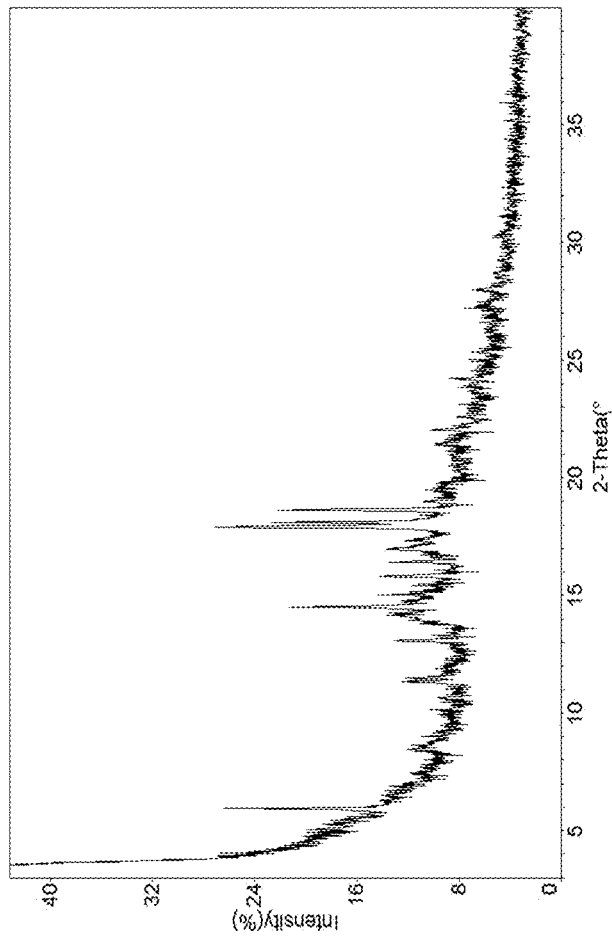
FIG. 75 shows an XRPD pattern of Compound 1 Isethionate (Form B).

In some embodiments, the Compound 1 Isethionate (Form B) exhibits an XRPD that is substantially similar to FIG. 75.

Gentisate Salt

In some embodiments, the present disclosure provides a gentisate salt of Compound 1 ("Compound 1 Gentisate"). In some embodiments, the present disclosure provides a crystalline form of Compound 1 Gentisate.

In one embodiment, the present disclosure provides Compound 1 Gentisate (Form A). In some embodiments, the Compound 1 Gentisate (Form A) exhibits an XRPD comprising one or more peaks at about 3.4, 3.6, 7.0, 14.6, and 21.4 degrees two-theta with the margin of error of about ±0.5; about ±0.4; about ±0.3; about ±0.2; about ±0.1; about ±0.05; or less. In another embodiment, the XRPD of the Compound 1 Gentisate (Form A) further comprises one or more peaks at about 16.0, 18.0, 18.5, 19.5, and 21.1 degrees two-theta with the margin of error of about ±0.5; about ±0.4; about ±0.3; about ±0.2; about ±0.1; about ±0.05; or less.

In some embodiments, the Compound 1 Gentisate (Form A) exhibits an XRPD comprising peaks shown in Table 35 below:

TABLE 35

XRPD Table of Compound 1 Gentisate (Form A)

| 2-Theta | Intensity % |
|---|---|
| 3.4 | 100 |
| 3.6 | 54.6 |
| 5.3 | 10.1 |
| 7.0 | 88.3 |
| 7.6 | 5.8 |
| 8.1 | 12.3 |
| 9.0 | 8.2 |
| 10.9 | 20 |
| 14.0 | 18.5 |
| 14.6 | 42.3 |
| 16.0 | 30.1 |
| 16.3 | 25.7 |
| 18.0 | 40.3 |
| 18.5 | 28.1 |
| 19.5 | 31.7 |
| 19.8 | 11.8 |
| 21.1 | 39.1 |
| 21.4 | 48 |
| 21.8 | 6.8 |
| 22.8 | 22.4 |
| 23.3 | 7.8 |

Figure 76:
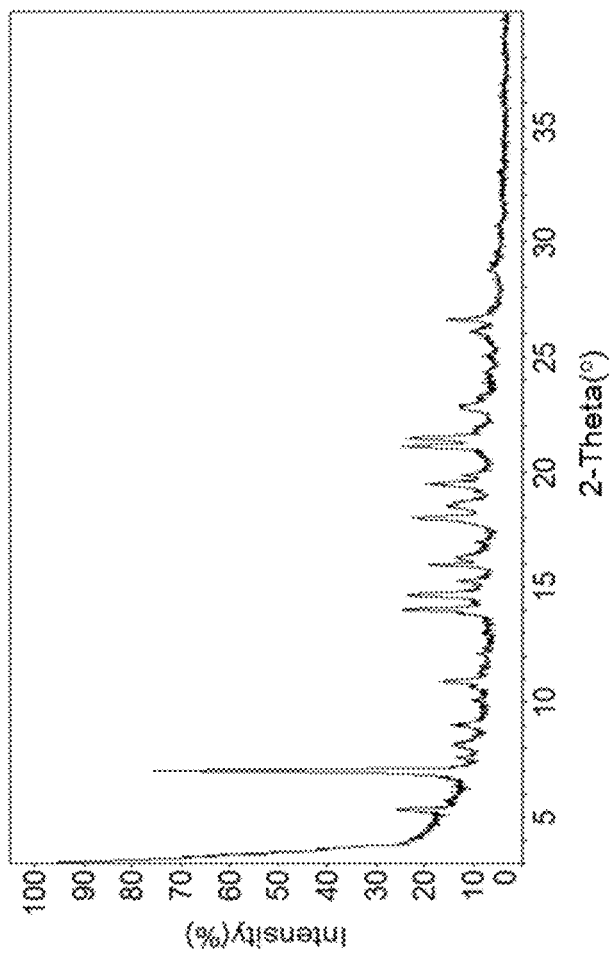
FIG. 76 shows an XRPD pattern of Compound 1 Gentisate (Form A).

In some embodiments, the Compound 1 Gentisate (Form A) exhibits an XRPD that is substantially similar to FIG. 76.

In some embodiments, the Compound 1 Gentisate (Form A) exhibits a DSC thermogram comprising a sharp endotherm at about 117.7° C. with the error of margin of about ±2.5; about ±2.0; about ±1.5; about ±1.0; about ±0.5; or less. In some embodiments, the Compound 1 Gentisate (Form A) exhibits a DSC thermogram that is substantially similar to FIG. 77.

Figure 77:
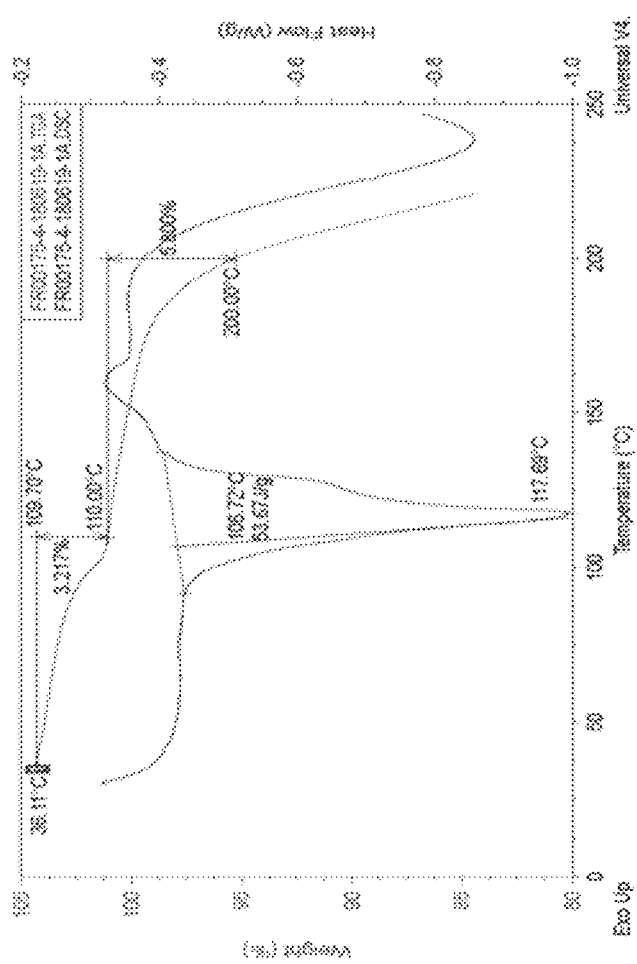
FIG. 77 shows a DSC thermogram and a TGA thermogram of Compound 1 Gentisate (Form A).

In some embodiments, the Compound 1 Gentisate (Form A) exhibits a TGA thermogram that is substantially similar to FIG. 77. In other embodiments, the TGA thermogram of the Compound 1 Gentisate (Form A) exhibits a weight loss of 0.0 to 9.0% in the temperature range of 25 to 200° C.

Figure 78:
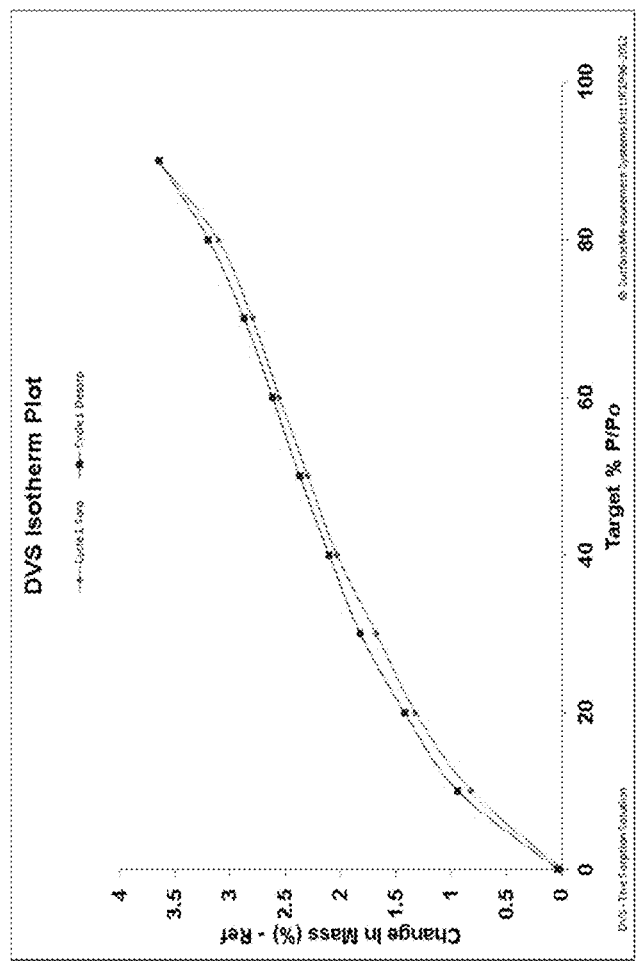
FIG. 78 shows a DVS isotherm plot for Compound 1 Gentisate (Form A).

In some embodiments, the Compound 1 Gentisate (Form A) exhibits a DVS isotherm plot that is substantially similar to FIG. 78. In other embodiments, the Compound 1 Gentisate (Form A) exhibits a gravimetric moisture sorption of about 3.1% (by weight) at 80% Relative Humidity.

In one embodiment, the present disclosure provides Compound 1 Gentisate (Form B). In some embodiments, the Compound 1 Gentisate (Form B) exhibits an XRPD comprising one or more peaks at about 5.5, 10.9, 16.4, 21.9, and 22.8 degrees two-theta with the margin of error of about ±0.5; about ±0.4; about ±0.3; about ±0.2; about ±0.1; about ±0.05; or less. In another embodiment, the XRPD of the Compound 1 Gentisate (Form B) further comprises one or more peaks at about 9.2, 13.0, 17.2, 18.7, and 27.8 degrees two-theta with the margin of error of about ±0.5; about ±0.4; about ±0.3; about ±0.2; about ±0.1; about ±0.05; or less.

In some embodiments, the Compound 1 Gentisate (Form B) exhibits an XRPD comprising peaks shown in Table 36 below:

TABLE 36

XRPD Table of Compound 1 Gentisate (Form B)

| 2-Theta | Intensity % |
|---|---|
| 5.5 | 100 |
| 9.2 | 12.5 |
| 10.9 | 25.5 |
| 11.6 | 2.7 |
| 13.0 | 5.4 |
| 14.8 | 3.1 |
| 16.4 | 70.6 |
| 17.2 | 11.2 |
| 18.3 | 5.2 |
| 18.7 | 11.2 |
| 20.5 | 1.7 |
| 21.9 | 12.8 |
| 22.8 | 20.9 |
| 23.2 | 4.5 |
| 23.8 | 2.6 |
| 26.0 | 1.5 |
| 26.2 | 2.1 |
| 27.2 | 2.7 |
| 27.5 | 2.6 |
| 27.8 | 5.6 |
| 28.7 | 1.8 |
| 28.9 | 2.3 |

Figure 79:
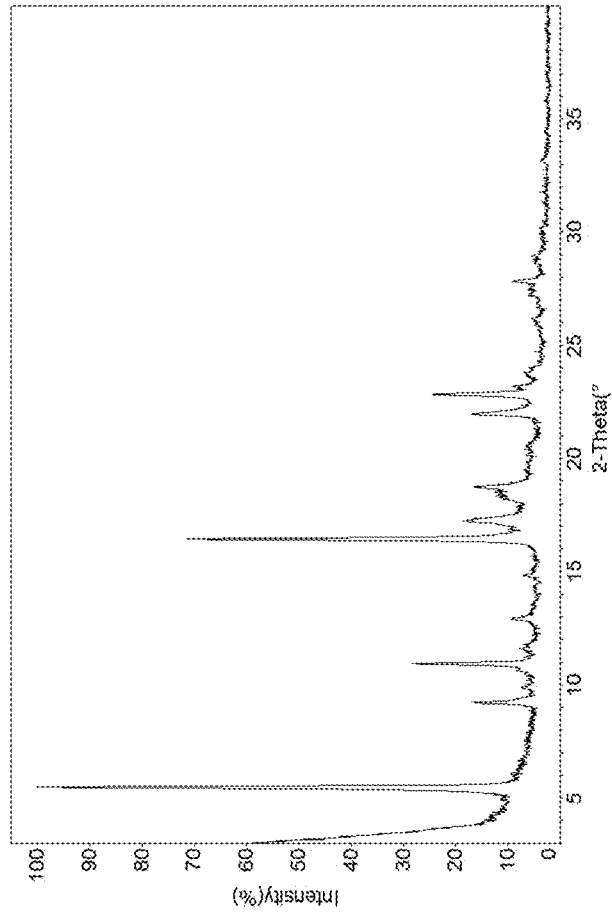
FIG. 79 shows an XRPD pattern of Compound 1 Gentisate (Form B).

In some embodiments, the Compound 1 Gentisate (Form B) exhibits an XRPD that is substantially similar to FIG. 79.

In one embodiment, the present disclosure provides Compound 1 Gentisate (Form C). In some embodiments, the Compound 1 Gentisate (Form C) exhibits an XRPD comprising one or more peaks at about 5.3, 15.2, 15.9, 21.4, and 26.6 degrees two-theta with the margin of error of about ±0.5; about ±0.4; about ±0.3; about ±0.2; about ±0.1; about ±0.05; or less. In another embodiment, the XRPD of the Compound 1 Gentisate (Form C) further comprises one or more peaks at about 7.6, 10.6, 13.8, 16.9, and 19.8 degrees two-theta with the margin of error of about ±0.5; about ±0.4; about ±0.3; about ±0.2; about ±0.1; about ±0.05; or less.

In some embodiments, the Compound 1 Gentisate (Form C) exhibits an XRPD comprising peaks shown in Table 37 below:

TABLE 37

XRPD Table of Compound 1 Gentisate (Form C)

| 2-Theta | Intensity % |
| --- | --- |
| 5.3 | 71.5 |
| 7.6 | 39.3 |
| 10.6 | 28.0 |
| 12.1 | 16.7 |
| 13.8 | 37.8 |
| 15.2 | 63.5 |
| 15.9 | 100 |
| 16.2 | 19.8 |
| 16.9 | 24.4 |
| 19.8 | 27.7 |
| 21.4 | 78.3 |
| 22.7 | 4.0 |
| 23.7 | 4.6 |
| 24.0 | 7.3 |
| 26.6 | 49.6 |
| 28.9 | 7.4 |

Figure 80:
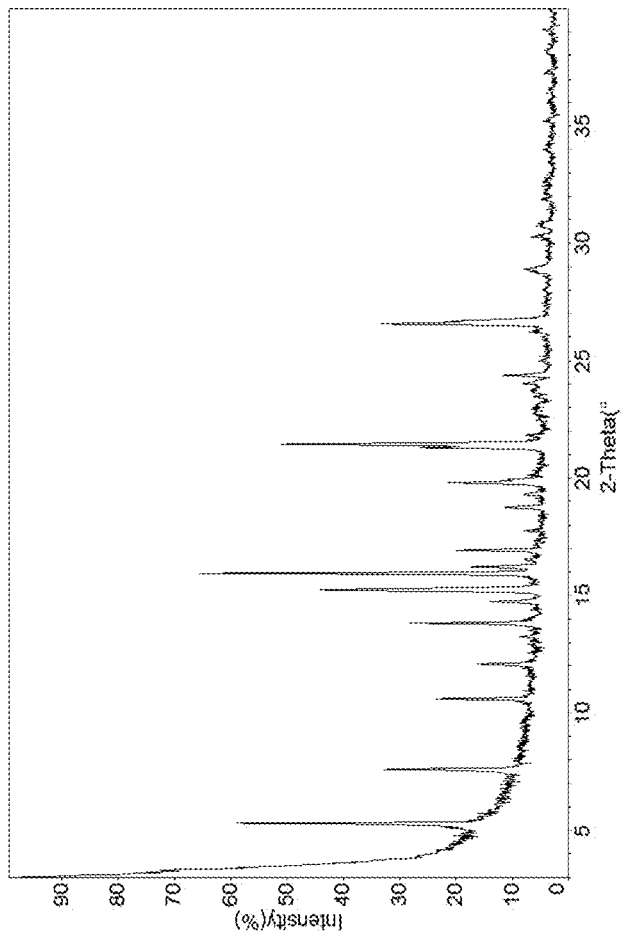
FIG. 80 shows an XRPD pattern of Compound 1 Gentisate (Form C).

In some embodiments, the Compound 1 Gentisate (Form C) exhibits an XRPD that is substantially similar to FIG. 80.

1-Hydroxy-2-Naphthoate Salt

In some embodiments, the present disclosure provides a 1-hydroxy-2-naphthoate salt of Compound 1 ("Compound 1 1-Hydroxy-2-naphthoate"). In some embodiments, the present disclosure provides a crystalline form of Compound 1 1-Hydroxy-2-naphthoate.

In one embodiment, the present disclosure provides Compound 1 1-Hydroxy-2-naphthoate (Form A). In some embodiments, the Compound 1 1-Hydroxy-2-naphthoate (Form A) exhibits an XRPD comprising one or more peaks at about 3.2, 6.2, 13.8, 21.2, and 21.6 degrees two-theta with the margin of error of about ±0.5; about ±0.4; about ±0.3; about ±0.2; about ±0.1; about ±0.05; or less. In another embodiment, the XRPD of the Compound 1 1-Hydroxy-2-naphthoate (Form A) further comprises one or more peaks at about 13.4, 16.2, 19.9, 20.2, and 24.7 degrees two-theta with the margin of error of about ±0.5; about ±0.4; about ±0.3; about ±0.2; about ±0.1; about ±0.05; or less.

In some embodiments, the Compound 1 1-Hydroxy-2-naphthoate (Form A) exhibits an XRPD comprising peaks shown in Table 38 below:

TABLE 38

XRPD Table of Compound 1 1-Hydroxy-2-napthoate (Form A)

| 2-Theta | Intensity % |
| --- | --- |
| 3.2 | 100 |
| 6.2 | 17.9 |
| 10.6 | 7.3 |
| 10.8 | 8.9 |
| 13.4 | 16.2 |
| 13.8 | 21.9 |
| 16.2 | 14.2 |
| 16.7 | 5.5 |
| 18.2 | 7.1 |
| 19.9 | 14.7 |
| 20.2 | 10.3 |
| 21.2 | 29.4 |
| 21.6 | 22.6 |
| 22.8 | 5.8 |
| 24.7 | 9.6 |

Figure 81:
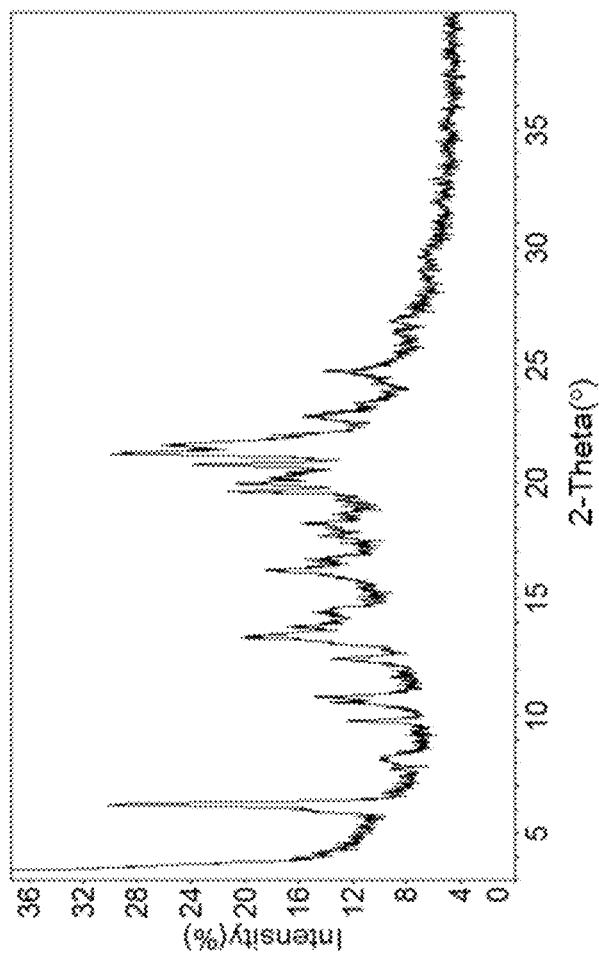
FIG. 81 shows an XRPD pattern of Compound 1 1-Hydroxy-2-naphthoate (Form A).

In some embodiments, the Compound 1 1-Hydroxy-2-naphthoate (Form A) exhibits an XRPD that is substantially similar to FIG. 81.

In some embodiments, the Compound 1 1-Hydroxy-2-naphthoate (Form A) exhibits a DSC thermogram comprising a endotherm at about 57.7° C. with the error of margin of about ±2.5; about ±2.0; about ±1.5; about ±1.0; about ±0.5; or less. In some embodiments, the Compound 1 1-Hydroxy-2-naphthoate (Form A) exhibits a DSC thermogram comprising a endotherm at about 79.1° C. with the error of margin of about ±2.5; about ±2.0; about ±1.5; about ±1.0; about ±0.5; or less. In some embodiments, the Compound 1 1-Hydroxy-2-naphthoate (Form A) exhibits a DSC thermogram comprising a endotherm at about 116.1° C. with the error of margin of about ±2.5; about ±2.0; about ±1.5; about ±1.0; about ±0.5; or less. In some embodiments, the Compound 1 1-Hydroxy-2-naphthoate (Form A) exhibits a DSC thermogram comprising a endotherm at about 164.7° C. with the error of margin of about ±2.5; about ±2.0; about ±1.5; about ±1.0; about ±0.5; or less. In some embodiments, the Compound 1 1-Hydroxy-2-naphthoate (Form A) exhibits a DSC thermogram that is substantially similar to FIG. 82.

Figure 82:
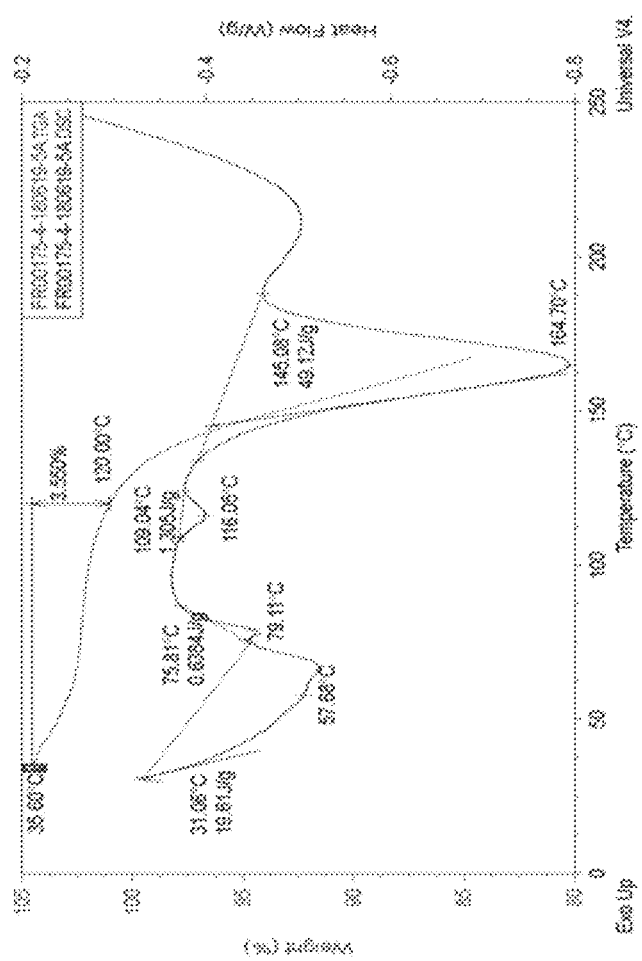
FIG. 82 shows a DSC thermogram and a TGA thermogram of Compound 1 1-Hydroxy-2-naphthoate (Form A).

In some embodiments, the Compound 1 1-Hydroxy-2-naphthoate (Form A) exhibits a TGA thermogram that is substantially similar to FIG. 82. In other embodiments, the TGA thermogram of the Compound 1 1-Hydroxy-2-naphthoate (Form A) exhibits a weight loss of 0.0 to 3.6% in the temperature range of 25 to 120° C.

Figure 83:
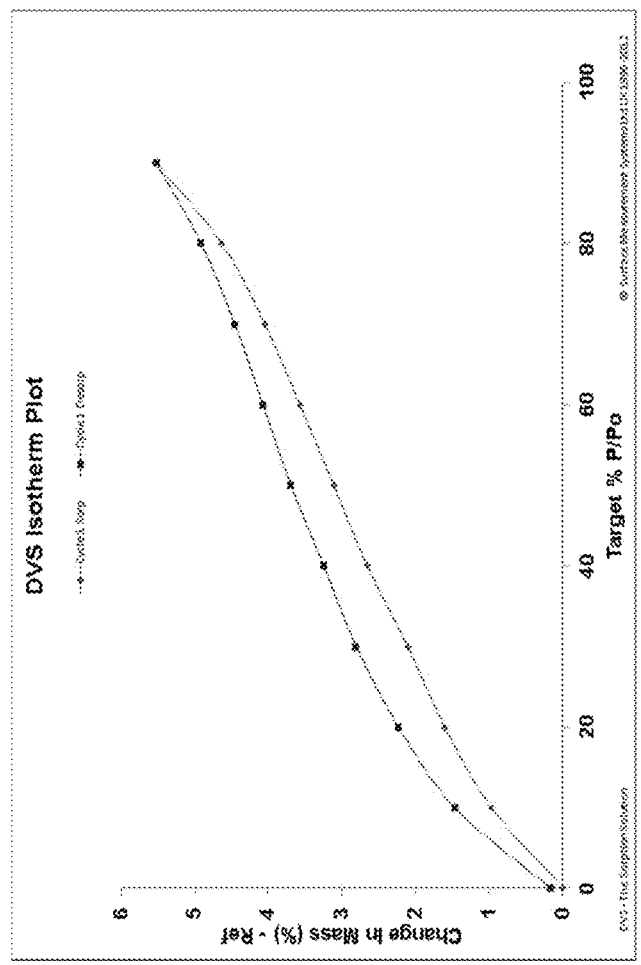
FIG. 83 shows a DVS isotherm plot for Compound 1 1-Hydroxy-2-naphthoate (Form A).

In some embodiments, the Compound 1 1-Hydroxy-2-naphthoate (Form A) exhibits a DVS isotherm plot that is substantially similar to FIG. 83. In other embodiments, the Compound 1 1-Hydroxy-2-naphthoate (Form A) exhibits a gravimetric moisture sorption of about 4.6% (by weight) at 80% Relative Humidity.

In one embodiment, the present disclosure provides Compound 1 1-Hydroxy-2-naphthoate (Form B). In some embodiments, the Compound 1 1-Hydroxy-2-naphthoate (Form B) exhibits an XRPD comprising one or more peaks at about 8.0, 8.6, 13.5, 13.8, and 20.6 degrees two-theta with the margin of error of about ±0.5; about ±0.4; about ±0.3; about ±0.2; about ±0.1; about ±0.05; or less. In another embodiment, the XRPD of the Compound 1 1-Hydroxy-2-naphthoate (Form B) further comprises one or more peaks at about 14.4, 15.2, 16.1, 21.4, and 23.8 degrees two-theta with the margin of error of about ±0.5; about ±0.4; about ±0.3; about ±0.2; about ±0.1; about ±0.05; or less.

In some embodiments, the Compound 1 1-Hydroxy-2-naphthoate (Form B) exhibits an XRPD comprising peaks shown in Table 39 below:

TABLE 39

XRPD Table of Compound 1 1-Hydroxy-2-napthoate (Form B)

| 2-Theta | Intensity % |
| --- | --- |
| 8.0 | 34.8 |
| 8.6 | 37.1 |
| 10.6 | 6.9 |
| 11.8 | 15 |
| 13.5 | 57.4 |
| 13.8 | 37 |
| 14.4 | 20.9 |
| 15.2 | 15.9 |
| 15.6 | 11.1 |
| 16.1 | 17.7 |
| 16.5 | 7.3 |
| 17.2 | 7.7 |
| 18.3 | 9.5 |
| 19.3 | 8.5 |
| 19.6 | 7 |
| 20.0 | 6.8 |
| 20.6 | 100 |
| 21.4 | 26.6 |
| 22.4 | 8.9 |
| 23.3 | 5.5 |

TABLE 39-continued

XRPD Table of Compound 1 1-Hydroxy-2-napthoate (Form B)

| 2-Theta | Intensity % |
|---------|-------------|
| 23.8 | 19.9 |
| 24.9 | 7 |
| 25.1 | 6.3 |
| 26.0 | 4.4 |
| 26.4 | 4.6 |
| 27.0 | 10.7 |
| 27.5 | 8.4 |
| 27.9 | 6.6 |
| 28.3 | 14.4 |
| 28.7 | 5.5 |
| 34.3 | 4.7 |
| 36.4 | 4.2 |
| 38.3 | 4.6 |
| 38.6 | 3.7 |

Figure 84:
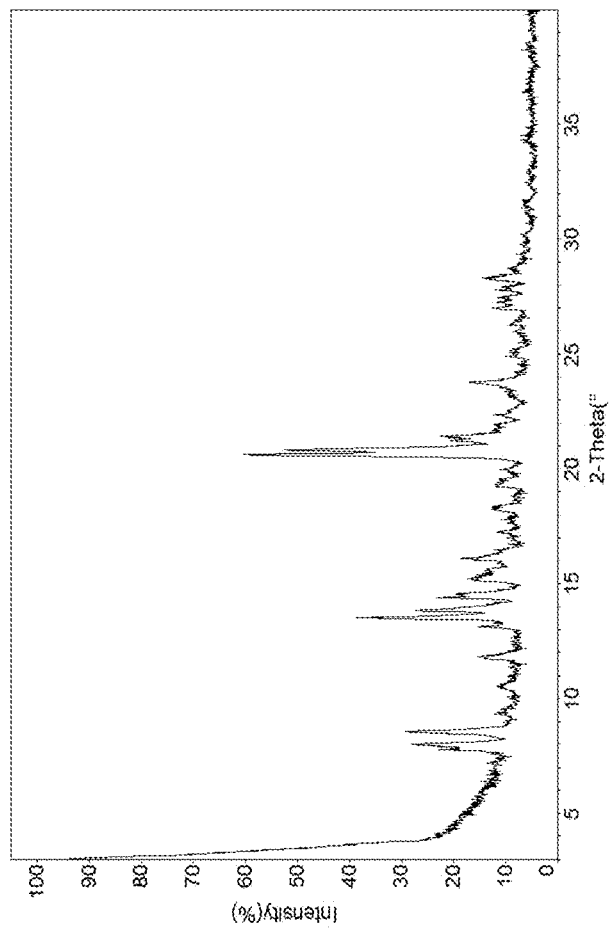
FIG. 84 shows an XRPD pattern of Compound 1 1-Hydroxy-2-naphthoate (Form B).

In some embodiments, the Compound 1 1-Hydroxy-2-naphthoate (Form B) exhibits an XRPD that is substantially similar to FIG. 84.

In one embodiment, the present disclosure provides Compound 1 1-Hydroxy-2-naphthoate (Form C). In some embodiments, the Compound 1 1-Hydroxy-2-naphthoate (Form C) exhibits an XRPD comprising one or more peaks at about 8.5, 13.7, 14.2, 17.3, and 21.4 degrees two-theta with the margin of error of about ±0.5; about ±0.4; about ±0.3; about ±0.2; about ±0.1; about ±0.05; or less. In another embodiment, the XRPD of the Compound 1 1-Hydroxy-2-naphthoate (Form C) further comprises one or more peaks at about 7.7, 15.4, 20.2, 20.6, and 21.1 degrees two-theta with the margin of error of about ±0.5; about ±0.4; about ±0.3; about ±0.2; about ±0.1; about ±0.05; or less.

In some embodiments, the Compound 1 1-Hydroxy-2-naphthoate (Form C) exhibits an XRPD comprising peaks shown in Table 40 below:

TABLE 40

XRPD Table of Compound 1 1-Hydroxy-2-napthoate (Form C)

| 2-Theta | Intensity % |
|---------|-------------|
| 5.0 | 20.3 |
| 5.4 | 22.3 |
| 7.7 | 43.6 |
| 8.0 | 27.8 |
| 8.5 | 77.3 |
| 10.5 | 17.5 |
| 10.7 | 18.6 |
| 11.0 | 15.1 |
| 12.5 | 25.1 |
| 13.7 | 80.1 |
| 14.2 | 100 |
| 15.4 | 62.2 |
| 16.1 | 22.7 |
| 17.3 | 72.9 |
| 17.6 | 28.5 |
| 17.8 | 18.2 |
| 18.2 | 22.7 |
| 19.2 | 13.4 |
| 20.2 | 35.1 |
| 20.6 | 42.3 |
| 20.8 | 29.2 |
| 21.1 | 46 |
| 21.4 | 70.4 |
| 27.5 | 15.5 |

Figure 85:
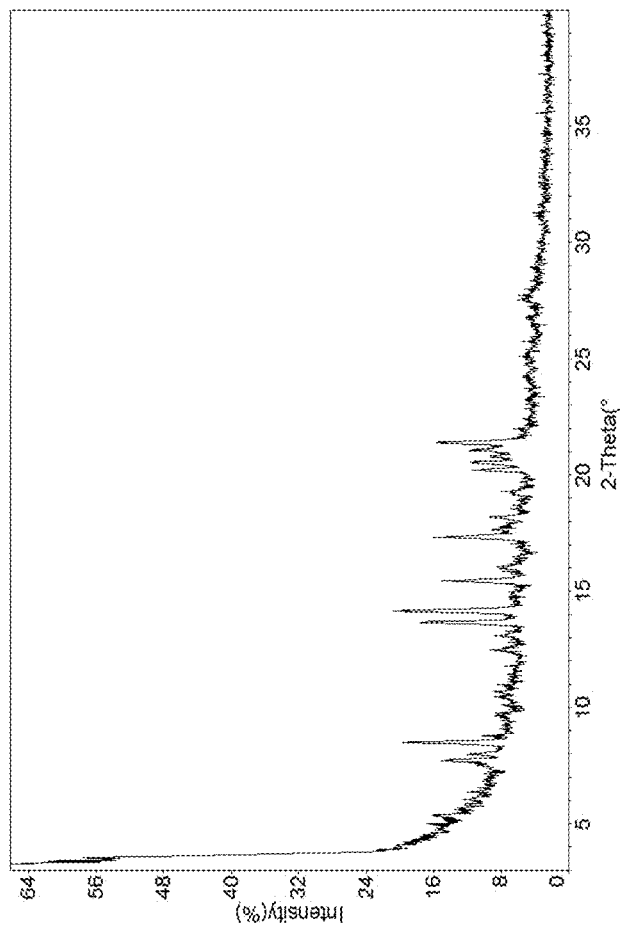
FIG. 85 shows an XRPD pattern of Compound 1 1-Hydroxy-2-naphthoate (Form C).

In some embodiments, the Compound 1 1-Hydroxy-2-naphthoate (Form C) exhibits an XRPD that is substantially similar to FIG. 85.

In one embodiment, the present disclosure provides Compound 1 1-Hydroxy-2-naphthoate (Form D). In some embodiments, the Compound 1 1-Hydroxy-2-naphthoate (Form D) exhibits an XRPD comprising one or more peaks at about 10.4, 12.9, 13.5, 20.4, and 20.9 degrees two-theta with the margin of error of about ±0.5; about ±0.4; about ±0.3; about ±0.2; about ±0.1; about ±0.05; or less. In another embodiment, the XRPD of the Compound 1 1-Hydroxy-2-naphthoate (Form D) further comprises one or more peaks at about 6.3, 9.1, 11.2, 13.2, and 19.9 degrees two-theta with the margin of error of about ±0.5; about ±0.4; about ±0.3; about ±0.2; about ±0.1; about ±0.05; or less.

In some embodiments, the Compound 1 1-Hydroxy-2-naphthoate (Form D) exhibits an XRPD comprising peaks shown in Table 41 below:

TABLE 41

XRPD Table of Compound 1 1-Hydroxy-2-napthoate (Form D)

| 2-Theta | Intensity % |
|---------|-------------|
| 6.3 | 20.2 |
| 9.1 | 14.6 |
| 10.4 | 46.3 |
| 11.2 | 16.5 |
| 12.1 | 11.3 |
| 12.9 | 29.9 |
| 13.2 | 22.5 |
| 13.5 | 40.5 |
| 19.5 | 14.4 |
| 19.9 | 21.1 |
| 20.4 | 40.1 |
| 20.9 | 100 |
| 22.6 | 7.7 |
| 28.2 | 6.1 |
| 31.5 | 5.6 |

Figure 86:
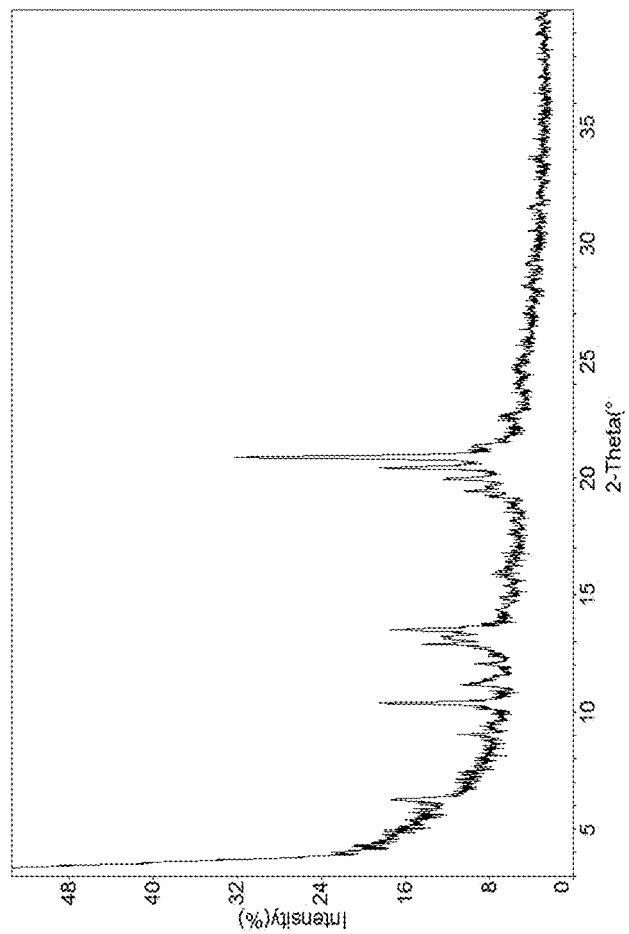
FIG. 86 shows an XRPD pattern of Compound 1 1-Hydroxy-2-naphthoate (Form D).

In some embodiments, the Compound 1 1-Hydroxy-2-naphthoate (Form D) exhibits an XRPD that is substantially similar to FIG. 86.

Cyclamate Salt

In some embodiments, the present disclosure provides a cyclamate salt of Compound 1 ("Compound 1 Cyclamate"). In some embodiments, the present disclosure provides a crystalline form of Compound 1 Cyclamate.

In one embodiment, the present disclosure provides Compound 1 Cyclamate (Form A). In some embodiments, the Compound 1 Cyclamate (Form A) exhibits an XRPD comprising one or more peaks at about 6.6, 7.2, 18.5, 19.5, and 21.6 degrees two-theta with the margin of error of about ±0.5; about ±0.4; about ±0.3; about ±0.2; about ±0.1; about ±0.05; or less. In another embodiment, the XRPD of the Compound 1 Cyclamate (Form A) further comprises one or more peaks at about 14.3, 14.8, 17.2, 17.6, and 18.2 degrees two-theta with the margin of error of about ±0.5; about ±0.4; about ±0.3; about ±0.2; about ±0.1; about ±0.05; or less.

In some embodiments, the Compound 1 Cyclamate (Form A) exhibits an XRPD comprising peaks shown in Table 42 below:

TABLE 42

XRPD Table of Compound 1 Cyclamate (Form A)

| 2-Theta | Intensity % |
|---------|-------------|
| 6.6 | 100 |
| 7.2 | 42.7 |
| 8.6 | 9.3 |
| 14.3 | 19.8 |
| 14.8 | 18.7 |
| 17.2 | 11.3 |
| 17.6 | 12.9 |

TABLE 42-continued

XRPD Table of Compound 1 Cyclamate (Form A)

| 2-Theta | Intensity % |
|---|---|
| 18.2 | 24.9 |
| 18.5 | 28.8 |
| 19.5 | 27 |
| 20.9 | 6.1 |
| 21.6 | 35.6 |
| 26.1 | 5 |

Figure 87:
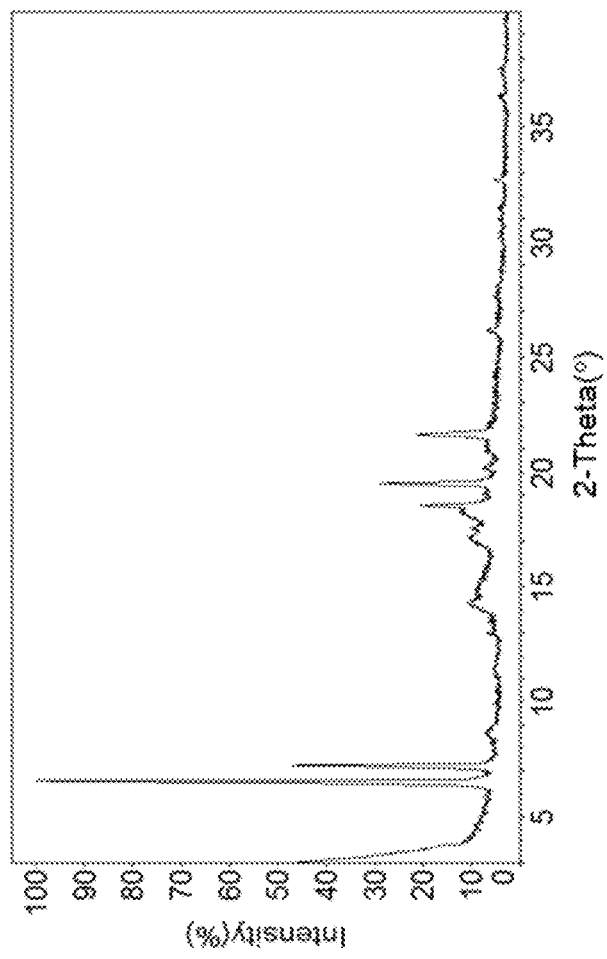
FIG. 87 shows an XRPD pattern of Compound 1 Cyclamate (Form A).

In some embodiments, the Compound 1 Cyclamate (Form A) exhibits an XRPD that is substantially similar to FIG. 87.

In some embodiments, the Compound 1 Cyclamate (Form A) exhibits a DSC thermogram comprising a endotherm at about 60.1° C. with the error of margin of about ±2.5; about ±2.0; about ±1.5; about ±1.0; about ±0.5; or less. In some embodiments, the Compound 1 Cyclamate (Form A) exhibits a DSC thermogram comprising a endotherm at about 168.5° C. with the error of margin of about ±2.5; about ±2.0; about ±1.5; about ±1.0; about ±0.5; or less. In some embodiments, the Compound 1 Cyclamate (Form A) exhibits a DSC thermogram that is substantially similar to FIG. 88.

Figure 88:
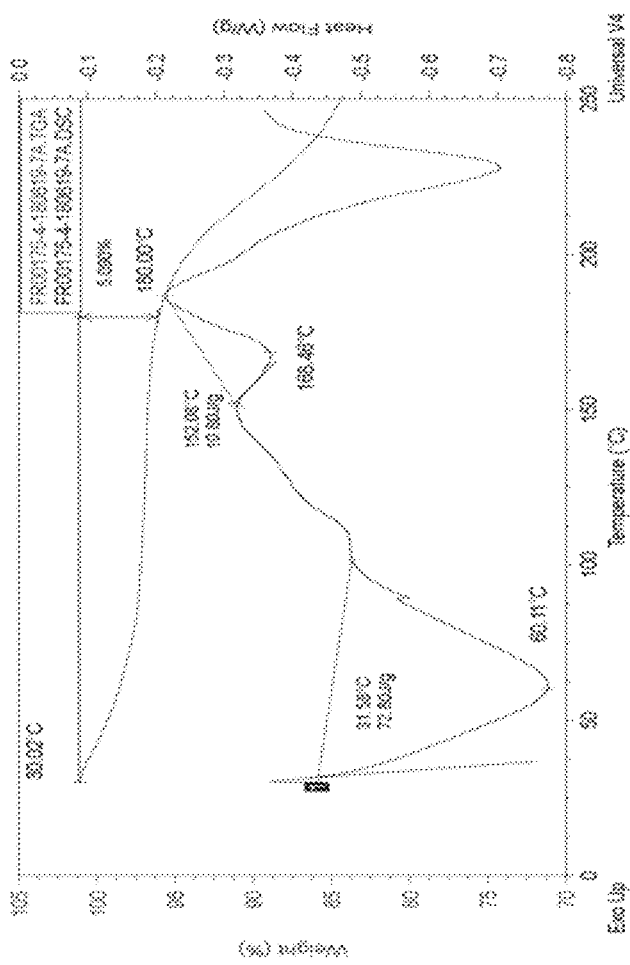
FIG. 88 shows a DSC thermogram and a TGA thermogram of Compound 1 Cyclamate (Form A).

In some embodiments, the Compound 1 Cyclamate (Form A) exhibits a TGA thermogram that is substantially similar to FIG. 88. In other embodiments, the TGA thermogram of the Compound 1 Cyclamate (Form A) exhibits a weight loss of 0.0 to 5.1% in the temperature range of 25 to 180° C.

Figure 89:
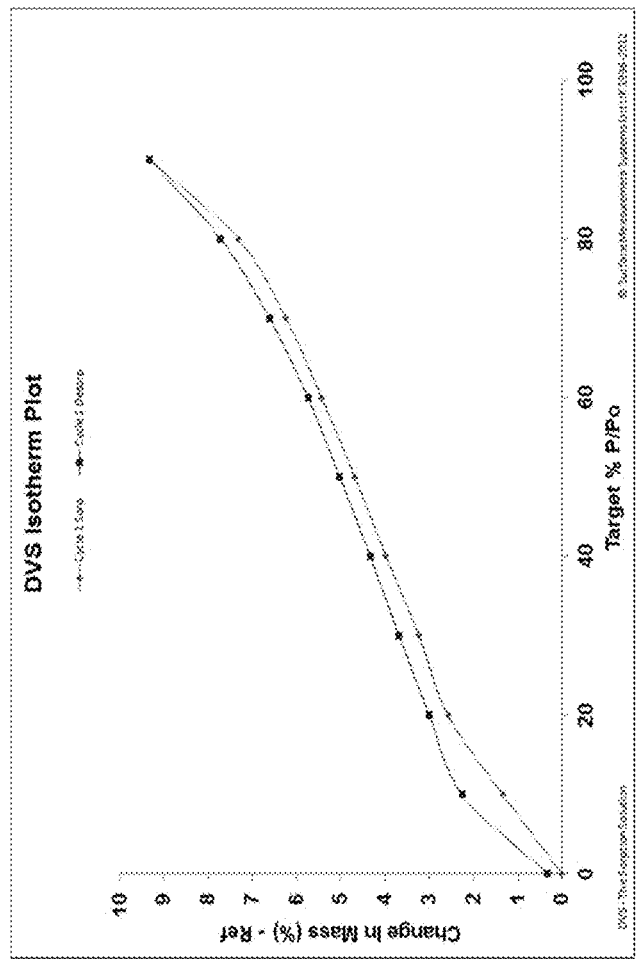
FIG. 89 shows a DVS isotherm plot for Compound 1 Cyclamate (Form A).

In some embodiments, the Compound 1 Cyclamate (Form A) exhibits a DVS isotherm plot that is substantially similar to FIG. 89. In other embodiments, the Compound 1 Cyclamate (Form A) exhibits a gravimetric moisture sorption of about 7.3% (by weight) at 80% Relative Humidity.

Ethane-1, 2-Disulfonate Salt

In some embodiments, the present disclosure provides an ethane-1, 2-disulfonate salt of Compound 1 ("Compound 1 Ethane-1,2-disulfonate"). In some embodiments, the present disclosure provides a crystalline form of Compound 1 Ethane-1,2-disulfonate.

In one embodiment, the present disclosure provides Compound 1 Ethane-1,2-disulfonate (Form A). In some embodiments, the Compound 1 Ethane-1,2-disulfonate (Form A) exhibits an XRPD comprising one or more peaks at about 16.2, 16.5, 17.5, 20.7, and 21.3 degrees two-theta with the margin of error of about ±0.5; about ±0.4; about ±0.3; about ±0.2; about ±0.1; about ±0.05; or less. In another embodiment, the XRPD of the Compound 1 Ethane-1,2-disulfonate (Form A) further comprises one or more peaks at about 3.7, 5.5, 13.8, 14.7, and 26.0 degrees two-theta with the margin of error of about ±0.5; about ±0.4; about ±0.3; about ±0.2; about ±0.1; about ±0.05; or less.

In some embodiments, the Compound 1 Ethane-1,2-disulfonate (Form A) exhibits an XRPD comprising peaks shown in Table 43 below:

TABLE 43

XRPD Table of Compound 1 Ethane-1,2-disulfonate (Form A)

| 2-Theta | Intensity % |
|---|---|
| 3.7 | 55.6 |
| 5.5 | 38.8 |
| 11.0 | 16.4 |
| 11.4 | 11 |
| 13.8 | 50.4 |
| 14.7 | 38 |
| 15.8 | 10.3 |

TABLE 43-continued

XRPD Table of Compound 1 Ethane-1,2-disulfonate (Form A)

| 2-Theta | Intensity % |
|---|---|
| 16.2 | 58 |
| 16.5 | 93.5 |
| 17.5 | 100 |
| 18.2 | 6.8 |
| 19.3 | 27.4 |
| 19.6 | 34.6 |
| 20.7 | 90.4 |
| 21.3 | 62.5 |
| 22.0 | 13.3 |
| 23.7 | 21.2 |
| 26.0 | 40.4 |
| 27.2 | 23.7 |
| 34.2 | 5.9 |
| 38.5 | 5.8 |

Figure 90:
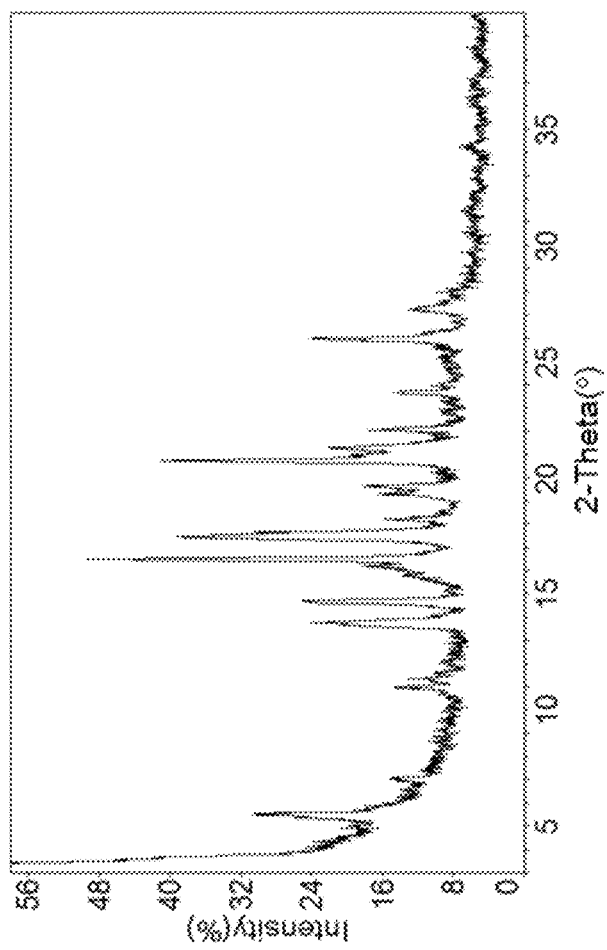
FIG. 90 shows an XRPD pattern of Compound 1 Ethane-1, 2-disulfonate (Form A).

In some embodiments, the Compound 1 Ethane-1,2-disulfonate (Form A) exhibits an XRPD that is substantially similar to FIG. 90.

In some embodiments, the Compound 1 Ethane-1,2-disulfonate (Form A) exhibits a DSC thermogram comprising a endotherm at about 59.0° C. with the error of margin of about ±2.5; about ±2.0; about ±1.5; about ±1.0; about ±0.5; or less. In some embodiments, the Compound 1 Ethane-1,2-disulfonate (Form A) exhibits a DSC thermogram comprising a endotherm at about 154.8° C. with the error of margin of about ±2.5; about ±2.0; about ±1.5; about ±1.0; about ±0.5; or less. In some embodiments, the Compound 1 Ethane-1, 2-disulfonate (Form A) exhibits a DSC thermogram that is substantially similar to FIG. 91.

Figure 91:
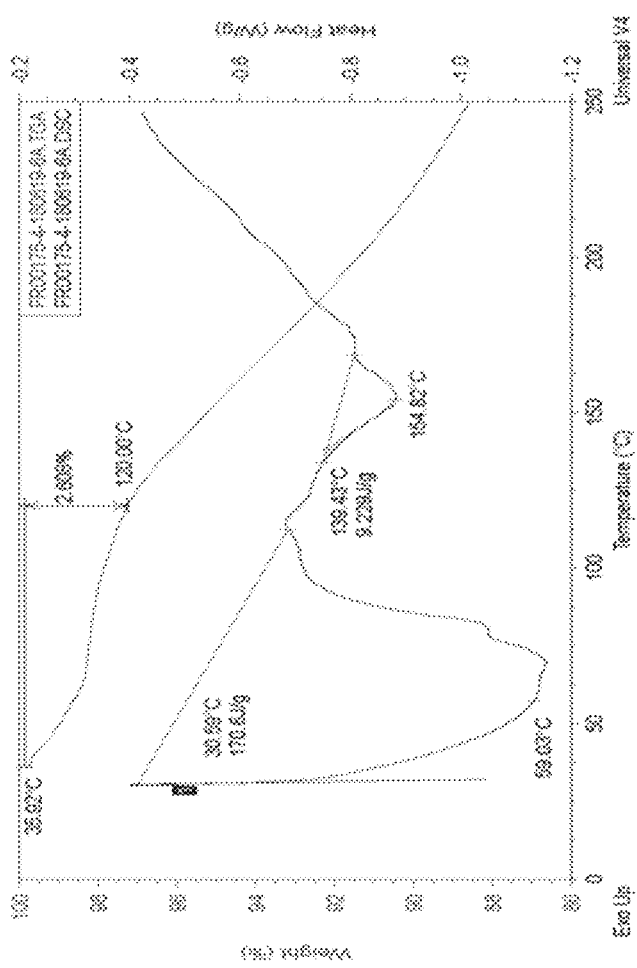
FIG. 91 shows a DSC thermogram and a TGA thermogram of Compound 1 Ethane-1, 2-disulfonate (Form A).

In some embodiments, the Compound 1 Ethane-1,2-disulfonate (Form A) exhibits a TGA thermogram that is substantially similar to FIG. 91. In other embodiments, the TGA thermogram of the Compound 1 Ethane-1,2-disulfonate (Form A) exhibits a weight loss of 0.0 to 0.7% in the temperature range of 25 to 120° C.

Figure 92:
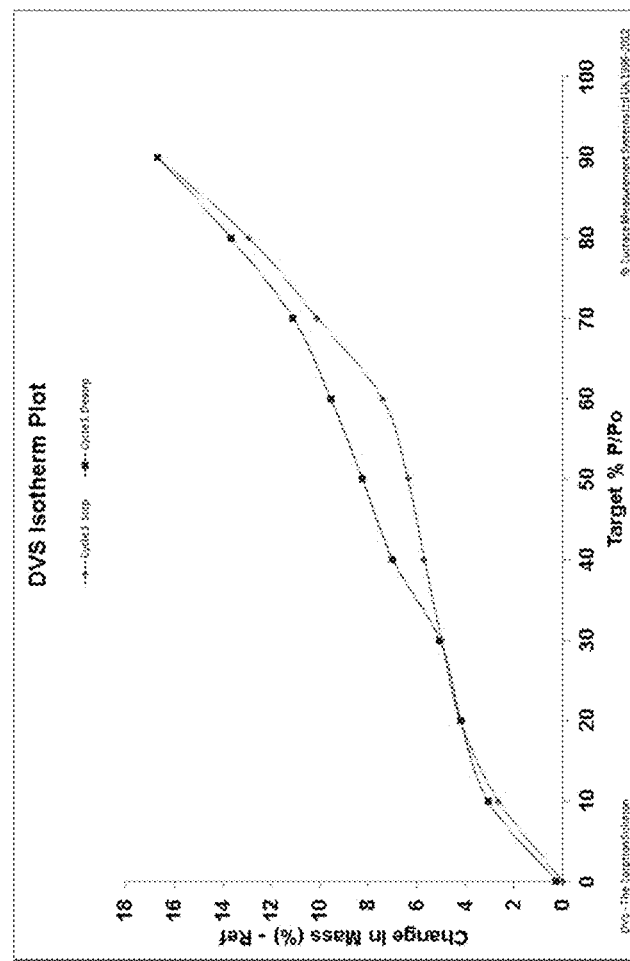
FIG. 92 shows a DVS isotherm plot for Compound 1 Ethane-1, 2-disulfonate (Form A).

In some embodiments, the Compound 1 Ethane-1,2-disulfonate (Form A) exhibits a DVS isotherm plot that is substantially similar to FIG. 92. In other embodiments, the Compound 1 Ethane-1,2-disulfonate (Form A) exhibits a gravimetric moisture sorption of about 12.9% (by weight) at 80% Relative Humidity.

In one embodiment, the present disclosure provides Compound 1 Ethane-1,2-disulfonate (Form B). In some embodiments, the Compound 1 Ethane-1,2-disulfonate (Form B) exhibits an XRPD comprising one or more peaks at about 5.5, 16.4, 17.4, 17.6, and 20.7 degrees two-theta with the margin of error of about ±0.5; about ±0.4; about ±0.3; about ±0.2; about ±0.1; about ±0.05; or less. In another embodiment, the XRPD of the Compound 1 Ethane-1,2-disulfonate (Form B) further comprises one or more peaks at about 10.9, 13.7, 14.6, 21.2, and 22.1 degrees two-theta with the margin of error of about ±0.5; about ±0.4; about ±0.3; about ±0.2; about ±0.1; about ±0.05; or less In some embodiments, the Compound 1 Ethane-1,2-disulfonate (Form B) exhibits an XRPD comprising peaks shown in Table 44 below:

TABLE 44

XRPD Table of Compound 1 Ethane-1,2-disulfonate (Form B)

| 2-Theta | Intensity % |
| --- | --- |
| 5.5 | 33.4 |
| 10.9 | 15.5 |
| 11.4 | 11.1 |
| 13.7 | 22.1 |
| 14.6 | 25.3 |
| 15.0 | 7.4 |
| 15.2 | 6.3 |
| 15.7 | 8.1 |
| 16.0 | 7.5 |
| 16.4 | 100 |
| 17.4 | 36.4 |
| 17.6 | 29.9 |
| 19.6 | 10.2 |
| 20.7 | 42.5 |
| 21.0 | 6.1 |
| 21.2 | 16.9 |
| 22.1 | 16.8 |
| 24.7 | 5.8 |
| 25.9 | 14.7 |
| 26.2 | 5.4 |
| 27.1 | 5.3 |
| 27.4 | 5.4 |
| 27.9 | 5.2 |

Figure 93:
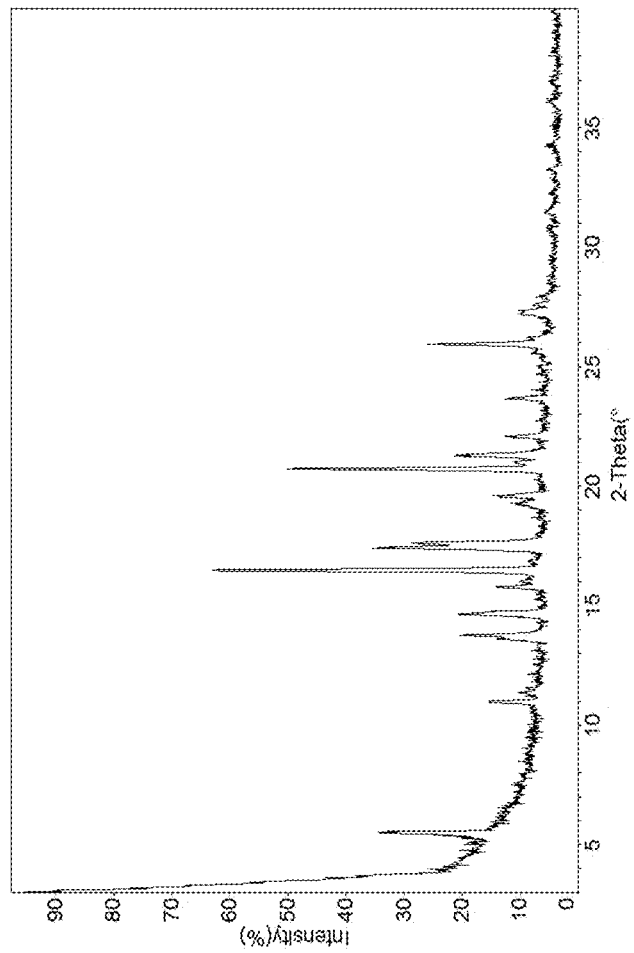
FIG. 93 shows an XRPD pattern of Compound 1 Ethane-1, 2-disulfonate (Form B).

In some embodiments, the Compound 1 Ethane-1,2-disulfonate (Form B) exhibits an XRPD that is substantially similar to FIG. 93.

Dichloroacetate Salt

In some embodiments, the present disclosure provides a dichloroacetate salt of Compound 1 ("Compound 1 Dichloroacetate"). In some embodiments, the present disclosure provides a crystalline form of Compound 1 Dichloroacetate.

In one embodiment, the present disclosure provides Compound 1 Dichloroacetate (Form A). In some embodiments, the Compound 1 Dichloroacetate (Form A) exhibits an XRPD comprising one or more peaks at about 3.4, 3.6, 16.2, 17.1 and 19.5 degrees two-theta with the margin of error of about ±0.5; about ±0.4; about ±0.3; about ±0.2; about ±0.1; about ±0.05; or less. In another embodiment, the XRPD of the Compound 1 Dichloroacetate (Form A) further comprises one or more peaks at about 8.1, 11.4, 12.8, 16.7 and 20.0 degrees two-theta with the margin of error of about ±0.5; about ±0.4; about ±0.3; about ±0.2; about ±0.1; about ±0.05; or less.

In some embodiments, the Compound 1 Dichloroacetate (Form A) exhibits an XRPD comprising peaks shown in Table 45 below:

TABLE 45

XRPD Table of Compound 1 Dichloroacetate (Form A)

| 2-Theta | Intensity % |
| --- | --- |
| 3.4 | 100 |
| 3.6 | 49.1 |
| 8.1 | 37.7 |
| 11.0 | 9.6 |
| 11.4 | 11.6 |
| 12.8 | 10.8 |
| 14.7 | 7.7 |
| 16.2 | 42.9 |
| 16.7 | 9.8 |
| 17.1 | 58.4 |
| 17.5 | 7.1 |
| 19.5 | 43.2 |
| 20.0 | 14.3 |
| 21.9 | 8.5 |
| 22.7 | 7.3 |
| 25.5 | 9.3 |
| 25.8 | 9.1 |
| 26.6 | 8.2 |
| 27.2 | 5.1 |
| 31.0 | 6.6 |

Figure 94:
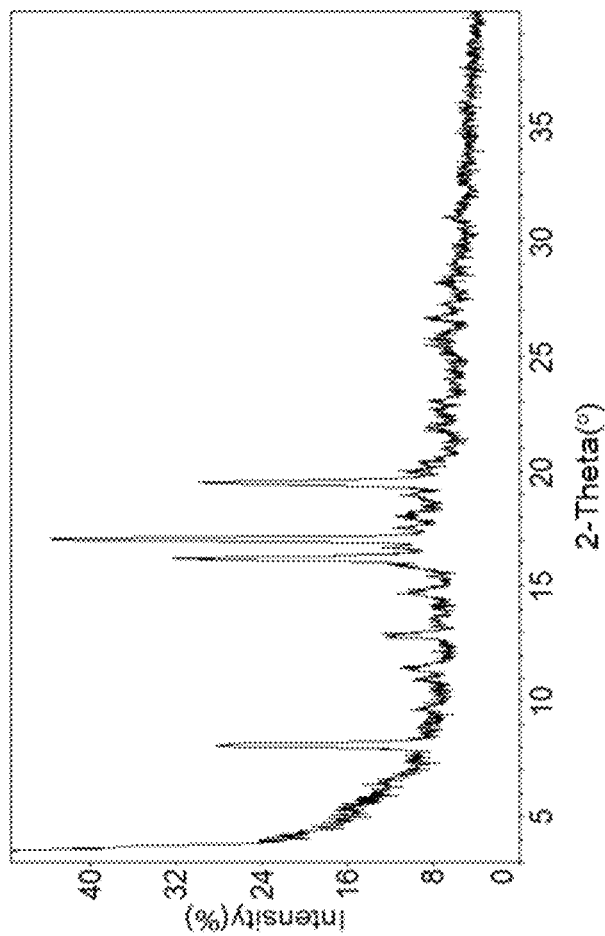
FIG. 94 shows an XRPD pattern of Compound 1 Dichloroacetate (Form A).

In some embodiments, the Compound 1 Dichloroacetate (Form A) exhibits an XRPD that is substantially similar to FIG. 94.

In some embodiments, the Compound 1 Dichloroacetate (Form A) exhibits a DSC thermogram comprising a sharp endotherm at about 117.7° C. with the error of margin of about ±2.5; about ±2.0; about ±1.5; about ±1.0; about ±0.5; or less. In some embodiments, the Compound 1 Dichloroacetate (Form A) exhibits a DSC thermogram that is substantially similar to FIG. 95.

Figure 95:
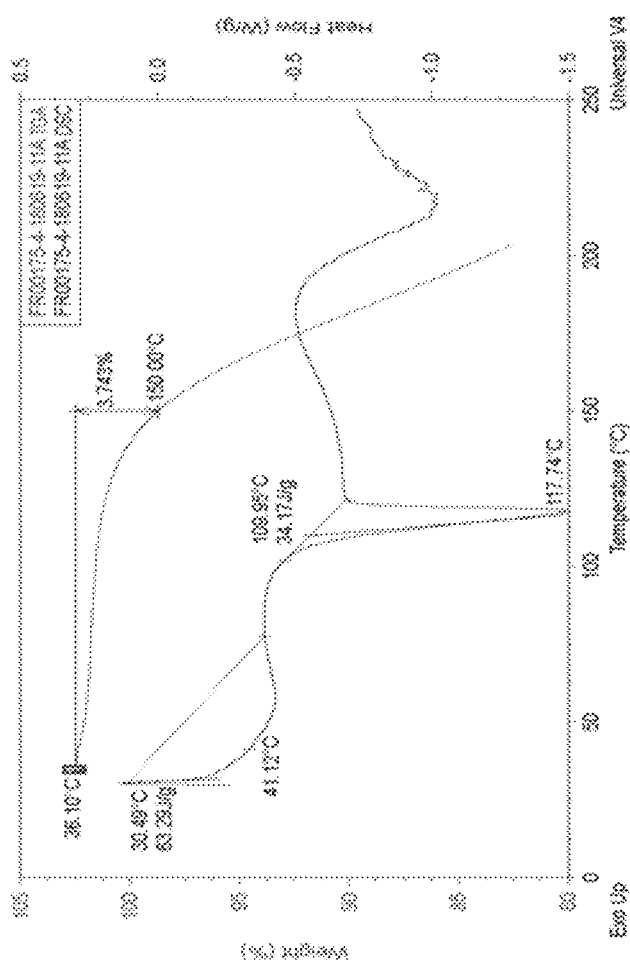
FIG. 95 shows a DSC thermogram and a TGA thermogram of Compound 1 Dichloroacetate (Form A).

In some embodiments, the Compound 1 Dichloroacetate (Form A) exhibits a TGA thermogram that is substantially similar to FIG. 95. In other embodiments, the TGA thermogram of the Compound 1 Dichloroacetate (Form A) exhibits a weight loss of 0.0 to 3.7% in the temperature range of 25 to 150° C.

Figure 96:
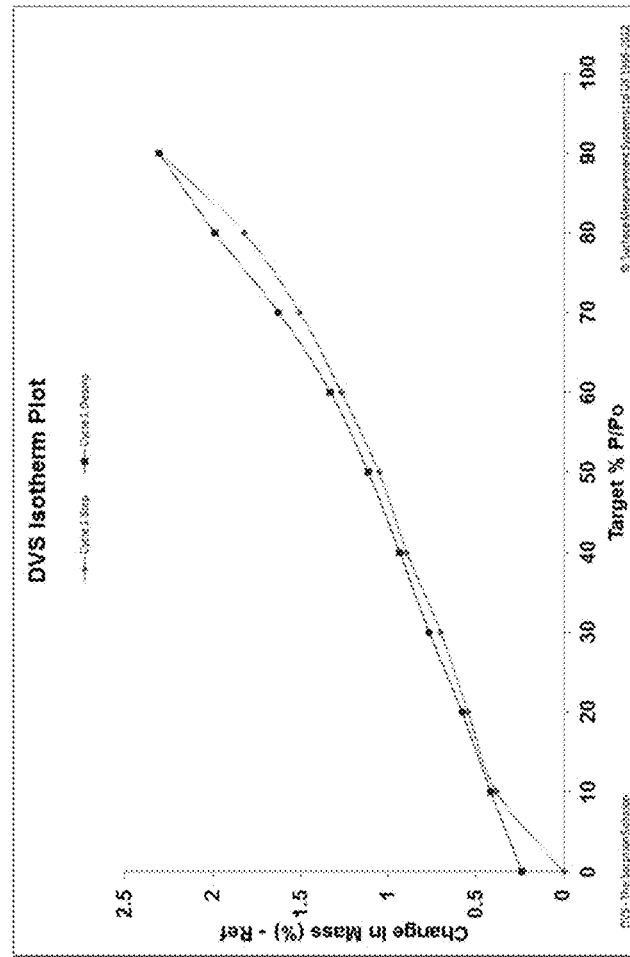
FIG. 96 shows a DVS isotherm plot for Compound 1 Dichloroacetate (Form A).

In some embodiments, the Compound 1 Dichloroacetate (Form A) exhibits a DVS isotherm plot that is substantially similar to FIG. 96. In other embodiments, the Compound 1 Dichloroacetate (Form A) exhibits a gravimetric moisture sorption of about 1.8% (by weight) at 80% Relative Humidity.

Malate Salt

In some embodiments, the present disclosure provides a malate salt of Compound 1 ("Compound 1 Malate"). In some embodiments, the present disclosure provides a D-malate salt of Compound 1 ("Compound 1 D-Malate"). In some embodiments, the present disclosure provides an L-malate salt of Compound 1 ("Compound 1 L-malate").

In some embodiments, the present disclosure provides a crystalline form of Compound 1 Malate. In some embodiments, the present disclosure provides a crystalline form of Compound 1 D-Malate. In some embodiments, the present disclosure provides a crystalline form of Compound 1 L-Malate.

In one embodiment, the present disclosure provides Compound 1 L-Malate (Form A). In some embodiments, the Compound 1 L-Malate (Form A) exhibits an XRPD comprising one or more peaks at about 3.2, 12.5, 14.4, 15.7, and 18.4 degrees two-theta with the margin of error of about ±0.5; about ±0.4; about ±0.3; about ±0.2; about ±0.1; about ±0.05; or less. In another embodiment, the XRPD of the Compound 1 L-Malate (Form A) further comprises one or more peaks at about 3.6, 6.1, 13.2, 18.9, and 21.1 degrees two-theta with the margin of error of about ±0.5; about ±0.4; about ±0.3; about ±0.2; about ±0.1; about ±0.05; or less.

In some embodiments, the Compound 1 L-Malate (Form A) exhibits an XRPD comprising peaks shown in Table 46 below:

TABLE 46

XRPD Table of Compound 1 L-Malate (Form A)

| 2-Theta | Intensity % |
|---|---|
| 3.2 | 93.3 |
| 3.6 | 45.4 |
| 6.1 | 42.2 |
| 8.4 | 9.8 |
| 10.4 | 5.9 |
| 10.6 | 6.2 |
| 11.1 | 14.2 |
| 12.2 | 19.5 |
| 12.5 | 68.8 |
| 13.2 | 47.8 |
| 14.1 | 7.2 |
| 14.4 | 53.1 |
| 15.5 | 16.6 |
| 15.7 | 63.1 |
| 16.9 | 12.3 |
| 17.1 | 27.8 |
| 17.8 | 7.6 |
| 18.0 | 9.5 |
| 18.4 | 100 |
| 18.9 | 43.6 |
| 19.2 | 11.5 |
| 20.7 | 16.7 |
| 21.1 | 32.6 |
| 21.2 | 17.9 |
| 22.6 | 7.7 |
| 23.1 | 6.3 |
| 23.4 | 20.3 |
| 23.9 | 8.8 |
| 24.5 | 8.9 |
| 24.9 | 6 |
| 26.0 | 8.5 |
| 26.4 | 13.8 |
| 26.8 | 6.9 |
| 27.4 | 5.5 |
| 28.5 | 3.5 |
| 28.9 | 4.6 |
| 29.2 | 3 |
| 29.9 | 4.5 |
| 32.3 | 3.9 |
| 32.6 | 6.3 |
| 33.0 | 2.4 |

Figure 97:
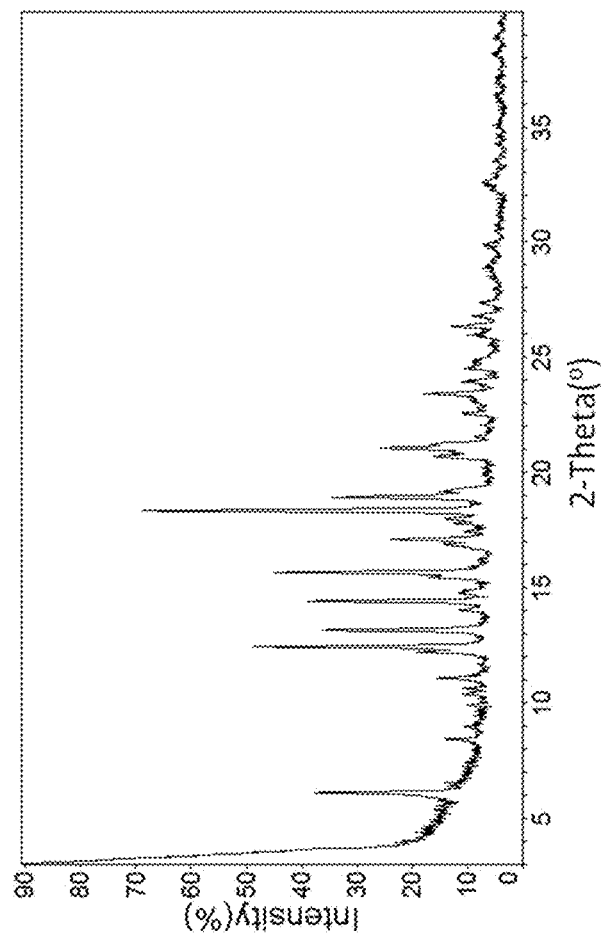
FIG. 97 shows an XRPD pattern of Compound 1 L-Malate (Form A).

In some embodiments, the Compound 1 L-Malate (Form A) exhibits an XRPD that is substantially similar to FIG. 97.

In some embodiments, the Compound 1 L-Malate (Form A) exhibits a DSC thermogram comprising a sharp endotherm at about 120.9° C. with the error of margin of about ±2.5; about ±2.0; about ±1.5; about ±1.0; about ±0.5; or less. In some embodiments, the Compound 1 L-Malate (Form A) exhibits a DSC thermogram comprising a sharp endotherm at about 142.3° C. with the error of margin of about ±2.5; about ±2.0; about ±1.5; about ±1.0; about ±0.5; or less. In some embodiments, the Compound 1 L-Malate (Form A) exhibits a DSC thermogram that is substantially similar to FIG. 98.

Figure 98:
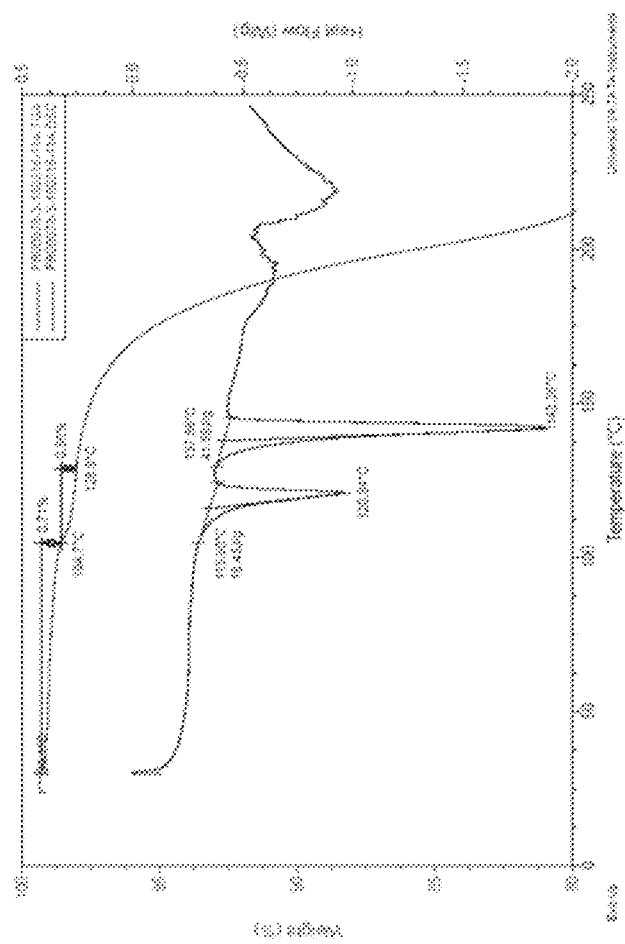
FIG. 98 shows a DSC thermogram and a TGA thermogram of Compound 1 L-Malate (Form A).

In some embodiments, the Compound 1 L-Malate (Form A) exhibits a TGA thermogram that is substantially similar to FIG. 98. In other embodiments, the TGA thermogram of the Compound 1 L-Malate (Form A) exhibits a weight loss of 0.0 to 0.7% in the temperature range of 25 to 105° C.

Figure 99:
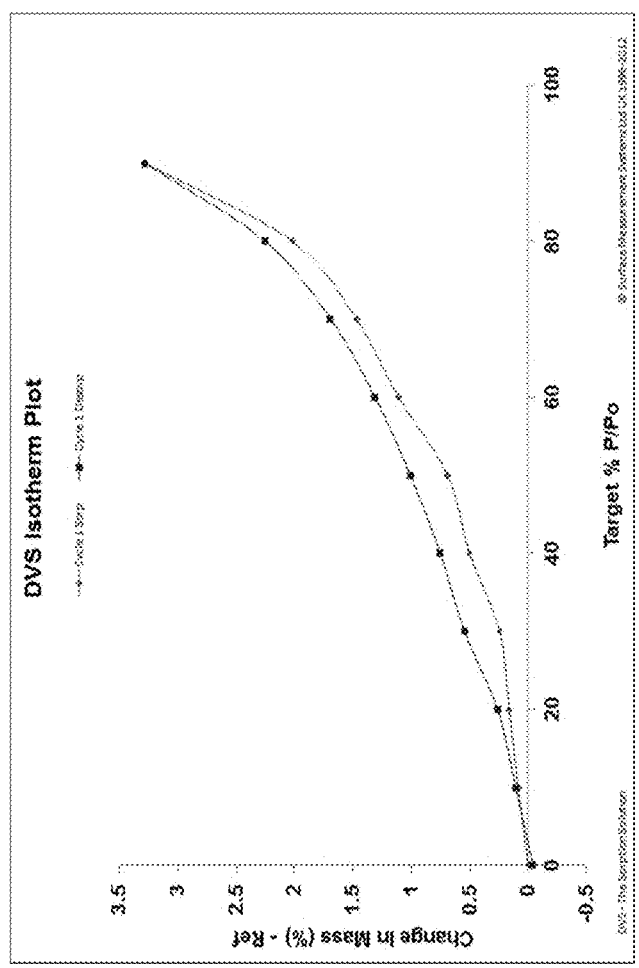
FIG. 99 shows a DVS isotherm plot for Compound 1 L-Malate (Form A).

In some embodiments, the Compound 1 L-Malate (Form A) exhibits a DVS isotherm plot that is substantially similar to FIG. 99. In other embodiments, the Compound 1 L-Malate (Form A) exhibits a gravimetric moisture sorption of about 2.0% (by weight) at 80% Relative Humidity.

In one embodiment, the present disclosure provides Compound 1 L-Malate (Form B). In some embodiments, the Compound 1 L-Malate (Form B) exhibits an XRPD comprising one or more peaks at about 5.6, 13.4, 17.3, 20.8 and 23.2 degrees two-theta with the margin of error of about ±0.5; about ±0.4; about ±0.3; about ±0.2; about ±0.1; about ±0.05; or less. In another embodiment, the XRPD of the Compound 1 L-Malate (Form B) further comprises one or more peaks at about 3.7, 11.2, 14.4, 14.9 and 17.8 degrees two-theta with the margin of error of about ±0.5; about ±0.4; about ±0.3; about ±0.2; about ±0.1; about ±0.05; or less.

In some embodiments, the Compound 1 L-Malate (Form B) exhibits an XRPD comprising peaks shown in Table 47 below:

TABLE 47

XRPD Table of Compound 1 L-Malate (Form B)

| 2-Theta | Intensity % |
|---|---|
| 3.7 | 57.5 |
| 5.6 | 100 |
| 6.0 | 23.7 |
| 8.3 | 12.1 |
| 9.2 | 19.4 |
| 11.2 | 56.7 |
| 11.9 | 14.1 |
| 13.4 | 63.7 |
| 14.4 | 44.5 |
| 14.9 | 53.1 |
| 16.0 | 39.4 |
| 16.6 | 34 |
| 17.3 | 83.5 |
| 17.8 | 62.3 |
| 18.6 | 14.3 |
| 19.2 | 28.2 |
| 20.0 | 13.7 |
| 20.8 | 77.2 |
| 21.3 | 44.5 |
| 23.2 | 69 |
| 25.7 | 10.6 |
| 26.1 | 29.5 |

Figure 100:
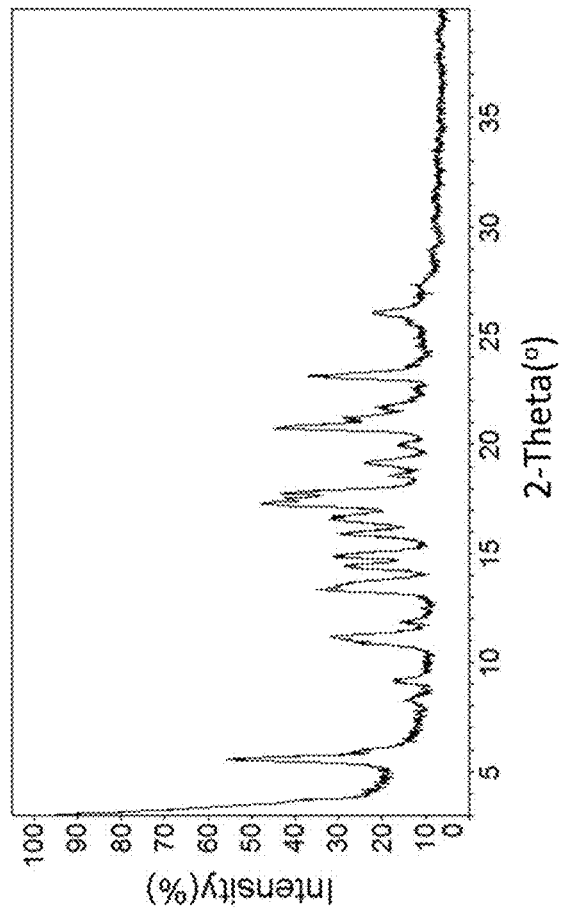
FIG. 100 shows an XRPD pattern of Compound 1 L-Malate (Form B).

In some embodiments, the Compound 1 L-Malate (Form B) exhibits an XRPD that is substantially similar to FIG. 100.

In some embodiments, the Compound 1 L-Malate (Form B) exhibits a DSC thermogram comprising an endotherm at about 108.7° C. with the error of margin of about ±2.5; about ±2.0; about ±1.5; about ±1.0; about ±0.5; or less. In some embodiments, the Compound 1 L-Malate (Form B) exhibits a DSC thermogram comprising a sharp endotherm at about 143.3° C. with the error of margin of about ±2.5; about ±2.0; about ±1.5; about ±1.0; about ±0.5; or less. In some embodiments, the Compound 1 L-Malate (Form B) exhibits a DSC thermogram that is substantially similar to FIG. 101.

Figure 101:
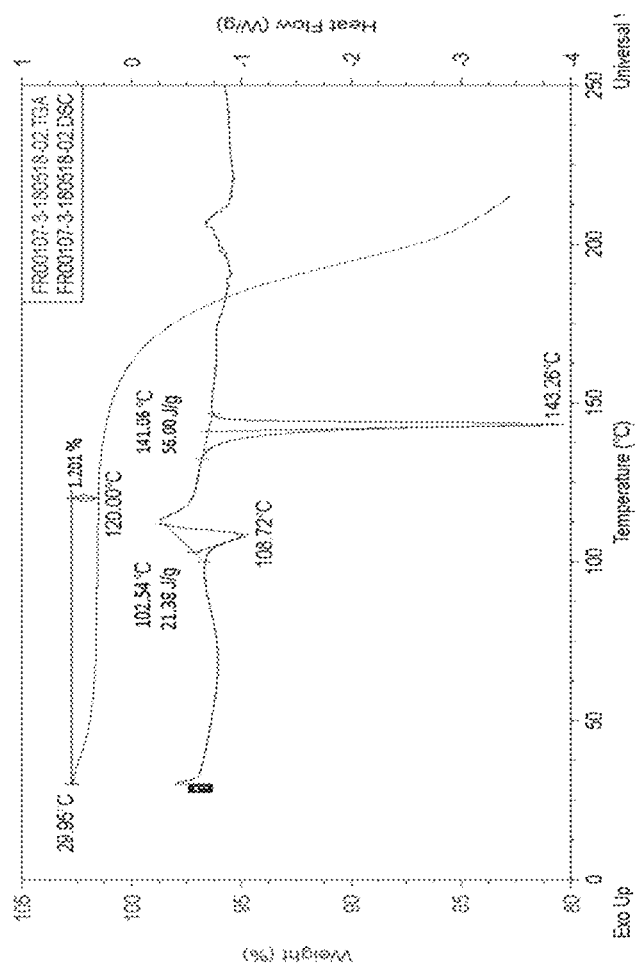
FIG. 101 shows a DSC thermogram and a TGA thermogram of Compound 1 L-Malate (Form B).

In some embodiments, the Compound 1 L-Malate (Form B) exhibits a TGA thermogram that is substantially similar to FIG. 101. In other embodiments, the TGA thermogram of the Compound 1 L-Malate (Form B) exhibits a weight loss of 0.0 to 1.2% in the temperature range of 25 to 120° C.

Figure 102:
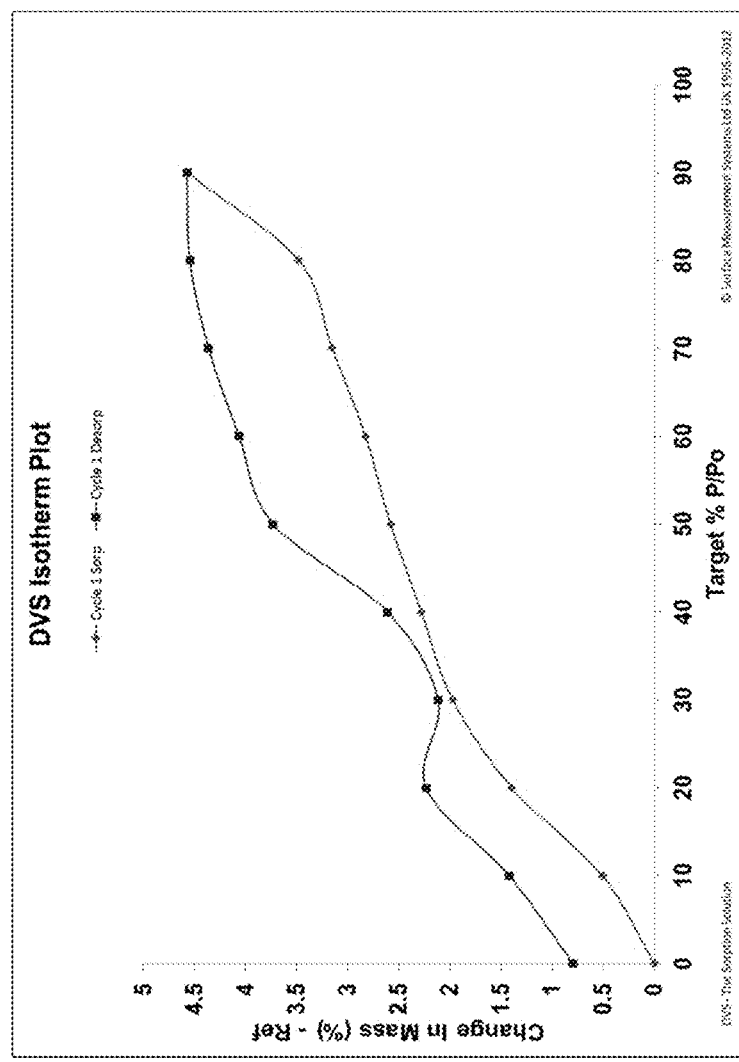
FIG. 102 shows a DVS isotherm plot for Compound 1 L-Malate (Form B).

In some embodiments, the Compound 1 L-Malate (Form B) exhibits a DVS isotherm plot that is substantially similar to FIG. 102. In other embodiments, the Compound 1 L-Malate (Form B) exhibits a gravimetric moisture sorption of about 3.5% (by weight) at 80% Relative Humidity.

Hydrochloride Salt

In some embodiments, the present disclosure provides a hydrochloride salt of Compound 1 ("Compound 1 Hydrochloride"). In some embodiments, the present disclosure provides a crystalline form of Compound 1 Hydrochloride.

In one embodiment, the present disclosure provides Compound 1 Hydrochloride (Form A). In some embodiments, the Compound 1 Hydrochloride (Form A) exhibits an XRPD comprising one or more peaks at about 3.6, 5.2, 14.2, 17.4 and 17.7 degrees two-theta with the margin of error of about ±0.5; about ±0.4; about ±0.3; about ±0.2; about ±0.1; about ±0.05; or less. In another embodiment, the XRPD of the Compound 1 Hydrochloride (Form A) further comprises one or more peaks at about 12.8, 13.4, 14.9, 18.9 and 20.4 degrees two-theta with the margin of error of about ±0.5; about ±0.4; about ±0.3; about ±0.2; about ±0.1; about ±0.05; or less.

In some embodiments, the Compound 1 Hydrochloride (Form A) exhibits an XRPD comprising peaks shown in Table 48 below:

TABLE 48

XRPD Table of Compound 1 Hydrochloride (Form A)

| 2-Theta | Intensity % |
|---|---|
| 3.6 | 88 |
| 5.2 | 100 |
| 8.7 | 11.2 |
| 12.1 | 15.1 |
| 12.8 | 22.6 |
| 13.4 | 19.5 |
| 13.8 | 10.1 |
| 14.2 | 57.8 |
| 14.9 | 29.7 |
| 15.5 | 9.8 |
| 16.1 | 11.2 |
| 17.1 | 13.7 |
| 17.4 | 79.6 |
| 17.7 | 54.6 |
| 18.3 | 10.6 |
| 18.9 | 16.4 |
| 20.4 | 21.1 |
| 21.2 | 9 |
| 22.0 | 15.9 |
| 22.5 | 6.1 |
| 28.2 | 8.7 |

Figure 103:
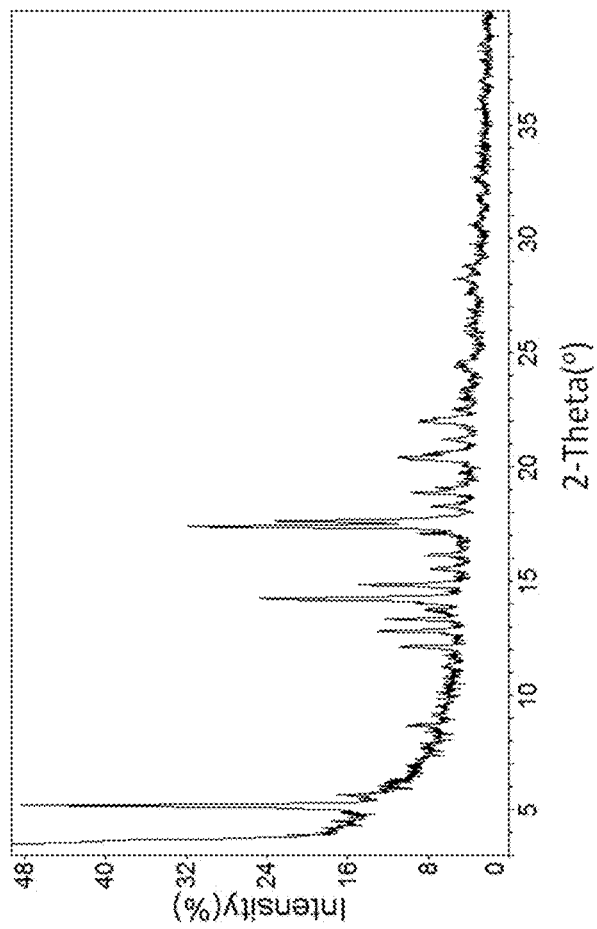
FIG. 103 shows an XRPD pattern of Compound 1 Hydrochloride (Form A).

In some embodiments, the Compound 1 Hydrochloride (Form A) exhibits an XRPD that is substantially similar to FIG. 103.

In some embodiments, the Compound 1 Hydrochloride (Form A) exhibits a DSC thermogram comprising an endotherm at about 225.0° C. with the error of margin of about ±2.5; about ±2.0; about ±1.5; about ±1.0; about ±0.5; or less. In some embodiments, the Compound 1 Hydrochloride (Form A) exhibits a DSC thermogram comprising an endotherm at about 232.7° C. with the error of margin of about ±2.5; about ±2.0; about ±1.5; about ±1.0; about ±0.5; or less. In some embodiments, the Compound 1 Hydrochloride (Form A) exhibits a DSC thermogram that is substantially similar to FIG. 104.

Figure 104:
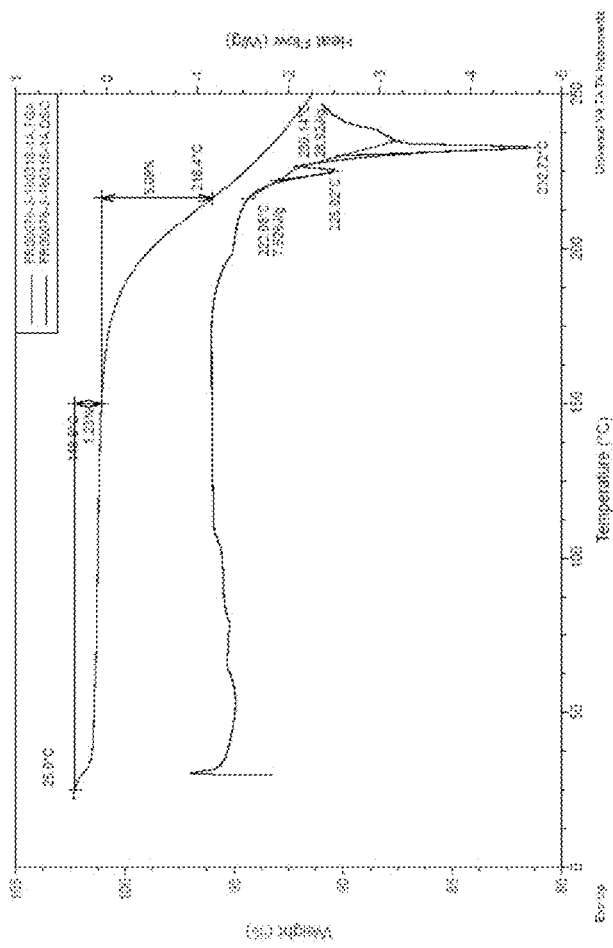
FIG. 104 shows a DSC thermogram and a TGA thermogram of Compound 1 Hydrochloride (Form A).

In some embodiments, the Compound 1 Hydrochloride (Form A) exhibits a TGA thermogram that is substantially similar to FIG. 104. In other embodiments, the TGA thermogram of the Compound 1 Hydrochloride (Form A) exhibits a weight loss of 0.0 to 1.2% in the temperature range of 25 to 150° C.

Figure 105:
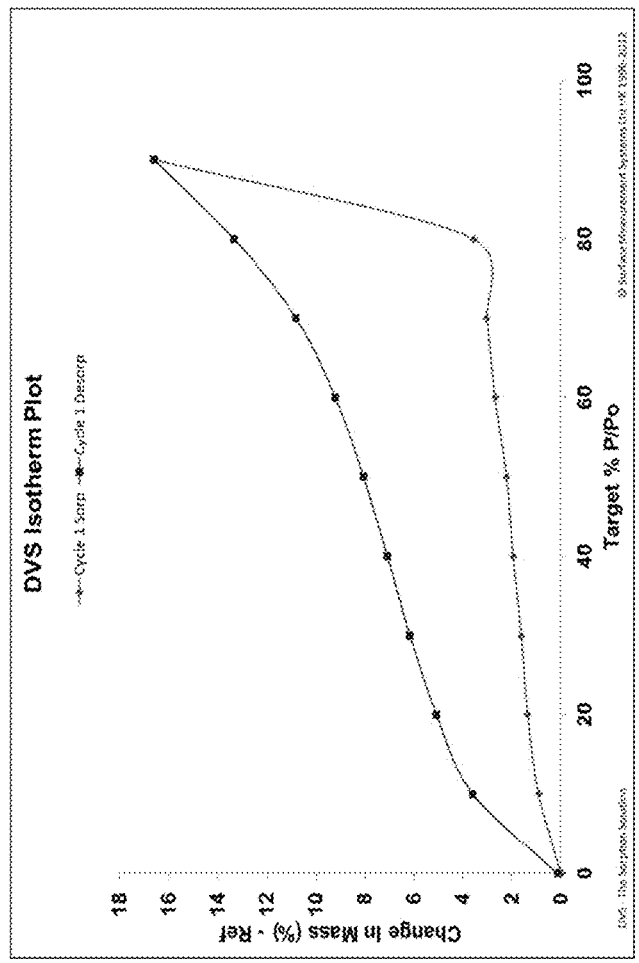
FIG. 105 shows a DVS isotherm plot for Compound 1 Hydrochloride (Form A).

In some embodiments, the Compound 1 Hydrochloride (Form A) exhibits a DVS isotherm plot that is substantially similar to FIG. 105. In other embodiments, the Compound 1 Hydrochloride (Form A) exhibits a gravimetric moisture sorption of about 3.6% (by weight) at 80% Relative Humidity.

In one embodiment, the present disclosure provides Compound 1 Hydrochloride (Form B). In some embodiments, the Compound 1 Hydrochloride (Form B) exhibits an XRPD comprising one or more peaks at about 3.3, 7.8, 15.4, 16.6 and 23.2 degrees two-theta with the margin of error of about ±0.5; about ±0.4; about ±0.3; about ±0.2; about ±0.1; about ±0.05; or less. In another embodiment, the XRPD of the Compound 1 Hydrochloride (Form B) further comprises one or more peaks at about 15.0, 18.8, 20.4, 23.5, and 26.5 degrees two-theta with the margin of error of about ±0.5; about ±0.4; about ±0.3; about ±0.2; about ±0.1; about ±0.05; or less.

In some embodiments, the Compound 1 Hydrochloride (Form B) exhibits an XRPD comprising peaks shown in Table 49 below:

TABLE 49

XRPD Table of Compound 1 Hydrochloride (Form B)

| 2-Theta | Intensity % |
|---|---|
| 3.3 | 58.7 |
| 4.9 | 12.3 |
| 7.8 | 34.4 |
| 9.8 | 14.2 |
| 15.0 | 25.8 |
| 15.4 | 100 |
| 16.6 | 57.7 |
| 17.6 | 7.3 |
| 18.8 | 16.1 |
| 20.4 | 14.6 |
| 22.7 | 5.8 |
| 23.2 | 59.2 |
| 23.5 | 32.2 |
| 26.5 | 15.4 |
| 26.9 | 8.4 |
| 28.4 | 5.8 |
| 31.7 | 9.3 |

Figure 106:
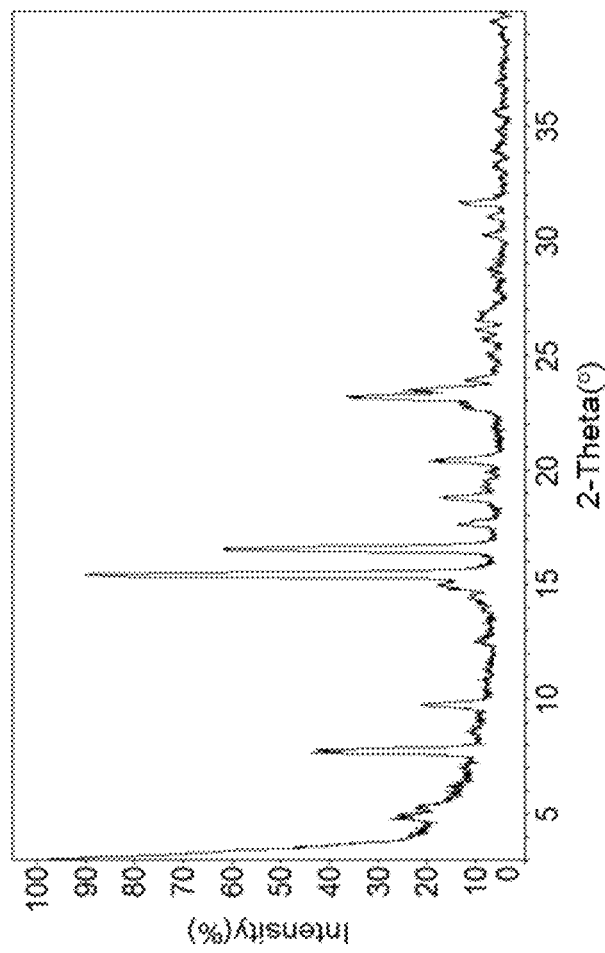
FIG. 106 shows an XRPD pattern of Compound 1 Hydrochloride (Form B).

In some embodiments, the Compound 1 Hydrochloride (Form B) exhibits an XRPD that is substantially similar to FIG. 106.

In some embodiments, the Compound 1 Hydrochloride (Form B) exhibits a DSC thermogram comprising an endotherm at about 87.1° C. with the error of margin of about ±2.5; about ±2.0; about ±1.5; about ±1.0; about ±0.5; or less. In some embodiments, the Compound 1 Hydrochloride (Form B) exhibits a DSC thermogram comprising a sharp endotherm at about 207.3° C. with the error of margin of about ±2.5; about ±2.0; about ±1.5; about ±1.0; about ±0.5; or less. In some embodiments, the Compound 1 Hydrochloride (Form B) exhibits a DSC thermogram that is substantially similar to FIG. 107.

Figure 107:
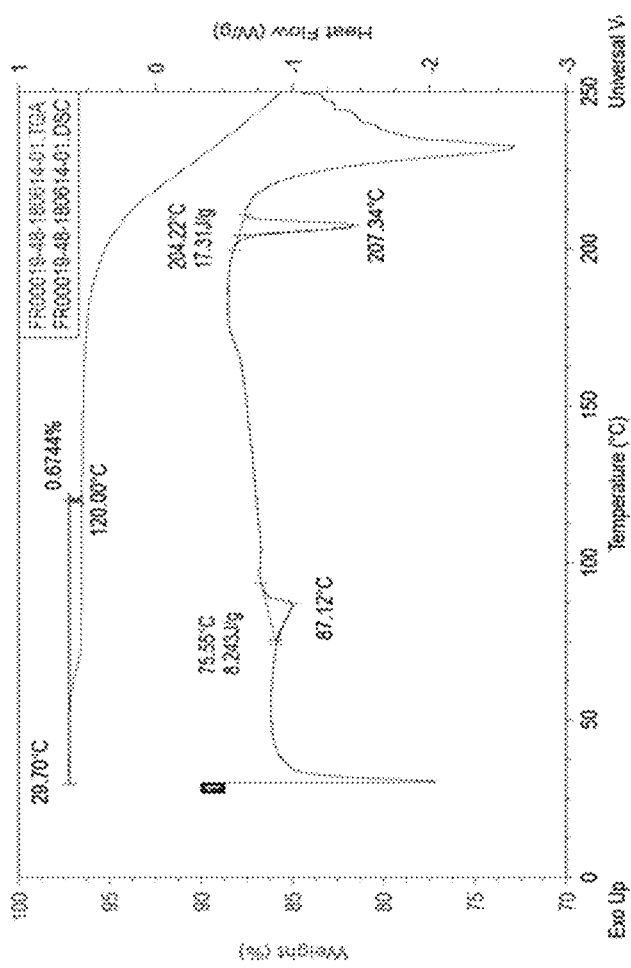
FIG. 107 shows a DSC thermogram and a TGA thermogram of Compound 1 Hydrochloride (Form B).

In some embodiments, the Compound 1 Hydrochloride (Form B) exhibits a TGA thermogram that is substantially similar to FIG. 107. In other embodiments, the TGA thermogram of the Compound 1 Hydrochloride (Form B) exhibits a weight loss of 0.0 to 0.7% in the temperature range of 25 to 120° C.

Figure 108:
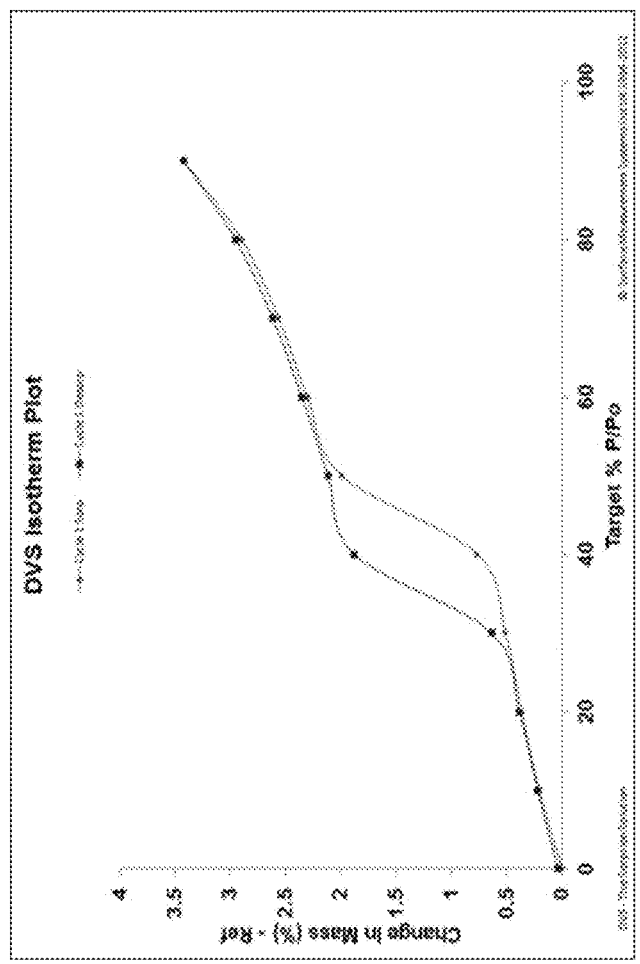
FIG. 108 shows a DVS isotherm plot for Compound 1 Hydrochloride (Form B).

In some embodiments, the Compound 1 Hydrochloride (Form B) exhibits a DVS isotherm plot that is substantially similar to FIG. 108. In other embodiments, the Compound 1 Hydrochloride (Form B) exhibits a gravimetric moisture sorption of about 2.9% (by weight) at 80% Relative Humidity.

In one embodiment, the present disclosure provides Compound 1 Hydrochloride (Form C). In some embodiments, the Compound 1 Hydrochloride (Form C) exhibits an XRPD comprising one or more peaks at about 14.6, 16.5, 18.0, 21.5, and 21.9 degrees two-theta with the margin of error of about ±0.5; about ±0.4; about ±0.3; about ±0.2; about ±0.1; about ±0.05; or less. In another embodiment, the XRPD of the Compound 1 Hydrochloride (Form C) further comprises one or more peaks at about 3.6, 18.8, 19.9, 22.1, and 23.7 degrees two-theta with the margin of error of about ±0.5; about ±0.4; about ±0.3; about ±0.2; about ±0.1; about ±0.05; or less.

In some embodiments, the Compound 1 Hydrochloride (Form C) exhibits an XRPD comprising peaks shown in Table 50 below:

TABLE 50

XRPD Table of Compound 1 Hydrochloride (Form C)

| 2-Theta | Intensity % |
|---|---|
| 3.6 | 36.5 |
| 9.1 | 13.5 |
| 10.8 | 8.4 |
| 12.0 | 16.4 |
| 13.3 | 24.3 |
| 14.2 | 27.6 |
| 14.6 | 62.6 |
| 16.1 | 9.1 |
| 16.5 | 100 |
| 16.9 | 30.1 |
| 18.0 | 46.2 |
| 18.8 | 32.2 |
| 19.6 | 17.7 |
| 19.9 | 31.3 |
| 20.5 | 16.4 |
| 21.5 | 94.7 |
| 21.9 | 61.3 |
| 22.1 | 41.1 |
| 22.9 | 7.1 |
| 23.7 | 32 |
| 24.4 | 8.9 |

Figure 109:
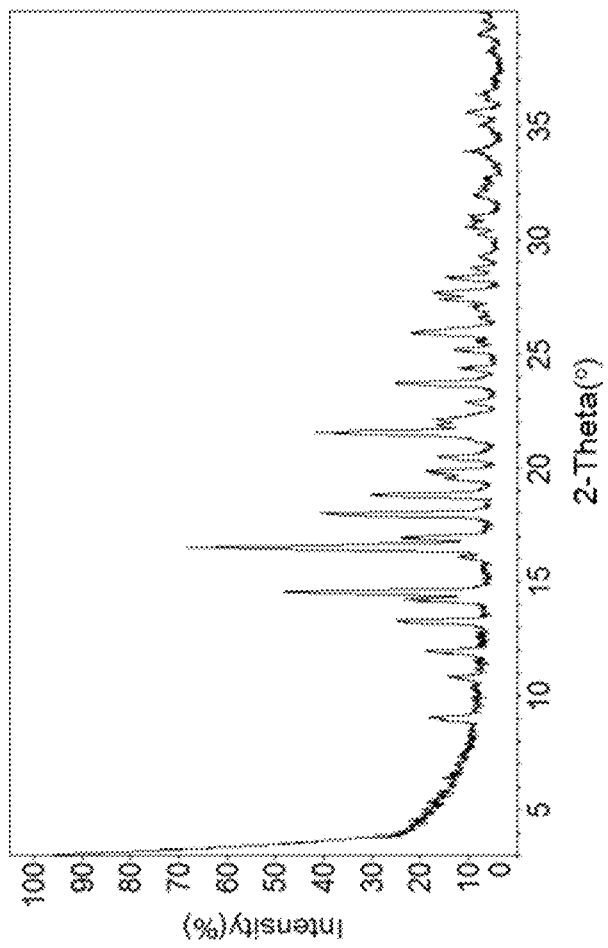
FIG. 109 shows an XRPD pattern of Compound 1 Hydrochloride (Form C).

In some embodiments, the Compound 1 Hydrochloride (Form C) exhibits an XRPD that is substantially similar to FIG. 109.

In some embodiments, the Compound 1 Hydrochloride (Form C) exhibits a DSC thermogram comprising an endotherm at about 132.9° C. with the error of margin of about ±2.5; about ±2.0; about ±1.5; about ±1.0; about ±0.5; or less. In some embodiments, the Compound 1 Hydrochloride (Form C) exhibits a DSC thermogram that is substantially similar to FIG. 110.

Figure 110:
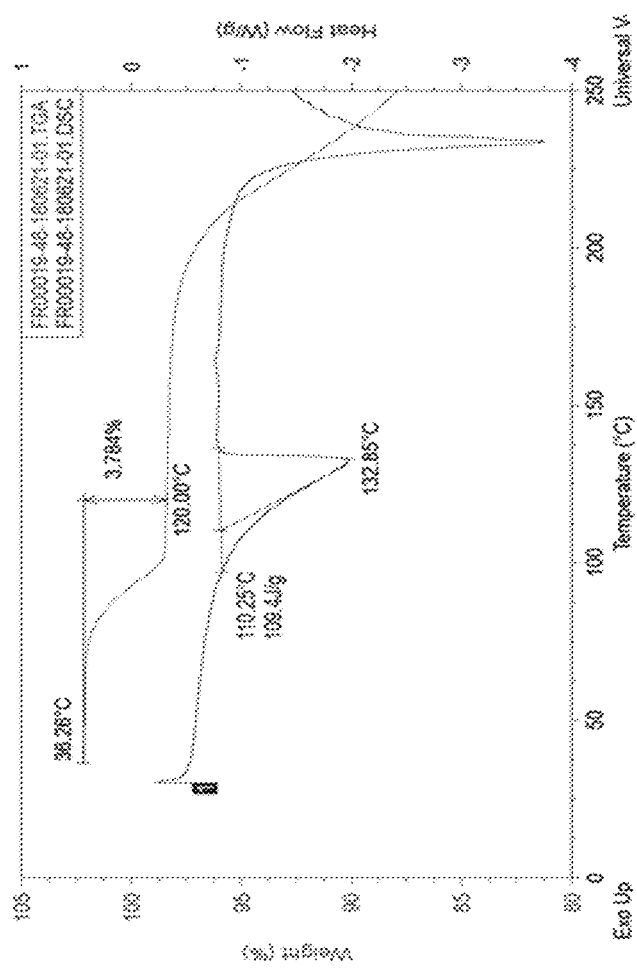
FIG. 110 shows a DSC thermogram and a TGA thermogram of Compound 1 Hydrochloride (Form C).

In some embodiments, the Compound 1 Hydrochloride (Form C) exhibits a TGA thermogram that is substantially similar to FIG. 110. In other embodiments, the TGA thermogram of the Compound 1 Hydrochloride (Form C) exhibits a weight loss of 0.0 to 3.8% in the temperature range of 25 to 120° C.

Figure 111:
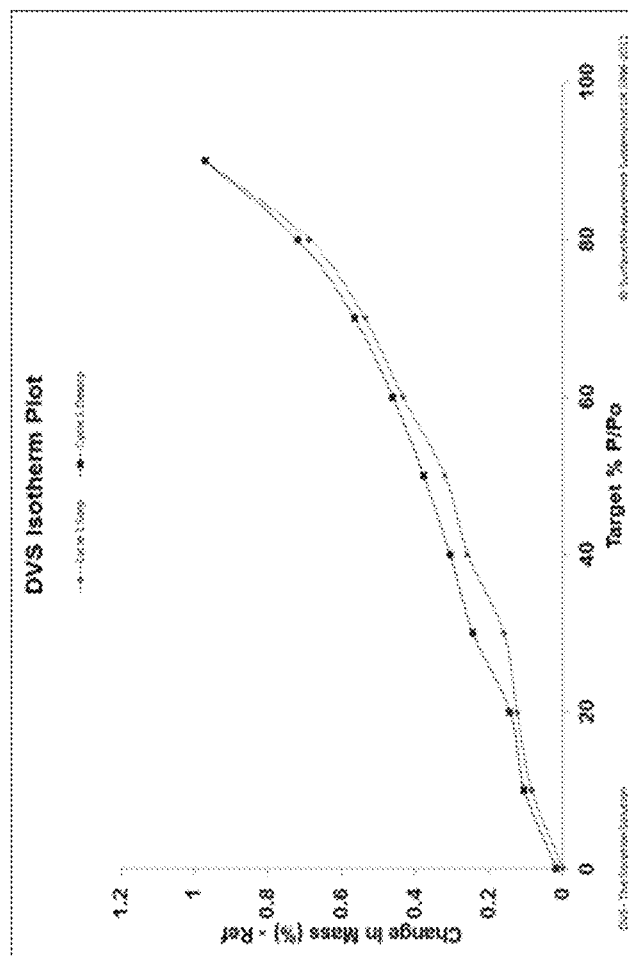
FIG. 111 shows a DVS isotherm plot for Compound 1 Hydrochloride (Form C).

In some embodiments, the Compound 1 Hydrochloride (Form C) exhibits a DVS isotherm plot that is substantially similar to FIG. 111. In other embodiments, the Compound 1 Hydrochloride (Form C) exhibits a gravimetric moisture sorption of about 0.7% (by weight) at 80% Relative Humidity.

Napsylate Salt

In some embodiments, the present disclosure provides a napsylate salt of Compound 1 ("Compound 1 Napsylate"). In some embodiments, the present disclosure provides a crystalline form of Compound 1 Napsylate.

In one embodiment, the present disclosure provides Compound 1 Napsylate (Form A). In some embodiments, the Compound 1 Napsylate (Form A) exhibits an XRPD comprising one or more peaks at about 3.4, 9.5, 16.6, 17.0, and 17.5 degrees two-theta with the margin of error of about ±0.5; about ±0.4; about ±0.3; about ±0.2; about ±0.1; about ±0.05; or less. In another embodiment, the XRPD of the Compound 1 Napsylate (Form A) further comprises one or more peaks at about 8.3, 8.7, 19.8, 25.0, and 25.5 degrees two-theta with the margin of error of about ±0.5; about ±0.4; about ±0.3; about ±0.2; about ±0.1; about ±0.05; or less.

In some embodiments, the Compound 1 Napsylate (Form A) exhibits an XRPD comprising peaks shown in Table 51 below:

TABLE 51

XRPD Table of Compound 1 Napsylate (Form A)

| 2-Theta | Intensity % |
|---|---|
| 3.4 | 100 |
| 8.3 | 5.3 |
| 8.7 | 5.1 |
| 9.5 | 5.8 |
| 16.6 | 22 |
| 17.0 | 31.5 |
| 17.5 | 11.5 |
| 19.8 | 4.4 |
| 25.0 | 4.5 |
| 25.5 | 5.4 |

Figure 112:
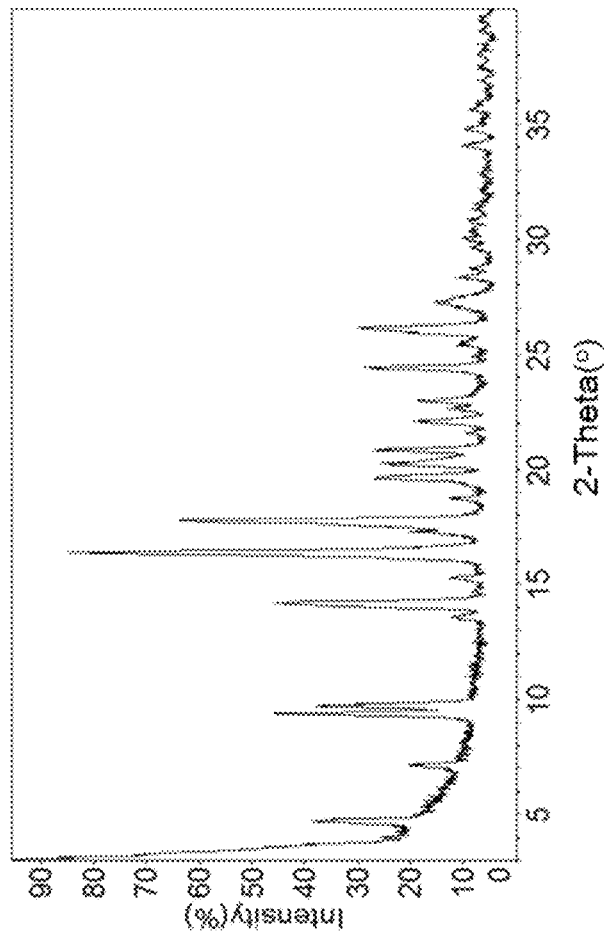
FIG. 112 shows an XRPD pattern of Compound 1 Napsylate (Form A).

In some embodiments, the Compound 1 Napsylate (Form A) exhibits an XRPD that is substantially similar to FIG. 112.

In some embodiments, the Compound 1 Napsylate (Form A) exhibits a DSC thermogram comprising an endotherm at about 100.1° C. with the error of margin of about ±2.5; about ±2.0; about ±1.5; about ±1.0; about ±0.5; or less. In some embodiments, the Compound 1 Napsylate (Form A) exhibits a DSC thermogram comprising a sharp endotherm at about 202.3° C. with the error of margin of about ±2.5; about ±2.0; about ±1.5; about ±1.0; about ±0.5; or less. In some embodiments, the Compound 1 Napsylate exhibits a DSC thermogram that is substantially similar to FIG. 113.

Figure 113:
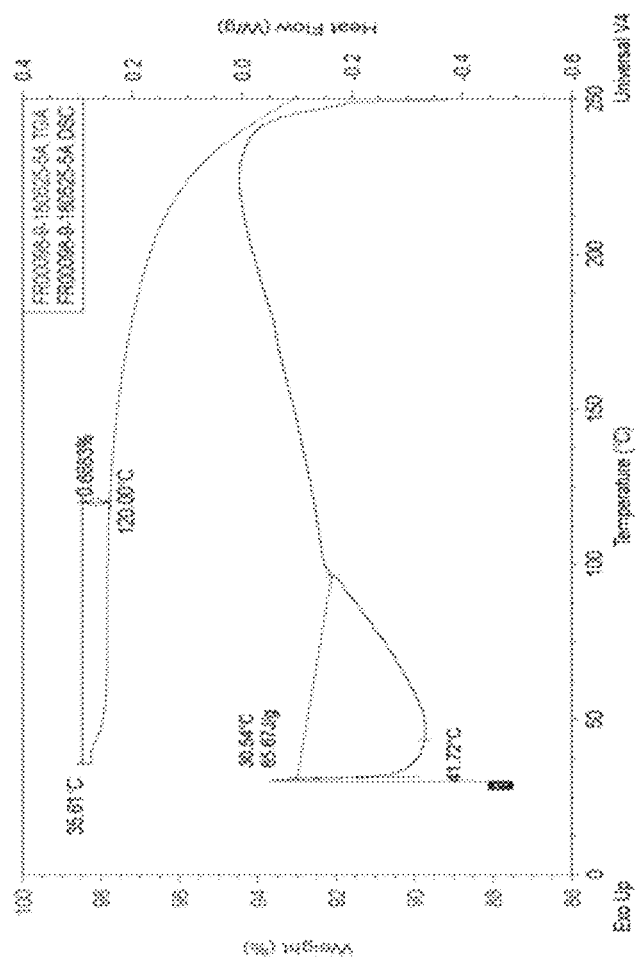
FIG. 113 shows a DSC thermogram and a TGA thermogram of Compound 1 Napsylate (Form A).

In some embodiments, the Compound 1 Napsylate (Form A) exhibits a TGA thermogram that is substantially similar to FIG. 113. In other embodiments, the TGA thermogram of the Compound 1 Napsylate exhibits a weight loss of 0.0 to 1.7% in the temperature range of 25 to 180° C.

Figure 114:
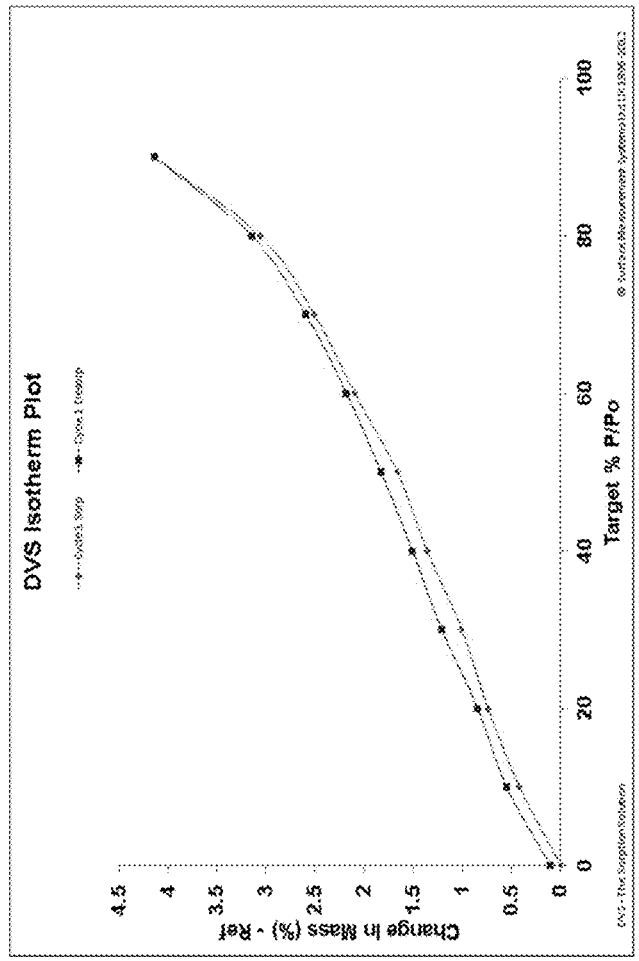
FIG. 114 shows a DVS isotherm plot for Compound 1 Napsylate (Form A).

In some embodiments, the Compound 1 Napsylate (Form A) exhibits a DVS isotherm plot that is substantially similar to FIG. 114. In other embodiments, the Compound 1 Napsylate (Form A) exhibits a gravimetric moisture sorption of about 3.9% (by weight) at 80% Relative Humidity.

In one embodiment, the present disclosure provides Compound 1 Napsylate (Form B). In some embodiments, the Compound 1 Napsylate (Form B) exhibits an XRPD comprising one or more peaks at about 9.1, 15.6, 16.1, 18.2, and 19.7 degrees two-theta with the margin of error of about ±0.5; about ±0.4; about ±0.3; about ±0.2; about ±0.1; about ±0.05; or less. In another embodiment, the XRPD of the Compound 1 Napsylate (Form B) further comprises one or more peaks at about 8.6, 12.9, 17.1, 25.8, and 26.2 degrees two-theta with the margin of error of about ±0.5; about ±0.4; about ±0.3; about ±0.2; about ±0.1; about ±0.05; or less.

In some embodiments, the Compound 1 Napsylate (Form B) exhibits an XRPD comprising peaks shown in Table 52 below:

TABLE 52

XRPD Table of Compound 1 Napsylate (Form B)

| 2-Theta | Intensity % |
|---|---|
| 8.6 | 29.7 |
| 9.1 | 100 |
| 12.9 | 34.5 |

TABLE 52-continued

XRPD Table of Compound 1 Napsylate (Form B)

| 2-Theta | Intensity % |
|---|---|
| 15.6 | 87.2 |
| 16.1 | 62.8 |
| 17.1 | 54.1 |
| 18.2 | 85.8 |
| 19.7 | 64.9 |
| 21.4 | 22.3 |
| 25.8 | 25.7 |
| 26.2 | 35.1 |

Figure 115:
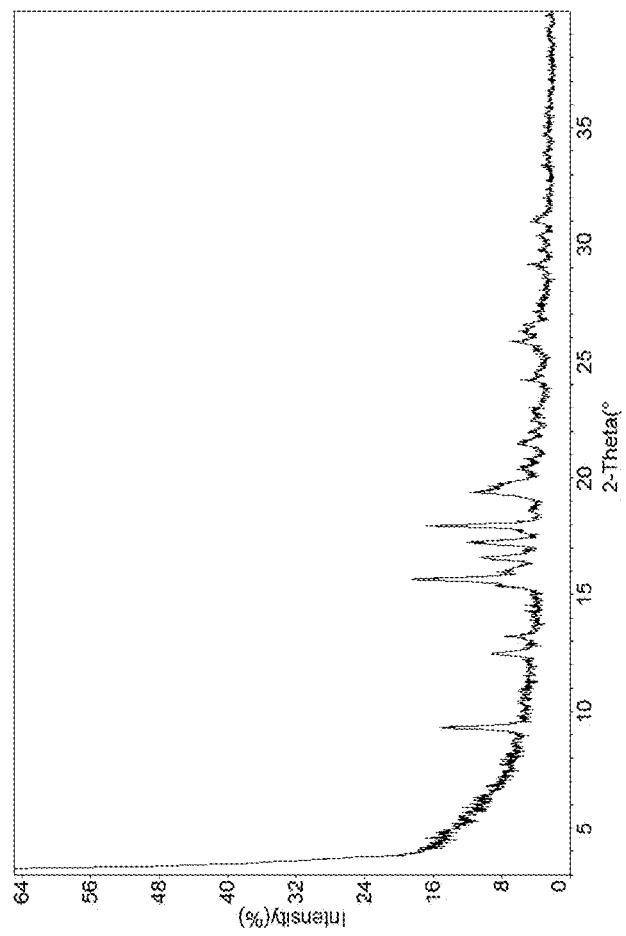
FIG. 115 shows an XRPD pattern of Compound 1 Napsylate (Form B).

In some embodiments, the Compound 1 Napsylate (Form B) exhibits an XRPD that is substantially similar to FIG. 115.

Oxalate Salt

In some embodiments, the present disclosure provides an oxalate salt of Compound 1 ("Compound 1 Oxalate"). In some embodiments, the present disclosure provides a crystalline form of Compound 1 Oxalate.

In one embodiment, the present disclosure provides Compound 1 Oxalate (Form A). In some embodiments, the Compound 1 Oxalate (Form A) exhibits an XRPD comprising one or more peaks at about 6.1, 18.2, 19.1, 19.8, and 24.3 degrees two-theta with the margin of error of about ±0.5; about ±0.4; about ±0.3; about ±0.2; about ±0.1; about ±0.05; or less. In another embodiment, the XRPD of the Compound 1 Oxalate (Form A) further comprises one or more peaks at about 12.1, 13.9, 21.1, 21.7, and 24.7 degrees two-theta with the margin of error of about ±0.5; about ±0.4; about ±0.3; about ±0.2; about ±0.1; about ±0.05; or less.

In some embodiments, the Compound 1 Oxalate (Form A) exhibits an XRPD comprising peaks shown in Table 53 below:

TABLE 53

XRPD Table of Compound 1 Oxalate (Form A)

| 2-Theta | Intensity % |
|---|---|
| 6.1 | 32.9 |
| 9.9 | 5.3 |
| 11.4 | 8.9 |
| 12.1 | 13.7 |
| 13.5 | 12.1 |
| 13.9 | 23.6 |
| 14.5 | 12.6 |
| 15.8 | 6.2 |
| 16.2 | 5.8 |
| 17.0 | 8.5 |
| 18.2 | 52.7 |
| 19.1 | 26.2 |
| 19.8 | 100 |
| 21.1 | 23.9 |
| 21.7 | 14.1 |
| 24.3 | 28.3 |
| 24.7 | 13.6 |
| 25.6 | 10.7 |
| 25.9 | 10.9 |
| 29.9 | 7.2 |
| 31.8 | 5.3 |
| 33.7 | 6 |
| 38.7 | 5.8 |

Figure 116:
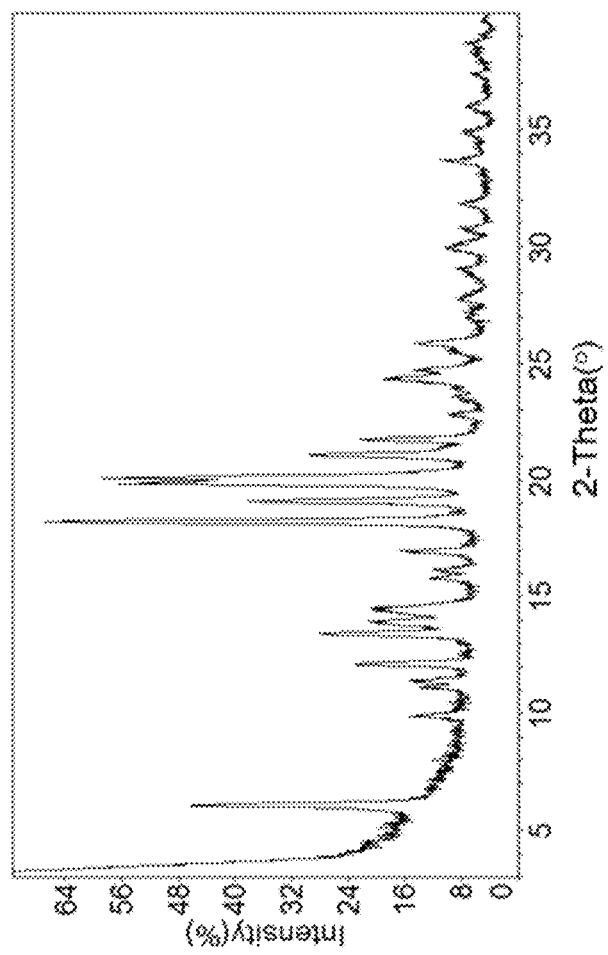
FIG. 116 shows an XRPD pattern of Compound 1 Oxalate (Form A).

In some embodiments, the Compound 1 Oxalate (Form A) exhibits an XRPD that is substantially similar to FIG. 116.

In some embodiments, the Compound 1 Oxalate (Form A) exhibits a DSC thermogram comprising an endotherm at about 163.8° C. with the error of margin of about ±2.5; about ±2.0; about ±1.5; about ±1.0; about ±0.5; or less. In some embodiments, the Compound 1 Oxalate (Form A) exhibits a DSC thermogram comprising a sharp endotherm at about 198.6° C. with the error of margin of about ±2.5; about ±2.0; about ±1.5; about ±1.0; about ±0.5; or less. In some embodiments, the Compound 1 Oxalate exhibits a DSC thermogram that is substantially similar to FIG. 117.

Figure 117:
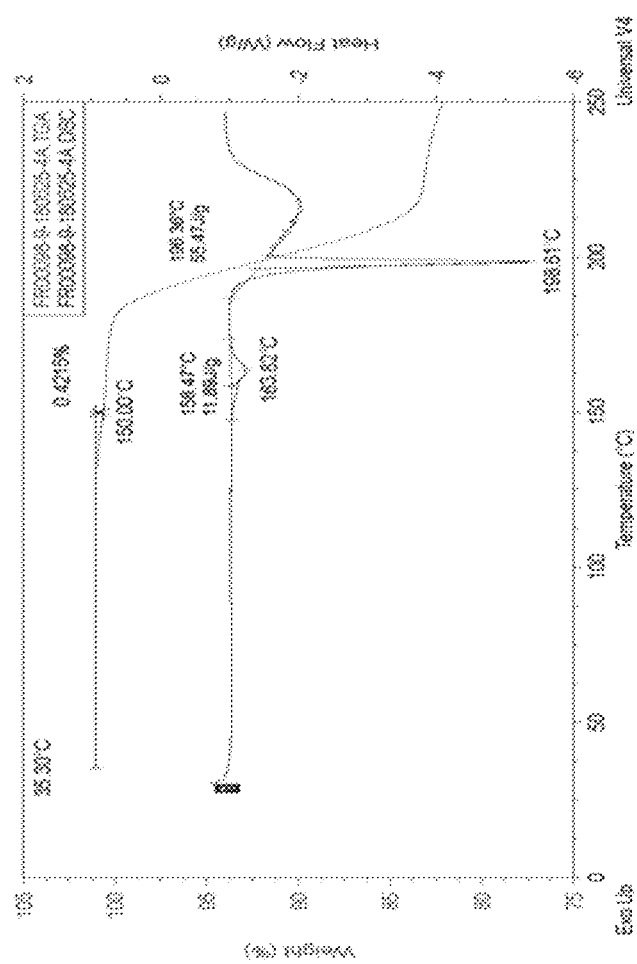
FIG. 117 shows a DSC thermogram and a TGA thermogram of Compound 1 Oxalate (Form A).

In some embodiments, the Compound 1 Oxalate (Form A) exhibits a TGA thermogram that is substantially similar to FIG. 117. In other embodiments, the TGA thermogram of the Compound 1 Oxalate exhibits a weight loss of 0.0 to 0.4% in the temperature range of 25 to 150° C.

Figure 118:
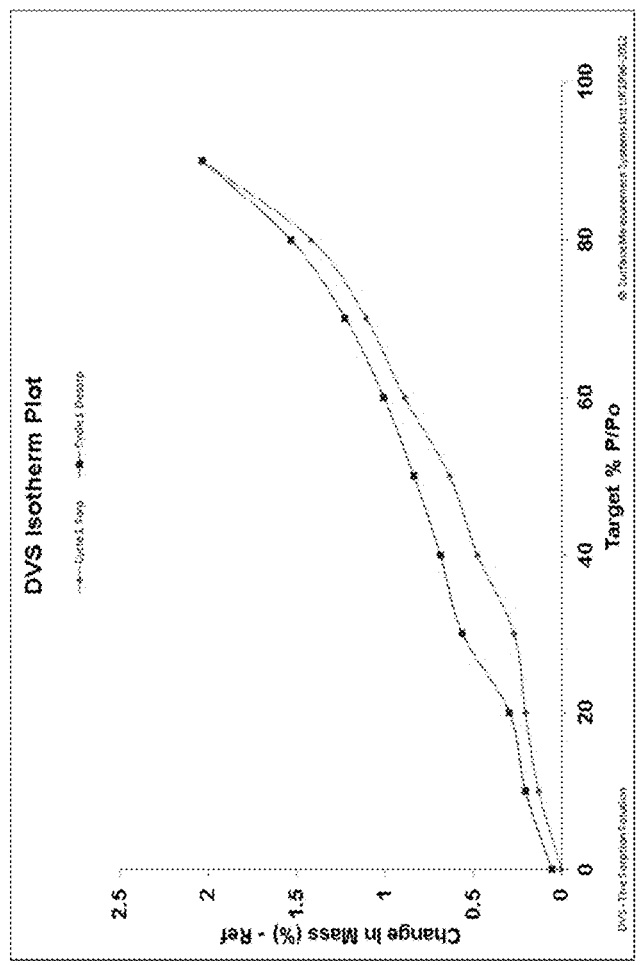
FIG. 118 shows a DVS isotherm plot for Compound 1 Oxalate (Form A).

In some embodiments, the Compound 1 Oxalate (Form A) exhibits a DVS isotherm plot that is substantially similar to FIG. 118. In other embodiments, the Compound 1 Oxalate (Form A) exhibits a gravimetric moisture sorption of about 1.4% (by weight) at 80% Relative Humidity.

In one embodiment, the present disclosure provides Compound 1 Oxalate (Form B). In some embodiments, the Compound 1 Oxalate (Form B) exhibits an XRPD comprising one or more peaks at about 6.0, 6.3, 18.2, 18.8, and 20.0 degrees two-theta with the margin of error of about ±0.5; about ±0.4; about ±0.3; about ±0.2; about ±0.1; about ±0.05; or less. In another embodiment, the XRPD of the Compound 1 Oxalate (Form B) further comprises one or more peaks at about 12.1, 12.5, 17.8, 20.7, and 23.5 degrees two-theta with the margin of error of about ±0.5; about ±0.4; about ±0.3; about ±0.2; about ±0.1; about ±0.05; or less.

In some embodiments, the Compound 1 Oxalate (Form B) exhibits an XRPD comprising peaks shown in Table 54 below:

TABLE 54

XRPD Table of Compound 1 Oxalate (Form B)

| 2-Theta | Intensity % |
|---|---|
| 6.0 | 37.1 |
| 6.3 | 56.6 |
| 9.7 | 13.9 |
| 9.9 | 13.2 |
| 12.1 | 27.1 |
| 12.5 | 34.1 |
| 13.4 | 23.2 |
| 14.0 | 22.5 |
| 14.9 | 22.5 |
| 16.9 | 21.6 |
| 17.8 | 30.4 |
| 18.2 | 47.3 |
| 18.8 | 100 |
| 19.8 | 23.4 |
| 20.0 | 42.9 |
| 20.7 | 28.3 |
| 22.7 | 16 |
| 23.5 | 33.6 |
| 25.5 | 9 |
| 29.5 | 10.2 |
| 29.9 | 7 |

Figure 119:
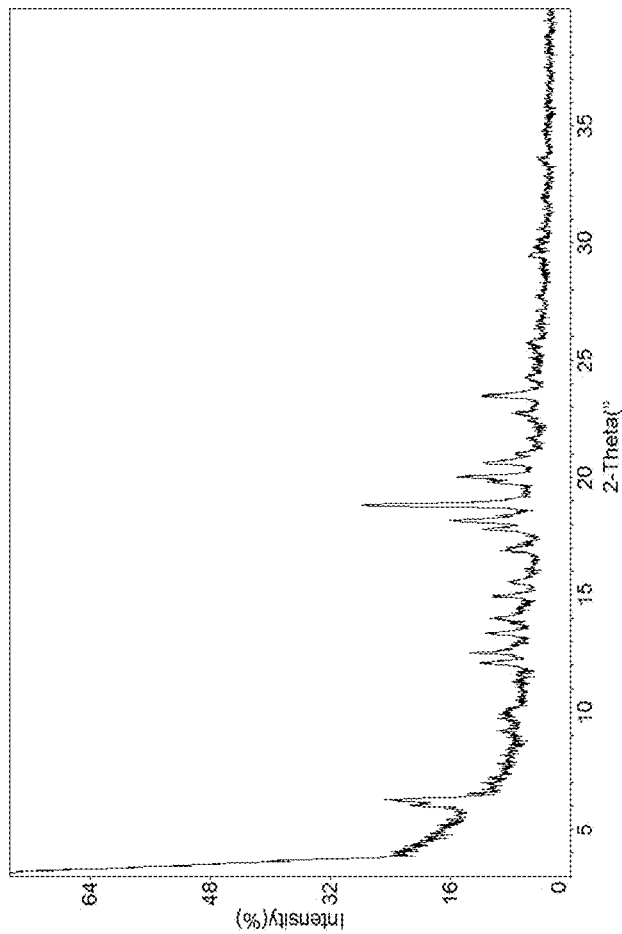
FIG. 119 shows an XRPD pattern of Compound 1 Oxalate (Form B).

In some embodiments, the Compound 1 Oxalate (Form B) exhibits an XRPD that is substantially similar to FIG. 119.

P-Aminosalicylate Salt

In some embodiments, the present disclosure provides a p-aminosalicylate salt of Compound 1 ("Compound 1 P-Aminosalicylate"). In some embodiments, the present disclosure provides a crystalline form of Compound 1 P-Aminosalicylate.

In one embodiment, the present disclosure provides Compound 1 P-Aminosalicylate (Form A). In some embodiments, the Compound 1 P-Aminosalicylate (Form A) exhibits an XRPD comprising one or more peaks at about 5.4, 13.8, 15.7, 20.7, and 21.2 degrees two-theta with the margin of error of about ±0.5; about ±0.4; about ±0.3; about ±0.2; about ±0.1; about ±0.05; or less. In another embodiment, the XRPD of the Compound 1 P-Aminosalicylate (Form A) further comprises one or more peaks at about 12.5, 13.5, 15.3, 19.2, and 27.6 degrees two-theta with the margin of error of about ±0.5; about ±0.4; about ±0.3; about ±0.2; about ±0.1; about ±0.05; or less.

In some embodiments, the Compound 1 P-Aminosalicylate (Form A) exhibits an XRPD comprising peaks shown in Table 55 below:

TABLE 55

XRPD Table of Compound 1 P-Aminosalicylate (Form A)

| 2-Theta | Intensity % |
| --- | --- |
| 5.4 | 46.7 |
| 7.0 | 8.2 |
| 9.9 | 6.4 |
| 12.5 | 27.2 |
| 13.0 | 18.7 |
| 13.5 | 18.8 |
| 13.8 | 42.3 |
| 14.9 | 5.6 |
| 15.3 | 20.5 |
| 15.7 | 32.9 |
| 16.6 | 18.3 |
| 17.5 | 5.7 |
| 18.5 | 10.8 |
| 18.9 | 10.9 |
| 19.2 | 25.3 |
| 19.9 | 10.9 |
| 20.7 | 91.8 |
| 21.2 | 100 |
| 21.8 | 9.1 |
| 22.1 | 9 |
| 23.0 | 9.1 |
| 23.3 | 8.9 |
| 24.2 | 13.3 |
| 27.6 | 29.6 |
| 28.1 | 15.2 |

Figure 120:
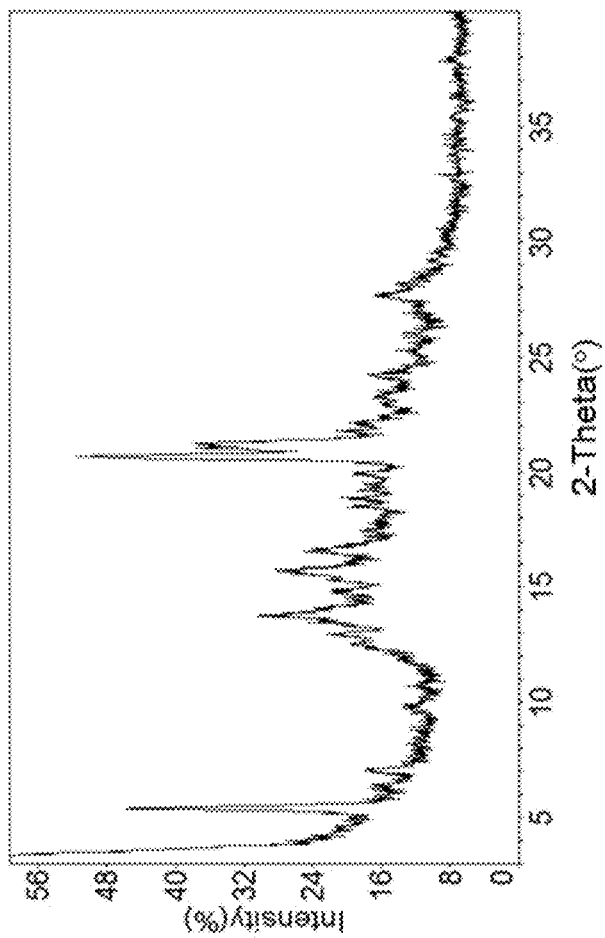
FIG. 120 shows an XRPD pattern of Compound 1 P-Aminosalicylate (Form A).

In some embodiments, the Compound 1 P-Aminosalicylate (Form A) exhibits an XRPD that is substantially similar to FIG. 120.

In some embodiments, the Compound 1 P-Aminosalicylate (Form A) exhibits a DSC thermogram comprising an endotherm at about 97.1° C. with the error of margin of about ±2.5; about ±2.0; about ±1.5; about ±1.0; about ±0.5; or less. In some embodiments, the Compound 1 P-Aminosalicylate (Form A) exhibits a DSC thermogram comprising a endotherm at about 146.8° C. with the error of margin of about ±2.5; about ±2.0; about ±1.5; about ±1.0; about ±0.5; or less. In some embodiments, the Compound 1 P-Aminosalicylate (Form A) exhibits a DSC thermogram that is substantially similar to FIG. 121.

Figure 121:
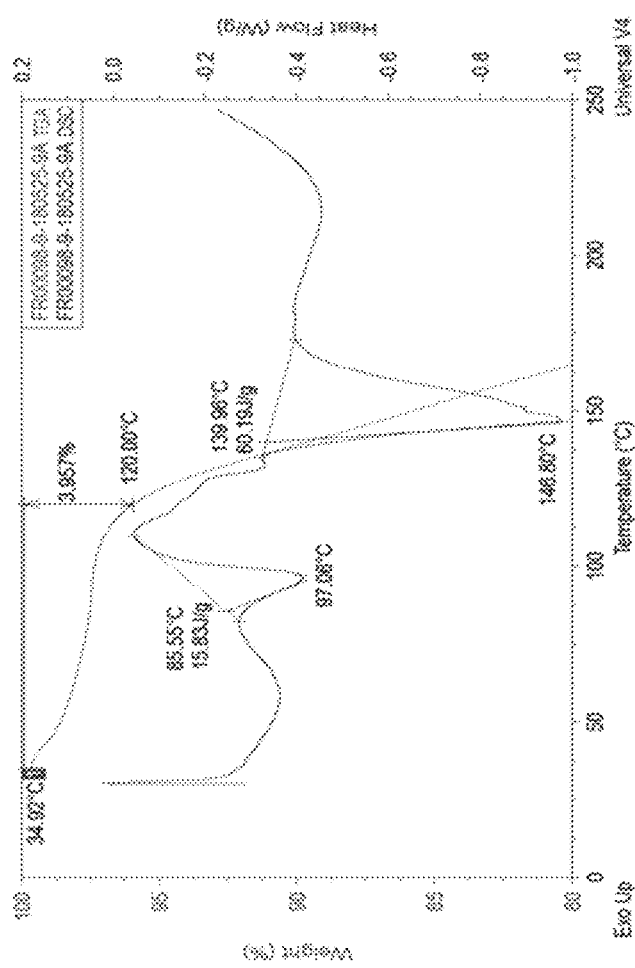
FIG. 121 shows a DSC thermogram and a TGA thermogram of Compound 1 P-Aminosalicylate (Form A).

In some embodiments, the Compound 1 P-Aminosalicylate (Form A) exhibits a TGA thermogram that is substantially similar to FIG. 121. In other embodiments, the TGA thermogram of the Compound 1 P-Aminosalicylate (Form A) exhibits a weight loss of 0.0 to 4.0% in the temperature range of 25 to 120° C.

Figure 122:
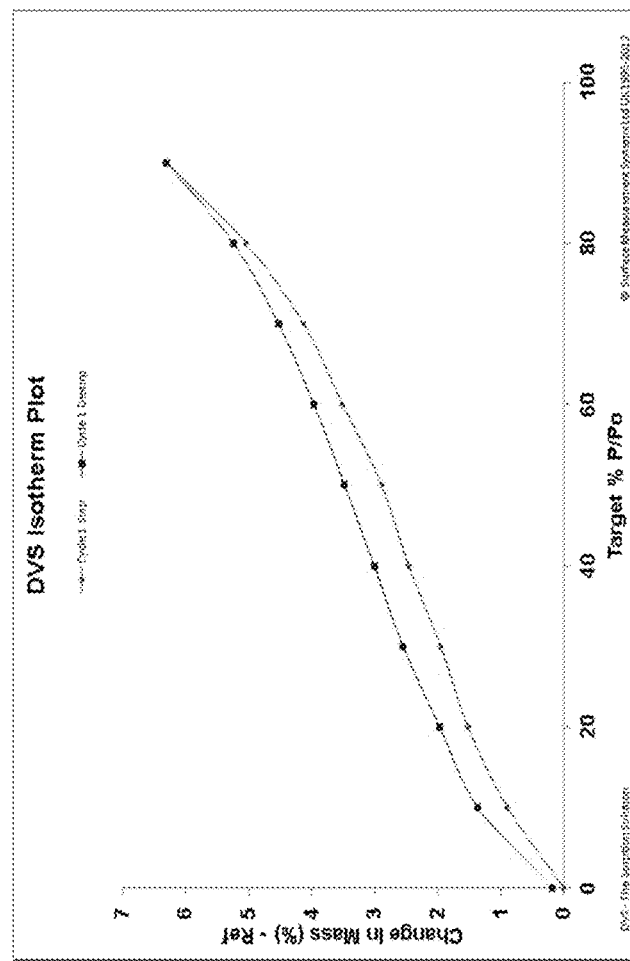
FIG. 122 shows a DVS isotherm plot for Compound 1 P-Aminosalicylate (Form A).

In some embodiments, the Compound 1 P-Aminosalicylate (Form A) exhibits a DVS isotherm plot that is substantially similar to FIG. 122. In other embodiments, the Compound 1 P-Aminosalicylate (Form A) exhibits a gravimetric moisture sorption of about 4.0% (by weight) at 80% Relative Humidity.

In one embodiment, the present disclosure provides Compound 1 P-Aminosalicylate (Form B). In some embodiments, the Compound 1 P-Aminosalicylate (Form B) exhibits an XRPD comprising one or more peaks at about 12.3, 15.2, 17.3, 19.9, and 22.9 degrees two-theta with the margin of error of about ±0.5; about ±0.4; about ±0.3; about ±0.2; about ±0.1; about ±0.05; or less. In another embodiment, the XRPD of the Compound 1 P-Aminosalicylate (Form B) further comprises one or more peaks at about 6.3, 12.5, 14.8, 16.4, and 20.7 degrees two-theta with the margin of error of about ±0.5; about ±0.4; about ±0.3; about ±0.2; about ±0.1; about ±0.05; or less.

In some embodiments, the Compound 1 P-Aminosalicylate (Form B) exhibits an XRPD comprising peaks shown in Table 56 below:

TABLE 56

XRPD Table of Compound 1 P-Aminosalicylate (Form B)

| 2-Theta | Intensity % |
| --- | --- |
| 6.3 | 47.2 |
| 12.3 | 100 |
| 12.5 | 44.8 |
| 14.0 | 18 |
| 14.8 | 42.6 |
| 15.2 | 83.7 |
| 16.4 | 47.8 |
| 16.9 | 31.3 |
| 17.3 | 66.8 |
| 18.3 | 17.9 |
| 18.9 | 17.7 |
| 19.5 | 41.3 |
| 19.9 | 84.9 |
| 20.7 | 42.4 |
| 22.0 | 19.9 |
| 22.9 | 65.1 |
| 23.2 | 31.9 |
| 25.9 | 21.4 |
| 28.1 | 19.6 |
| 29.1 | 23 |

Figure 123:
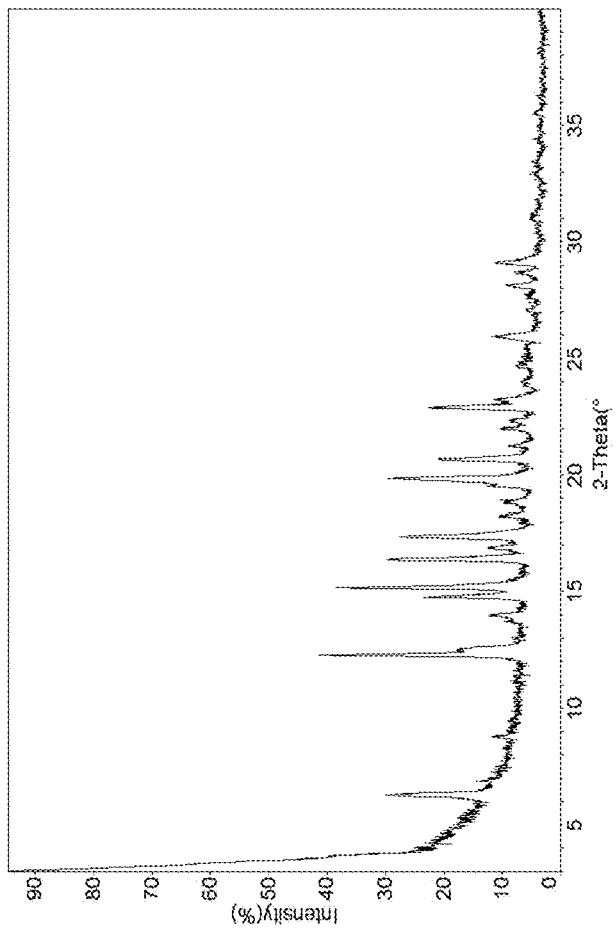
FIG. 123 shows an XRPD pattern of Compound 1 P-Aminosalicylate (Form B).

In some embodiments, the Compound 1 P-Aminosalicylate (Form B) exhibits an XRPD that is substantially similar to FIG. 123.

Maleate Salt

In some embodiments, the present disclosure provides a maleate salt of Compound 1 ("Compound 1 Maleate"). In some embodiments, the present disclosure provides a crystalline form of Compound 1 maleate.

In one embodiment, the present disclosure provides Compound 1 Maleate (Form A). In some embodiments, the Compound 1 Maleate (Form A) exhibits an XRPD comprising one or more peaks at about 6.4, 9.5, 11.2, 13.1, 15.0, and 17.6 degrees two-theta with the margin of error of about ±0.5; about ±0.4; about ±0.3; about ±0.2; about ±0.1; about ±0.05; or less. In another embodiment, the XRPD of the Compound 1 Maleate (Form A) further comprises one or more peaks at about 11.2, 12.6, 14.0, 16.7, and 19.2 degrees two-theta with the margin of error of about ±0.5; about ±0.4; about ±0.3; about ±0.2; about ±0.1; about ±0.05; or less.

In some embodiments, the Compound 1 Maleate (Form A) exhibits an XRPD comprising peaks shown in Table 57 below:

TABLE 57

XRPD Table of Compound 1 Maleate (Form A)

| 2-Theta | Intensity % |
| --- | --- |
| 6.4 | 100 |
| 8.1 | 24.2 |

TABLE 57-continued

XRPD Table of Compound 1 Maleate (Form A)

| 2-Theta | Intensity % |
|---|---|
| 9.5 | 74.6 |
| 11.2 | 54.4 |
| 11.6 | 24.6 |
| 12.6 | 31.0 |
| 13.1 | 57.1 |
| 14.0 | 39.7 |
| 15.0 | 86.5 |
| 16.7 | 46.4 |
| 17.6 | 65.1 |
| 19.2 | 44.4 |
| 23.6 | 21.0 |
| 24.2 | 16.3 |
| 24.8 | 15.9 |

Figure 124:
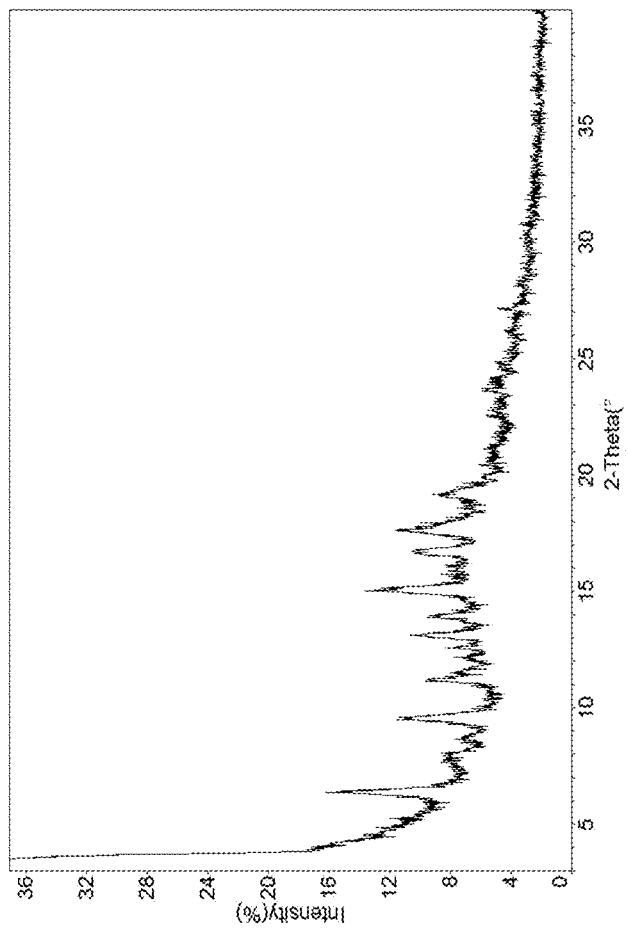
FIG. 124 shows an XRPD pattern of Compound 1 Maleate (Form A).

In some embodiments, the Compound 1 Maleate (Form A) exhibits an XRPD that is substantially similar to FIG. 124.

Methods of Preparing Salts of Compound 1

Salts of Compound 1 (and crystalline forms thereof) may be prepared, for example, by mixing Compound 1 free base and an acid (such as hydrochloric acid) in a suitable solvent to provide the Compound 1 salt as a suspension in the suitable solvent. In some embodiments, the Compound 1 salts may be prepared by slow evaporation, slow cooling or antisolvent addition to the mixture of Compound 1 free base and an acid.

In some embodiments, the present disclosure provides methods of making crystalline forms of salts of Compound 1. In some embodiments, a salt of Compound 1 is suspended in a suitable solvent for a time sufficient to provide a suspension of a crystalline form of the salt of Compound 1.

In some embodiments, a salt of Compound 1 is dissolved in a suitable solvent to provide a solution and a crystalline form of the salt of Compound 1 is precipitated from the solution. In some further embodiments, the salt of Compound 1 is dissolved by heating a mixture of a salt of Compound 1 and a suitable solvent. In some further embodiments, a crystalline form of the salt of Compound 1 is precipitated from the solution by cooling the solution. In other further embodiments, the crystalline form of the salt of Compound 1 is precipitated from the solution by adding an anti-solvent (i.e., a solvent that decreases the solubility of the crystalline form of the salt of Compound 1) the solution. In still other further embodiments, a crystalline form of the salt of Compound 1 is precipitated from the solution by evaporating a portion of the suitable solvent from the solution. In certain further embodiments, the suitable solvent comprises water.

In some embodiments, a salt of Compound 1 is heated to provide a melt and the melt is cooled to provide a crystalline form of the salt of Compound 1. In some embodiments, a salt of Compound 1 is compressed at a pressure and for a time sufficient (for example, 5 mPa for 5 minutes) to provide a crystalline form of the salt of Compound 1. In some embodiments, a salt of Compound 1 is ground (for example, using a mortar and pestle or a mill) to provide a crystalline form of the salt of Compound 1. In some further embodiments, a salt of Compound 1 is ground in the presence of a suitable solvent to provide crystalline form of the salt of Compound 1. In some embodiments, a salt of Compound 1 is subjected to a relative humidity and temperature (for example, 75% relative humidity at 45° C.), for a time sufficient to provide a crystalline form of the salt of Compound 1.

In some embodiments, the suitable solvent comprises a non-protic solvent. In some embodiments, the non-protic solvent comprises at least one solvent selected from dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethylsulfoxide, propionitrile, ethyl formate, methyl acetate, methyl ethyl ketone (MEK), hexachloroacetone, acetone, ethyl methyl ketone, ethyl acetate, sulfolane, N,N-dimethylpropionamide, tetramethylurea, nitromethane, nitrobenzene, or hexamethylphosphoramide, diethoxymethane, tetrahydrofuran, toluene, 1,3-dioxane, 1,4-dioxane, furan, diethyl ether, tetrahydropyran, diisopropyl ether, dibutyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether. In some embodiments, the non-protic solvent is acetone. In some embodiments, the non-protic solvent is ethyl acetate. In some embodiments, the non-protic solvent is acetonitrile.

In some embodiments, the suitable solvent comprises protic solvent. In some embodiments, the protic solvent comprises at least one solvent selected from water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, and glycerol. In some embodiments, the protic solvent comprises a mixture of 2-propanol and water.

In some embodiments, the suitable solvent is a single solvent. In some embodiments, the solvent is a mixture of solvents. In some embodiments, the suitable solvent is a mixture of a protic solvent and a non-protic solvent.

In certain embodiments, the Compound 1 salts (or crystalline forms of the salts) are isolated after they are prepared. The isolation of the salts (or crystalline forms of the salts) may be accomplished using methods such as filtration, decantation, centrifugation or other suitable separation technique.

In certain embodiments, the isolated salts (or crystalline forms of the salts) are optionally washed with a liquid such as an anti-solvent, acetonitrile, methanol, ethanol, ethyl acetate, methyl ethyl ketone, acetone, tetrahydrofuran, or a combination thereof.

In certain embodiments, the salts of Compound 1 prepared by the embodiments above are substantially pure. For example, in some embodiments, the chemical purity of the salt of Compound 1 (for example Compound 1 Hydrochloride) may comprise at least about 99.9%, about 99.8%, about 99.7%, about 99.6%, about 99.5%, about 99.4%, about 99.3%, about 99.2%, about 99.1%, about 99.0%, about 98%, about 97%, about 96%, or about 95% of the salt of Compound 1. Chemical purity may be determined using methods known to those skilled in the area (for example, HPLC chromatography with a suitable solvent and column detecting a wavelength of 210 nm). In some embodiments, the substantial purity is determined on a weight percent basis. In some embodiments, the substantial purity is determined on an area under the curve basis.

In some embodiments, the salts of Compound 1 prepared by the embodiments above are crystalline. In certain embodiments, the crystalline salts of Compound 1 prepared by the embodiments above are substantially pure. For example, in some embodiments, the polymorphic purity of the crystalline salt of Compound 1 (for example Compound 1 Hydrochloride) may comprise at least about 99.9%, about 99.8%, about 99.7%, about 99.6%, about 99.5%, about 99.4%, about 99.3%, about 99.2%, about 99.1%, about 99.0%, about 98%, about 97%, about 96%, about 95%, about 94%, about 93%, about 92%, about 91%, about 90%, ab out 85%, ab out 80%, ab out 75%, ab out 70%, ab out 65%, ab out 60%, ab out 55% or ab out 50% of a single crystalline form (for example, Compound 1 Hydrochloride (Form A)). Polymorphic purity may be determined using methods known to those skilled in the art (including, among others, X-ray powder crystallography as described in Shah, B., et al., Analytical techniques for quantification of amorphous/crystalline phases in pharmaceutical solids, J. Pharm. Sci. 2006, 95(8), pages 1641-1665 which is hereby incorporated by reference in its entirety).

In some embodiments, the salts of Compound 1 prepared by the embodiments above are epimerically enriched at one or more positions compared to the epimeric purity of the Compound 1 free base starting material. For example, in some embodiments, the salt of Compound 1 may comprise at least about 8:1, about 9:1, about 10:1, about 11:1, about 12:1, about 13:1, about 14:1, about 15:1, or about 20:1 of 17-β:17α epimer of Compound 1. In some embodiments, the salt of Compound 1 may comprise at least about 8:1, about 9:1, about 10:1, about 11:1, about 12:1, about 13:1, about 14:1, about 15:1, or about 20:1 of 3α-hydroxy:3β-hydroxy of Compound 1. In other embodiments, the epimeric purity of the salts of Compound 1 as described herein is substantially the same as the epimeric purity of the Compound 1 free base starting material.

Pharmaceutical Compositions

In one aspect, the present disclosure provides a pharmaceutical composition comprising a salt of Compound 1. In some embodiments, the salt of Compound 1 is Compound 1 Hydrobromide, Compound 1 Citrate, Compound 1 L-Malate, Compound 1 Mesylate, Compound 1 Phosphate, Compound 1 L(+)-Tartrate, Compound 1 Hydrochloride, Compound 1 Tosylate, Compound 1 Glucuronate, or Compound 1 Ethanesulfonate. In some embodiments, the salt of Compound 1 is Compound 1 Hydrobromide (Form A). In some embodiments, the salt of Compound 1 is Compound 1 Hydrobromide (Form B). In some embodiments, the salt of Compound 1 is Compound 1 Hydrobromide (Form C). In some embodiments, the salt of Compound 1 is Compound 1 Hydrobromide (Form D). In some embodiments, the salt of Compound 1 is Compound 1 Hydrobromide (Form E). In some embodiments, the salt of Compound 1 is Compound 1 Citrate (Form A). In some embodiments, the salt of Compound 1 is Compound 1 Citrate (Form B). In some embodiments, the salt of Compound 1 is Compound 1 Citrate (Form C).

The compositions may be administered by a suitable route, including, but not limited to, orally, parenterally, rectally, topically and locally. The compositions may be in liquid, semi-liquid or solid form and may be formulated using methods known to those skilled in the art in a manner suitable for each route of administration.

Orally administered dosage forms include, for example, solid dosage forms (such as tablets, capsules, pills, granules, and the like) and liquid dosage forms (such as oral solutions, oral suspensions, syrups and the like).

In some embodiments, the pharmaceutical composition comprises a therapeutically effective amount of a salt of Compound 1 or solvate thereof and a pharmaceutically acceptable excipient.

Methods of Use

In one aspect, the present invention provides methods of treating a disease or condition in a subject in need thereof comprising administering to the subject a therapeutically effective amount of a salt of Compound 1.

In some embodiments, the disease or condition is depression. In some embodiments, the disease or condition is treatment resistant depression. In some embodiments, the disease or condition is post-partum depression. In some embodiments, the disease or condition is major depressive disorder. In some embodiments, the disease or condition is bipolar disorder. In some embodiments, the disease or condition is epilepsy. In some embodiments, the disease or condition is anxiety.

EXAMPLES

The present invention is further illustrated by reference to the following Examples. However, it is noted that these Examples, like the embodiments described above, are illustrative and are not to be construed as restricting the scope of the invention in any way.

"EtOAc" means ethyl acetate. "(m)DSC" means (modulated) differential scanning calorimetry. "ACN" means acetonitrile. "AR" means analytically pure. "DCM" means dichloromethane. "DMF" means dimethyl formamide. "DMSO" means dimethylsulfoxide. "DI" means distilled. "DSC" means differential scanning calorimetry. "DVS" means dynamic vapor sorption. "e.q." means equivalents. "EtOH" means ethyl alcohol. "FaSSIF" means fasted state simulated intestinal fluids. "FeSSIF" means fed state simulated intestinal fluids. "1H-NMR" means proton nuclear magnetic resonance. "IPA" means isopropanol. "IPAC" means isopropyl acetate. "IPE" means diisopropyl ether. "LC" means low crystallinity. "MEK" means methyl ethyl ketone. "MeOH" means methyl alcohol. "MIBK" means methyl isobutyl ketone. "MTBE" means Methyl Tert-Butyl ether. "NMR" means nuclear magnetic resonance. "PLM" means polarized light microscope. "RH" means relative humidity. "RRT" means relative retention time. "RT" means Room temperature. "RT(min)" means Retention time. "SGF" means simulated gastric fluids. "TGA" means Thermal gravimetric analysis. "THF" means Tetrahydrofuran. "UPLC" means ultra performance liquid chromatography. "XRPD" means X-ray Powder Diffractometer.

In some instances, the ratio of Compound 1:acid in the Compound 1 salts described herein was determined by the ion chromatography (IC) using the following method: 25 μL of 10.0 μg/mL sample or standard were injected into a Dionex IonPac AG18 column with a flow rate of 1.0 mL/min and detected by a Thermo ICS-2100 Conductivity detector. ASRS-4 mm suppressor was set at 38 mA and the column temperature was 30° C. The chromatographic elution was 15 mM KOH with a total run time of 20 minutes.

X-Ray Powder Diffraction patterns were collected on a Rigaku D/Max-2200/PC or a Bruker D8 Advance powder diffractometer. The samples were irradiated with copper K-alpha X-rays ($\lambda$=1.54179 Å) with the generator operated at 40 kV/40 mA. The samples were scanned in continuous mode from 3° to 40° with a sample rotation speed of 15 rpm and a scanning rate of 10°/min.

Single crystal x-ray analysis: The single crystal X-ray diffraction data were obtained was using Rigaku XtaLAB Synergy-R(Cu) (Micro-Max007HF Cu mode, CuKα: $\lambda$=1.54184 Å, Hypix6000HE detector) diffractometer.

The following SCXRD Instrument parameters were used:

| Instrument | Rigaku XtaLAB Synergy R |
|---|---|
| X-Ray sources generator | MicroMax-007HF X-ray source (Cu/kα: 1.54184 Å) |
| Detector | HyPix 6000HE detector |
| Goniometer | Four-circle Kappa Goniometer |
| Low Temperature Devices | Cryostream-700 (Oxford Cryosystems) |
| Software package | CrysAlisPro (V1.171.40.14e) |

A suitable single crystal with good diffraction quality was separated out of the block-like crystal sample and was wrapped with Paratone-N(an oil based cryoprotectant). The crystal was mounted on a mylar loop in a random orientation and immersed in a stream of nitrogen at the temperature specified in the Example, below. Preliminary examination and data collection were performed on a Rigaku XtaLAB Synergy R (CuKα radiation, λ=1.54184 Å) diffractometer and analyzed with the CrysAlisPro (Rigaku, V1.171.40.14e, 2018) software package.

Structures were solved in the ShelXT (Sheldrick, G. M. Acta Cryst. 2015, A71, 3-8.) structure solution program using Intrinsic Phasing and refined with ShelXL (Version 2017/1; Sheldrick, G. M. Acta Cryst. 2015, C71, 3-8) refinement package using full-matrix least-squares on $F^2$ contained in OLEX2 (Dolomanov, O. V., Bourhis, L. J., Gildea, R. J, Howard, J. A. K. & Puschmann, H. J. Appl. Cryst. 2009, 42, 339-341). All non-hydrogen atoms were refined anisotropically. The positions of the hydrogen atoms connected with the carbon atoms were calculated geometrically and refined using the riding model, but the hydrogen atoms connected with nitrogen atom and oxygen atom were refined freely based on the Difference Fourier Map.

DSC data were collected on a TA Q2000. For each sample analyzed approximately 1 mg of the sample was placed in a hermetic aluminum pan containing a pinhole and heated from 25° C. to 250° C. ramped at 10° C./min.

TGA data were collected on TA Q5000. For each sample analyzed approximately 4 mg of material was placed in an open platinum pan and heated from 30° C. to 300° C. or weight %<80% at a rate of 10° C./min.

Dynamic Vapor Sorption (DVS) were collected conducted using an SMS DVS Advantage 1 system. For each sample analyzed approximately 10 mg of material was transferred into the DVS instrument and recorded the weight change with respect to the atmospheric humidity at 25° C. using the following parameters: Equilibrium dm/dt: 0.01%/min, (for min: 10 min and max: 180 min); drying setting were 0% RH for 120 min; RH (%) measurement step at 10% and RH (%) measurement step scope of 0-90-0%.

$^1$H-NMR were collected on a Bruker 400 MHz magnet. For each sample analyzed, approximately 6 mg of material was dissolved in 0.6 mL of $d_6$-DMSO for analysis. As is known to those skilled in the art, the relative ppm shift and integration values for $^1$H-NMR resonances may vary depending on various sample factors, including, for example, water content in the $d_6$-DMSO, ion concentration in the sample, etc. Thus, the $^1$H-NMR values reported in the following examples should not be considered characteristic for the respective salt and polymorphic form.

UPLC data were collected by injecting a 0.5 μL of sample or standard into a Waters Acquity UPLC Shield RP18 column with a flow rate of 0.8 mL/min by an Agilent 1290 UPLC (detection wavelength: 210 nm). The column was equilibrated with mobile phase A which consisted of 0.1% $H_3PO_4$ in water. Mobile phase B was acetonitrile (ACN). The chromatographic elution was programed as follows with an additional minute after for re-equilibration and a total run time of 6 minutes:

| Time (mm) | A(%) | B(%) |
|---|---|---|
| 0 | 90 | 10 |
| 4 | 10 | 90 |
| 5 | 10 | 90 |

The crystalline salts described herein were characterized by polarized light microscopy. In some embodiments, the crystalline salts described herein exhibit birefringence, which indicates crystallinity.

Example 1: Preparation of Hydrobromide Salt of Compound 1

Hydrobromide Salts of Compound 1 may be prepared from Compound 1 using the following exemplary methods.

Compound 1 HBr (Form A):

500 mg of Compound 1 (Pattern A, see XRPD in FIG. 1) was dissolved in 16.0 mL of acetone at 60° C. while stirring at 500 rpm and held at 60° C. for 1.5 hrs. 1.1 e.q. hydrobromic acid in acetone (2.565 mL, 0.5 mol/L) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs resulting in 532.16 mg of powder with a yield of 72.05%.

The resulting solid is Compound 1 HBr (Form A). The ratio of Compound 1:HBr in Compound 1 HBr (Form A) is 1:1.02 as determined by ion chromatography. The XPRD is shown in FIG. 2; the DSC and TGA are shown in FIG. 3; and the DVS is shown in FIG. 4.

Compound 1 HBr (Form B):

1 g of Compound 1 HBr (Form A) was suspended in 20 mL of 0.603 water activity solution (14.5% water in acetone, v/v) to generate a suspension of 50 mg/mL. The suspension was stirred at 700 rpm and held at 50° C. for 26 hours. The suspension was centrifuged and the precipitate collected. The obtained wet product was vacuum dried at 30° C. for three days resulting in powder with yield of 70.82%. The ratio of Compound 1:HBr in Compound 1 HBr (Form B) is 1:1.01 as determined by ion chromatography. The XPRD is shown in FIG. 5; the DSC and TGA are shown in FIG. 6; and the DVS is shown in FIG. 7.

Compound 1 HBr (Form C):

500 mg of Compound 1 HBr (Form A) was dissolved in 4.5 mL of DMSO to generate a clear solution, then 31.5 mL of water (anti-solvent) was added to the DMSO solution. The solution was left at room temperature for seven days. Afterward, the precipitated material was isolated. The obtained wet product was vacuum dried at 30° C. for three days resulting in powder with yield of 66.1%. The ratio of Compound 1:HBr in Compound 1 HBr (Form C) is 1:1.09 as determined by ion chromatography. The XPRD is shown in FIG. 8; the DSC and TGA are shown in FIG. 9; and the DVS is shown in FIG. 10.

Compound 1 HBr (Form D):

Form D is observed by VT-XRPD when heating Form B to 160° C. The XRPD is shown in FIG. 11; the TGA and DSC are shown in FIG. 12.

Compound 1 HBr (Form E):

In a 20 mL vial with stir bar, Compound 1 (1.00 g, 1.0 equiv.) in EtOH (5 mL) was stirred at 60° C. for 30 mins. HBr (48% w/w in water, 0.3 mL, 1.1 equiv.) was added to the mixture and stirred at 60° C. for 1 hr. The reaction mixture was cooled to 25° C. and ethyl acetate anti-solvent (5 mL) was added to the reaction mixture and stirred for 1 hr. The mixture was kept in an ice bath for 30 mins followed by filtration and solids were collected and dried under vacuum at 25° C. overnight to afford Compound 1 HBr (876 mg, 73.7% yield). The XRPD is shown in FIG. 13; the DSC and TGA are shown in FIG. 14.

General Procedures to Prepare Compound 1 HBr

The following general procedures were conducted to prepare Compound 1 HBr.

General Procedure 1

In a 20 mL vial with stir bar, Compound 1 (1.00 g, 1.0 equiv.) in solvent (15 mL, 15 mL/g Compound 1), was stirred at 60° C. for 30 mins. HBr (48% w/w in water, 0.3 mL, 1.1 equiv.) was added to the reaction and stirred at 60° C. for 1 hr. The reaction was cooled to 25° C. and stirred for 1 hr. The mixture was kept in ice bath for 30 mins (procedure 1-2 was kept at 25° C.) followed by filtration and solids were collected and dried under vacuum at 25° C. overnight to afford Compound 1 HBr.

General Procedure 2

In a 20 mL vial with stir bar, Compound 1 (1.00 g, 1.0 equiv.) in solvent (3.5 mL, 3.5 mL/g Compound 1), was stirred at 60° C. for 30 mins. HBr (48% w/w in water, 0.3 mL, 1.1 equiv.) in acetone (3.5 mL, 3.5 mL/g Compound 1) was added to the reaction and stirred at 60° C. for 1 hr. The reaction was cooled to 25° C. and stirred for 1 hr. The mixture was kept in ice bath for 30 mins followed by filtration and solids were collected and dried under vacuum at 25° C. overnight to afford Compound 1 HBr.

General Procedure 3

In a 20 mL vial with stir bar, Compound 1 (1.00 g, 1.0 equiv.) in EtOH (5 mL, 5 mL/g Compound 1), was stirred at 60° C. for 30 mins. HBr (48% w/w in water, 0.3 mL, 1.1 equiv.) was added to the mixture and stirred at 60° C. for 1 hr. The reaction mixture was cooled to 25° C., then anti-solvent (5 mL, 5 mL/g Compound 1) was added to the reaction mixture and stirred for 1 hr. The mixture was kept in an ice bath for 30 mins followed by filtration and solids were collected and dried under vacuum at 25° C. overnight to afford Compound 1 HBr.

The following table summarizes preparations of Compound 1 HBr according to these general procedures:

| General Procedure | 1-2 | 1-2 | 1 | 1 | 1 | 3 |
|---|---|---|---|---|---|---|
| Solvent (mL/g Compound 1) | Acetone (15X) | 2-propanol (15X) | EtOH (15X) | EtOH/H$_2$O (1:1, 15X) | MeOH (15X) | EtOH/EtOAc (1:1, 14X) |
| Weight Yield | 88.1% | 66.0% | 50.9% | 48.0% | 38.0% | 73.7% |
| Purity | 98.5% | 99.2% | 99.1% | 98.0% | 99.6% | 99.0% |
| Form by XRPD | Form A | Form A | Form A | Form A | Form A + E | Form E |

| General Procedure | 1 | 1-2 | 2 | 2 | 3 | 3 |
|---|---|---|---|---|---|---|
| Solvent (mL/g Compound 1) | MeOH/Acetone (1:1, 15X) | EtOH/Acetone (1:1, 15X) | EtOH/Acetone (1:2, 10.5X) | EtOH/Acetone (1:4, 17.5X) | EtOH/IPE (1:2, 10.5X) | EtOH/EtOAc (1:1, 20X) |
| Weight Yield | 48.2% | 64.7% | 77.4% | 80.2% | 80.3% | 65.1% |
| Purity | 99.8% | 99.7% | 99.7% | 99.6% | 99.7% | 99.4% |
| Form by XRPD | Form E | Form A | Form A | Form A | Form A + E | Form E |

| General Procedure | 3 | 3 | 3 | 3 | 3 | 3 |
|---|---|---|---|---|---|---|
| Solvent (mL/g Compound 1) | EtOH/IPE (1:4, 17.5X) | EtOH/EtOAc (1:1, 10X) | EtOH/IPAc (1:1, 10X) | EtOH/MTBE (1:1, 10X) | EtOH/MIBK (1:1, 10X) | EtOH/Toluene (1:1, 10X) |
| Weight Yield | 86.8% | 74.4% | 79.2% | 82.0% | 77.2% | 64.4% |
| Purity | 99.6% | 99.7% | 99.8% | 99.8 % | 99.8% | 99.9% |
| Form by XRPD | Form A + E | Form E | Form A + E | Form A + E | Form E | Form A + E |

Chemical and Physical Stability Test

For each salt, approximately 5 mg compound was added into an 8 mL glass vial with a multi-hole aluminum foil cap, and kept at 60° C., 40° C./75% RH for 1 week. For photostability test, the compound in vial without cap was kept in photo-stability chamber and exposed to a total illumination of 1.2 million lux-hrs, while the sample in vial covered with aluminum foil completely was considered as the dark control. Appearance by visual observation were recorded followed by purity assessment and XPRD data collection on the residual solids.

The chemical and physical stability test results for Compound 1 HBr (Form A), Compound 1 HBr (Form B), Compound 1 HBr (Form C) and Compound 1 free base are shown in the following table:

| Test Material | Conditions | XRPD pattern | Final purity |
|---|---|---|---|
| Compound 1 | 60° C., 1 w | Pattern A | 98.2 |
| | 40° C./75% RH, 1 w | Pattern A | 98.2 |
| | 1.2 million lux-hrs | Pattern A | 97.9 |
| | Dark control | Pattern A | 98.3 |
| Hydrobromide (Form A) | 60° C., 1 w | Form A | 98.0 |
| | 40° C./75% RH, 1 w | Form A | 98.2 |
| | 1.2 million lux-hrs | Form A | 98.2 |
| | Dark control | Form A | 97.9 |
| Hydrobromide (Form B) | 60° C., 1 w | Form B | 98.8 |
| | 40° C./75% RH, 1 w | Form B | 98.9 |
| | 1.2 million lux-hrs | Form B | 98.4 |
| | Dark control | Form B | 97.8 |
| Hydrobromide (Form C) | 60° C., 1 w | Form C + B | 98.1 |
| | 40° C./75% RH, 1 w | Form C + B | 98.4 |
| | 1.2 million lux-hrs | Form C + B | 98.1 |
| | Dark control | Form C + B | 98.0 |

Solubility Tests in Simulated Gastric and Intestinal Fluids

For each salt, between about 4~6 mg of Compound 1 or the salt was added into a 2-mL vial in triplicate. Then 1 mL of bio-relevant media (SGF, FaSSIF or FeSSIF) was added into the vial. All the vials were placed on the thermo-mixer and kept at 37° C. while shaking at 700 rpm. If the compounds were completely dissolved in the media, then more compound was added until the system became a suspension, no additional material was added if the concentration of the compound exceeded 25 mg/mL. After shaking at 37° C. for 24 hrs, 300 μL of suspension from each system were isolated for analysis. The samples were centrifuged at 12000 rpm for 5 mins and the supernatant were analyzed by UPLC after dilution by ACN:$H_2O$ (4/1, V/V) for 10 times. The final pH values of bio-relevant media were measured and recorded. The solubility results (mg/mL) in bio-relevant solutions for Compound 1 HBr (Form A), Compound 1 HBr (Form B), Compound 1 HBr (Form C) and Compound 1 free base are shown in the following table:

| Solute tested | SGF (original pH = 1.82) | | FaSSIF (original pH = 6.51) | | FeSSIF (original pH = 4.99) | |
|---|---|---|---|---|---|---|
| | 24 h | Final pH | 24 h | Final pH | 24 h | Final pH |
| Compound 1 | 4.44 | 3.10 | 0.05 | 6.48 | 0.84 | 5.11 |
| Hydrobromide (Form A) | 2.60 | 1.91 | 1.04 | 4.11 | 0.88 | 5.01 |
| Hydrobromide (Form B) | 1.28 | 1.89 | 0.09 | 5.51 | 0.74 | 4.89 |
| Hydrobromide (Form C) | 1.32 | 1.99 | 0.42 | 4.90 | 0.41 | 5.05 |

Single Crystal X-Ray Analysis of Compound 1 HBr Form B

The block-like single crystal of Compound 1 Hydrobromide Form B used for SCXRD characterization were crystallized from MeOH/MEK (1:3, v/v) solvent mixture by slow evaporation method.

Characterization of the salt by PLM and XRPD showed it to be Compound 1 HBr Form B.

Cell parameters and an orientation matrix for data collection were retrieved and refined (least-squares refinement) by CrysAlisPro (Rigaku, V1.171.40.14e, 2018) software using the setting angles of 45416 reflections in the range 3.4880°<θ<75.8360°. The data were collected to a minimum diffraction angle (θ) of 3.506° and a maximum diffraction angle (θ) of 68.243° at 120.00 K. The final completeness is 100%. The mean I/σ of the data is 91.7 and the maximum resolution that was achieved was 0.83 Å.

SCXRD data obtained by the methods described herein is provided in the table below.

| Temperature | 120.00 (10) K |
|---|---|
| a | 9.28522 (4) Å |
| b | 10.84366 (4) Å |
| c | 25.21443 (11) Å |
| α | 90° |
| β | 90° |
| γ | 90° |
| Space group | $P2_12_12_1$ |
| Crystal system | Orthorhombic |
| Volume | 2538.734 (18) Å$^3$ |
| Empirical formula | $C_{26}H_{41}BrN_2O_3 \cdot H_2O$ |

Single Crystal X-Ray Analysis of Compound 1 HBr Form E

The block-like single crystal of Compound 1 Hydrobromide Form E used for SCXRD characterization were crystallized from MeOH/MEK (1:3, v/v) solvent mixture by slow evaporation method. Characterization of the salt by PLM and XRPD showed it to be Compound 1 HBr Form E.

Data collection at 120 K: Cell parameters and an orientation matrix for data collection were retrieved and refined (least-squares refinement) by CrysAlisPro (Rigaku, V1.171.40.14e, 2018) software using the setting angles of 10196 reflections in the range 3.4990°<θ<75.6570°. The data were collected to a minimum diffraction angle (θ) of 3.508° and a maximum diffraction angle (θ) of 66.553° at 120.00(10) K. The final completeness is 100%. The mean I/σ of the data is 19.3 and the maximum resolution that was achieved was 0.84 Å.

Data collection at Room Temperature: Cell parameters and an orientation matrix for data collection were retrieved and refined (least-squares refinement) by CrysAlisPro (Rigaku, V1.171.40.14e, 2018) software using the setting angles of 17551 reflections in the range 3.4830°<θ<75.8250°. The data were collected to a minimum diffraction angle (θ) of 3.496° and a maximum diffraction angle (θ) of 66.597° at room temperature. The final completeness is 99.8%. The mean I/σ of the data is 40.0 and the maximum resolution that was achieved was 0.84 Å.

SCXRD data obtained by the methods described herein is provided in the table below.

| Temperature | 120.00 (10) K | Room Temperature |
|---|---|---|
| a | 7.49140 (10) Å | 23.3046 (5) Å |
| b | 15.0483 (2) Å | 15.0483 (3) Å |
| c | 23.0349 (2) Å | 7.53530 (10) Å |
| α | 90° | 90° |
| β | 90° | 90° |
| γ | 90° | 90° |
| Space group | P2$_1$2$_1$2$_1$ | P2$_1$2$_1$2$_1$ |
| Crystal system | Orthorhombic | Orthorhombic |
| Volume | 2596.79 (5) Å$^3$ | 2642.59 (8) Å$^3$ |
| Empirical formula | C$_{26}$H$_{41}$BrN$_2$O$_3$ | C$_{26}$H$_{41}$BrN$_2$O$_3$ |

Example 2: Preparation of Citrate Salt of Compound 1

Citrate Salts of Compound 1 may be prepared from Compound 1 using the following exemplary methods.

Compound 1 Citrate (Form A):

200 mg of Compound 1 was dissolved in 10.0 mL of acetone at 60° C. while stirring at 500 rpm and held at 60° C. for 1.5 hrs. 1.1 e.q. Citric acid in acetone (1.027 mL, 0.5 mol/L) was then added into the Compound 1 solution and incubated at 60° C. for 3 hrs, then cooled to 25° C. and held at 25° C. for 20 hrs. The solution was evaporated by nitrogen to remove the organic solvent. The obtained wet product was vacuum dried at 25° C. for 42 hrs resulting in 218.85 mg of powder with a yield of 71.1%.

The resulting solid is Compound 1 Citrate (Form A). The ratio of Compound 1:citric acid in Compound 1 Citrate (Form A) is 1:1.23 as determined by ion chromatography. The XPRD is shown in FIG. 15; the DSC and TGA are shown in FIG. 16; and the DVS is shown in FIG. 17.

Compound 1 Citrate (Form A) was analyzed by $^1$H-NMR in deuterated DMSO resulting in the following chemical shifts: $^1$H NMR (400 MHz, DMSO-d$_6$): δ 0.48-0.88 (m, 7H) 2.03-2.22 (m, 2H) 2.46-2.86 (m, 28H) 3.00-3.17 (m, 3H) 3.19-3.46 (m, 5H) 4.74-5.35 (m, 2H) 7.09 (s, 1H) 7.19 (s, 1H) 7.86 (s, 1H).

Compound 1 Citrate (Form B):

500 mg of Compound 1 Citrate (Form A) was dissolved in 4.0 mL of 0.901 water activity solution (65% water in acetone, v/v) to generate a suspension targeting 125 mg/mL. The suspension was stirred at 300 rpm and held at 50° C. for 3 days. The suspension was centrifuged and the precipitate collected. The wet crude product was vacuum dried at 30° C. for one day resulting in powder with yield of 56.9%. The ratio of Compound 1:citric acid in Compound 1 Citrate (Form B) is 1:1.17 as determined by ion chromatography. The XPRD is shown in FIG. 18; the DSC and TGA are shown in FIG. 19; and the DVS is shown in FIG. 20.

Compound 1 Citrate (Form B) was analyzed by $^1$H-NMR in deuterated DMSO resulting in the following chemical shifts: $^1$H NMR (400 MHz, DMSO-d$_6$): δ 0.53-0.79 (m, 7H) 0.85-1.76 (m, 24H) 1.99-2.14 (m, 3H) 2.32-2.35 (m, 1H) 2.61-2.74 (m, 6H) 3.00-3.09 (m, 2H) 4.89-5.13 (m, 1H) 6.99 (s, 1H) 7.11 (s, 1H) 7.74 (s, 1H).

Compound 1 Citrate (Form C):

A sample of Compound 1 Citrate Form A was stirred as a suspension in acetonitrile at 50° C. The resultant solids were isolated by filtration.

General Procedures to Prepare Compound 1 Citrate

The following general procedures were conducted to prepare Compound 1 Citrate.

General Procedure A

To a 20 mL vial equipped with stir bar, Compound (1.00 g, 1.0 equiv.) and solvent or co-solvent were charged. The resulting mixture was heated to 60° C. for 30 mins. To the mixture was added citric acid monohydrate (0.54 g, 1.1 equiv.) in solvent or co-solvent (pre-heated to dissolution) at 60° C. and stirred for 1 hr. The reaction was cooled to 25° C. and stirred overnight. The suspension was filtered and the wet cake was washed with acetone. The solids were collected and dried under vacuum at 25° C. overnight to afford Compound 1 Citrate.

General Procedure A-2

To a 20 mL vial equipped with stir bar, Compound 1 (1.00 g, 1.0 equiv.) and co-solvent (10 mL, 10 mL/g Compound 1) were charged. The resulting mixture was heated to 60° C. for 30 mins. To the mixture was added citric acid monohydrate (0.54 g, 1.1 equiv.) in co-solvent (2 mL, 2 mL/g Compound 1) (pre-heated to dissolution) at 60° C. and stirred for 1 hr. The reaction was cooled to 0° C. (no ppt.). The mixture was dried under vacuum and added co-solvent (3 mL, 3 mL/g Compound 1) at 60° C. The reaction was cooled to 25° C. and stirred overnight. The suspension was filtered and the wet cake was washed with acetone. The solids were collected and dried under vacuum at 25° C. overnight to afford Compound 1 Citrate.

General Procedure B

To a 20 mL vial equipped with stir bar, Compound 1 (1.00 g, 1.0 equiv.) and EtOH (3.5 mL, 3.5 mL/g Compound 1) were charged. The resulting mixture was heated to 60° C. for 30 mins. To the mixture was added citric acid monohydrate (0.54 g, 1.1 equiv.) in EtOH (1.5 mL, 1.5 mL/g Compound 1) (pre-heated to dissolution) at 60° C. and stirred for 1 hr. The reaction was cooled to 25° C. and added anti-solvent (5 mL, 5 mL/g Compound 1) at 25° C. The reaction was cooled to 0° C. and then stirred for 1 hr. The mixture was stirred at 25° C. overnight. The reaction was cooled to 0° C. and then stirred for 1 hr. The suspension was filtered and the wet cake was washed with acetone. The solids were collected and dried under vacuum at 25° C. overnight to afford Compound 1 Citrate.

General Procedure C

To a four-neck 250 mL flask equipped with a mechanical stirrer (5.5 cm paddle; 100 rpm), thermometer, and N2 inlet, Compound 1 (5.00 g, 1.0 equiv.) and EtOH/IPAc (1:1, 40 mL, 8 mL/g Compound 1) were charged. The resulting mixture was heated to 60° C. for 30 mins. To the mixture was added citric acid monohydrate (2.73 g, 1.1 equiv.) in EtOH/IPAc (1:1, 10 mL, 2 mL/g Compound 1) (pre-heated to dissolution) at 60° C., and stirred for 1 hr. The reaction was cooled to 25° C. and then stirred for 1 hr. The reaction was cooled to 0° C. and then stirred for 30 mins. The suspension was filtered and the wet cake was washed with acetone. The solids were collected and dried under vacuum at 50° C. overnight to afford Compound 1 Citrate.

The following table summarizes preparations of Compound 1 Citrate according to these general procedures:

| Preparation General Procedure | 1<br>A | 2<br>C | 3<br>A | 4<br>A | 5<br>A | 6<br>A-2 | 7<br>B |
|---|---|---|---|---|---|---|---|
| Solvent (mL/g Compound 1) | Acetone (30X) | EtOH/ IPAc (1:1, 10X) | 10-20% EtOH in H$_2$O (20X) | 1-butanol (10X) | EtOH (5X) | EtOH/ Acetone (1:1, 12X→3X) | EtOH/ EtOAc (1:1, 10X) |
| Weight Yield | 67.0% | 90.0% | 60.7% | 75.1% | 66.1% | 63.8% | 67.5% |
| Purity | 99.0% | 99.6 % | 98.2% | 99.01% | 99.4% | 99.6 % | 99.6 % |
| Form by XRPD | Form A | Form A | Form C | Form A | Form A | Form A | Form A |

| Preparation General Procedure | 8<br>B | 9<br>B | 10<br>B | 11<br>B | 12<br>B | 13<br>B | 14<br>B |
|---|---|---|---|---|---|---|---|
| Solvent (mL/g Compound 1) | EtOH/ IPE (1:1, 10X) | EtOH/ IPAc (1:1, 10X) | EtOH/ IPAc (1:1, 10X) | EtOH/ MTBE (1:1, 10X) | EtOH/ MIBK (1:1, 10X) | EtOH/ Toluene (1:1, 10X) | EtOH/ H$_2$O (1:1, 10X) |
| Weight Yield | 82.2% | 74.8% | 76.2% | 75.2% | 71.5% | 66.0% | 47.7% |
| Purity | 99.0% | 99.1% | 99.80% | 99.0% | 99.2% | 99.7% | 99.4% |
| Form by XRPD | Form A | Form A | Form A | Form A | Form A | Form A | Form A |

N.R. means that free base was recovered from the experiment.

Chemical and Physical Stability Test

Chemical and physical stability testing was carried out using the procedures set forth in Example 1. The chemical and physical stability test results for Compound 1 Citrate (Form A), Compound 1 Citrate (Form B) and Compound 1 free base are shown in the following table:

| Test Material | Conditions | XRPD patterns | Final purity |
|---|---|---|---|
| Compound 1 | 60° C., 1 w | Pattern A | 99.3 |
| | 40° C./75% RH, 1 w | Pattern A | 99.1 |
| | 1.2 million lux-hrs | Pattern A | 99.2 |
| | Dark control | Pattern A | 99.1 |
| Citrate (Form A) | 60° C., 1 w | Form A | 99.5 |
| | 40° C./75% RH, 1 w | Form A | 99.4 |
| | 1.2 million lux-hrs | Form A | 99.5 |
| | Dark control | Form A | 99.5 |
| Citrate (Form B) | 60° C., 1 w | Form B | 97.7 |
| | 40° C./75% RH, 1 w | Form B | 98.3 |
| | 1.2 million lux-hrs | Form B | 99.3 |
| | Dark control | Form B | 99.1 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Citrate (Form A), Compound 1 Citrate (Form B) and Compound 1 free base are shown in the following table:

| | SGF (original pH = 1.82) | | | FaSSIF (original pH = 6.50) | | | FeSSIF (original pH = 4.99) | | |
|---|---|---|---|---|---|---|---|---|---|
| Solute tested | 1 h | 24 h | Final pH | 1 h | 24 h | Final pH | 1 h | 24 h | Final pH |
| Compound 1 | 3.41 | 2.81 | 2.07 | 0.03 | 0.03 | 6.47 | 0.87 | 0.95 | 5.00 |
| Citrate (Form A) | 4.23 | 4.27 | 3.00 | 0.18 | 0.16 | 4.85 | 2.18 | 0.38 | 4.71 |
| Citrate (Form B) | N/A | 8.00 | 2.79 | N/A | 0.33 | 5.05 | N/A | 0.37 | 5.13 |

Single Crystal X-Ray Structure of Compound 1 Citrate Form A

A block-like single crystal sample Compound 1 Citrate Form A used for SCXRD characterization was crystallized from THF solvent by slow evaporation method.

Characterization of the salt by PLM and XRPD showed it to be Compound 1 Citrate Form A.

Cell parameters and an orientation matrix for data collection were retrieved and refined (least-squares refinement) by CrysAlisPro (Rigaku, V1.171.40.14e, 2018) software using the setting angles of 64393 reflections in the range $3.7580°<\theta<75.8720°$. The data were collected to a minimum diffraction angle ($\theta$) of 3.785° and a maximum diffraction angle ($\theta$) of 66.597° at 120.00 K. The final completeness is 99.3%. The mean I/$\sigma$ of the data is 81.3 and the maximum resolution that was achieved was 0.84 Å.

SCXRD data obtained by the methods described herein is provided in the table below.

| Temperature | 120.00 (10) K |
|---|---|
| a | 8.85550 (10) Å |
| b | 12.18980 (10) Å |
| c | 16.49670 (10) Å |
| α | 73.6770 (10)° |
| β | 76.5960 (10)° |
| γ | 83.2390 (10)° |
| Space group | P1 |

-continued

| Temperature | 120.00 (10) K |
| --- | --- |
| Crystal system | Triclinic |
| Volume | 1659.80 (3) Å$^3$ |
| Empirical formula | $(C_{26}H_{42}N_2O_3)^+ \cdot (C_6H_6O_7)^- \cdot H_2O$ |

Example 3: Preparation of Mesylate Salt of Compound 1

A Mesylate Salt of Compound 1 may be prepared from Compound 1 using the following exemplary methods.
Compound 1 Mesylate (Form A):
200 mg of Compound 1 was dissolved in 10.0 mL of EtOAc at 60° C. while stirring at 500 rpm and held at 60° C. for 1 hr. 1.1 e.q. methanesulfonic acid in EtOAc (1.027 mL, 0.5 mol/L) was then added into the Compound 1 solution and incubated at 60° C. for 3 hrs, then cooled to 25° C. and held at 25° C. for 20 hrs. This suspension was centrifuged and the precipitate collected and washed with EtOAc. The obtained wet product was vacuum dried at 35° C. for 22 hrs resulting in 234.52 mg of powder with a yield of 94.1%.

The resulting solid is Compound 1 Mesylate (Form A). The ratio of Compound 1:methanesulfonic acid in Compound 1 Mesylate (Form A) is 1:1.08 as determined by ion chromatography. The XPRD is shown in FIG. 22; the DSC and TGA are shown in FIG. 23; and the DVS is shown in FIG. 24.

Compound 1 Mesylate (Form A) was analyzed by $^1$H-NMR in deuterated DMSO resulting in the following chemical shifts: $^1$H NMR (400 MHz, DMSO-d$_6$): δ 0.54-0.81 (m, 7H) 0.84 (t, J=7.44 Hz, 1H) 1.84-2.17 (m, 3H) 2.31 (s, 3H) 2.41-2.59 (m, 20H) 2.65-2.83 (m, 1H) 3.05 (s, 2H) 3.22-3.48 (m, 1H) 3.23-3.51 (m, 6H) 4.96-5.52 (m, 1H) 4.96-5.52 (m, 1H) 7.62 (s, 1H) 7.55-7.64 (m, 1H) 7.62-7.77 (m, 1H) 9.01 (s, 1H).

Compound 1 Mesylate (Form B):
200 mg of Compound 1 was dissolved in 10.0 mL of EtOAc at 60° C. while stirring at 500 rpm and held at 60° C. for 1 hr. 1.1 e.q. methane sulfonic acid in EtOAc (1.027 mL, 0.5 mol/L) was then added into the Compound 1 solution and incubated at 60° C. for 3 hrs, then cooled to 25° C. and held at 25° C. for 20 hrs. This suspension was centrifuged and the precipitate collected and washed with EtOAc. The obtained wet product was vacuumed dried at 35° C. for 22 hrs resulting in 234.52 mg powder with a yield of 94.1%.

The resulting solid is Compound 1 Mesylate (Form B). The XPRD is shown in FIG. 25A.

Compound 1 Mesylate (Form C):
Compound 1 Mesylate (Form C) was prepared using solvent ACN solvent and methane sulfonic acid. For liquid counter-ion, 50 mg Compound 1 was weighed into 2 mL vials, and 743 μL solvents were added in the vials subsequently. Then 1.1 e.q. counter-ions solutions of corresponding solvent (257 μL, concentration: 0.5 mol/L) was added to the vial. The vial was placed on the thermo-mixer with a stirrer bar and heated to 50° C. After keeping at 50° C. under stirring at 900 rpm for 18 hrs, the vial was then cooled to 25° C. After keeping at 25° C. for 1 hr, the solids in suspensions were isolated by centrifugation and dried in the vacuum oven at 30° C. overnight.

The resulting solid is Compound 1 Mesylate (Form C). The XPRD is shown in FIG. 25B.

Compound 1 Mesylate (Form D):
Approximately 5 mg Compound 1 Mesylate (Form A) was added into an 8 mL glass vial with a multi-hole aluminum foil cap, and kept at 60° C., 40° C./75% RH for 1 week. Appearance by visual observation were recorded followed by purity assessment and XPRD data collection on the residual solids. The resulting solid is Compound 1 Mesylate (Form D). The dried solids were characterized by PLM and XRPD.

The XPRD is shown in FIG. 26.

Chemical and Physical Stability Test

Chemical and physical stability testing was carried out using the procedures set forth in Example 1. The chemical and physical stability test results for Compound 1 Mesylate (Form A) and Compound 1 free base are shown in the following table:

| Test material | Conditions | XRPD patterns | Final purity |
| --- | --- | --- | --- |
| Compound 1 | 60° C., 1 w | Pattern A | 99.3 |
| | 40° C./75% RH, 1 w | Pattern A | 99.1 |
| | 1.2 million lux-hrs | Pattern A | 99.2 |
| | Dark control | Pattern A | 99.1 |
| Mesylate (Form A) | 60° C., 1 w | Form A | 99.4 |
| | 40° C./75% RH, 1 w | Form D (see FIG. 26) | 99.4 |
| | 1.2 million lux-hrs | Form A | 99.3 |
| | Dark control | Form A | 99.4 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Mesylate (Form A) and Compound 1 free base are shown in the following table:

| | SGF (original pH = 1.82) | | | FaSSIF (original pH = 6.50) | | | FeSSIF (original pH = 4.99) | | |
| --- | --- | --- | --- | --- | --- | --- | --- | --- | --- |
| Solute tested | 1 h | 24 h | Final pH | 1 h | 24 h | Final pH | 1 h | 24 h | Final pH |
| Compound 1 | 3.41 | 2.81 | 2.07 | 0.03 | 0.03 | 6.47 | 0.87 | 0.95 | 5.00 |
| Mesylate (Form A) | >29.38 | >26.49 | 2.07 | 0.10 | 0.09 | 5.16 | 1.66 | 0.004 | 5.05 |

Example 4: Preparation of Phosphate Salt of Compound 1

A Phosphate Salt of Compound 1 may be prepared from Compound 1 using the following exemplary method.

200 mg of Compound 1 was dissolved in 10.0 mL of acetone at 60° C. while stirring at 500 rpm and held at 60° C. for 1.5 hrs. 1.1 e.q. phosphoric acid in acetone (1.027 mL, 0.5 mol/L) was then added into the Compound 1 solution and incubated at 60° C. for 3 hrs, then cooled to 25° C. and held at 25° C. for 20 hrs. This suspension was centrifuged and the precipitate collected and washed with acetone. The obtained wet product was vacuum dried at 30° C. for 42 hrs resulting in 233.51 mg of powder with a yield of 93.3%.

The resulting solid is Compound 1 Phosphate (Form A). The ratio of Compound 1:phosphoric acid in Compound 1 Phosphate (Form A) is 1:0.9 as determined by ion chromatography. The XPRD is shown in FIG. 27; the DSC and TGA are shown in FIG. 28; and the DVS is shown in FIG. 29.

Chemical and Physical Stability Test

Chemical and physical stability testing was carried out using the procedures set forth in Example 1. The chemical and physical stability test results for Compound 1 Phosphate (Form A) and Compound 1 free base are shown in the following table:

| Test Material | Conditions | XRPD patterns | Final purity |
|---|---|---|---|
| Compound 1 | 60° C., 1 w | Pattern A | 99.3 |
|  | 40° C./75% RH, 1 w | Pattern A | 99.1 |
|  | 1.2 million lux-hrs | Pattern A | 99.2 |
|  | Dark control | Pattern A | 99.1 |
| Phosphate (Form A) | 60° C., 1 w | Form A | 99.2 |
|  | 40° C./75% RH, 1 w | Form A | 99.2 |
|  | 1.2 million lux-hrs | Form A | 98.9 |
|  | Dark control | Form A | 99.2 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Phosphate (Form A) and Compound 1 free base are shown in the following table:

| Solute tested | SGF (original pH = 1.82) | | | FaSSIF (original pH = 6.50) | | | FeSSIF (original pH = 4.99) | | |
|---|---|---|---|---|---|---|---|---|---|
|  | 1 h | 24 h | Final pH | 1 h | 24 h | Final pH | 1 h | 24 h | Final pH |
| Compound 1 | 3.41 | 2.81 | 2.07 | 0.03 | 0.03 | 6.47 | 0.87 | 0.95 | 5.00 |
| Phosphate (Form A) | 18.94 | 14.26 | 2.47 | 0.72 | 0.70 | 4.28 | 1.62 | 0.004 | 4.94 |

Example 5: Preparation of L(+)-Tartrate Salt of Compound 1

L(+)-Tartrate Salts of Compound 1 may be prepared from Compound 1 using the following exemplary methods.

Compound 1 L(+)-Tartrate (Form A):

200 mg of Compound 1 was dissolved in 10.0 mL of acetone at 60° C. while stirring at 500 rpm and held at 60° C. for 1.5 hrs. 1.1 e.q. L(+)-tartaric acid powder (77 mg, 0.5 mmol) was then added into the Compound 1 solution and incubated at 60° C. for 3 hrs, then cooled to 25° C. and held at 25° C. for 20 hrs. The suspension was centrifuged and the precipitate collected and washed with acetone. The obtained wet product was vacuum dried at 30° C. for 42 hrs resulting in 237.95 mg of powder with a yield of 85.9%.

The resulting solid is Compound 1 L(+)-Tartrate (Form A). The ratio of Compound 1:tartaric acid in Compound 1 L(+)-Tartrate (Form A) is 1:1.15 as determined by ion chromatography. The XPRD is shown in FIG. 30; the DSC and TGA are shown in FIG. 31; and the DVS is shown in FIG. 32.

Compound 1 L(+)-Tartrate (Form A) was analyzed by $^1$H-NMR in deuterated DMSO resulting in the following chemical shifts: $^1$H NMR (400 MHz, DMSO-$d_6$): δ 0.49-0.84 (m, 7H) 0.90-1.75 (m, 21H) 1.94-2.21 (m, 3H) 2.35-2.58 (m, 14H) 2.66-2.80 (m, 1H) 3.10 (s, 2H) 3.23-3.34 (m, 3H) 4.24-4.39 (m, 2H) 4.80-5.19 (m, 2H) 6.98 (s, 1H) 7.12 (s, 1H) 7.67 (s, 1H).

Compound 1 L(+)-Tartrate (Form B):

200 mg of Compound 1 was dissolved in 10.0 mL of EtOAc at 60° C. while stirring at 500 rpm and held at 60° C. for 1 hr. 1.1 e.q. L(+)-tartaric acid powder (77 mg, 0.5 mmol) was then added into the RX-0001175 solution and incubated at 60° C. for 3 hrs, then cooled to 25° C. and held at 25° C. for 20 hrs. The suspension was centrifuged and the precipitate collected and washed with EtOAc. The obtained wet product was vacuum dried at 35° C. for 22 hrs resulting in 254.08 mg of powder with a yield of 91.7%.

The resulting solid is Compound 1 L(+)-Tartrate (Form B). The ratio of Compound 1:tartaric acid in Compound 1 L(+)-Tartrate (Form B) is 1:1.19 as determined by ion chromatography. The XPRD is shown in FIG. 33; the DSC and TGA are shown in FIG. 34; and the DVS is shown in FIG. 35.

Compound 1 L(+)-Tartrate (Form B) was analyzed by $^1$H-NMR in deuterated DMSO resulting in the following chemical shifts: $^1$H NMR (400 MHz, DMSO-$d_6$): δ 0.50-0.82 (m, 6H) 1.91-2.22 (m, 2H) 3.03 (s, 2H) 3.24 (s, 2H) 3.14-3.53 (m, 1H) 4.27 (s, 2H) 4.54-5.21 (m, 2H) 6.71-7.18 (m, 2H) 7.59 (s, 1H).

Chemical and Physical Stability Test

Chemical and physical stability testing was carried out using the procedures set forth in Example 1. The chemical and physical stability test results for Compound 1 L(+)-Tartrate (Form A), Compound 1 L(+)-Tartrate (Form B), and Compound 1 free base are shown in the following table:

| Starting materials | Conditions | XRPD patterns | Final purity |
|---|---|---|---|
| Compound 1 | 60° C., 1 w | Pattern A | 99.3 |
|  | 40° C./75% RH, 1 w | Pattern A | 99.1 |
|  | 1.2 million lux-hrs | Pattern A | 99.2 |
|  | Dark control | Pattern A | 99.1 |
| L(+)-Tartrate (Form A) | 60° C., 1 w | Form A | 99.3 |
|  | 40° C./75% RH, 1 w | Form A | 99.3 |
|  | 1.2 million lux-hrs | Form A | 99.4 |
|  | Dark control | Form A | 99.2 |
| L(+)-Tartrate (Form B) | 60° C., 1 w | Form B | 99.2 |
|  | 40° C./75% RH, 1 w | Form B | 99.2 |
|  | 1.2 million lux-hrs | Form B | 99.3 |
|  | Dark control | Form B | 99.2 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 L(+)-Tartrate (Form A), Compound 1 L(+)-Tartrate (Form B), and Compound 1 free base are shown in the following table:

| Solute tested | SGF (original pH = 1.82) | | | FaSSIF (original pH = 6.50) | | | FeSSIF (original pH = 4.99) | | |
|---|---|---|---|---|---|---|---|---|---|
| | 1 h | 24 h | Final pH | 1 h | 24 h | Final pH | 1 h | 24 h | Final pH |
| Compound 1 | 3.41 | 2.81 | 2.07 | 0.03 | 0.03 | 6.47 | 0.87 | 0.95 | 5.00 |
| L(+)-Tartrate (Form A) | 5.76 | 5.82 | 2.91 | 0.58 | 0.54 | 4.32 | 1.98 | 1.07 | 4.79 |
| L(+)-Tartrate (Form B) | 6.03 | 5.42 | 2.77 | 0.61 | 0.56 | 4.35 | 2.11 | 0.98 | 4.79 |

Example 6: Preparation of Fumarate of Compound 1

Fumarate Salts of Compound 1 may be prepared from Compound 1 using the following exemplary method.

Compound 1 Fumarate (Form A):

200 mg of Compound 1 was dissolved in 10.0 mL of acetone at 60° C. while stirring at 500 rpm and held at 60° C. for 1.5 hrs. 1.1 e.q. fumaric acid powder (60 mg, 0.51 mmol) was then added into the Compound 1 solution and incubated at 60° C. for 3 hrs, then cooled to 25° C. and held at 25° C. for 20 hrs. A 2-fold volume of heptane was then added to the acetone mixture which produced a suspension. This suspension was centrifuged and the precipitate collected, then vacuum dried at 25° C. for 42 hrs resulting in 75.58 mg of powder with a yield of 29.1%.

The resulting solid is Compound 1 Fumarate (Form A). The ratio of Compound 1:fumaric acid in Compound 1 Fumarate (Form A) is 1:1.37 as determined by ion chromatography. The XPRD is shown in FIG. 36 and the DSC and TGA are shown in FIG. 37.

Compound 1 Fumarate (Form A) was analyzed by $^1$H-NMR in deuterated DMSO resulting in the following chemical shifts: $^1$H NMR (400 MHz, DMSO-$d_6$): δ 0.45-0.80 (m, 7H) 1.97-2.13 (m, 3H) 2.47-2.58 (m, 12H) 2.63-2.78 (m, 1H) 2.63-2.78 (m, 1H) 3.04 (s, 2H) 3.25 (s, 3H) 4.80-5.14 (m, 1H) 4.80-5.14 (m, 1H) 6.63 (s, 3H) 6.91 (s, 1H) 7.05 (s, 1H) 7.52-7.69 (m, 1H).

Compound 1 Fumarate (Form B):

200 mg of Compound 1 was dissolved in 10.0 mL of ethyl acetate at 60° C. while stirring at 500 rpm and held at 60° C. for 1 hr. 1.1 e.q. fumaric acid powder (60 mg, 0.51 mmol) was added into the Compound 1 solution. The solution was held at 60° C. for 3 hrs, then cooled to 25° C. and held at 25° C. for 20 hrs. During the cooling process, the clear solution became suspension. This suspension was subsequently centrifuged and the precipitate collected and vacuumed dried at 35° C. for 22 hrs resulting in 156.78 mg of powder with a yield of 60.4%.

The resulting solid is Compound 1 Fumarate (Form B). The ratio of Compound 1:fumaric acid in Compound 1 Fumarate (Form B) is 1:1.55 as determined by ion chromatography. The XPRD is shown in FIG. 38; the DSC and TGA are shown in FIG. 39; and the DVS is FIG. 40.

$^1$H NMR (400 MHz, DMSO-$d_6$): δ 0.43-0.79 (m, 8H) 1.88-2.13 (m, 2H) 3.03 (s, 2H) 3.10-3.39 (m, 4H) 4.38-5.21 (m, 3H) 6.61 (s, 2H) 6.59-6.64 (m, 1H) 6.74-7.16 (m, 2H) 7.56 (s, 1H).

Compound 1 Fumarate (Form C):

50 mg Compound 1 and 1.1 e.q. counter ion of fumaric acid in solid form were weighed into 2 mL vials individually, followed by adding 1 mL solvent ACN into the vial. The vial was placed on the thermo-mixer with a stir bar and heated to 50° C. After keeping at 50° C. under constant stirring at 900 rpm for 18 hrs, the vial was then cooled to 25° C. After keeping at 25° C. for 1 hr, the solids in suspension were isolated by centrifugation and dried in the vacuum oven at 30° C. for 48 hrs.

The resulting solid is Compound 1 Fumarate (Form C). The dried solids were characterized by PLM and XRPD.

The XPRD is shown in FIG. 41.

Compound 1 Fumarate (Form D):

Approximately 5 mg Compound 1 Fumarate (Form A) was added into an 8 mL glass vial with a multi-hole aluminum foil cap, and kept at 60° C., 40° C./75% RH for 1 week. Appearance by visual observation were recorded followed by purity assessment and XPRD data collection on the residual solids. The resulting solid is Compound 1 Fumarate (Form D). The dried solids were characterized by PLM and XRPD. The XPRD is shown in FIG. 42.

Chemical and Physical Stability Test

Chemical and physical stability testing was carried out using the procedures set forth in Example 1. The chemical and physical stability test results for Compound 1 Fumarate (Form A), and Compound 1 free base are shown in the following table:

| Start material | Condition | XRPD pattern | Final purity |
|---|---|---|---|
| Compound 1 | 60° C., 1 w | Pattern A | 99.3 |
| | 40° C./75% RH, 1 w | Pattern A | 99.1 |
| | 1.2 million lux-hrs | Pattern A | 99.2 |
| | Dark control | Pattern A | 99.1 |
| Fumarate (Form A) | 60° C., 1 w | Form A | 88.4 |
| | 40° C./75% RH, 1 w | Form D (see FIG. 42) | 97.9 |
| | 1.2 million lux-hrs | Form A | 97.7 |
| | Dark control | Form A | 97.1 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Fumarate (Form A), and Compound 1 free base are shown in the following table:

| Solute tested | SGF (original pH = 1.82) | | | FaSSIF (original pH = 6.50) | | | FeSSIF (original pH = 4.99) | | |
|---|---|---|---|---|---|---|---|---|---|
| | 1 h | 24 h | Final pH | 1 h | 24 h | Final pH | 1 h | 24 h | Final pH |
| Compound 1 | 3.41 | 2.81 | 2.07 | 0.03 | 0.03 | 6.47 | 0.87 | 0.95 | 5.00 |
| Fumarate (Form A) | 2.90 | 3.03 | 2.39 | 0.25 | 0.32 | 4.63 | 2.06 | 0.72 | 4.58 |

Example 7: Preparation of Tosylate Salt of Compound 1

A Tosylate Salt of Compound 1 may be prepared from Compound 1 using the following exemplary methods.

Compound 1 Tosylate (Form A):

200 mg of Compound 1 was dissolved in 10.0 mL of ACN at 60° C. while stirring at 500 rpm and held at 60° C. for 1 hr. 1.1 e.q. p-toluenesulfonic acid in ACN (1.027 mL, 0.5 mol/L) was then added into the Compound 1 solution and incubated at 60° C. for 3 hrs, then cooled to 25° C. and held at 25° C. for 20 hrs. The suspension was centrifuged and the precipitate collected and washed with ACN. The obtained wet product was vacuum dried at 35° C. for 22 hrs resulting in 141.85 mg of powder with a yield of 49.2%.

The resulting solid is Compound 1 Tosylate (Form A). The ratio of Compound 1:toluenesulfonic acid in Compound 1 Tosylate (Form A) is 1:1.09 as determined by ion chromatography. The XPRD is shown in FIG. 43; the DSC and TGA are shown in FIG. 44; and the DVS is shown in FIG. 45.

Compound 1 Tosylate (Form A) was analyzed by $^1$H-NMR in deuterated DMSO resulting in the following chemical shifts: $^1$H NMR (400 MHz, DMSO-$d_6$): δ 0.50-0.79 (m, 7H) 1.98-2.15 (m, 3H) 2.28 (s, 4H) 2.49 (s, 23H) 2.60-2.76 (m, 1H) 3.03 (s, 2H) 3.21-3.34 (m, 5H) 4.85-5.45 (m, 2H) 7.10 (d, J=7.78 Hz, 2H) 7.45 (s, 1H) 7.46-7.73 (m, 3H) 8.99 (s, 1H).

Compound 1 Tosylate (Form B):

50 mg Compound 1 and 1.1 e.q. counter ion of para-toluenesulfonic acid in solid form were weighed into 2 mL vials individually, and then 1 mL EtOAc solvent was added into the vial. The vial was placed on the thermo-mixer with a stir bar and heated to 50° C. After keeping at 50° C. under constant stirring at 900 rpm for 18 hrs, the vial was then cooled to 25° C. After keeping at 25° C. for 1 hr, the solids in suspension were isolated by centrifugation and dried in the vacuum oven at 30° C. overnight.

The resulting solid is Compound 1 Tosylate (Form B). The XPRD is shown in FIG. 46.

Compound 1 Tosylate (Form C):

Approximately 5 mg Compound 1 Tosylate (Form A) was added into an 8 mL glass vial with a multi-hole aluminum foil cap, and kept at 60° C., 40° C./75% RH for 1 week. Appearance by visual observation were recorded followed by purity assessment and XPRD data collection on the residual solids. The resulting solid is Compound 1 Tosylate (Form C). The dried solids were characterized by PLM and XRPD.

The resulting solid is Compound 1 Tosylate (Form C). The XPRD is shown in FIG. 47.

Chemical and Physical Stability Test

Chemical and physical stability testing was carried out using the procedures set forth in Example 1. The chemical and physical stability test results for Compound 1 Tosylate (Form A) and Compound 1 free base are shown in the following table:

| Starting materials | Conditions | XRPD patterns | Final purity |
|---|---|---|---|
| Compound 1 | 60° C., 1 w | Pattern A | 99.3 |
| | 40° C./75% RH, 1 w | Pattern A | 99.1 |
| | 1.2 million lux-hrs | Pattern A | 99.2 |
| | Dark control | Pattern A | 99.1 |
| Tosylate (Form A) | 60° C., 1 w | Form A | 99.5 |
| | 40° C./75% RH, 1 w | Form C (see FIG. 47) | 99.5 |
| | 1.2 million lux-hrs | Form A | 99.0 |
| | Dark control | Form A | 99.5 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Tosylate (Form A) and Compound 1 free base are shown in the following table:

| Solute tested | SGF (original pH = 1.82) | | | FaSSIF (original pH = 6.50) | | | FeSSIF (original pH = 4.99) | | |
|---|---|---|---|---|---|---|---|---|---|
| | 1 h | 24 h | Final pH | 1 h | 24 h | Final pH | 1 h | 24 h | Final pH |
| Compound 1 | 3.41 | 2.81 | 2.07 | 0.03 | 0.03 | 6.47 | 0.87 | 0.95 | 5.00 |
| Tosylate (Form A) | 0.64 | 0.62 | 2.10 | 0.02 | 0.03 | 6.33 | 1.61 | 1.69 | 4.94 |

Example 8: Preparation of Glucuronate Salt of Compound 1

A Glucuronate Salt of Compound 1 may be prepared from Compound 1 using the following exemplary method.

Compound 1 Glucuronate (Form A)

500 mg of Compound 1 was dissolved in 16.0 mL of acetone at 60° C. while stirring at 500 rpm and held at 60° C. for 1.5 hrs. 1.1 e.q. D-glucuronic acid solid (248.62 mg) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs resulting in 739.32 mg of powder with a yield of 98.76%.

The resulting solid is Compound 1 Glucuronate (Form A). The ratio of Compound 1:glucuronic acid in Compound 1 Glucuronate (Form A) is 1:1.09 as determined by ion chromatography. The XPRD is shown in FIG. 48; the DSC and TGA are shown in FIG. 49; and the DVS is shown in FIG. 50.

Compound 1 Glucuronate (Form A) was analyzed by $^1$H-NMR in deuterated DMSO resulting in the following chemical shifts: $^1$H NMR (400 MHz, DMSO-d6) δ ppm 0.49-0.81 (m, 7H) 0.83-1.73 (m, 22H) 1.98-2.13 (m, 2H) 2.68 (br t, J=8.76 Hz, 1H) 2.90-3.08 (m, 3H) 3.10-3.20 (m, 2H) 3.57 (d, J=9.76 Hz, 1H) 3.95-4.14 (m, 2H) 4.33 (d, J=7.75 Hz, 1H) 4.78-5.11 (m, 4H) 6.51 (br s, 1H) 6.88 (s, 1H) 7.03 (s, 1H) 7.54 (s, 1H).

Chemical and Physical Stability Test

Chemical and physical stability testing was carried out using the procedures set forth in Example 1. The chemical and physical stability test results for Compound 1 Glucuronate (Form A) and Compound 1 free base are shown in the following table:

| Starting materials | Conditions | XRPD patterns | Final purity |
|---|---|---|---|
| Compound 1 | 60° C., 1 w | Pattern A | 98.2 |
|  | 40° C./75% RH, 1 w | Pattern A | 98.2 |
|  | 1.2 million lux-hrs | Pattern A | 97.9 |
|  | Dark control | Pattern A | 98.3 |
| Glucoronate (Form A) | 60° C., 1 w | Form A | 96.7 |
|  | 40° C./75% RH, 1 w | Form A | 98.0 |
|  | 1.2 million lux-hrs | Form A | 97.5 |
|  | Dark control | Form A | 97.5 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Glucuronate (Form A) and Compound 1 free base are shown in the following table:

| Solute tested | SGF (original pH = 1.82) | | FaSSIF (original pH = 6.51) | | FeSSIF (original pH = 4.99) | |
|---|---|---|---|---|---|---|
|  | 24 h | Final pH | 24 h | Final pH | 24 h | Final pH |
| Compound 1 | 4.44 | 3.10 | 0.05 | 6.48 | 0.84 | 5.11 |
| Glucuronate (Form A) | 5.40 | 2.82 | 0.65 | 4.28 | 0.47 | 4.97 |

Compound 1 Glucuronate (Form B)

50 mg Compound 1 and 1.1 e.q. counter ion of D-Glucuronic acid in solid form were weighed into 2 mL vials individually, and then 1 mL solvent EtOAc/ACN was added into the vial. The vial was placed on the thermo-mixer with a stir bar and heated to 50° C. After keeping at 50° C. under constant stirring at 900 rpm for 18 hrs, the vial was then cooled to 25° C. After keeping at 25° C. for 1 hr, the solids in suspension were isolated by centrifugation and dried in the vacuum oven at 30° C. for 18 hrs.

The dried solids were characterized by PLM and XRPD (FIG. 51).

Example 9: Preparation of Ethanesulfonate Salt of Compound 1

An Ethanesulfonate Salt of Compound 1 may be prepared from Compound 1 using the following exemplary method.

500 mg of Compound 1 was dissolved in 16.0 mL of acetone at 60° C. while stirring at 500 rpm and held at 60° C. for 1.5 hrs. 1.1 e.q. ethanesulfonic acid in acetone (2.565 mL, 0.5 mol/L) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs resulting in 546.88 mg of powder with a yield of 84.68%.

The resulting solid is Compound 1 Ethanesulfonate (Form A). The ratio of Compound 1:ethanesulfonic acid in Compound 1 Ethanesulfonate (Form A) is 1:1.17 as determined by ion chromatography. The XPRD is shown in FIG. 52; the DSC and TGA are shown in FIG. 53; and the DVS is shown in FIG. 54.

Compound 1 Ethanesulfonate (Form A) was analyzed by $^1$H-NMR in deuterated DMSO resulting in the following chemical shifts: $^1$H NMR (400 MHz, DMSO-d$_6$) δ ppm 0.52-0.81 (m, 7H) 0.83-1.78 (m, 25H) 1.99-2.17 (m, 3H) 2.39 (q, J=7.42 Hz, 2H) 2.69-2.80 (m, 1H) 3.05 (s, 2H) 3.43 (br s, 4H) 5.11-5.46 (m, 2H) 7.54-7.77 (m, 2H) 9.02 (s, 1H).

Chemical and Physical Stability Test

Chemical and physical stability testing was carried out using the procedures set forth in Example 1. The chemical and physical stability test results for Compound 1 Ethanesulfonate (Form A) and Compound 1 free base are shown in the following table:

| Starting materials | Conditions | XRPD patterns | Final purity |
|---|---|---|---|
| Compound 1 | 60° C., 1 w | Pattern A | 98.2 |
|  | 40° C./75% RH, 1 w | Pattern A | 98.2 |
|  | 1.2 million lux-hrs | Pattern A | 97.9 |
|  | Dark control | Pattern A | 98.3 |
| Ethanesulfonate (Form A) | 60° C., 1 w | Form A | 98.2 |
|  | 40° C./75% RH, 1 w | Form A | 98.0 |
|  | 1.2 million lux-hrs | Form A | 97.7 |
|  | Dark control | Form A | 97.4 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Ethanesulfonate (Form A) and Compound 1 free base are shown in the following table:

| Solute tested | SGF (original pH = 1.82) | | FaSSIF (original pH = 6.51) | | FeSSIF (original pH = 4.99) | |
|---|---|---|---|---|---|---|
|  | 24 h | Final pH | 24 h | Final pH | 24 h | Final pH |
| Compound 1 | 4.44 | 3.10 | 0.05 | 6.48 | 0.84 | 5.11 |
| Ethanesulfonate (Form A) | 5.85 | 1.88 | 0.39 | 4.59 | 0.76 | 5.02 |

Example 10: Preparation of Sulfate Salt of Compound 1

A Sulfate Salt of Compound 1 may be prepared from Compound 1 using the following exemplary method.

200 mg of Compound 1 was dissolved in 10.0 mL of ACN at 60° C. while stirring at 500 rpm and held at 60° C. for 1 hr. 1.1 e.q. sulfuric acid in ACN (1.027 mL, 0.5 mol/L) was then added into the Compound 1 solution and incubated at 60° C. for 3 hrs, then cooled to 25° C. and held at 25° C. for 20 hrs. The suspension was centrifuged and the precipitate collected and washed with ACN. The obtained wet product was vacuum dried at 35° C. for 22 hrs resulting in 177.38 mg of powder with a yield of 70.9%.

The resulting solid is Compound 1 Sulfate (Form A). The ratio of Compound 1:sulfuric acid in Compound 1 Sulfate (Form A) is 1:1.03 as determined by ion chromatography. The XPRD is shown in FIG. 55; the DSC and TGA are shown in FIG. 56; and the DVS is shown in FIG. 57.

Chemical and Physical Stability Test

Chemical and physical stability testing was carried out using the procedures set forth in Example 1. The chemical and physical stability test results for Compound 1 Sulfate (Form A) and Compound 1 free base are shown in the following table:

| Starting materials | Conditions | XRPD patterns | Final purity |
|---|---|---|---|
| Compound 1 | 60° C., 1 w | Pattern A | 99.3 |
|  | 40° C./75% RH, 1 w | Pattern A | 99.1 |
|  | 1.2 million lux-hrs | Pattern A | 99.2 |
|  | Dark control | Pattern A | 99.1 |
| Sulfate (Form A) | 60° C., 1 w | Form A | 96.2 |
|  | 40° C./75% RH, 1 w | Form A | 97.5 |
|  | 1.2 million lux-hrs | Form A | 97.1 |
|  | Dark control | Form A | 97.6 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Sulfate (Form A) and Compound 1 free base are shown in the following table:

| | SGF (original pH = 1.82) | | | FaSSIF (original pH = 6.50) | | | FeSSIF (original pH = 4.99) | | |
|---|---|---|---|---|---|---|---|---|---|
| Solute tested | 1 h | 24 h | Final pH | 1 h | 24 h | Final pH | 1 h | 24 h | Final pH |
| Compound 1 | 3.41 | 2.81 | 2.07 | 0.03 | 0.03 | 6.47 | 0.87 | 0.95 | 5.00 |
| Sulfate (Form A) | 1.95 | 1.75 | 1.75 | 2.27 | 1.55 | 2.33 | 0.98 | 0.64 | 4.77 |

Example 11: Preparation of Ascorbate Salt of Compound 1

An Ascorbate Salt of Compound 1 may be prepared from Compound 1 using the following exemplary method.

Compound 1 Ascorbate (Form A):

500 mg of Compound 1 was dissolved in 16.0 mL of acetone at 60° C. while stirring at 500 rpm and held at 60° C. for 1.5 hrs. 1.1 e.q. ascorbic acid powder (226 mg) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs resulting in 264.1 mg of powder with a yield of 36.3%.

The resulting solid is Compound 1 Ascorbate (Form A). The ratio of Compound 1:ascorbic acid in Compound 1 Ascorbate (Form A) is 1:0.98 as determined by ion chromatography. The XPRD is shown in FIG. 58; the DSC and TGA are shown in FIG. 59; and the DVS is shown in FIG. 60.

Compound 1 Ascorbate (Form A) was analyzed by $^1$H-NMR in deuterated DMSO resulting in the following chemical shifts: $^1$H NMR (400 MHz, DMSO-$d_6$) δ ppm 0.51-0.81 (m, 7H) 0.83-1.76 (m, 22H) 1.98-2.14 (m, 4H) 2.33 (br s, 1H) 2.64-2.72 (m, 1H) 3.04 (s, 2H) 3.25 (s, 3H) 3.41-3.45 (m, 3H) 3.73 (br t, J=7.65 Hz, 1H) 4.71 (d, J=1.51 Hz, 1H) 4.87-5.11 (m, 3H) 6.98 (s, 1H) 7.10 (s, 1H) 7.71 (s, 1H).

Chemical and Physical Stability Test

Chemical and physical stability testing was carried out using the procedures set forth in Example 1. The chemical and physical stability test results for Compound 1 Ascorbate (Form A) and Compound 1 free base are shown in the following table:

| Starting materials | Conditions | XRPD patterns | Final purity |
|---|---|---|---|
| Compound 1 | 60° C., 1 w | Pattern A | 98.2 |
|  | 40° C./75% RH, 1 w | Pattern A | 98.2 |
|  | 1.2 million lux-hrs | Pattern A | 97.9 |
|  | Dark control | Pattern A | 98.3 |
| Ascorbate (Form A) | 60° C., 1 w | Form A | 95.7 |
|  | 40° C./75% RH, 1 w | Form A | 96.4 |
|  | 1.2 million lux-hrs | Form A | 96.8 |
|  | Dark control | Form A | 96.8 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Ascorbate (Form A) and Compound 1 free base are shown in the following table:

| | SGF (original pH = 1.82) | | FaSSIF (original pH = 6.51) | | FeSSIF (original pH = 4.99) | |
|---|---|---|---|---|---|---|
| Solute tested | 24 h | Final pH | 24 h | Final pH | 24 h | Final pH |
| Compound 1 | 4.44 | 3.10 | 0.05 | 6.48 | 0.84 | 5.11 |
| Ascorbate (Form A) | 4.34 | 2.56 | 0.48 | 5.06 | 1.86 | 4.58 |

Compound 1 Ascorbate (Form B):

50 mg Compound 1 and 1.1 e.q. counter ion of ascorbic acid in solid form were weighed into 2 mL vials individually, and then 1 mL ACN solvent was added into the vial. The vial was placed on the thermo-mixer with a stir bar and heated to 50° C. After keeping at 50° C. under constant stirring at 500 rpm for 21 hrs, the vial was then cooled to 25° C. After keeping at 25° C. for 1 hr, the solids in suspension were isolated by centrifugation and dried in the vacuum oven at 30° C. for 18 hrs.

The obtained dried solids were characterized by PLM and XRPD (FIG. 61).

Example 12: Preparation of Napadisylate Salt of Compound 1

A Napadisylate Salt of Compound 1 may be prepared from Compound 1 using the following exemplary method.
Compound 1 Napadisylate (Form A)

500 mg of Compound 1 was dissolved in 16.0 mL of acetone at 60° C. while stirring at 500 rpm and held at 60° C. for 1.5 hrs. 1.1 e.q. naphthalene-1,5-disulfonic acid tetrahydrate in acetone (2.565 mL, 0.5 mol/L) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs resulting in 675.62 mg of light pink powder with a yield of 69.38%.

The resulting solid is Compound 1 Napadisylate (Form A). The ratio of Compound 1:naphthalene-1, 5-disulfonic acid in Compound 1 Napadisylate (Form A) is 1:0.7 as determined by ion chromatography. The XPRD is shown in FIG. 62; the DSC and TGA are shown in FIG. 63; and the DVS is shown in FIG. 64.

Compound 1 Napadisylate (Form A) was analyzed by $^1$H-NMR in deuterated DMSO resulting in the following chemical shifts: $^1$H NMR (400 MHz, DMSO-$d_6$) δ ppm 0.51-0.81 (m, 7H) 0.85-1.76 (m, 21H) 2.00-2.15 (m, 2H) 2.34 (s, 1H) 2.64-2.78 (m, 1H) 3.05 (s, 2H) 3.25 (s, 4H) 5.16-5.38 (m, 2H) 7.37-7.45 (m, 1H) 7.62 (s, 1H) 7.68 (s, 1H) 7.93 (d, J=6.88 Hz, 1H) 8.86 (d, J=8.63 Hz, 1H) 9.01 (s, 1H).

Chemical and Physical Stability Test

Chemical and physical stability testing was carried out using the procedures set forth in Example 1. The chemical and physical stability test results for Compound 1 Napadisylate (Form A) and Compound 1 free base are shown in the following table:

| Starting materials | Conditions | XRPD patterns | Final purity |
| --- | --- | --- | --- |
| Compound 1 | 60° C., 1 w | Pattern A | 98.2 |
| | 40° C./75% RH, 1 w | Pattern A | 98.2 |
| | 1.2 million lux-hrs | Pattern A | 97.9 |
| | Dark control | Pattern A | 98.3 |
| Napadisylate (Form A) | 60° C., 1 w | Form A | 96.6 |
| | 40° C./75% RH, 1 w | Form A | 97.4 |
| | 1.2 million lux-hrs | Form A | 98.0 |
| | Dark control | Form A | 97.8 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Napadisylate (Form A) and Compound 1 free base are shown in the following table:

| | SGF (original pH = 1.82) | | FaSSIF (original pH = 6.51) | | FeSSIF (original pH = 4.99) | |
| --- | --- | --- | --- | --- | --- | --- |
| Solute tested | 24 h | Final pH | 24 h | Final pH | 24 h | Final pH |
| Compound 1 | 4.44 | 3.10 | 0.05 | 6.48 | 0.84 | 5.11 |
| Napadisylate (Form A) | 0.13 | 1.88 | 0.10 | 5.61 | 1.06 | 5.59 |

Compound 1 Napadisylate (Form B)

50 mg Compound 1 and 1.1 e.q. counter ion of naphthalene-1,5-disulfonic acid tetrahydrate in solid form were weighed into 2 mL vials individually, and then 1 mL solvent IPA/water (95/5, V/V) was added into the vial. The vial was placed on the thermo-mixer with a stir bar and heated to 50° C. After keeping at 50° C. under constant stirring at 500 rpm for 21 hrs, the vial was then cooled to 25° C. After keeping at 25° C. for 1 hr, the solids in suspension were isolated by centrifugation and dried in the vacuum oven at 30° C. for 18 hrs.

The dried solids were characterized by PLM and XRPD (FIG. 65).

Example 13: Preparation of Malonate Salt of Compound 1

A Malonate Salt of Compound 1 may be prepared from Compound 1 using the following exemplary method.

500 mg of Compound 1 was dissolved in 16.0 mL of acetone at 60° C. while stirring at 500 rpm and held at 60° C. for 1.5 hrs. 1.1 e.q. malonic acid in acetone (2.565 mL, 0.5 mol/L) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs.

The resulting solid is Compound 1 Malonate (Form A). The ratio of Compound 1:malonic acid in Compound 1 Malonate (Form A) is 1:1.28 as determined by ion chromatography. The XPRD is shown in FIG. 66; and the DSC and TGA are shown in FIG. 67.

Compound 1 Malonate (Form A) was analyzed by $^1$H-NMR in deuterated DMSO resulting in the following chemical shifts: $^1$H-NMR (400 MHz, DMSO-$d_6$) δ ppm 0.50-0.79 (m, 7H) 0.84-1.75 (m, 20H) 1.91 (s, 1H) 2.00-2.12 (m, 2H) 2.65-2.73 (m, 1H) 3.04 (s, 2H) 3.13 (s, 3H) 4.92-5.15 (m, 2H) 7.03-7.20 (m, 2H) 7.91 (s, 1H).

Chemical and Physical Stability Test

Chemical and physical stability testing was carried out using the procedures set forth in Example 1. The chemical and physical stability test results for Compound 1 Malonate (Form A) and Compound 1 free base are shown in the following table:

| Starting materials | Conditions | XRPD patterns | Final purity |
| --- | --- | --- | --- |
| Compound 1 | 60° C., 1 w | Pattern A | 98.2 |
| | 40° C./75% RH, 1 w | Pattern A | 98.2 |
| | 1.2 million lux-hrs | Pattern A | 97.9 |
| | Dark control | Pattern A | 98.3 |
| Malonate (Form A) | 60° C., 1 w | Form A | 97.0 |
| | 40° C./75% RH, 1 w | Form A | 98.5 |
| | 1.2 million lux-hrs | Form A | 98.2 |
| | Dark control | Form A | 99.0 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Malonate (Form A) and Compound 1 free base are shown in the following table:

| Solute tested | SGF (original pH = 1.82) | | FaSSIF (original pH = 6.51) | | FeSSIF (original pH = 4.99) | |
|---|---|---|---|---|---|---|
| | 24 h | Final pH | 24 h | Final pH | 24 h | Final pH |
| Compound 1 | 4.44 | 3.10 | 0.05 | 6.48 | 0.84 | 5.11 |
| Malonate (Form A) | 4.99 | 2.26 | 0.80 | 4.30 | 2.42 | 4.96 |

Example 14: Preparation of Besylate Salt of Compound 1

A Besylate Salt of Compound 1 may be prepared from Compound 1 using the following exemplary method.
Compound 1 Besylate (Form A)

500 mg of Compound 1 was dissolved in 16.0 mL of acetone at 60° C. while stirring at 500 rpm and held at 60° C. for 1.5 hrs. 1.1 e.q. benzenesulfonic acid in acetone (2.565 mL, 0.5 mol/L) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs resulting in 654.68 mg of powder with a yield of 92.56%.

The resulting solid is Compound 1 Besylate (Form A). The ratio of Compound 1:benzenesulfonic acid in Compound 1 Besylate (Form A) is 1:0.94 as determined by ion chromatography. The XPRD is shown in FIG. 68; the DSC and TGA are shown in FIG. 69; and the DVS is shown in FIG. 70.

Compound 1 Besylate (Form A) was analyzed by $^1$H-NMR in deuterated DMSO resulting in the following chemical shifts: $^1$H NMR (400 MHz, DMSO-$d_6$) δ ppm 0.53-0.80 (m, 7H) 0.83-1.78 (m, 21H) 1.99-2.15 (m, 3H) 2.29-2.36 (m, 1H) 2.56 (br s, 1H) 2.66-2.77 (m, 1H) 3.05 (s, 2H) 3.25 (s, 4H) 4.03 (br s, 1H) 5.15-5.39 (m, 2H) 7.27-7.36 (m, 3H) 7.55-7.70 (m, 4H) 8.97 (s, 1H).

Chemical and Physical Stability Test

Chemical and physical stability testing was carried out using the procedures set forth in Example 1. The chemical and physical stability test results for Compound 1 Besylate (Form A) and Compound 1 free base are shown in the following table:

| Starting materials | Conditions | XRPD patterns | Final purity |
|---|---|---|---|
| Compound 1 | 60° C., 1 w | Pattern A | 98.2 |
| | 40° C./75% RH, 1 w | Pattern A | 98.2 |
| | 1.2 million lux-hrs | Pattern A | 97.9 |
| | Dark control | Pattern A | 98.3 |
| Besylate (Form A) | 60° C., 1 w | Form A | 98.3 |
| | 40° C./75% RH, 1 w | Form A | 98.3 |
| | 1.2 million lux-hrs | Form A | 98.7 |
| | Dark control | Form A | 98.4 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Besylate (Form A) and Compound 1 free base are shown in the following table:

| Solute tested | SGF (original pH = 1.82) | | FaSSIF (original pH = 6.51) | | FeSSIF (original pH = 4.99) | |
|---|---|---|---|---|---|---|
| | 24 h | Final pH | 24 h | Final pH | 24 h | Final pH |
| Compound 1 | 4.44 | 3.10 | 0.05 | 6.48 | 0.84 | 5.11 |
| Besylate (Form A) | 0.85 | 1.84 | 0.28 | 4.78 | 0.78 | 5.04 |

Compound 1 Besylate (Form B)

50 mg Compound 1 and 1.1 e.q. counter ion of benzenesulfonic acid in solid form were weighed into 2 mL vials individually, and then 1 mL ACN solvent was added into the vial. The vial was placed on the thermo-mixer with a stir bar and heated to 50° C. After keeping at 50° C. under constant stirring at 500 rpm for 21 hrs, the vial was then cooled to 25° C. After keeping at 25° C. for 1 hr, the solids in suspension were isolated by centrifugation and dried in the vacuum oven at 30° C. for 18 hrs.

The obtained dried solids were characterized by PLM and XRPD (FIG. 71).

Example 15: Preparation of Isethionate Salt of Compound 1

An Isethionate Salt of Compound 1 may be prepared from Compound 1 using the following exemplary method.
Compound 1 Isethionate (Form A)

500 mg of Compound 1 was dissolved in 16.0 mL of acetone at 60° C. while stirring at 500 rpm and held at 60° C. for 1.5 hrs. 1.1 e.q. 2-hydroxyethanesulphonic acid in acetone (2.565 mL, 0.5 mol/L) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs resulting in 493.12 mg of powder with a yield of 74.64%.

The resulting solid is Compound 1 Isethionate (Form A). The ratio of Compound 1:2-hydroxyethanesulphonic acid in Compound 1 Isethionate (Form A) is 1:1.09 as determined by ion chromatography. The XPRD is shown in FIG. 72; the DSC and TGA are shown in FIG. 73; and the DVS is shown in FIG. 74.

Compound 1 Isethionate (Form A) was analyzed by $^1$H-NMR in deuterated DMSO resulting in the following chemical shifts: $^1$H NMR (400 MHz, DMSO-$d_6$) δ ppm 0.53-0.81 (m, 7H) 0.84-1.78 (m, 22H) 2.01-2.15 (m, 3H) 2.34 (br s, 1H) 2.61 (t, J=6.82 Hz, 2H) 2.66-2.78 (m, 1H) 3.05 (s, 2H) 3.25 (s, 3H) 3.63 (t, J=6.75 Hz, 2H) 5.14-5.38 (m, 2H) 7.58-7.69 (m, 2H) 8.99 (s, 1H).

Chemical and Physical Stability Test

Chemical and physical stability testing was carried out using the procedures set forth in Example 1. The chemical and physical stability test results for Compound 1 Isethionate (Form A) and Compound 1 free base are shown in the following table:

| Starting materials | Conditions | XRPD patterns | Final purity |
|---|---|---|---|
| Compound 1 | 60° C., 1 w | Pattern A | 98.2 |
| | 40° C./75% RH, 1 w | Pattern A | 98.2 |
| | 1.2 million lux-hrs | Pattern A | 97.9 |
| | Dark control | Pattern A | 98.3 |
| Isethionate (Form A) | 60° C., 1 w | Form A | 98.7 |
| | 40° C./75% RH, 1 w | Form A | 98.5 |
| | 1.2 million lux-hrs | Form A | 98.9 |
| | Dark control | Form A | 98.8 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Isethionate (Form A) and Compound 1 free base are shown in the following table:

| Solute tested | SGF (original pH = 1.82) | | FaSSIF (original pH = 6.51) | | FeSSIF (original pH = 4.99) | |
|---|---|---|---|---|---|---|
| | 24 h | Final pH | 24 h | Final pH | 24 h | Final pH |
| Compound 1 | 4.44 | 3.10 | 0.05 | 6.48 | 0.84 | 5.11 |
| Isethionate (Form A) | 4.45 | 1.93 | 1.12 | 4.05 | 0.76 | 4.98 |

Compound 1 Isethionate (Form B)

50 mg Compound 1 was weighed into 2 mL vials, and 743 µL solvent IPA/water (95/5, V/V) was added in the vials subsequently. Then 1.1 e.q. counter-ion of 2-hydroxyethane-sulphonic acid (257 µL, concentration: 0.5 mol/L) was added to the vial. The vial was placed on the thermo-mixer with a stir bar and heated to 50° C. After keeping at 50° C. under constant stirring at 500 rpm for 21 hrs, the vial was then cooled to 25° C. After keeping at 25° C. for 1 hr, the vial showed a clear solution. The solvent was evaporated by vacuum oven at 30° C.

The resulting solids were characterized by PLM and XRPD (FIG. 75).

Example 16: Preparation of Gentisate Salt of Compound 1

A Gentisate Salt of Compound 1 may be prepared from Compound 1 using the following exemplary method.

Compound 1 Gentisate (Form A)

500 mg of Compound 1 was dissolved in 16.0 mL of acetone at 60° C. while stirring at 500 rpm and held at 60° C. for 1.5 hrs. 1.1 e.q. gentisic acid in acetone (2.565 mL, 0.5 mol/L) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs resulting in 281.5 mg of powder with a yield of 31.39%.

The resulting solid is Compound 1 Gentisate (Form A). The ratio of Compound 1:gentisic acid in Compound 1 Gentisate (Form A) is 1:1.03 as determined by ion chromatography. The XPRD is shown in FIG. 76; the DSC and TGA are shown in FIG. 77; and the DVS is shown in FIG. 78.

Compound 1 Gentisate (Form A) was analyzed by $^1$H-NMR in deuterated DMSO resulting in the following chemical shifts: $^1$H NMR (400 MHz, DMSO-d6) δ ppm 0.53-0.80 (m, 7H) 0.85-1.72 (m, 20H) 2.00-2.13 (m, 5H) 2.66-2.74 (m, 1H) 3.04 (s, 2H) 4.02 (br s, 1H) 4.90-5.12 (m, 2H) 6.71 (d, J=8.76 Hz, 1H) 6.88 (dd, J=8.82, 3.06 Hz, 1H) 7.03 (s, 1H) 7.13-7.17 (m, 2H) 7.78-7.86 (m, 1H) 7.81 (s, 1H) 9.01 (br s, 1H).

Chemical and Physical Stability Test

Chemical and physical stability testing was carried out using the procedures set forth in Example 1. The chemical and physical stability test results for Compound 1 Gentisate (Form A) and Compound 1 free base are shown in the following table:

| Starting materials | Conditions | XRPD patterns | Final purity |
|---|---|---|---|
| Compound 1 | 60° C., 1 w | Pattern A | 98.2 |
| | 40° C./75% RH, 1 w | Pattern A | 98.2 |
| | 1.2 million lux-hrs | Pattern A | 97.9 |
| | Dark control | Pattern A | 98.3 |
| Gentisate salt (Form A) | 60° C., 1 w | Form A | 97.0 |
| | 40° C./75% RH, 1 w | Form A | 97.6 |
| | 1.2 million lux-hrs | Form A | 96.0 |
| | Dark control | Form A | 97.6 |

Compound 1 Gentisate (Form B)

50 mg Compound 1 and 1.1 e.q. counter ion of gentisic acid in solid form were weighed into 2 mL vials individually, and then 1 mL EtOAc solvent was added into the vial. The vial was placed on the thermo-mixer with a stir bar and heated to 50° C. After keeping at 50° C. under constant stirring at 900 rpm for 18 hrs, the vial was then cooled to 25° C. After keeping at 25° C. for 1 hr, the solids in suspension were isolated by centrifugation and dried in the vacuum oven at 30° C. for 18 hrs.

The dried solids were characterized by PLM and XRPD (FIG. 79).

Compound 1 Gentisate (Form C)

50 mg Compound 1 and 1.1 e.q. counter ion of gentisic acid in solid form were weighed into 2 mL vials individually, and then 1 mL IPA/water (95/5, V/V) solvent was added into the vial. The vial was placed on the thermo-mixer with a stir bar and heated to 50° C. After keeping at 50° C. under constant stirring at 900 rpm for 18 hrs, the vial was then cooled to 25° C. After keeping at 25° C. for 1 hr, the solids in suspension were isolated by centrifugation and dried in the vacuum oven at 30° C. for 18 hrs.

The dried solids were characterized by PLM and XRPD (FIG. 80).

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Gentisate (Form A) and Compound 1 free base are shown in the following table:

| Solute tested | SGF (original pH = 1.82) | | FaSSIF (original pH = 6.51) | | FeSSIF (original pH = 4.99) | |
|---|---|---|---|---|---|---|
| | 24 h | Final pH | 24 h | Final pH | 24 h | Final pH |
| Compound 1 | 4.44 | 3.10 | 0.05 | 6.48 | 0.84 | 5.11 |
| Gentisate (Form A) | 1.16 | 1.93 | 0.15 | 5.23 | 1.20 | 5.01 |

Example 17: Preparation of 1-Hydroxy-2-Naphthoate Salt of Compound 1

A 1-Hydroxy-2-Naphthoate Salt of Compound 1 may be prepared from Compound 1 using the following exemplary method.

Compound 1 1-Hydroxy-2-Naphthoate (Form A)

500 mg of Compound 1 was dissolved in 16.0 mL of acetone at 60° C. while stirring at 500 rpm and held at 60° C. for 1.5 hrs. 1.1 e.q. 1-hydroxy-2-napthoic acid in acetone (2.565 mL, 0.5 mol/L) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs resulting in 675.36 mg of powder with a yield of 68.15%.

The resulting solid is Compound 1 1-Hydroxy-2-Naphthoate (Form A). The ratio of Compound 1:1-Hydroxy-2-Napthoic acid in Compound 1 1-Hydroxy-2-Naphthoate (Form A) is 1:1.15 as determined by ion chromatography. The XPRD is shown in FIG. 81; the DSC and TGA are shown in FIG. 82; and the DVS is shown in FIG. 83.

Compound 1 1-Hydroxy-2-Naphthoate (Form A) was analyzed by $^1$H-NMR in deuterated DMSO resulting in the following chemical shifts: $^1$H NMR (400 MHz, DMSO-$d_6$) δ ppm 0.49-0.79 (m, 7H) 0.82-1.76 (m, 22H) 1.96-2.16 (m, 4H) 2.63-2.76 (m, 1H) 2.95-3.11 (m, 2H) 4.98-5.22 (m, 2H) 7.19-7.32 (m, 3H) 7.46-7.62 (m, 2H) 7.72-7.86 (m, 2H) 8.16-8.29 (m, 2H).

Chemical and Physical Stability Test

Chemical and physical stability testing was carried out using the procedures set forth in Example 1. The chemical and physical stability test results for Compound 1 1-Hydroxy-2-Naphthoate (Form A) and Compound 1 free base are shown in the following table:

| Starting materials | Conditions | XRPD patterns | Final purity |
|---|---|---|---|
| Compound 1 | 60° C., 1 w | Pattern A | 98.15 |
|  | 40° C./75% RH, 1 w | Pattern A | 98.23 |
|  | 1.2 million lux-hrs | Pattern A | 97.92 |
|  | Dark control | Pattern A | 98.30 |
| 1-hydroxy-2-napthoate (Form A) | 60° C., 1 w | Form A | 88.91 |
|  | 40° C./75% RH, 1 w | Form A | 92.64 |
|  | 1.2 million lux-hrs | Form A | 92.64 |
|  | Dark control | Form A | 91.96 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 1-Hydroxy-2-Naphthoate (Form A) and Compound 1 free base are shown in the following table:

| Solute tested | SGF (original pH = 1.82) | | FaSSIF (original pH = 6.51) | | FeSSIF (original pH = 4.99) | |
|---|---|---|---|---|---|---|
|  | 24 h | Final pH | 24 h | Final pH | 24 h | Final pH |
| Compound 1 | 4.44 | 3.10 | 0.05 | 6.48 | 0.84 | 5.11 |
| 1-hydroxy-2-napthoate (Form A) | 1.04 | 2.05 | 0.08 | 5.74 | 2.32 | 4.98 |

Compound 1 1-Hydroxy-2-Naphthoate (Form B)

50 mg Compound 1 and 1.1 e.q. counter ion of 1-hydroxy-2-napthoic acid in solid form were weighed into 2 mL vials individually, and then 1 mL EtOAc solvent was added into the vial. The vial was placed on the thermo-mixer with a stir bar and heated to 50° C. After keeping at 50° C. under constant stirring at 900 rpm for 18 hrs, the vial was then cooled to 25° C. After keeping at 25° C. for 1 hr, the solids in suspension were isolated by centrifugation and dried in the vacuum oven at 30° C. for 18 hrs.

The dried solids were characterized by PLM and XRPD (FIG. 84).

Compound 1 1-Hydroxy-2-Naphthoate (Form C)

50 mg Compound 1 and 1.1 e.q. counter ion of 1-hydroxy-2-napthoic acid in solid form were weighed into 2 mL vials individually, and then 1 mL ACN solvent was added into the vial. The vial was placed on the thermo-mixer with a stir bar and heated to 50° C. After keeping at 50° C. under constant stirring at 900 rpm for 18 hrs, the vial was then cooled to 25° C. After keeping at 25° C. for 1 hr, the solids in suspension were isolated by centrifugation and dried in the vacuum oven at 30° C. for 18 hrs.

The dried solids were characterized by PLM and XRPD (FIG. 85).

Compound 1 1-Hydroxy-2-Naphthoate (Form D)

50 mg Compound 1 and 1.1 e.q. counter ion of 1-hydroxy-2-napthoic acid in solid form were weighed into 2 mL vials individually, and then 1 mL solvent IPA/water (95/5, V/V) was added into the vial. The vial was placed on the thermo-mixer with a stir bar and heated to 50° C. After keeping at 50° C. under constant stirring at 900 rpm for 18 hrs, the vial was then cooled to 25° C. After keeping at 25° C. for 1 hr, the solids in suspension were isolated by centrifugation and dried in the vacuum oven at 30° C. for 18 hrs.

The dried solids were characterized by PLM and XRPD (FIG. 86).

Example 18: Preparation of Cyclamate Salt of Compound 1

A Cyclamate Salt of Compound 1 may be prepared from Compound 1 using the following exemplary method.

500 mg of Compound 1 was dissolved in 16.0 mL of acetone at 60° C. while stirring at 500 rpm and held at 60° C. for 1.5 hrs. 1.1 e.q. cyclamic acid in acetone (2.565 mL, 0.5 mol/L) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs resulting in 715.81 mg of powder with a yield of 74.48%.

The resulting solid is Compound 1 Cyclamate (Form A). The ratio of Compound 1:cyclamic acid in Compound 1 Cyclamate (Form A) is 1:1.00 as determined by ion chromatography. The XPRD is shown in FIG. 87; the DSC and TGA are shown in FIG. 88; and the DVS is shown in FIG. 89.

Compound 1 Cyclamate (Form A) was analyzed by $^1$H-NMR in deuterated DMSO resulting in the following chemical shifts: $^1$H NMR (400 MHz, DMSO-d$_6$) δ ppm 0.49-0.80 (m, 7H) 0.84-1.77 (m, 30H) 1.83-2.14 (m, 5H) 2.65-2.74 (m, 1H) 2.90-3.09 (m, 3H) 3.35-3.60 (m, 2H) 4.03 (br s, 1H) 4.87-5.16 (m, 2H) 6.97-7.18 (m, 2H) 7.54-7.91 (m, 3H).

Chemical and Physical Stability Test

Chemical and physical stability testing was carried out using the procedures set forth in Example 1. The chemical and physical stability test results for Compound 1 Cyclamate (Form A) and Compound 1 free base are shown in the following table:

| Starting materials | Conditions | XRPD patterns | Final purity |
|---|---|---|---|
| Compound 1 | 60° C., 1 w | Pattern A | 98.2 |
|  | 40° C./75% RH, 1 w | Pattern A | 98.2 |
|  | 1.2 million lux-hrs | Pattern A | 97.9 |
|  | Dark control | Pattern A | 98.3 |
| Cyclamate (Form A) | 60° C., 1 w | Form A | 97.6 |
|  | 40° C./75% RH, 1 w | Form A | 97.5 |
|  | 1.2 million lux-hrs | Form A | 97.2 |
|  | Dark control | Form A | 97.5 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Cyclamate (Form A) and Compound 1 free base are shown in the following table:

| Solute tested | SGF (original pH = 1.82) | | FaSSIF (original pH = 6.51) | | FeSSIF (original pH = 4.99) | |
|---|---|---|---|---|---|---|
|  | 24 h | Final pH | 24 h | Final pH | 24 h | Final pH |
| Compound 1 | 4.44 | 3.10 | 0.05 | 6.48 | 0.84 | 5.11 |
| Cyclamate (Form A) | 1.99 | 2.05 | 0.57 | 4.50 | 0.83 | 5.00 |

Example 19: Preparation of Ethane-1,2-Disulfonate Salt of Compound 1

A Ethane-1,2-Disulfonate Salt of Compound 1 may be prepared from Compound 1 using the following exemplary method.

Compound 1 Ethane-1,2-Disulfonate (Form A)

500 mg of Compound 1 was dissolved in 16.0 mL of acetone at 60° C. while stirring at 500 rpm and held at 60° C. for 1.5 hrs. 1.1 e.q. ethane-1,2-disulfonic acid in acetone (2.565 mL, 0.5 mol/L) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs resulting in 704.45 mg of powder with a yield of 71.61%.

The resulting solid is Compound 1 Ethane-1,2-Disulfonate (Form A). The ratio of Compound 1:Ethane-1,2-Disulfonic acid in Compound 1 Ethane-1,2-Disulfonate (Form A) is 1:2.4 as determined by ion chromatography. The XPRD is shown in FIG. 90; the DSC and TGA are shown in FIG. 91; and the DVS is shown in FIG. 92.

Compound 1 Ethane-1,2-Disulfonate (Form A) was analyzed by $^1$H-NMR in deuterated DMSO resulting in the following chemical shifts: $^1$H NMR (400 MHz, DMSO-d$_6$) δ ppm 0.52-0.79 (m, 7H) 0.82-1.77 (m, 22H) 1.97-2.15 (m, 2H) 2.58-2.78 (m, 4H) 3.03 (s, 2H) 3.23 (s, 4H) 5.13-5.40 (m, 2H) 7.56-7.71 (m, 2H) 9.00 (s, 1H).

Chemical and Physical Stability Test

Chemical and physical stability testing was carried out using the procedures set forth in Example 1. The chemical and physical stability test results for Compound 1 Ethane-1,2-Disulfonate (Form A) and Compound 1 free base are shown in the following table:

| Starting materials | Conditions | XRPD patterns | Final purity |
|---|---|---|---|
| Compound 1 | 60° C., 1 w | Pattern A | 98.2 |
|  | 40° C./75% RH, 1 w | Pattern A | 98.2 |
|  | 1.2 million lux-hrs | Pattern A | 97.9 |
|  | Dark control | Pattern A | 98.3 |
| Ethane-1,2-disulfonate salt (Form A) | 60° C., 1 w | Form A | 95.6 |
|  | 40° C./75% RH, 1 w | Form A | 96.0 |
|  | 1.2 million lux-hrs | Form A | 96.6 |
|  | Dark control | Form A | 96.8 |

Compound 1 Ethane-1,2-Disulfonate (Form B)

50 mg Compound 1 and 1.1 e.q. counter ion of ethane-1,2-disulfonic acid in solid form were weighed into 2 mL vials individually, and then 1 mL solvent EtOAc/IPA/water (95/5, V/V) was added into the vial. The vial was placed on the thermo-mixer with a stir bar and heated to 50° C. After keeping at 50° C. under constant stirring at 900 rpm for 18 hrs, the vial was then cooled to 25° C. After keeping at 25° C. for 1 hr, the solids in suspension were isolated by centrifugation and dried in the vacuum oven at 30° C. for 18 hrs.

The dried solids were characterized by PLM and XRPD (FIG. 93).

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Ethane-1,2-Disulfonate (Form A) and Compound 1 free base are shown in the following table:

| Solute tested | SGF (original pH = 1.82) | | FaSSIF (original pH = 6.51) | | FeSSIF (original pH = 4.99) | |
|---|---|---|---|---|---|---|
|  | 24 h | Final pH | 24 h | Final pH | 24 h | Final pH |
| Compound 1 | 4.44 | 3.10 | 0.05 | 6.48 | 0.84 | 5.11 |
| Ethane-1,2-disulfonate (Form A) | 1.66 | 1.86 | 0.55 | 4.53 | 0.06 | 4.97 |

Example 20: Preparation of Dichloroacetate Salt of Compound 1

A Dichloroacetate Salt of Compound 1 may be prepared from Compound 1 using the following exemplary method.

500 mg of Compound 1 was dissolved in 16.0 mL of acetone at 60° C. while stirring at 500 rpm and held at 60°

C. for 1.5 hrs. 1.1 e.q. dichloroacetic acid in acetone (2.565 mL, 0.5 mol/L) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs resulting in 559.98 mg of powder with a yield of 83.41%.

The resulting solid is Compound 1 Dichloroacetate (Form A). The ratio of Compound 1:Dichloroacetic acid in Compound 1 Dichloroacetate (Form A) is 1:1.14 as determined by ion chromatography. The XPRD is shown in FIG. 94; the DSC and TGA are shown in FIG. 95; and the DVS is shown in FIG. 96.

Compound 1 Dichloroacetate (Form A) was analyzed by $^1$H-NMR in deuterated DMSO resulting in the following chemical shifts: $^1$H NMR (400 MHz, DMSO-$d_6$) δ ppm 0.46-0.79 (m, 7H) 0.82-1.75 (m, 21H) 1.96-2.15 (m, 2H) 2.62-2.75 (m, 1H) 3.02 (s, 2H) 4.98-5.27 (m, 3H) 6.30 (s, 1H) 7.31 (d, J=12.80 Hz, 2H) 8.32 (s, 1H).

Chemical and Physical Stability Test

Chemical and physical stability testing was carried out using the procedures set forth in Example 1. The chemical and physical stability test results for Compound 1 Dichloroacetate (Form A) and Compound 1 free base are shown in the following table:

| Starting materials | Conditions | XRPD patterns | Final purity |
|---|---|---|---|
| Compound 1 | 60° C., 1 w | Pattern A | 98.2 |
| | 40° C./75% RH, 1 w | Pattern A | 98.2 |
| | 1.2 million lux-hrs | Pattern A | 97.9 |
| | Dark control | Pattern A | 98.3 |
| Dichloroacetate (Form A) | 60° C., 1 w | Form A | 96.3 |
| | 40° C./75% RH, 1 w | Form A | 98.0 |
| | 1.2 million lux-hrs | Form A | 96.4 |
| | Dark control | Form A | 97.3 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Dichloroacetate (Form A) and Compound 1 free base are shown in the following table:

| | SGF (original pH = 1.82) | | FaSSIF (original pH = 6.51) | | FeSSIF (original pH = 4.99) | |
|---|---|---|---|---|---|---|
| Solute tested | 24 h | Final pH | 24 h | Final pH | 24 h | Final pH |
| Compound 1 | 4.44 | 3.10 | 0.05 | 6.48 | 0.84 | 5.11 |
| Dichloroacetate (Form A) | 5.96 | 1.90 | 0.60 | 4.41 | 1.20 | 4.00 |

Example 21: Preparation of L-Malate Salt of Compound 1

L-Malate Salts of Compound 1 may be prepared from Compound 1 using the following exemplary method.

Compound 1 L-Malate (Form A):

200 mg of Compound 1 was dissolved in 10.0 mL of acetone at 60° C. while stirring at 500 rpm and held at 60° C. for 1.5 hrs. 1.1 e.q. L-malic acid in acetone (1.027 mL, 0.5 mol/L) was then added into the Compound 1 solution and incubated at 60° C. for 3 hrs, then cooled to 25° C. and held at 25° C. for 20 hrs. The solution was evaporated by nitrogen to remove the organic solvent. The obtained wet product was vacuum dried at 25° C. for 42 hrs resulting in 230.93 mg of powder with a yield of 85.9%.

The resulting solid is Compound 1 L-Malate (Form A). The ratio of Compound 1:Malic acid in Compound 1 L-Malate (Form A) is 1:1.35 as determined by ion chromatography. The XPRD is shown in FIG. 97; the DSC and TGA are shown in FIG. 98; and the DVS is shown in FIG. 99.

Compound 1 L-Malate (Form A) was analyzed by $^1$H-NMR in deuterated DMSO resulting in the following chemical shifts: $^1$H NMR (400 MHz, DMSO-$d_6$): δ 0.57-0.86 (m, 4H) 0.70-0.86 (m, 4H) 0.89-1.79 (m, 21H) 2.00-2.21 (m, 3H) 2.33-2.78 (m, 13H) 3.10 (s, 2H) 3.31 (s, 3H) 4.28 (dd, J=7.32, 5.44 Hz, 1H) 4.85-5.19 (m, 2H) 7.00 (s, 1H) 7.13 (s, 1H) 7.53-7.84 (m, 1H).

Compound 1 L-Malate (Form B):

10 g of Compound 1 was suspended in 350 mL of acetone at 60° C. while stirring at 200 rpm and held at 60° C. for 0.5 hrs. 1.1 e.q. L-malic acid in acetone (50 mL, 0.5 mol/L) was then added into the Compound 1 suspension and incubated at 60° C. for 3 hrs, then cooled to 25° C. and held at 25° C. for 72 hrs with vial openly. The suspension was centrifuged and the precipitate was collected and vacuum dried at 30° C. for 24 hrs resulting in 4.44 g of powder with a yield of 33.86%.

The resulting solid is Compound 1 L-Malate (Form B). The ratio of Compound 1:Malic acid in Compound 1 L-Malate (Form B) is 1:1.26 as determined by ion chromatography. The XPRD is shown in FIG. 100; the DSC and TGA are shown in FIG. 101; and the DVS is shown in FIG. 102.

Compound 1 L-Malate (Form B) was analyzed by $^1$H-NMR in deuterated DMSO resulting in the following chemical shifts: $^1$H NMR (400 MHz, DMSO-$d_6$) δ ppm 0.45-0.79 (m, 7H) 0.83-1.73 (m, 20H) 1.98-2.12 (m, 2H) 2.43 (dd, J=15.69, 7.40 Hz, 1H) 2.56-2.72 (m, 2H) 3.04 (s, 2H) 4.22 (dd, J=7.28, 5.52 Hz, 1H) 4.86-5.10 (m, 2H) 6.94 (s, 1H) 7.07 (s, 1H) 7.65 (s, 1H).

Chemical and Physical Stability Test

Chemical and physical stability testing was carried out using the procedures set forth in Example 1. The chemical and physical stability test results for Compound 1 L-Malate (Form A), Compound 1 L-Malate (Form B), and Compound 1 free base are shown in the following table:

| Starting materials | Conditions | XRPD patterns | Final purity |
|---|---|---|---|
| Compound 1 | 60° C., 1 w | Pattern A | 99.3 |
| | 40° C./75% RH, 1 w | Pattern A | 99.1 |
| | 1.2 million lux-hrs | Pattern A | 99.2 |
| | Dark control | Pattern A | 99.1 |
| L-Malate (Form A) | 60° C., 1 w | Form A | 99.6 |
| | 40° C./75% RH, 1 w | Form A | 99.2 |
| | 1.2 million lux-hrs | Form A | 99.3 |
| | Dark control | Form A | 99.3 |

| Starting materials | Conditions | XRPD patterns | Final purity |
|---|---|---|---|
| L-Malate (Form B) | 60° C., 1 w | Form B | 97.8 |
| | 40° C./75% RH, 1 w | Similar to Form A | 98.5 |
| | 1.2 million lux-hrs | Form B | 97.6 |
| | Dark control | Form B | 97.5 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 L-Malate (Form A), Compound 1 L-Malate (Form B), and Compound 1 free base are shown in the following table:

| Solute tested | SGF (original pH = 1.82) | | | FaSSIF (original pH = 6.50) | | | FeSSIF (original pH = 4.99) | | |
|---|---|---|---|---|---|---|---|---|---|
| | 1 h | 24 h | Final PH | 1 h | 24 h | Final pH | 1 h | 24 h | Final PH |
| Compound 1 | 3.41 | 2.81 | 2.07 | 0.03 | 0.03 | 6.47 | 0.87 | 0.95 | 5.00 |
| L-Malate (Form A) | 5.35 | 4.69 | 3.26 | 0.10 | 0.08 | 6.02 | 1.66 | 0.73 | 4.79 |
| L-Malate (Form B) | N/A | 6.53 | 2.63 | N/A | 1.12 | 3.98 | N/A | 1.25 | 4.01 |

Example 22: Preparation of Hydrochloride Salt of Compound 1

Hydrochloride Salts of Compound 1 may be prepared from Compound 1 using the following exemplary methods.

Compound 1 Hydrochloride (Form A):

200 mg of Compound 1 was dissolved in 10.0 mL of acetone at 60° C. while stirring at 500 rpm and held at 60° C. for 1.5 hrs. 1.1 e.q. hydrochloric acid in acetone (1.027 mL, 0.5 mol/L) was then added into the Compound 1 solution and incubated at 60° C. for 3 hrs, then cooled to 25° C. and held at 25° C. for 20 hrs. This suspension was centrifuged and the precipitate collected and washed with acetone. The obtained wet product was vacuum dried at 25° C. for 42 hrs resulting in 168.15 mg of powder with a yield of 76.9%.

The resulting solid is Compound 1 Hydrochloride (Form A). The ratio of Compound 1:hydrochloric acid in Compound 1 Hydrochloride (Form A) is 1:0.94 as determined by ion chromatography. The XPRD is shown in FIG. 103; the DSC and TGA are shown in FIG. 104; and the DVS is shown in FIG. 105.

Compound 1 Hydrochloride (Form B):

500 mg of hydrochloride (Form A) was dissolved in 4.0 mL of ethanol at 50° C. The solution was filtered and a 6.25 fold volume of heptane was then added dropwise to the solution which produced a suspension. This suspension was kept constant stirring at 500 rpm and held at 50° C. for 24 hrs. The suspension was then centrifuged and the precipitate collected, vacuum dried at 30° C. for 24 hrs resulting in 365 mg of powder with a yield of 73.0%.

The resulting solid is Compound 1 Hydrochloride (Form B). The ratio of Compound 1:hydrochloric acid in Compound 1 Hydrochloride (Form B) is 1:0.96 as determined by ion chromatography. The XPRD is shown in FIG. 106; the DSC and TGA are shown in FIG. 107; and the DVS is shown in FIG. 108.

Compound 1 Hydrochloride (Form C):

300 mg of hydrochloride salt (Form A) was suspended in 6.0 mL of 0.901 water activity solution at 50° C. under stirring at 700 rpm which produced a clear solution. Then 200 mg of the hydrochloride salt was added which produced a suspension. The suspension remained under constant stirring at 700 rpm and held at 50° C. for 1 week. Then the suspension was centrifuged and the precipitate collected, vacuum dried at 30° C. for 24 hrs resulting in 400 mg of powder with a yield of 80.0%.

The resulting solid is Compound 1 Hydrochloride (Form C). The ratio of Compound 1:Hydrochloric acid in Compound 1 Hydrochloride (Form C) is 1:0.97 as determined by ion chromatography. The XPRD is shown in FIG. 109; the DSC and TGA are shown in FIG. 110; and the DVS is shown in FIG. 111.

Chemical and Physical Stability Test

Chemical and physical stability testing was carried out using the procedures set forth in Example 1. The chemical and physical stability test results for Compound 1 Hydrochloride (Form A), Compound 1 Hydrochloride (Form B), Compound 1 Hydrochloride (Form C) and Compound 1 free base are shown in the following table:

| Starting materials | Conditions | XRPD patterns | Final purity |
|---|---|---|---|
| Compound 1 | 60° C., 1 w | Pattern A | 99.3 |
| | 40° C./75% RH, 1 w | Pattern A | 99.1 |
| | 1.2 million lux-hrs | Pattern A | 99.2 |
| | Dark control | Pattern A | 99.1 |
| Hydrochloride (Form A) | 60° C., 1 w | Form A | 99.5 |
| | 40° C./75% RH, 1 w | Form A | 99.4 |
| | 1.2 million lux-hrs | Form A | 99.5 |
| | Dark control | Form A | 99.5 |
| Hydrochloride (Form B) | 60° C., 1 w | Form B | 100.0 |
| | 40° C./75% RH, 1 w | Similar to Form C | 100.0 |
| | 1.2 million lux-hrs | Form B | 98.2 |
| | Dark control | Form B | 98.59 |
| Hydrochloride (Form C) | 60° C., 1 w | Form C | 98.6 |
| | 40° C./75% RH, 1 w | Form C | 100.0 |
| | 1.2 million lux-hrs | Form C | 100.0 |
| | Dark control | Form C | 99.2 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Hydrochloride (Form A), Compound 1 Hydrochloride (Form B), Compound 1 Hydrochloride (Form C) and Compound 1 free base are shown in the following table:

| | SGF (original pH = 1.82) | | | FaSSIF (original pH = 6.50) | | | FeSSIF (original pH = 4.99) | | |
|---|---|---|---|---|---|---|---|---|---|
| Solute tested | 1 h | 24 h | Final pH | 1 h | 24 h | Final pH | 1 h | 24 h | Final pH |
| Compound 1 | 3.41 | 2.81 | 2.07 | 0.03 | 0.03 | 6.47 | 0.87 | 0.95 | 5.00 |
| Hydrochloride (Form A) | 6.28 | 6.28 | 2.05 | 0.86 | 0.84 | 4.05 | 1.17 | 0.67 | 4.93 |
| Hydrochloride (Form B) | N/A | 3.00 | 1.73 | N/A | 1.70 | 3.76 | N/A | 1.32 | 3.94 |
| Hydrochloride (Form C) | N/A | 1.58 | 1.69 | N/A | 0.95 | 4.03 | N/A | 1.12 | 3.99 |

Example 22: Preparation of Napsylate Salt of Compound 1

A Napsylate Salt of Compound 1 may be prepared from Compound 1 using the following exemplary method.

Compound 1 Napsylate (Form A):

500 mg of Compound 1 was dissolved in 16.0 mL of acetone at 60° C. while stirring at 500 rpm and held at 60° C. for 1.5 hrs. 1.1 e.q. naphthalene-2-sulfonic acid hydrate in acetone (2.565 mL, 0.5 mol/L) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs resulting in 690.41 mg of powder with a yield of 89.17%.

The resulting solid is Compound 1 Napsylate (Form A). The ratio of Compound 1:naphthalene-2-sulfonic acid in Compound 1 Napsylate (Form A) is 1:1.04 as determined by ion chromatography. The XPRD is shown in FIG. 112; the DSC and TGA are shown in FIG. 113; and the DVS is shown in FIG. 114.

Compound 1 Napsylate (Form A) was analyzed by $^1$H-NMR in deuterated DMSO resulting in the following chemical shifts: $^1$H NMR (400 MHz, DMSO-$d_6$) δ ppm 0.51-0.80 (m, 8H) 0.82-1.77 (m, 25H) 2.33 (br d, J=1.75 Hz, 2H) 2.54-2.78 (m, 3H) 3.05 (s, 3H) 3.20-3.30 (m, 6H) 4.04 (br s, 1H) 5.15-5.36 (m, 2H) 7.49-7.73 (m, 5H) 7.83-8.01 (m, 3H) 8.14 (s, 1H) 8.94 (s, 1H).

Chemical and Physical Stability Test

Chemical and physical stability testing was carried out using the procedures set forth in Example 1. The chemical and physical stability test results for Compound 1 Napsylate (Form A) and Compound 1 free base are shown in the following table:

| Starting materials | Conditions | XRPD patterns | Final purity |
|---|---|---|---|
| Compound 1 | 60° C., 1 w | Pattern A | 98.2 |
| | 40° C./75% RH, 1 w | Pattern A | 98.2 |
| | 1.2 million lux-hrs | Pattern A | 97.9 |
| | Dark control | Pattern A | 98.3 |
| Napsylate (Form A) | 60° C., 1 w | Form A | 99.1 |
| | 40° C./75% RH, 1 w | Form A | 99.1 |
| | 1.2 million lux-hrs | Form A | 99.0 |
| | Dark control | Form A | 99.1 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Napsylate (Form A) and Compound 1 free base are shown in the following table:

| | SGF (original pH = 1.82) | | FaSSIF (original pH = 6.51) | | FeSSIF (original pH = 4.99) | |
|---|---|---|---|---|---|---|
| Solute tested | 24 h | Final pH | 24 h | Final pH | 24 h | Final pH |
| Compound 1 | 4.44 | 3.10 | 0.05 | 6.48 | 0.84 | 5.11 |
| Napsylate (Form A) | 0.40 | 1.86 | 0.06 | 5.42 | 1.00 | 5.04 |

Compound 1 Napsylate (Form B):

50 mg Compound 1 and 1.1 e.q. counter ion of naphthalene-2-sulfonic acid hydrate in solid form were weighed into 2 mL vials individually, and then 1 mL solvent EtOAc/ACN was added into the vial. The vial was placed on the thermomixer with a stir bar and heated to 50° C. After keeping at 50° C. under constant stirring at 500 rpm for 21 hrs, the vial was then cooled to 25° C. After keeping at 25° C. for 1 hr, the solids in suspension were isolated by centrifugation and dried in the vacuum oven at 30° C. for 18 hrs.

The obtained dried solids were characterized by PLM and XRPD (FIG. 115).

Example 23: Preparation of Oxalate Salt of Compound 1

An Oxalate Salt of Compound 1 may be prepared from Compound 1 using the following exemplary method.

Compound 1 Oxalate (Form A)

500 mg of Compound 1 was dissolved in 16.0 mL of acetone at 60° C. while stirring at 500 rpm and held at 60° C. for 1.5 hrs. 1.1 e.q. oxalic acid in acetone (2.565 mL, 0.5 mol/L) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs resulting in 595.76 mg of powder with a yield of 96.32%.

The resulting solid is Compound 1 Oxalate (Form A). The ratio of Compound 1:oxalic acid in Compound 1 Oxalate (Form A) is 1:0.91 as determined by ion chromatography. The XPRD is shown in FIG. 116; the DSC and TGA are shown in FIG. 117; and the DVS is shown in FIG. 118.

Chemical and Physical Stability Test

Chemical and physical stability testing was carried out using the procedures set forth in Example 1. The chemical and physical stability test results for Compound 1 Oxalate (Form A) and Compound 1 free base are shown in the following table:

| Starting materials | Conditions | XRPD patterns | Final purity |
|---|---|---|---|
| Compound 1 | 60° C., 1 w | Pattern A | 98.2 |
| | 40° C./75% RH, 1 w | Pattern A | 98.2 |
| | 1.2 million lux-hrs | Pattern A | 97.9 |
| | Dark control | Pattern A | 98.3 |
| Oxalate (Form A) | 60° C., 1 w | Form A | 98.3 |
| | 40° C./75% RH, 1 w | Form A | 98.4 |
| | 1.2 million lux-hrs | Form A | 98.2 |
| | Dark control | Form A | 98.9 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 Oxalate (Form A) and Compound 1 free base are shown in the following table:

| Solute tested | SGF (original pH = 1.82) | | FaSSIF (original pH = 6.51) | | FeSSIF (original pH = 4.99) | |
|---|---|---|---|---|---|---|
| | 24 h | Final pH | 24 h | Final pH | 24 h | Final pH |
| Compound 1 | 4.44 | 3.10 | 0.05 | 6.48 | 0.84 | 5.11 |
| Oxalate (Form A) | 3.76 | 1.95 | 1.84 | 4.86 | 0.75 | 3.73 |

Compound 1 Oxylate (Form B)

50 mg Compound 1 and 1.1 e.q. counter ion of oxalic acid in solid form were weighed into 2 mL vials individually, and then 1 mL EtOAc solvent was added into the vial. The vial was placed on the thermo-mixer with a stir bar and heated to 50° C. After keeping at 50° C. under constant stirring at 500 rpm for 21 hrs, the vial was then cooled to 25° C. After keeping at 25° C. for 1 hr, the solids in suspension were isolated by centrifugation and dried in the vacuum oven at 30° C. for 18 hrs.

The dried solids were characterized by PLM and XRPD (FIG. 119).

Example 24: Preparation of P-Aminosalicylate Salt of Compound 1

A P-Aminosalicylate Salt of Compound 1 may be prepared from Compound 1 using the following exemplary method.

Compound 1 P-Aminosalicylate (Form A)

500 mg of Compound 1 was dissolved in 16.0 mL of acetone at 60° C. while stirring at 500 rpm and held at 60° C. for 1.5 hrs. 1.1 eq. 4-aminosalicylic acid in acetone (2.565 mL, 0.5 mol/L) was then added into the Compound 1 solution and incubated at 60° C. for 3 hrs, then cooled to 25° C. and held at 25° C. for overnight. This suspension was centrifuged and the precipitate collected and washed with acetone. The obtained wet product was vacuum dried at 25° C. for 72 hrs resulting in 583.32 mg of powder with a yield of 83.37%.

The resulting solid is Compound 1 P-Aminosalicylate (Form A). The ratio of Compound 1:4-aminosalicylic acid in Compound 1 P-Aminosalicylate (Form A) is 1:1.03 as determined by ion chromatography. The XPRD is shown in FIG. 120; the DSC and TGA are shown in FIG. 121; and the DVS is shown in FIG. 122.

Compound 1 P-Aminosalicylate (Form A) was analyzed by $^1$H-NMR in deuterated DMSO resulting in the following chemical shifts: $^1$H NMR (400 MHz, DMSO-$d_6$) δ ppm 0.51-0.80 (m, 7H) 0.83-1.74 (m, 22H) 1.97-2.15 (m, 3H) 2.34 (s, 1H) 2.68 (br t, J=8.69 Hz, 1H) 2.99-3.09 (m, 2H) 3.25 (s, 4H) 4.83-5.10 (m, 2H) 5.88-6.11 (m, 3H) 6.76 (t, J=8.19 Hz, 1H) 6.90 (s, 1H) 7.04 (s, 1H) 7.42 (d, J=8.63 Hz, 1H) 7.57 (s, 1H)

Chemical and Physical Stability Test

Chemical and physical stability testing was carried out using the procedures set forth in Example 1. The chemical and physical stability test results for Compound 1 P-Aminosalicylate (Form A) and Compound 1 free base are shown in the following table:

| Starting materials | Conditions | XRPD patterns | Final purity |
|---|---|---|---|
| Compound 1 | 60° C., 1 w | Pattern A | 98.2 |
| | 40° C./75% RH, 1 w | Pattern A | 98.2 |
| | 1.2 million lux-hrs | Pattern A | 97.9 |
| | Dark control | Pattern A | 98.3 |
| P-aminosalicylate (Form A) | 60° C., 1 w | Form A | 91.5 |
| | 40° C./75% RH, 1 w | Form A | 97.0 |
| | 1.2 million lux-hrs | Form A | 95.7 |
| | Dark control | Form A | 95.8 |

Solubility Tests in Simulated Gastric and Intestinal Fluids

Solubility Tests in Simulated Gastric and Intestinal Fluids was carried out using the procedures set forth in Example 1. The solubility results (mg/mL) in bio-relevant solutions for Compound 1 P-Aminosalicylate (Form A) and Compound 1 free base are shown in the following table:

| Solute tested | SGF (original pH = 1.82) | | FaSSIF (original pH = 6.51) | | FeSSIF (original pH = 4.99) | |
|---|---|---|---|---|---|---|
| | 24 h | Final pH | 24 h | Final pH | 24 h | Final pH |
| Compound 1 | 4.44 | 3.10 | 0.05 | 6.48 | 0.84 | 5.11 |
| P-Aminosalicylate (Form A) | 2.86 | 3.73 | 0.20 | 5.12 | 1.77 | 5.06 |

Compound 1 P-Aminosalicylate (Form B)

50 mg Compound 1 and 1.1 e.q. counter ion of 4-aminosalicylic acid in solid form were weighed into 2 mL vials individually, and then 1 mL solvent EtOAc/ACN was added into the vial. The vial was placed on the thermo-mixer with a stir bar and heated to 50° C. After keeping at 50° C. under constant stirring at 500 rpm for 21 hrs, the vial was then cooled to 25° C. After keeping at 25° C. for 1 hr, the solids in suspension were isolated by centrifugation and dried in the vacuum oven at 30° C. for 18 hrs.

The dried solids were characterized by PLM and XRPD (FIG. 123).

Example 25: Preparation of Maleate Salt of Compound 1

Maleate Salts of Compound 1 may be prepared from Compound 1 using the following exemplary methods.

Compound 1 Maleate (Form A):

50 mg of compound 1 and 1.1 e.q. counter ion of maleic acid in solid form were weighed into 2 mL vials individually, and then 1 mL acetone solvent was added into the vial. The vial was placed on the thermo-mixer with a stir bar and heated to 50° C. After keeping at 50° C. under constant stirring at 900 rpm for 18 hrs, the vial was then cooled to 25° C. After keeping at 25° C. for 1 hr, the solids in suspension were isolated by centrifugation and dried in the vacuum oven at 30° C. overnight.

The obtained dried solids were characterized by PLM and XRPD (FIG. 124).

Example 26: Attempts to Prepare Salts of Compound 1

The following acids formed non-crystalline salts under some conditions:

| Acid | Solvent |
| --- | --- |
| Maleic Acid | Ethyl Acetate; IPA/Water (95:5 V:V) |
| L-Malic Acid | IPA/Water (95:5 V:V) |
| Succinic Acid | Acetone; ACN; IPA/Water (95:5 V:V) |
| Naphthalene-2-sulfonic Acid | IPA/Water (95:5 V:V) |
| Ascorbic Acid | IPA/Water (95:5 V:V) |
| Salicylic Acid | Acetone; ACN; IPA/Water (95:5 V:V) |
| Lactic Acid | Acetone |
| 2-Hydroxyethanesulfonic acid | Acetone, Ethyl acetate |
| D-Mandelic Acid | Acetone; ACN; IPA/Water (95:5 V:V) |
| Cyclamic Acid | IPA/Water (95:5 V:V) |
| Dichloroacetic acid | Ethyl acetate; ACN; IPA/Water (95:5 V:V) |

Although multiple conditions (shown below) were attempted, the acids in the following table did not provide isolable salts of Compound 1.

| Acid | Solvent |
| --- | --- |
| Hydrochloric Acid | IPA/Water (95:5 V:V) |
| Sulfuric Acid | IPA/Water (95:5 V:V) |
| Acetic Acid | Acetone; Ethyl acetate; ACN; IPA/Water (95:5 V:V) |
| Succinic Acid | Ethyl Acetate |
| Pamoic Acid | Acetone; Ethyl acetate; ACN; IPA/Water (95:5 V:V) |
| Oleic Acid | Acetone; Ethyl acetate; ACN; IPA/Water (95:5 V:V) |
| L-Lysine Acid | Acetone; Ethyl acetate; ACN; IPA/Water (95:5 V:V) |
| L-Arginine | Acetone; Ethyl acetate; ACN; IPA/Water (95:5 V:V) |
| L-Aspartic Acid | Acetone; Ethyl acetate; ACN; IPA/Water (95:5 V:V) |
| Mucic Acid | Acetone; Ethyl acetate; ACN; IPA/Water (95:5 V:V) |
| Hipuric Acid | Acetone; Ethyl acetate; ACN; IPA/Water (95:5 V:V) |
| L-Pyroglutamic Acid | Acetone; Ethyl acetate; ACN; IPA/Water (95:5 V:V) |
| Gluconic Acid | Acetone; Ethyl acetate; ACN; IPA/Water (95:5 V:V) |
| Glyconic Acid | Acetone; Ethyl acetate; ACN; IPA/Water (95:5 V:V) |
| Lactic Acid | Ethyl acetate; ACN; IPA/Water (95:5 V:V) |
| D-Mandelic Acid | Ethyl Acetate |
| Lactobionic Acid | Acetone; Ethyl Acetate; ACN; IPA/Water (95:5 V:V) |
| Alginic Acid | Acetone; Ethyl acetate; ACN; IPA/Water (95:5 V:V) |
| Glycerophosphoric Acid | Acetone; Ethyl acetate; ACN; IPA/Water (95:5 V:V) |
| DL-Valine | Acetone; Ethyl acetate; ACN; IPA/Water (95:5 V:V) |
| DL-Leucine | Acetone; Ethyl acetate; ACN; IPA/Water (95:5 V:V) |
| L-Isoleucine | Acetone; Ethyl acetate; ACN; IPA/Water (95:5 V:V) |

Experimental conditions: For each of the twenty acids listed in the table above, four solvents (acetone, EtOAc, ACN and IPA/water (95/5, V/V)) were used according to following procedure to determine whether isolable salts of Compound 1 were provided by the particular solvent-acid combination.

Approximately 50 mg of Compound 1 and 1.1 molar equivalents of the acid were placed in a 2 mL vial. Approximately 1 mL solvent was added into the vial. The vials were placed on the thermomixer with a stir bar and heated to 50° C. After stirring (500 rpm) at 50° C. for 21 hrs, the vials were cooled to 25° C. and held at 25° C. for 1 hr and vials were monitored for the formation of solids. None of the experiments provided solids after stirring for approximately one hour. For each experiment, the solvent was evaporated in vacuum oven at 30° C. Under these conditions, none of the acids listed in the table above provided an isolable salt of Compound 1.

| Example 27. Bulk Density for salts of Compound 1. | | | |
| --- | --- | --- | --- |
| Salt | Form | Bulk Density (g/mL) | Tapped Density (g/mL) |
| Citrate | A | 0.49 | 0.70 |
| Phosphate | A | 0.15 | 0.33 |
| Tartrate | A | 0.13 | 0.32 |
| HBr | A | 0.27 | 0.50 |
| Free Base | A | 0.25 | 0.45 |

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as acknowledgment or any form of suggestion that they constitute valid prior art or form part of the common general knowledge in any country in the world.

What is claimed is:

1. A method of treating a disease or condition selected from epilepsy, bipolar disorder, and anxiety, the method comprising administering to a patient in need thereof an effective amount of a pharmaceutical composition comprising crystalline Form A of the citrate salt of 3α-hydroxy-3α-methoxymethyl-21-(1'-imidazolyl)-5α-pregnan-20-one, wherein the crystalline Form A exhibits an X-ray powder diffraction (XRPD) pattern comprising peaks at 5.7±0.2, 12.5±0.2 and 20.1±0.2 degrees two-theta using copper K-alpha radiation.

2. The method according to claim 1, wherein the disease or condition is epilepsy.

3. The method according to claim 1, wherein the pharmaceutical composition is in the form of an orally administered dosage form.

4. The method according to claim 3, wherein the pharmaceutical composition is in the form of a tablet.

5. The method according to claim 1, wherein the XRPD pattern further comprises a peak at about 13.0+0.2 degrees two-theta.

6. The method according to claim 1, wherein XRPD pattern further comprises a peak at about 11.9±0.2 degrees two-theta.

7. The method according to claim 1, wherein the XRPD pattern further comprises a peak at about 20.3±0.2 degrees two-theta.

8. The method according to claim 1, wherein the XRPD pattern further comprises a peak at about 17.1±0.2 degrees two-theta.

9. The method according to claim 1, wherein the crystalline Form A exhibits a differential scanning calorimetry thermogram having a peak value at about 89.0±2.0° C. or about 139.5±2.0° C.

10. A method of treating epilepsy, the method comprising administering to a patient in need thereof an effective amount of a pharmaceutical composition comprising crystalline Form A of the citrate salt of 3α-hydroxy-3α-methoxymethyl-21-(1'-imidazolyl)-5α-pregnan-20-one, wherein the crystalline Form A exhibits an X-ray powder diffraction (XRPD) pattern comprising peaks at 5.7±0.2, 12.5±0.2 and 20.1±0.2 degrees two-theta using copper K-alpha radiation.

11. The method according to claim 10, wherein the pharmaceutical composition is in the form of an orally administered dosage form.

12. The method according to claim 11, wherein the pharmaceutical composition is in the form of a tablet.

13. The method according to claim 10, wherein the XRPD pattern further comprises a peak at about 13.0±0.2 degrees two-theta.

14. The method according to claim 10, wherein the XRPD pattern further comprises a peak at about 11.9±0.2 degrees two-theta.

15. The method according to claim 10, wherein the XRPD pattern further comprises a peak at about 20.3±0.2 degrees two-theta.

16. The method according to claim 10, wherein the XRPD pattern further comprises a peak at about 17.1±0.2 degrees two-theta.

17. The method according to claim 10, wherein the crystalline Form A exhibits a differential scanning calorimetry thermogram having a peak value at about 89.0 ±2.0° C. or about 139.5±2.0° C.

* * * * *

UNITED STATES PATENT AND TRADEMARK OFFICE
CERTIFICATE OF CORRECTION

| | | |
|---|---|---|
| PATENT NO. | : 12,404,297 B2 | Page 1 of 1 |
| APPLICATION NO. | : 18/529117 | |
| DATED | : September 2, 2025 | |
| INVENTOR(S) | : Nelson B. Olivier et al. | |

It is certified that error appears in the above-identified patent and that said Letters Patent is hereby corrected as shown below:

In the Claims

Column 104, Line 39, Claim 1:
"3α-hydroxy-3α-methoxymethyl-21-(1′-imidazolyl)-5α-pregnan-20-one"
Should be:
-- 3α-hydroxy-3β-methoxymethyl-21-(1′-imidazolyl)-5α-pregnan-20-one --, Column 105, Line 4, Claim 10:
"3α-hydroxy-3α-methoxymethyl-21-(1′-imidazolyl)-5α-pregnan-20-one"
Should be:
-- "3α-hydroxy-3β-methoxymethyl-21-(1′-imidazolyl)-5α-pregnan-20-one" --.

Signed and Sealed this
Sixteenth Day of December, 2025

John A. Squires
*Director of the United States Patent and Trademark Office*